(12) United States Patent
Hayoz et al.

(10) Patent No.: US 9,748,487 B2
(45) Date of Patent: Aug. 29, 2017

(54) POLYMERS BASED ON NAPHTHODIONES

(71) Applicant: BASF SE, Ludwigshafen (DE)

(72) Inventors: Pascal Hayoz, Hofstetten (CH); Bernd Tieke, Bruehl (DE); Haichang Zhang, Huerth (DE)

(73) Assignee: BASF SE, Ludwigshafen (DE)

( * ) Notice: Subject to any disclaimer, the term of this patent is extended or adjusted under 35 U.S.C. 154(b) by 314 days.

(21) Appl. No.: 14/435,619

(22) PCT Filed: Nov. 5, 2013

(86) PCT No.: PCT/EP2013/073060
§ 371 (c)(1),
(2) Date: Apr. 14, 2015

(87) PCT Pub. No.: WO2014/072292
PCT Pub. Date: May 15, 2014

(65) Prior Publication Data
US 2016/0049588 A1 Feb. 18, 2016

Related U.S. Application Data

(60) Provisional application No. 61/723,334, filed on Nov. 7, 2012.

(30) Foreign Application Priority Data

Nov. 7, 2012 (EP) ..................................... 12191575

(51) Int. Cl.
*C08F 30/06* (2006.01)
*C08F 28/06* (2006.01)
(Continued)

(52) U.S. Cl.
CPC ........ *H01L 51/0035* (2013.01); *C07D 487/04* (2013.01); *C07D 493/04* (2013.01);
(Continued)

(58) Field of Classification Search
CPC ............. H01L 51/0036; H01L 51/0035; H01L 51/0043; H01L 51/0058; H01L 51/0007; H01L 51/42; C07D 519/00; C07D 493/04; C07D 487/04; C08G 61/124; C08G 61/125; C08G 61/126; C08G 2261/1412; C08G 2261/312; C08G 2261/314; C08G 2261/3222; C08G 2261/3241; C08G 2261/3327; C08G 2261/344; C08G 2261/364; C08G 2261/411; C08G 2261/51; C08G 2261/91; C08G 2261/92;
(Continued)

(56) References Cited

U.S. PATENT DOCUMENTS 6,013,811 A    1/2000 Milner et al.
6,690,029 B1   2/2004 Anthony et al.
(Continued)

FOREIGN PATENT DOCUMENTS

EP    0 648 770 A2    4/1995
EP    0 648 817 A1    4/1995
(Continued)

OTHER PUBLICATIONS

International Search Report issued Jul. 8, 2014 in PCT/EP2013/073060.
(Continued)

*Primary Examiner* — William Cheung
(74) *Attorney, Agent, or Firm* — Oblon, McClelland, Maier & Neustadt, L.L.P.

(57) ABSTRACT

The present invention relates to polymers comprising one or more (repeating) unit(s) of the formula (I), and compounds of formula (III), wherein Y, $Y^{15}$, $Y^{16}$ and $Y^{17}$ are independently of each other a group of formula and their use as IR absorber, organic semiconductor in organic devices, especially in organic photovoltaics and photodiodes, or in a device containing a diode and/or an organic field effect transistor. The polymers and compounds according to the invention can have excellent solubility in organic solvents and excellent film-forming properties. In addition, high efficiency of energy conversion, excellent field-effect mobility, good on/off current ratios and/or excellent stability can be observed, when the polymers and compounds according to the invention are used in organic field effect transistors, organic photovoltaics and photodiodes.

$$-\!\!\!+\!\text{Ar}^3\!\!+\!\!_c\!-\!\!+\!\text{Ar}^2\!\!+\!\!_b\!-\!\!+\!\text{Ar}^1\!\!+\!\!_a\!-\!\text{Y}\!-\!\!+\!\text{Ar}^{1\prime}\!\!+\!\!_{a\prime}\!-\!\!+\!\text{Ar}^{2\prime}\!\!+\!\!_{b\prime}\!-\!\!+\!\text{Ar}^{3\prime}\!\!+\!\!_{c\prime}\!-\!\!, \quad \text{(I)}$$

$$A^1\!-\!Y\!-\!\!+\!A^3\!-\!Y^{15}\!\!+\!\!_o\!-\!\!+\!A^4\!-\!Y^{16}\!\!+\!\!_p\!-\!\!+\!A^5\!-\!Y^{17}\!\!+\!\!_q\!-\!A^2, \quad \text{(III)}$$

16 Claims, No Drawings

(51) Int. Cl.

| | |
|---|---|
| H01L 21/00 | (2006.01) |
| C07D 487/00 | (2006.01) |
| C07D 307/77 | (2006.01) |
| H01L 51/00 | (2006.01) |
| C08G 61/12 | (2006.01) |
| C07D 519/00 | (2006.01) |
| C07D 487/04 | (2006.01) |
| C07D 493/04 | (2006.01) |
| C08F 226/10 | (2006.01) |
| C08F 232/00 | (2006.01) |
| C08F 234/02 | (2006.01) |
| C08F 234/04 | (2006.01) |
| H01L 51/05 | (2006.01) |
| H01L 51/42 | (2006.01) |

(52) U.S. Cl.
CPC .......... *C07D 519/00* (2013.01); *C08F 226/10* (2013.01); *C08F 232/00* (2013.01); *C08F 234/02* (2013.01); *C08F 234/04* (2013.01); *C08G 61/124* (2013.01); *C08G 61/125* (2013.01); *C08G 61/126* (2013.01); *H01L 51/0036* (2013.01); *H01L 51/0043* (2013.01); *C08G 2261/1412* (2013.01); *C08G 2261/312* (2013.01); *C08G 2261/314* (2013.01); *C08G 2261/3222* (2013.01); *C08G 2261/3223* (2013.01); *C08G 2261/3241* (2013.01); *C08G 2261/3327* (2013.01); *C08G 2261/344* (2013.01); *C08G 2261/364* (2013.01); *C08G 2261/411* (2013.01); *C08G 2261/51* (2013.01); *C08G 2261/59* (2013.01); *C08G 2261/91* (2013.01); *C08G 2261/92* (2013.01); *H01L 51/0007* (2013.01); *H01L 51/0558* (2013.01); *H01L 51/42* (2013.01); *Y02E 10/549* (2013.01)

(58) Field of Classification Search
CPC .... C08F 232/00; C08F 234/04; C08F 226/10; C08F 234/02; Y02E 10/549
USPC .................. 526/239, 256; 438/82; 548/421; 549/298
See application file for complete search history.

(56) References Cited

U.S. PATENT DOCUMENTS

| | | | |
|---|---|---|---|
| 2003/0021913 A1 | 1/2003 | O'Neill et al. | |
| 2006/0013549 A1 | 1/2006 | Shtein et al. | |
| 2006/0223993 A1* | 10/2006 | Connor | C07D 471/14 540/200 |
| 2007/0079867 A1 | 4/2007 | Chittibabu et al. | |
| 2008/0241492 A1 | 10/2008 | Demartin Maeder et al. | |

FOREIGN PATENT DOCUMENTS

| | | |
|---|---|---|
| EP | 0 742 255 A1 | 11/1996 |
| EP | 0 761 772 A1 | 3/1997 |
| EP | 1 086 984 A2 | 3/2001 |
| GB | 2 299 811 A | 10/1996 |
| WO | WO 97/28211 A1 | 8/1997 |
| WO | WO 97/28221 A1 | 8/1997 |
| WO | WO 98/32802 A1 | 7/1998 |
| WO | WO 98/45757 A1 | 10/1998 |
| WO | WO 98/58027 A1 | 12/1998 |
| WO | WO 99/01511 A1 | 1/1999 |
| WO | WO 00/17275 A1 | 3/2000 |
| WO | WO 00/36210 A1 | 6/2000 |
| WO | WO 00/39221 A1 | 7/2000 |
| WO | WO 00/63297 A1 | 10/2000 |
| WO | WO 03/052841 A1 | 6/2003 |
| WO | WO 2004/101581 A2 | 11/2004 |
| WO | WO 2004/112161 A2 | 12/2004 |
| WO | WO 2007/082584 A1 | 7/2007 |
| WO | WO 2008/001123 A1 | 1/2008 |
| WO | WO 2008/107089 A1 | 9/2008 |
| WO | WO 2009/047104 A2 | 4/2009 |
| WO | WO 2010/108873 A1 | 9/2010 |
| WO | WO 2010/136352 A1 | 12/2010 |
| WO | WO 2012/003918 A1 | 1/2012 |

OTHER PUBLICATIONS

John L. Carey, et al., "Naphthoquinone Mono- and Di-methide Lactones" Journal of the Chemical Society, Perkin Transactions 1, XP055059127, Jan. 1984, pp. 1957-1962.

Chun Yoon, et al., "Dyeing and fastness properties of benzodifuranones, naphthodifuranones and naphthofuranonepyrrolidones" Coloration Technology, Society of Dyers and Colourists, vol. 118, No. 3, XP001200570, Jan. 2002, pp. 125-130.

G. Hallas, et al., "The synthesis and properties of naphthodifuranones and naphthofuranonepyrrolidones" Dyes and Pigments, vol. 48, No. 2, XP004313977, Feb. 2001, pp. 121-132.

Kai Zhang, et al., "Low-Bandgap Benzodifuranone-Based Polymers" Macromolecules, American Chemical Society, vol. 44, Jun. 7, 2011, pp. 4596-4599.

Stanislav Lunak, et al., "DFT and TD DFT study of isomeric linear benzodifuranones, benzodipyrrolinones and their homologues" Journal of Molecular Structure, vol. 935, Jul. 2, 2009, pp. 82-91.

\* cited by examiner

POLYMERS BASED ON NAPHTHODIONES

This application is a U.S. National Stage Application under 35 U.S.C. §371 of International Application No. PCT/EP2013/073060 filed on Nov. 5, 2013, which claims benefit of U.S. Provisional Application No. 61/723,334 filed Nov. 7, 2012, and claims benefit to European Patent Application No. EP 1219157.5 filed on Nov. 7, 2012.

DESCRIPTION

The present invention relates to polymers comprising one or more (repeating) unit(s) of the formula (I), and compounds of formula (III) and their use as IR absorber, organic semiconductor in organic devices, especially in organic photovoltaics and photodiodes, or in a device containing a diode and/or an organic field effect transistor. The polymers and compounds according to the invention can have excellent solubility in organic solvents and excellent film-forming properties. In addition, high efficiency of energy conversion, excellent field-effect mobility, good on/off current ratios and/or excellent stability can be observed, when the polymers and compounds according to the invention are used in organic field effect transistors, organic photovoltaics and photodiodes.

US20060223993 discloses naphthalene centered-dilactone bismethines, dilactames and dithiolactones of formula

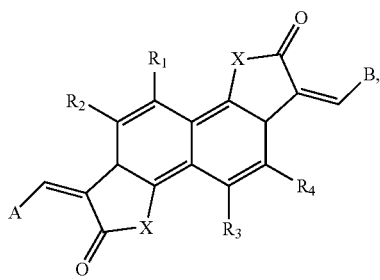

wherein X is O, S, or $NR_1$, which can be used as colorants for polyethylene terephthalate.

J. L. Carey et al., J. Chem. Soc. Perkin Trans. I (1984) 1957-62 relates to naphtoquinone mono- and di-methide lactones. The following compound has been synthesized:

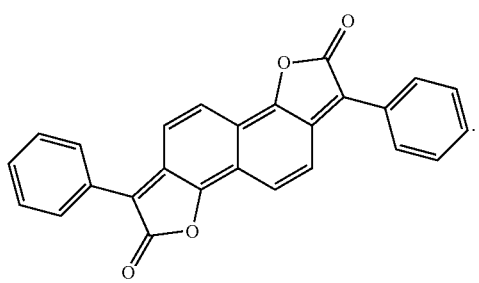

GB2299811 relates to compounds of the formula

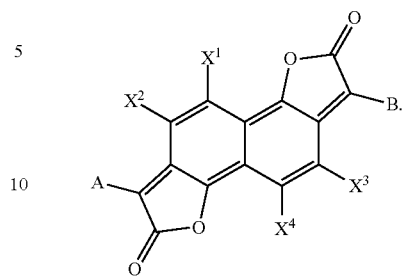

A and B are optionally substituted (hetero)aryl and $X^1$, $X^2$, $X^3$ and $X^4$ are independently of each other H, halo, alkyl, or alkoxy, provided that A and B are not unsubstituted phenyl. The use of such compounds is as dyes for synthetic textile materials and fibre blends or for the mass coloration of plastics.

G. Hallas et al., Dyes and Pigments 48 (2001) 121-132 relates to compounds of the formula

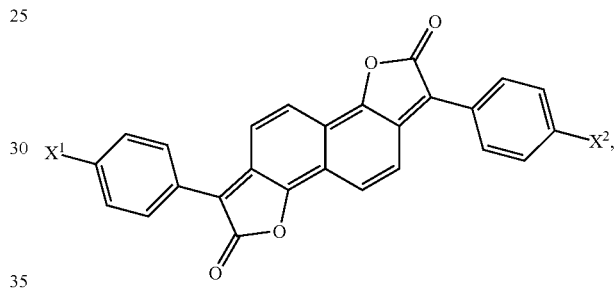

wherein $X^1$ is hydrogen, $CH_3$, Cl, $CH_3O$ and $X^2$ is $OCH^3$, $OCH_2CH_3$, $O(CH_2)_2CH_3$, $OCH(CH_3)_2$, $O(CH_2)_3CH_3$, $O(CH_2)_2OC_2H_5$, and

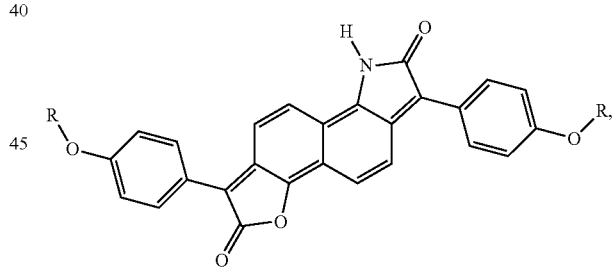

where R is $CH_3$, $C_2H_5$, Pr, iPr, Bu.

G. Hallas et al., Coloration Technology 118 (2002) 125-130 relates to compounds of the formula

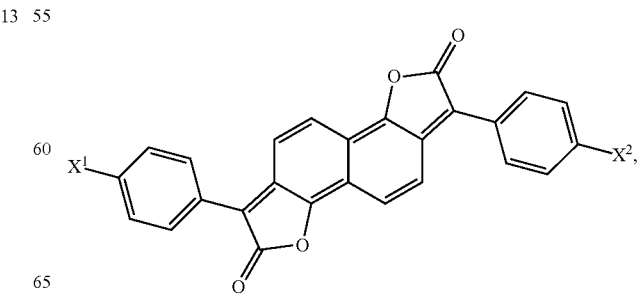

$X^1$ is hydrogen, $CH_3$, Cl, $CH_3O$, $O(CH_2)_2CH_3$, $O(CH_2)_3CH_3$, and $X^2$ is hydrogen, $OCH_3$, $OCH_2CH_3$, $O(CH_2)_2CH_3$, $OCH(CH_3)_2$, $O(CH_2)_3CH_3$, $O(CH_2)_2OC_2H_5$, and

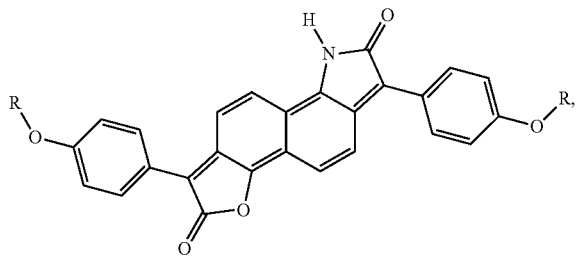

where R is $CH_3$, $C_2H_5$, $(CH_2)_2CH_3$, $CH(CH_3)_2$, or $(CH_2)_3CH_3$.

Stanislav Lunak et al., Journal of Molecular Structure 935 (2009) 82-91 relates to a theoretical density functional theory (DFT) and time dependent (TD) DFT study of isomeric linear benzodifuranones, benzodipyrrolinones and their homologues. No synthesis method for the claimed compounds is given. In addition no polymers are reported.

WO9728211 relates to a preparation process for benzodifuranone dyes.

WO2012/003918 relates to polymers comprising repeating units of formula

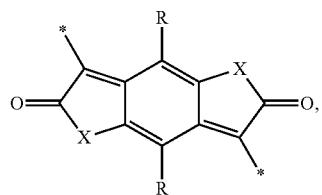

wherein X is O, S, or $NR^x$.

Kai Zhang and Bernd Tieke, Macromolecules 44 (2011) 4596-4599 relates to π-conjugated monomers and polymers containing benzodifuranone units in the main chain:

The polymers show very broad absorption bands with a high extinction coefficient up to 32 500 L mol$^{-1}$ cm$^{-1}$. The polymers also show reversible redox behavior, giving small HOMO-LUMO gaps up to 1.30 eV with strong donor-acceptor character.

It is one object of the present invention to provide polymers and compounds, which show high efficiency of energy conversion, excellent field-effect mobility, good on/off current ratios and/or excellent stability, when used in organic field effect transistors, organic photovoltaics (solar cells) and photodiodes. Another object of the invention is to provide polymers and compounds with very low band gap, which can also be used as infrared (IR) absorbers. Still another object of the invention is to provide a new synthesis route to benzodiones with 5-ring-heterocycles (instead of (substituted)phenyl) directly attached to the benzodione basic structure to form structures where the benzodione core and the directly attached 5-ring-heterocycles are arranged in a planar manner.

In a first aspect of the present invention, said object has been solved by polymers, comprising one or more (repeating) unit(s) Y, preferably in the form of the formula

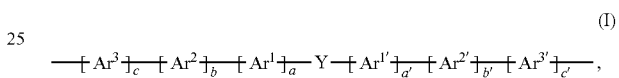

wherein Y is a group of formula

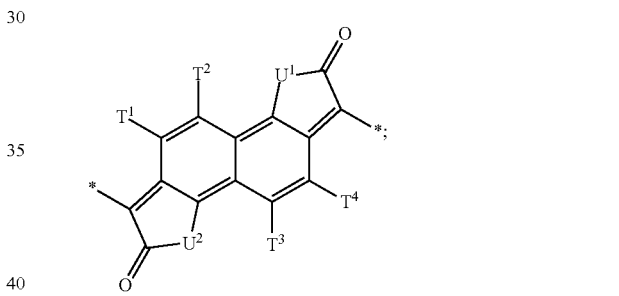

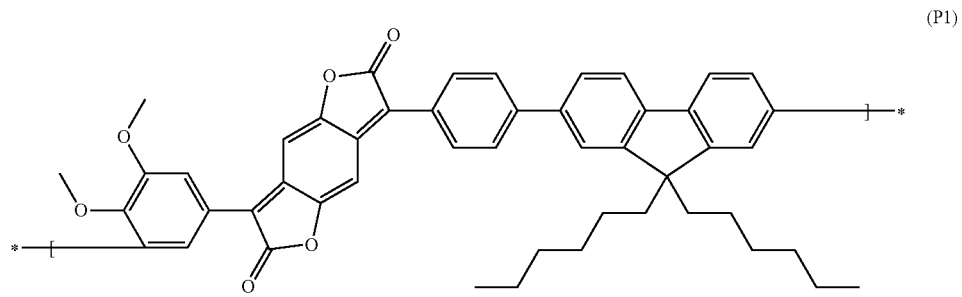

(P1)

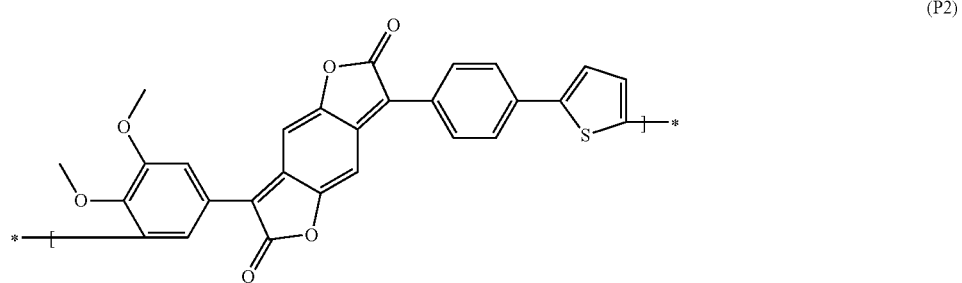

(P2)

a is 1, 2, or 3, a' is 1, 2, or 3; b is 0, 1, 2, or 3; b' is 0, 1, 2, or 3; c is 0, 1, 2, or 3; c' is 0, 1, 2, or 3;

$U^1$ is O, S, or $NR^1$;

$U^2$ is O, S, or $NR^2$;

$T^1$, $T^2$, $T^3$ and $T^4$ are independently of each other hydrogen, halogen, hydroxyl, cyano, —$COOR^{103}$, —$OCOR^{103}$, —$NR^{112}COR^{103}$, —$CONR^{112}R^{113}$, —$OR^{103'}$, —$SR^{103'}$, —$SOR^{103'}$, —$SO_2R^{103'}$, —$NR^{112}SO_2R^{103'}$, —$NR^{112}R^{113}$, $C_1$-$C_{25}$alkyl, which may be substituted by E and/or interrupted by D, $C_5$-$C_{12}$cycloalkyl, which can be substituted one to three times with $C_1$-$C_8$alkyl and/or $C_1$-$C_8$alkoxy; $C_7$-$C_{25}$arylalkyl, $C_6$-$C_{24}$aryl, $C_6$-$C_{24}$aryl which is substituted by G, $C_2$-$C_{20}$heteroaryl, or $C_2$-$C_{20}$heteroaryl which is substituted by G;

$R^1$ and $R^2$ may be the same or different and are selected from hydrogen, a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —$NR^{39}$—, $CONR^{39}$—, $NR^{39}CO$—, —COO—, —CO— or —OCO—, a $C_2$-$C_{100}$alkenyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —$NR^{39}$—, $CONR^{39}$—, $NR^{39}CO$—, —COO—, —CO— or —OCO—, a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —$NR^{39}$—, $CONR^{39}$—, $NR^{39}CO$—, —COO—, —CO— or —OCO—, a $C_3$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group; and/or can optionally be interrupted by —O—, —S—, —$NR^{39}$—, $CONR^{39}$—, $NR^{39}CO$—, —COO—, —CO— or —OCO—, a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group;

a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, a silyl group, or a siloxanyl group;

a —CO—$C_1$-$C_{18}$alkyl group, a —CO—$C_5$-$C_{12}$cycloalkyl group, or —COO—$C_1$-$C_{18}$alkyl group;

$R^{39}$ is hydrogen, $C_1$-$C_{18}$alkyl, $C_1$-$C_{18}$haloalkyl, $C_7$-$C_{25}$arylalkyl, or $C_1$-$C_{18}$alkanoyl, $Ar^1$, $Ar^{1'}$, $Ar^2$, $Ar^{2'}$, $Ar^3$ and $Ar^{3'}$ are independently of each other

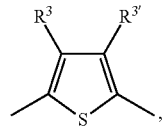
(XIa)

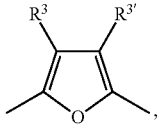
(XIb)

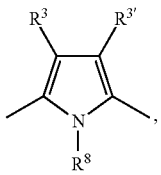
(XIc)

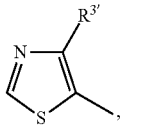
(XId)

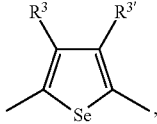
(XIe)

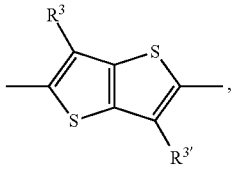
(XIf)

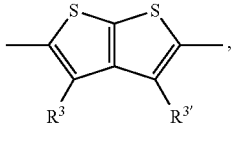
(XIg)

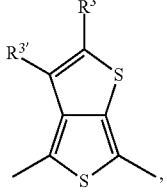
(XIh)

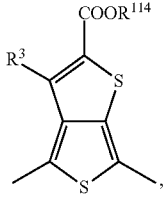
(XIi)

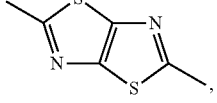
(XIj)

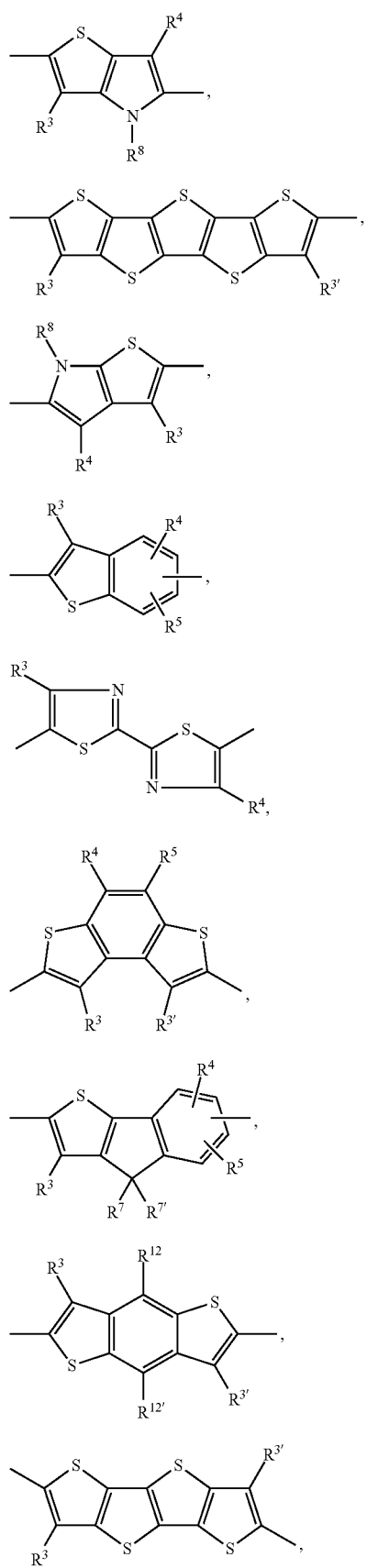
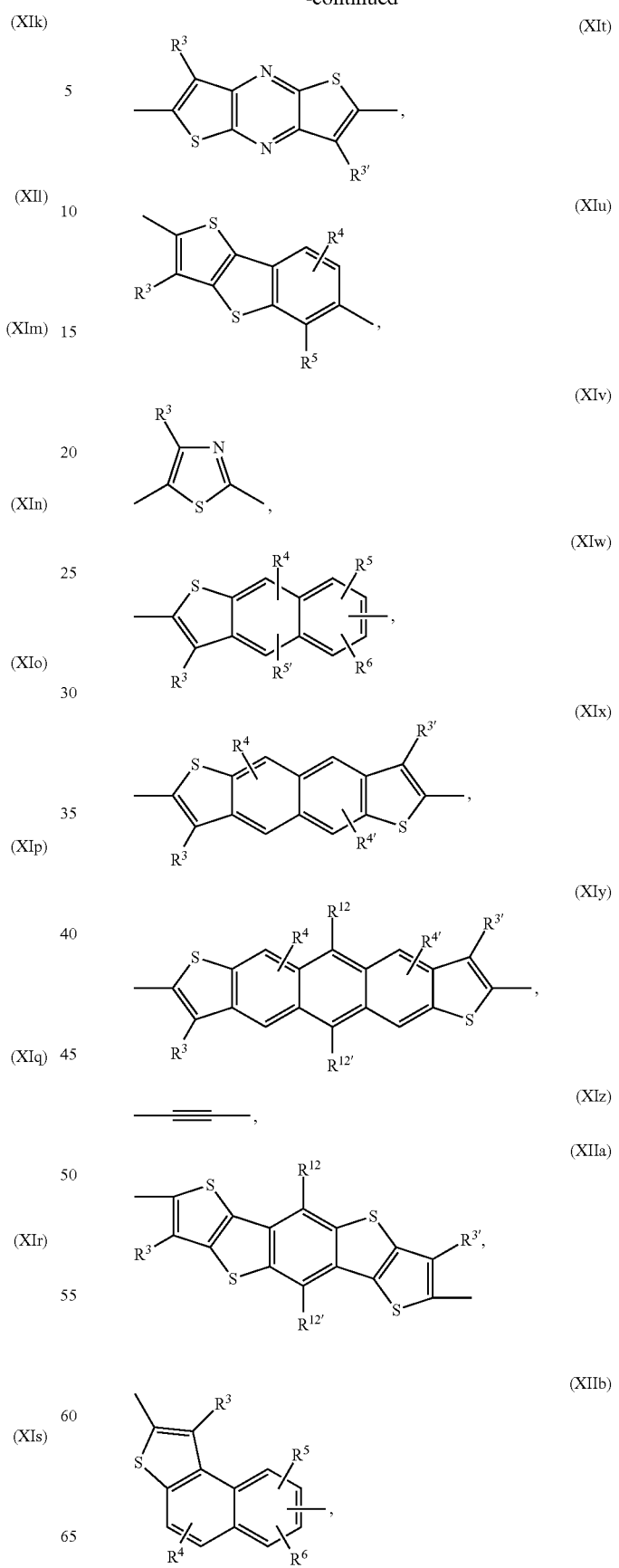

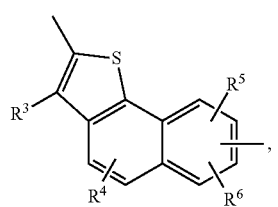
(XIIc)
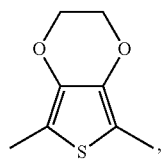
(XIId)
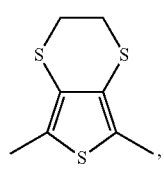
(XIIe)
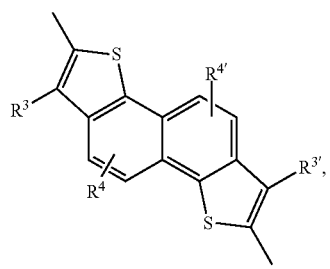
(XIIf)
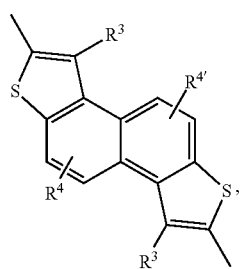
(XIIg)
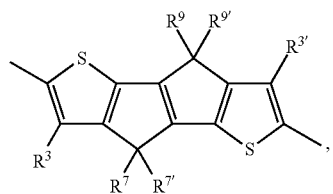
(XIIh)
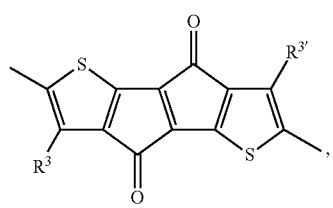
(XIIi)
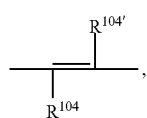
(XIIj)
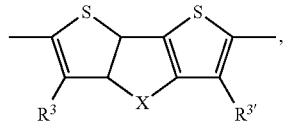
(XIII)
such as, for example,
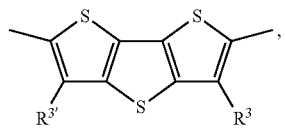
(XIIIa)
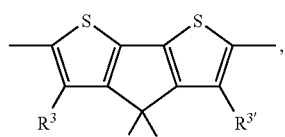
(XIIIb)
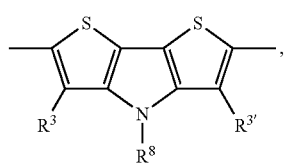
(XIIIc)
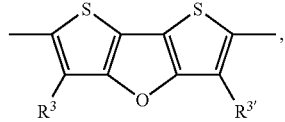
(XIIId)
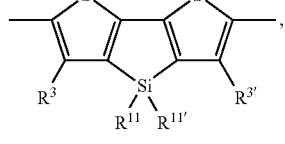
(XIIIe)
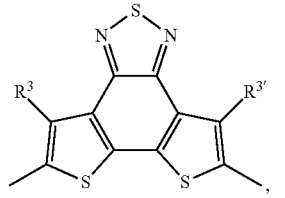
(XIIIf)
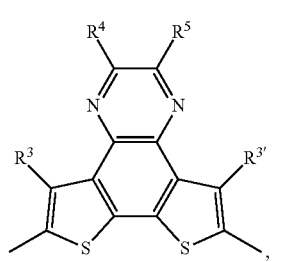
(XIIIg)

-continued
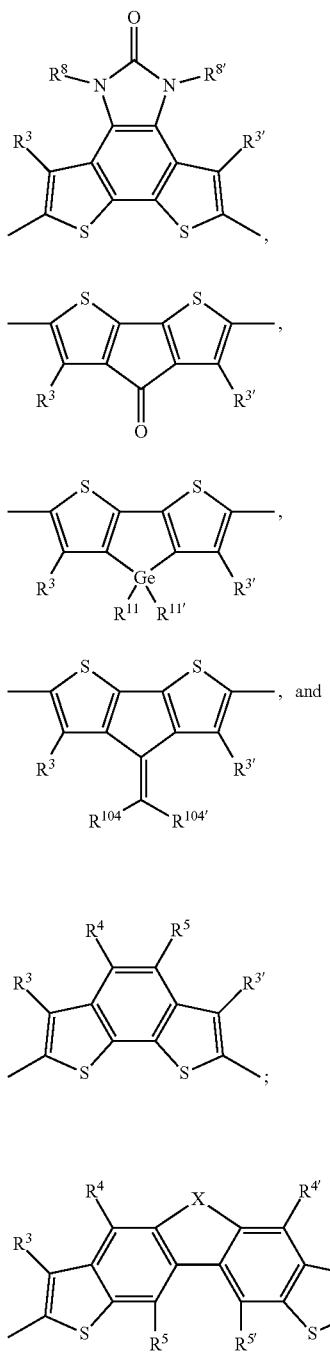
such as, for example,
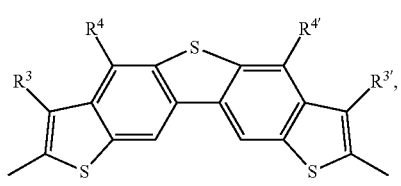
-continued
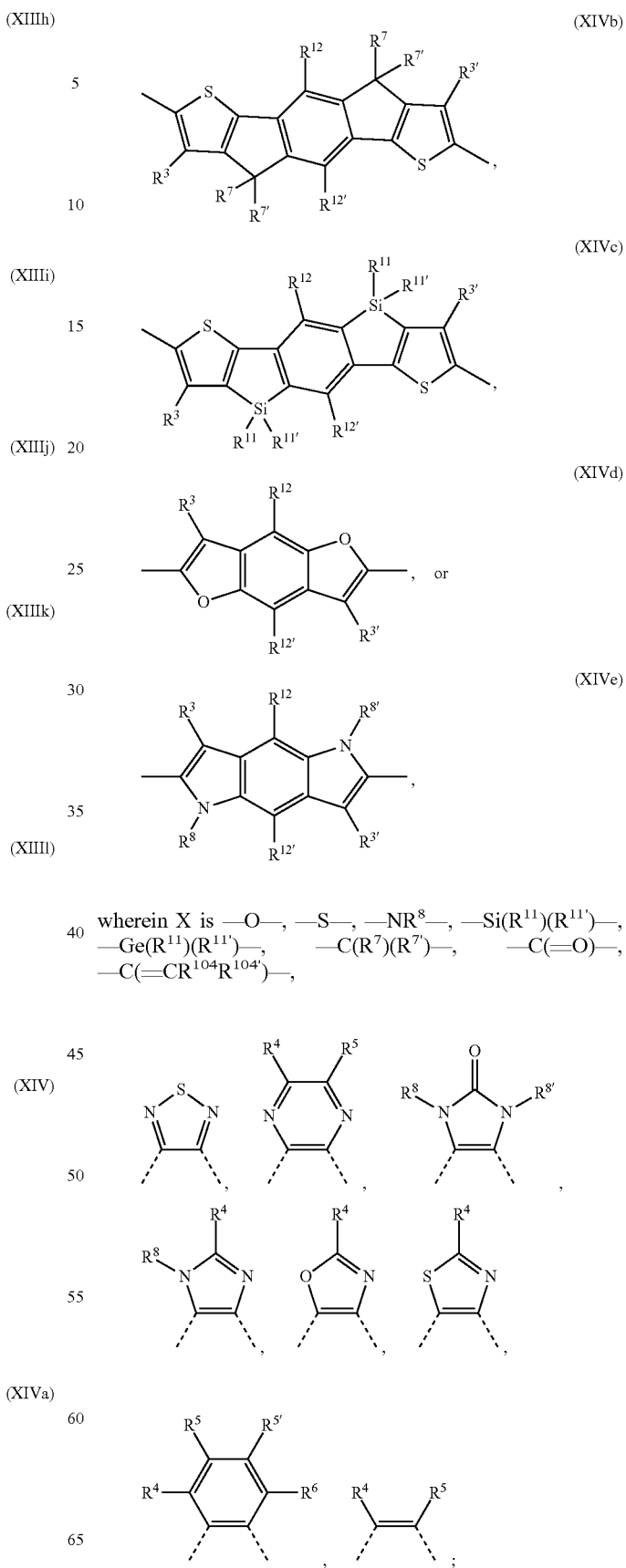
wherein X is —O—, —S—, —NR$^8$—, —Si(R$^{11}$)(R$^{11'}$)—, —Ge(R$^{11}$)(R$^{11'}$)—, —C(R$^7$)(R$^{7'}$)—, —C(=O)—, —C(=CR$^{104}$R$^{104'}$)—,

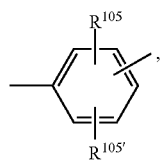 (XVa)
especially
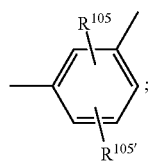, or (Xva')
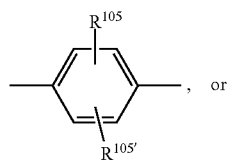; (Xva")
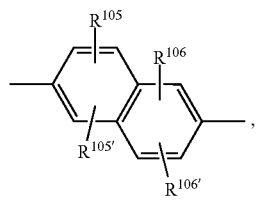, (XVb)
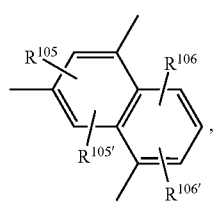, (XVc)
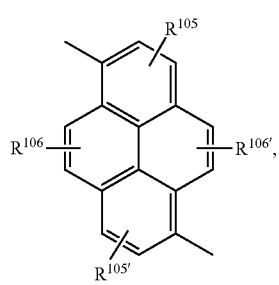, (XVd)
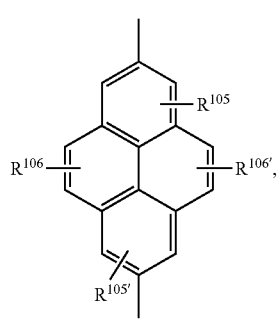, (XVe)
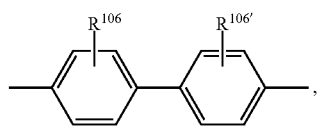, (XVf)
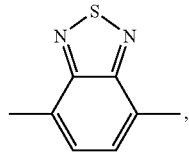, (XVg)
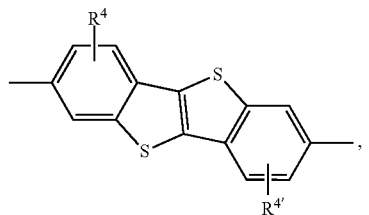, (XVh)
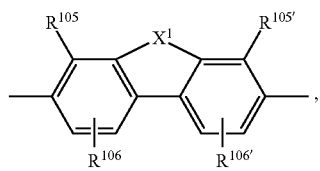, (XVI)
such as, for example,
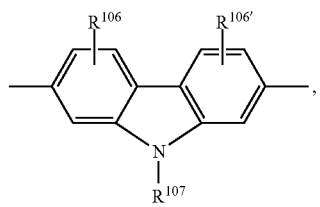, (XVIa)
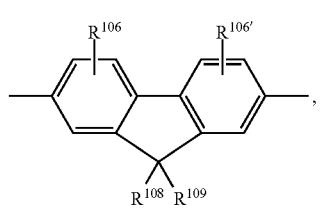, (XVIb)
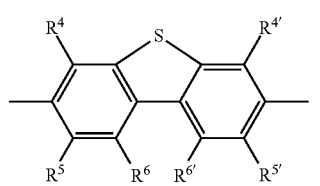 and (XVIc)
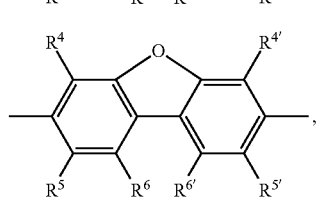, (XVId)

-continued

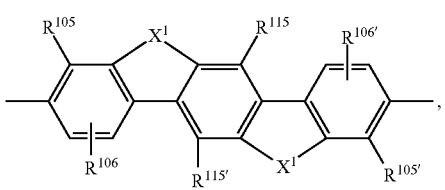
(XVII)

such as, for example,

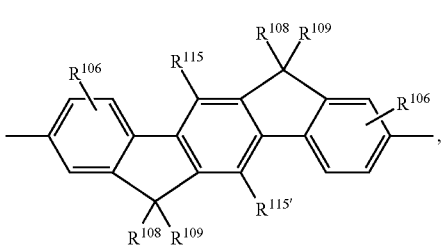
(XVIIa)

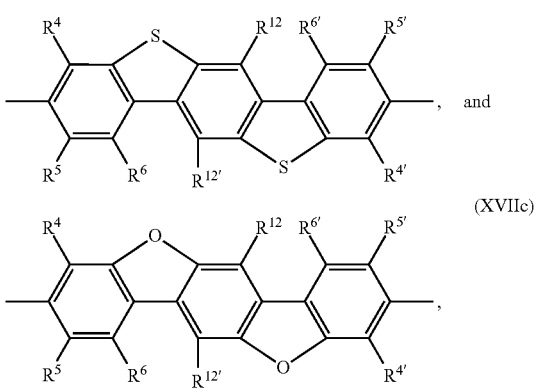
(XVIIb)

and (XVIIc)

wherein $X^1$ is S, O, $NR^{107}$—, —Si($R^{117}$)($R^{117'}$)—, —Ge($R^{117}$)($R^{117'}$)—, —C($R^{106}$)($R^{109}$)—, —C(=O)—, —C(=C$R^{104}R^{104'}$)—,

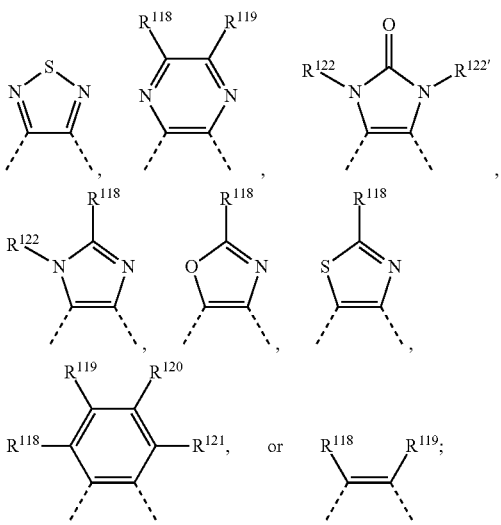

$R^3$ and $R^{3'}$ are independently of each other hydrogen, halogen, halogenated $C_1$-$C_{25}$alkyl, especially $CF_3$, cyano, $C_1$-$C_{25}$alkyl, especially $C_3$-$C_{25}$alkyl, which may optionally be interrupted by one or more oxygen or sulphur atoms; $C_7$-$C_{25}$arylalkyl, or $C_1$-$C_{25}$alkoxy;

$R^4$, $R^{4'}$, $R^5$, $R^{5'}$, $R^6$, and $R^{6'}$ are independently of each other hydrogen, halogen, halogenated $C_1$-$C_{25}$alkyl, especially $CF_3$, cyano, $C_1$-$C_{25}$alkyl, especially $C_3$-$C_{25}$alkyl, which may optionally be interrupted by one or more oxygen or sulphur atoms; $C_7$-$C_{25}$arylalkyl, or $C_1$-$C_{25}$alkoxy;

$R^7$, $R^{7'}$, $R^9$ and $R^{9'}$ are independently of each other hydrogen, $C_1$-$C_{25}$alkyl, especially $C_3$-$C_{25}$alkyl, which may optionally be interrupted by one, or more oxygen, or sulphur atoms; or $C_7$-$C_{25}$arylalkyl, $R^8$ and $R^{8'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_3$-$C_{25}$alkyl, which may optionally be interrupted by one or more oxygen or sulphur atoms; or $C_7$-$C_{25}$arylalkyl, $R^{11}$ and $R^{11'}$ are independently of each other $C_1$-$C_{25}$alkyl group, especially a $C_1$-$C_8$alkyl group, $C_7$-$C_{25}$arylalkyl, or a phenyl group, which can be substituted one to three times with $C_1$-$C_8$alkyl and/or $C_1$-$C_8$alkoxy;

$R^{12}$ and $R^{12'}$ are independently of each other hydrogen, halogen, cyano, $C_1$-$C_{25}$alkyl, especially $C_3$-$C_{25}$alkyl, which may optionally be interrupted by one, or more oxygen, or sulphur atoms, $C_1$-$C_{25}$alkoxy, $C_7$-$C_{25}$arylalkyl, or $$\mathrm{-\!\!\!=\!\!\!-\!\!\!R^{13}},$$

wherein $R^{13}$ is a $C_1$-$C_{10}$alkyl group, or a tri($C_1$-$C_8$alkyl)silyl group;

$R^{103}$ and $R^{103'}$ are independently of each other $C_1$-$C_{100}$alkyl, especially $C_3$-$C_{25}$alkyl, $C_1$-$C_{25}$alkyl substituted by E and/or interrupted with D, $C_7$-$C_{25}$arylalkyl, $C_6$-$C_{24}$aryl, $C_6$-$C_{24}$aryl which is substituted by G, $C_2$-$C_{20}$heteroaryl, or $C_2$-$C_{20}$heteroaryl which is substituted by G, $R^{104}$ and $R^{104'}$ are independently of each other hydrogen, $C_1$-$C_{18}$alkyl, cyano, $COOR^{103}$, $C_6$-$C_{10}$aryl, which may optionally be substituted by G, or $C_2$-$C_8$heteroaryl, which may optionally be substituted by G, $R^{105}$, $R^{105'}$, $R^{106}$ and $R^{106'}$ are independently of each other hydrogen, halogen, cyano, $C_1$-$C_{25}$alkyl, which may optionally be interrupted by one or more oxygen or sulphur atoms; $C_7$-$C_{25}$arylalkyl, or $C_1$-$C_{18}$alkoxy, $R^{107}$ is hydrogen, $C_7$-$C_{25}$arylalkyl, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$perfluoroalkyl; $C_1$-$C_{25}$alkyl; especially $C_3$-$C_{25}$alkyl, which may be interrupted by —O—, or —S—; or —COOR$^{103}$; $R^{103}$ is as defined above;

$R^{108}$ and $R^{109}$ are independently of each other H, $C_1$-$C_{25}$alkyl, $C_1$-$C_{25}$alkyl which is substituted by E and/or interrupted by D, $C_7$-$C_{25}$arylalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{108}$ and $R^{109}$ together form a group of formula =$CR^{110}R^{111}$, wherein $R^{110}$ and $R^{111}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{108}$ and $R^{109}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, D is —CO—, —COO—, —S—, —O—, or —$NR^{112}$—, E is $C_1$-$C_8$thioalkoxy, $C_1$-$C_8$alkoxy, CN, —$NR^{112}R^{113}$, —$CONR^{112}R^{113}$, or halogen, G is E, or $C_1$-$C_{18}$alkyl, and $R^{112}$ and $R^{113}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{114}$ is $C_1$-$C_{25}$alkyl, especially $C_3$-$C_{25}$alkyl, which may optionally be interrupted by one, or more oxygen, or sulphur atoms, $R^{115}$ and $R^{115'}$ are independently of each other hydrogen, halogen, cyano, $C_1$-$C_{25}$alkyl, especially $C_3$-$C_{25}$alkyl, which may optionally be interrupted by one, or more oxygen, or sulphur atoms, $C_1$-$C_{25}$alkoxy, $C_7$-$C_{25}$arylalkyl, or

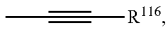$R^{116}$, wherein $R^{116}$ is a $C_1$-$C_{10}$alkyl group, or a tri($C_1$-$C_8$alkyl)silyl group;

$R^{117}$ and $R^{117'}$ are independently of each other $C_1$-$C_{25}$alkyl group, especially a $C_1$-$C_8$alkyl group, $C_7$-$C_{25}$arylalkyl, or a phenyl group, which can be substituted one to three times with $C_1$-$C_8$alkyl and/or $C_1$-$C_8$alkoxy;

$R^{118}$, $R^{119}$, $R^{120}$ and $R^{121}$ are independently of each other hydrogen, halogen, halogenated $C_1$-$C_{25}$alkyl, especially $CF_3$, cyano, $C_1$-$C_{25}$alkyl, especially $C_3$-$C_{25}$alkyl, which may optionally be interrupted by one or more oxygen or sulphur atoms; $C_7$-$C_{25}$arylalkyl, or $C_1$-$C_{25}$alkoxy;

$R^{122}$ and $R^{122'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_3$-$C_{25}$alkyl, which may optionally be interrupted by one or more oxygen or sulphur atoms; or $C_7$-$C_{25}$arylalkyl.

Polymers, comprising a repeating unit of the formula (I) are preferred.

In a preferred embodiment the present invention is directed to polymers comprising a repeating unit of formula (I), wherein Y is a group of formula

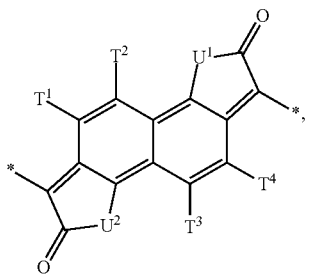

a is 1, a' is 1, b is 0, b' is 0, c is 0 and c' is 0; $T^1$, $T^2$, $T^3$ and $T^4$ are independently of each other a hydrogen atom, a halogen atom, CN, $COOR^{103}$, or $C_1$-$C_8$ alkyl, $U^1$ is $NR^1$ and $U^2$ is $NR^2$ and $Ar^1$ and $Ar^{1'}$ are as defined above.

In a preferred embodiment $Ar^1$ and $Ar^{1'}$ are independently of each other a group of formula (XIa), (XIb), (XIc), (XIe), (XIf), (XIk), (XIm), (XIn), (XIq), (XIr), (XIu), (XIw), (XIx), (XIII), such as, for example, (XIIIa) and (XIIIb); or (XIV), such as, for example, (XIVb). Preferably, $Ar^1$ and $Ar^{1'}$ are independently of each other a group of formula XIa, XIb, XIe, XIf, XIr, or XIIIa. More preferably, $Ar^1$ and $Ar^{1'}$ are independently of each other a group of formula XIa, XIb, or XIf, most preferred a group of formula XIa.

In another preferred embodiment of the present invention $Ar^1$ and $Ar^{1'}$ are independently of each other a group of formula XVa' or XVa''.

Preferably, $T^1$, $T^2$, $T^3$ and $T^4$ are independently of each other hydrogen, halogen, cyano, —$COOR^{103}$, —$OR^{103'}$, —$SR^{103'}$, or $C_1$-$C_{25}$alkyl. More preferably, $T^1$, $T^2$, $T^3$ and $T^4$ are independently of each other hydrogen, halogen, —$OR^{103'}$, or $C_1$-$C_{25}$alkyl. $T^1$, $T^2$, $T^3$ and $T^4$ are even more preferably hydrogen, or $C_1$-$C_{25}$alkyl, most preferred hydrogen.

$R^1$ and $R^2$ are preferably selected from hydrogen, a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl; and/or can optionally be interrupted by —O—, —S—, —$NR^{39}$—, —COO—, —CO— or —OCO—, a $C_2$-$C_{100}$alkenyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl; and/or can optionally be interrupted by —O—, —S—, —$NR^{39}$—, —COO—, —CO— or —OCO—, a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl; and/or can optionally be interrupted by —O—, —S—, —$NR^{39}$—, —COO—, —CO— or —OCO—, a $C_3$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl; and/or can optionally be interrupted by —O—, —S—, —$NR^{39}$—, —COO—, —CO— or —OCO—, a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl;

a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, or $C_2$-$C_{20}$heteroaryl;

a —CO—$C_1$-$C_{18}$alkyl group, a —CO—$C_5$-$C_{12}$cycloalkyl group, or —COO—$C_1$-$C_{18}$alkyl group.

$R^{39}$ is hydrogen, $C_1$-$C_{18}$alkyl, $C_7$-$C_{25}$arylalkyl, or $C_1$-$C_{18}$alkanoyl.

In a second aspect of the present invention, said object has been solved by compounds of formula (III), which are described in more detail below.

Advantageously, the polymer, or compound of the present invention, or an organic semiconductor material, layer or component, comprising the polymer, or compound of the present invention can be used in organic photovoltaics (solar cells), photodiodes, in an organic field effect transistor (OFET), as IR absorber, in thin film transistors (TFT), intergrated circuits (IC), radio frequency identification (RFID) tags, devices or components, organic light emitting diodes (OLED), organic light emitting transistors (OLET), flat panel displays, backlights of displays, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

The polymers of this invention preferably have a weight average molecular weight of 4,000 Daltons or greater, especially 4,000 to 2,000,000 Daltons, more preferably 10,000 to 1,000,000 and most preferably 10,000 to 100,000 Daltons. Molecular weights are determined according to high-temperature gel permeation chromatography (HT-GPC) using polystyrene standards. The polymers of this invention preferably have a polydispersity of 1.01 to 10, more preferably 1.1 to 3.0, most preferred 1.5 to 2.5. The polymers of the present invention are preferably conjugated.

Oligomers of the present invention preferably have a weight average molecular weight below 4,000 Daltons.

In an embodiment of the present invention the polymer is a polymer of formula

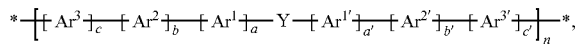

wherein n is usually in the range of 4 to 1000, especially 4 to 200, very especially 5 to 150.

$U^1$ is preferably O or $NR^1$; more preferably $NR^1$.

$U^2$ is preferably O or $NR^1$; more preferably $NR^1$.

Preferably $T^1$ and $T^2$ are independently of each other hydrogen, halogen, cyano, $-COOR^{103}$, $-OCOR^{103}$, $-OR^{103}$, $-SR^{103}$, $C_1$-$C_{25}$alkyl, which may be substituted by E and/or interrupted by D, $C_6$-$C_{24}$aryl, $C_6$-$C_{24}$aryl which is substituted by G, $C_2$-$C_{20}$heteroaryl, or $C_2$-$C_{20}$heteroaryl which is substituted by G;

More preferably, $T^1$ and $T^2$ are independently of each other hydrogen, halogen, cyano, $-COOR^{103}$, $-OCOR^{103}$, $-OR^{103}$, or $C_1$-$C_{25}$alkyl, which may be substituted by E and/or interrupted by D; more preferably hydrogen, halogen, cyano, $-OR^{103}$, $C_1$-$C_{25}$alkyl. Most preferred $T^1$ and $T^2$ are hydrogen, or $C_1$-$C_{25}$alkyl, especially hydrogen.

In the definition of $R^1$ and $R^2$ a silyl group or a siloxanyl group means $-SiR^{161}R^{162}R^{163}$, or $-O-SiR^{161}R^{162}R^{163}$.

$R^{161}$, $R^{162}$ and $R^{163}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, $-O-SiR^{164}R^{165}R^{166}$, $-(O-SiR^{164}R^{165})_d-R^{166}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{24}$ alkyl, halogen, cyano or $C_1$-$C_{25}$alkoxy; preferably hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, $-O-SiR^{164}R^{165}R^{166}$, $-O-(SiR^{164}R^{165})_d-R^{166}$ or phenyl; more preferably $C_1$-$C_8$alkyl, $C_5$-$C_6$cycloalkyl, which might optionally be substituted with $C_1$-$C_4$alkyl; $C_1$-$C_8$haloalkyl, $C_2$-$C_8$alkenyl, $-O-SiR^{164}R^{165}R^{166}$, $-(O-SiR^{164}R^{165})_d-R^{166}$ or phenyl; most preferably $C_1$-$C_8$alkyl, $C_1$-$C_8$haloalkyl, especially $C_1$-$C_8$alkyl which is substituted one, or more times with fluorine atoms; $-O-SiR^{164}R^{165}R^{166}$ or $-(O-SiR^{164}R^{165})_d-R^{166}$.

$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, $-O-SiR^{169}R^{170}R^{171}$, $-(O-SiR^{169}R^{170})_d-R^{171}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{24}$ alkyl, halogen, cyano or $C_1$-$C_{25}$alkoxy; preferably hydrogen, $C_1$-$C_{25}$alkyl, $C_1$-$C_{25}$haloalkyl, $C_2$-$C_{25}$alkenyl, $-O-SiR^{169}R^{170}R^{171}$, $-(O-SiR^{169}R^{170})_d-R^{171}$, or phenyl; more preferably $C_1$-$C_8$alkyl, $C_1$-$C_8$haloalkyl, $C_2$-$C_8$alkenyl, $-(O-SiR^{169}R^{170})_d-R^{171}$, or phenyl; most preferably $C_1$-$C_8$alkyl, $C_1$-$C_8$haloalkyl, especially $C_1$-$C_8$alkyl which is substituted one or more times with fluorine atoms; $-O-SiR^{169}R^{170}R^{171}$ or $-(O-SiR^{169}R_{170})_d-R^{171}$.

$R^{169}$, $R^{170}$ and $R^{171}$ are independently of each other hydrogen, $C_1$-$C_{25}$alkyl, $C_3$-$C_{12}$cycloalkyl, which might optionally be substituted with $C_1$-$C_4$alkyl, $C_1$-$C_{25}$haloalkyl, $C_2$-$C_{25}$alkenyl, $-O-Si(CH_3)_3$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{25}$alkyl, halogen, cyano, or $C_1$-$C_{25}$alkoxy; preferably hydrogen, $C_1$-$C_{25}$alkyl, $C_1$-$C_{25}$haloalkyl, $C_2$-$C_{25}$alkenyl, $-O-Si(CH_3)_3$, or phenyl; more preferably $C_1$-$C_8$alkyl, $C_1$-$C_8$haloalkyl, $C_2$-$C_8$alkenyl, $-O-Si(CH_3)_3$, or phenyl; most preferably $C_1$-$C_8$alkyl, $C_1$-$C_8$haloalkyl, especially $C_1$-$C_8$alkyl which is substituted one or more times with fluorine atoms; or $-O-Si(CH_3)_3$.

d is an integer from 1 to 50, preferably 1 to 40, even more preferably 1 to 30, still more preferably 1 to 20, more preferably 1 to 15, still more preferably 1 to 10 and even more preferably 1 to 5 and most preferably 1 to 3.

$R^{167}$ and $R^{168}$ are independently of each other hydrogen, $C_1$-$C_{25}$alkyl, $C_1$-$C_{25}$haloalkyl, $C_3$-$C_{25}$alkenyl, or phenyl; preferably $C_1$-$C_{25}$alkyl, $C_1$-$C_{25}$haloalkyl, or phenyl; most preferably $C_1$-$C_{25}$alkyl.

In a particularly preferred embodiment $R^{161}$, $R^{162}$ and $R^{163}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, $-CF_3$, $-(CH_2)_2CF_3$, $-(CH_2)_2qj$ $(CF_2)_5CF_3$ and $-(CH_2)_2(CF_2)_6CF_3$; $C_2$-$C_{25}$alkenyl, especially $C_2$-$C_8$alkenyl; $C_3$-$C_{12}$cycloalkyl, especially $C_5$-$C_6$cycloalkyl, which might optionally be substituted with $C_1$-$C_4$alkyl; phenyl, $-O-SiR^{164}R^{165}R^{166}$, or $-(O-SiR^{164}R^{165})_d-R^{166}$. In case of a group $-O-SiR^{164}R^{165}R^{166}$ $R^{164}$, $R^{165}$ and $R^{166}$ are independently of each other $C_1$-$C_8$alkyl, $C_1$-$C_8$haloalkyl, $C_2$-$C_8$alkenyl, or phenyl. In case of a group $-(O-SiR^{164}R^{165})_d-R^{166}$ $R^{164}$ and $R^{166}$ are independently of each other $C_1$-$C_8$alkyl, $R^{166}$ is $C_1$-$C_8$alkyl, or phenyl and d is an integer of 2 to 5.

Examples of groups of formula $-SiR^{161}R^{162}R^{163}$, or $-O-SiR^{161}R^{162}R^{163}$ are shown below:

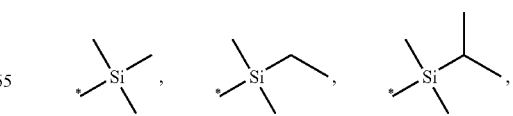

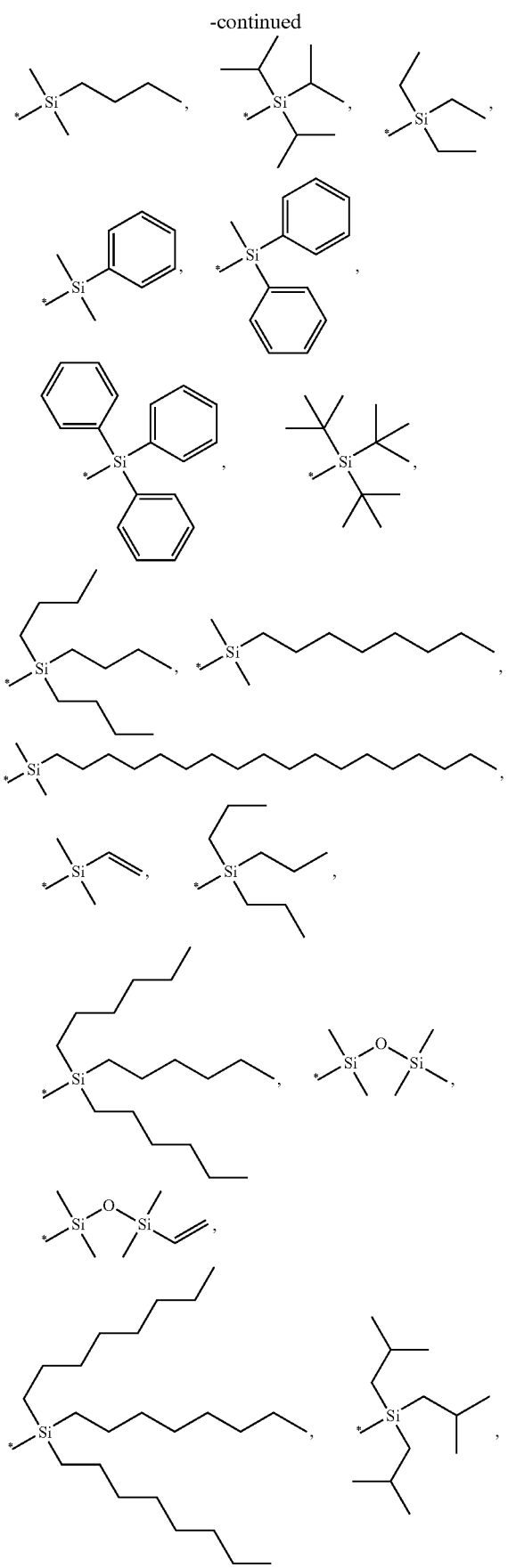
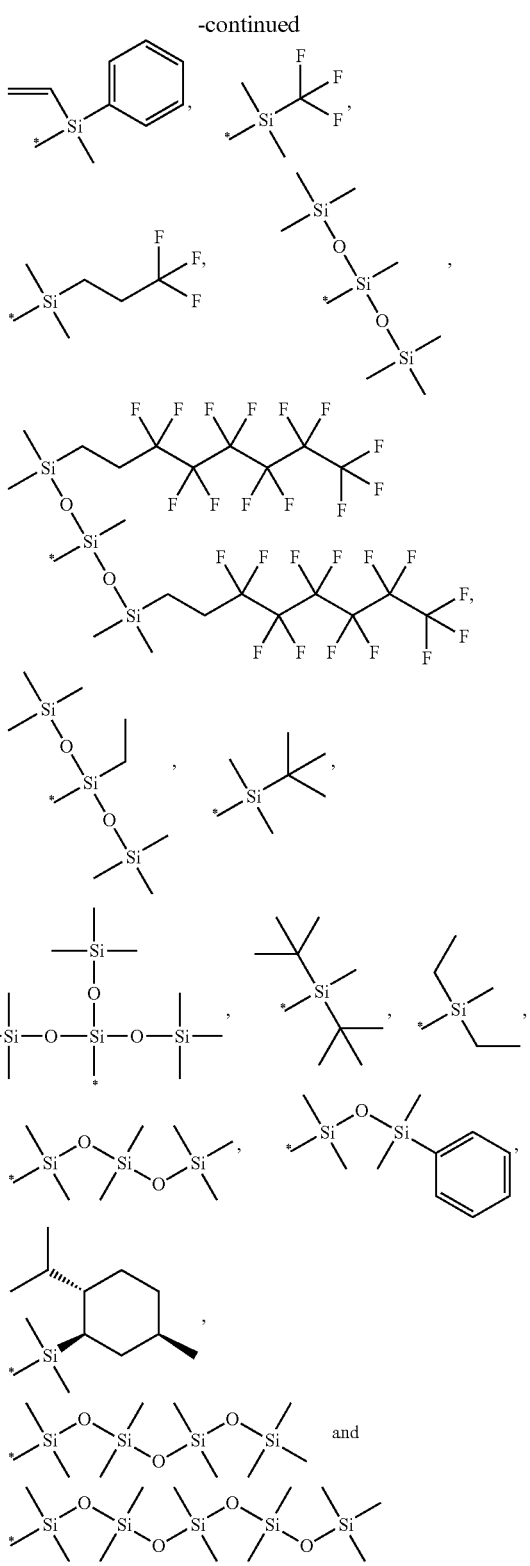
(*- indicates the bond to the carbon atom, to which the silyl group or siloxanyl group is connected).
$R^1$ and $R^2$ may be the same or different and are preferably selected from hydrogen, a $C_1$-$C_{100}$alkyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_2$-$C_{100}$alkenyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_3$-$C_{100}$alkinyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_4$-$C_{12}$cycloalkyl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl and/or can optionally be interrupted by —O—, —S—, —COO— or —OCO—, a $C_6$-$C_{24}$aryl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl, a $C_2$-$C_{20}$heteroaryl group which can optionally be substituted one or more times with $C_1$-$C_{12}$alkyl, $C_1$-$C_{12}$alkoxy, halogen, $C_5$-$C_{12}$cycloalkyl, cyano, $C_6$-$C_{24}$aryl, $C_2$-$C_{20}$heteroaryl, —CO—$C_1$-$C_{18}$alkyl, —CO—$C_5$-$C_{12}$cycloalkyl, and —COO—$C_1$-$C_{18}$alkyl.

More preferably $R^1$ and $R^2$ are selected from hydrogen, $C_1$-$C_{50}$alkyl, $C_1$-$C_{50}$haloalkyl, $C_7$-$C_{25}$arylalkyl, $C_2$-$C_{50}$alkenyl, $C_2$-$C_{50}$haloalkenyl, allyl, $C_5$-$C_{12}$cycloalkyl, phenyl, or naphthyl which can optionally be substituted one or more times with $C_1$-$C_{12}$alkyl or $C_1$-$C_{12}$alkoxy, —CO—$C_1$-$C_{18}$alkyl, —CO—$C_5$-$C_{12}$cycloalkyl and —COO—$C_1$-$C_{18}$alkyl. Even more preferably $R^1$ and $R^2$ are a $C_1$-$C_{50}$alkyl group. Still more preferably $R^1$ and $R^2$ are a $C_1$-$C_{36}$alkyl group, such as, for example, methyl, ethyl, n-propyl, iso-propyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, especially n-dodecyl, tridecyl, tetradecyl, pentadecyl, hexadecyl, 2-ethylhexyl, 2-butyl-hexyl, 2-butyl-octyl, 2-hexyldecyl, 2-decyl-tetradecyl, heptadecyl, octadecyl, eicosyl, heneicosyl, docosyl, or tetracosyl. Preferably $R^1$ and $R^2$ have the same meaning.

Advantageously, the groups $R^1$ and $R^2$ can be represented by formula

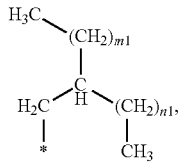

wherein m1=n1+2 and m1+n1≤24. Chiral side chains, such as $R^1$, $R^2$, $R^{1'}$, $R^{2'}$, $R^{1''}$, $R^{2''}$, $R^{1'''}$ and $R^{2'''}$, can either be homochiral, or racemic, which can influence the morphology of the compounds.

Preferably, $R^{103}$ and $R^{103'}$ are independently of each other $C_1$-$C_{25}$alkyl, $C_1$-$C_{25}$alkyl substituted by halogen, $C_7$-$C_{25}$arylalkyl, or phenyl; more preferably $C_1$-$C_{25}$alkyl.

In a preferred embodiment $Ar^1$ and $Ar^{1'}$ are independently of each other a group of formula (XIa), (XIb), (XIc), (XIe), (XIf), (XIk), (XIm), (XIn), (XIq), (XIr), (XIu), (XIw), (XIx), (XIII), such as, for example, (XIIIa) and (XIIIb); or (XIV), such as, for example, (XIVb). Preferably, $Ar^1$ and $Ar^{1'}$ are independently of each other a group of formula XIa, XIb, XIe, XIf, XIr, or XIIIa. More preferably, $Ar^1$ and $Ar^{1'}$ are independently of each other a group of formula XIa, XIb, or XIf, most preferred a group of formula XIa.

In another preferred embodiment of the present invention $Ar^1$ and $Ar^{1'}$ are independently of each other a group of formula XVa' or XVa".

Preferably, $R^3$ and $R^{3'}$ are independently of each other hydrogen, halogen, $CF_3$, cyano, $C_1$-$C_{25}$alkyl or $C_1$-$C_{25}$alkoxy; more preferably $CF_3$, cyano or $C_1$-$C_{25}$alkyl; most preferred hydrogen, or $C_1$-$C_{25}$alkyl.

Preferably, $R^{104}$ and $R^{104'}$ are independently of each other hydrogen, cyano or a $C_1$-$C_{25}$alkyl group, more preferably hydrogen, or a $C_1$-$C_{25}$alkyl group, most preferred hydrogen.

Preferably, $R^4$, $R^{4'}$, $R^5$, $R^{5'}$, $R^6$ and $R^{6'}$ are independently of each other hydrogen, halogen, $CF_3$, cyano, $C_1$-$C_{25}$alkyl or $C_1$-$C_{25}$alkoxy, more preferably hydrogen, $CF_3$, cyano or $C_1$-$C_{25}$alkyl; most preferred hydrogen, or $C_1$-$C_{25}$alkyl.

Preferably $R^7$, $R^{7'}$, $R^9$ and $R^{9'}$ are independently of each other hydrogen, $C_1$-$C_{25}$alkyl, more preferably $C_4$-$C_{25}$alkyl.

Preferably, $R^8$ and $R^{8'}$ are independently of each other hydrogen, $C_1$-$C_{25}$alkyl, $C_1$-$C_{25}$alkyl, which may optionally be interrupted by one or more oxygen or sulphur atoms; or $C_7$-$C_{25}$arylalkyl, more preferably hydrogen, or $C_1$-$C_{25}$alkyl.

Preferably, $R^{11}$ and $R^{11'}$ are independently of each other a $C_1$-$C_{25}$alkyl group, especially a $C_1$-$C_8$alkyl group, or phenyl; more preferably a $C_1$-$C_8$alkyl group.

Preferably, $R^{12}$ and $R^{12'}$ are independently of each other hydrogen, $C_1$-$C_{25}$alkyl, $C_1$-$C_{25}$alkoxy, or $$\equiv\!\!-R^{13},$$

wherein $R^{13}$ is a $C_1$-$C_{10}$alkyl group, or a tri($C_1$-$C_8$alkyl)silyl group, more preferably hydrogen, $C_1$-$C_{25}$alkyl, or $C_1$-$C_{25}$alkoxy.

Preferably, $Ar^2$, $Ar^{2'}$, $Ar^3$, $Ar^{3'}$, $Ar^4$ and $Ar^{4'}$ have independently of each other the meaning of $Ar^1$.

In a preferred embodiment $Ar^2$, $Ar^{2'}$, $Ar^3$, $Ar^{3'}$, $Ar^4$ and $Ar^{4'}$ are independently of each other a group of formula (XIa), (XIb), (XIc), (XIe), (XIf), (XIk), (XIm), (XIn), (XIr), (XIx), (XIz), (XIIj), (XIII), such as, for example, (XIIIa), or (XIIIb); or (XIV), such as, for example, (XIVb). Preferably, $Ar^2$, $Ar^{2'}$, $Ar^3$, $Ar^{3'}$, $Ar^4$ and $Ar^{4'}$ are independently of each other a group of formula XIa, XIb, XIf, XIr, XIIj, or XIIIa. More preferably, $Ar^2$, $Ar^{2'}$, $Ar^3$, $Ar^{3'}$, $Ar^4$ and $Ar^{4'}$ are independently of each other a group of formula XIa, XIb, XIf, or XIIj, Most preferred a group of formula XIa.

In another preferred embodiment of the present invention $Ar^1$ and $Ar^{1'}$ are independently of each other a group of formula XVa' or XVa".

Preferably, $R^{105}$, $R^{105'}$, $R^{106}$ and $R^{106'}$ are independently of each other hydrogen, halogen, cyano, $C_1$-$C_{25}$alkyl or $C_1$-$C_{18}$alkoxy, more preferably $C_1$-$C_{25}$alkyl or $C_1$-$C_{18}$alkoxy, most preferred hydrogen, or $C_1$-$C_{25}$alkyl.

$R^{107}$ is preferably hydrogen, $C_1$-$C_{25}$alkyl, $C_1$-$C_{25}$alkyl, which may optionally be interrupted by one or more oxygen or sulphur atoms; or $C_7$-$C_{25}$arylalkyl, more preferably hydrogen, or $C_1$-$C_{25}$alkyl, most preferred $C_4$-$C_{25}$alkyl.

Preferably, $R^{108}$ and $R^{109}$ are independently of each other H, $C_1$-$C_{25}$alkyl, $C_1$-$C_{25}$alkyl which is substituted by E and/or interrupted by D, $C_7$-$C_{25}$arylalkyl, $C_2$-$C_{18}$alkenyl, or $C_7$-$C_{25}$aralkyl, or $R^{108}$ and $R^{109}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, D is —CO—, —COO—, —S— or —O—, E is $C_1$-$C_8$thioalkoxy, $C_1$-$C_8$alkoxy, CN or halogen, G is E, or $C_1$-$C_{18}$alkyl. More preferably, $R^{108}$ and $R^{109}$ are independently of each other H, $C_1$-$C_{25}$alkyl or $C_7$-$C_{25}$arylalkyl. Most preferred $R^{108}$ and $R^{109}$ are independently of each other H, or $C_1$-$C_{25}$alkyl.

D is preferably —CO—, —COO—, —S— or —O—, more preferably —COO—, —S— or —O—, most preferred —S— or —O—.

Preferably, E is $C_1$-$C_8$thioalkoxy, $C_1$-$C_8$alkoxy, CN, or halogen, more preferably $C_1$-$C_8$alkoxy, CN, or halogen, most preferred halogen, especially F.

Preferably, $R^{112}$ and $R^{113}$ are independently of each other H; $C_1$-$C_{18}$alkyl; or $C_1$-$C_{18}$alkyl which is interrupted by —O—, more preferably H, or $C_1$-$C_{18}$alkyl; most preferred $C_1$-$C_{18}$alkyl. $U^1$ and $U^2$ are preferably O, more preferably $NR^1$.

$T^1$, $T^2$, $T^3$ and $T^4$ are preferably independently of each other hydrogen, CN, or $COOR^{103}$, more preferably hydrogen.

In a preferred embodiment the present invention is directed to polymers comprising one or more (repeating) unit(s) of the formula

 (I')

wherein Y is a group of formula

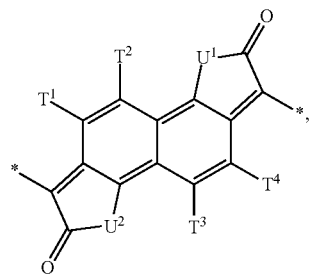

$U^1$ is O, S, or $NR^1$;
$U^2$ is O, S, or $NR^2$,
$T^1$, $T^2$, $T^3$ and $T^4$ may be different, but are preferably the same and are preferably independently of each other hydrogen, halogen, cyano, $—COOR^{103}$, $—OCOR^{103}$, $—OR^{103}$, $—SR^{103}$, $C_1$-$C_{25}$alkyl, which may be substituted by E and/or interrupted by D; more preferably hydrogen, halogen, cyano, $—OR^{103}$, or $C_1$-$C_{25}$alkyl; most preferred hydrogen, or $C_1$-$C_{25}$alkyl, especially hydrogen;
$R^1$ and $R^2$ may be different, but are preferably the same are preferably selected from hydrogen, $C_1$-$C_{50}$alkyl, $C_1$-$C_{50}$haloalkyl, $C_7$-$C_{25}$arylalkyl, $C_2$-$C_{50}$alkenyl, $C_2$-$C_{50}$haloalkenyl, allyl, $C_5$-$C_{12}$cycloalkyl, phenyl and naphthyl, which can optionally be substituted one or more times with $C_1$-$C_{12}$alkyl or $C_1$-$C_{12}$alkoxy, —CO—$C_1$-$C_{18}$alkyl, —CO—$C_5$-$C_{12}$cycloalkyl and —COO—$C_1$-$C_{18}$alkyl; more preferably $C_1$-$C_{50}$alkyl; most preferred $C_1$-$C_{38}$alkyl group;
a is 1, 2, or 3, a' is 1, 2, or 3; wherein $Ar^1$, $Ar^{1'}$, $R^{103}$, $R^{103'}$, D and E are as defined above.

$U^1$ and $U^2$ may be different, but are preferably the same. $U^1$ is preferably O or $NR^1$; more preferably $NR^1$. $U^2$ is preferably O or $NR^1$; more preferably $NR^1$. Polymers, comprising a repeating unit of the formula (I'), are preferred.

$T^1$, $T^2$, $T^3$ and $T^4$ may be different, but are preferably the same. $T^1$, $T^2$, $T^3$ and $T^4$ are preferably independently of each other hydrogen, halogen, cyano, $—COOR^{103}$, $—OCOR^{103}$, $—OR^{103}$, $—SR^{103}$, $C_1$-$C_{25}$alkyl, which may be substituted by E and/or interrupted by D; more preferably hydrogen, halogen, cyano, $—OR^{103}$, or $C_1$-$C_{25}$alkyl; most preferred hydrogen, or $C_1$-$C_{25}$alkyl, very especially hydrogen.

$R^1$ and $R^2$ may be different, but are preferably the same. More preferably $R^1$ and $R^2$ are selected from hydrogen, $C_1$-$C_{50}$alkyl, $C_1$-$C_{50}$haloalkyl, $C_7$-$C_{25}$arylalkyl, $C_2$-$C_{50}$alkenyl, $C_2$-$C_{50}$haloalkenyl, allyl, $C_5$-$C_{12}$cycloalkyl, phenyl, or naphthyl which can optionally be substituted one or more times with $C_1$-$C_{12}$alkyl or $C_1$-$C_{12}$alkoxy, —CO—$C_1$-$C_{18}$alkyl, —CO—$C_5$-$C_{12}$cycloalkyl and —COO—$C_1$-$C_{18}$alkyl. More preferably $R^1$ and $R^2$ are $C_1$-$C_{50}$alkyl group. Most preferred $R^1$ and $R^2$ are a $C_1$-$C_{38}$alkyl group.

a and a' may be different, but are preferably the same. a and a' are preferably 1, or 2, more preferably 1.

In a preferred embodiment $Ar^1$ and $Ar^{1'}$ are independently of each other a group of formula (XIa), (XIb), (XIc), (XIe), (XIf), (XIk), (XIm), (XIn), (XIq), (XIr), (XIu), (XIw), (XIx), (XIII), such as, for example, (XIIIa) and (XIIIb); or (XIV), such as, for example, (XIVb). Preferably, $Ar^1$ and $Ar^{1'}$ are independently of each other a group of formula XIa, XIb, XIe, XIf, XIr, or XIIIa. More preferably, $Ar^1$ and $Ar^{1'}$ are independently of each other a group of formula XIa, XIb, or XIf, most preferred a group of formula XIa.

In another preferred embodiment of the present invention $Ar^1$ and $Ar^{1'}$ are independently of each other a group of formula XVa' or XVa".

In a further preferred embodiment the present invention is directed to polymers, comprising one or more (repeating) unit(s) of the formula (Ia), (Ib), (Ic), (Id), and/or (Ie) as defined in claim 3.

$U^1$ is O, or $NR^1$; preferably $NR^1$;
$U^2$ is O, or $NR^2$; preferably $NR^2$;
$T^1$ and $T^2$ are independently of each other hydrogen, or $C_1$-$C_{25}$alkyl, especially hydrogen;
$R^1$ and $R^2$ may be the same or different and are selected from a $C_1$-$C_{38}$alkyl group, especially $C_8$-$C_{36}$alkyl group;
$R^3$ and $R^{3'}$ are independently of each other hydrogen or $C_1$-$C_{25}$alkyl; and
$R^8$ and $R^{8'}$ are independently of each other hydrogen or $C_1$-$C_{25}$alkyl, especially $C_1$-$C_{25}$alkyl.

Polymers, comprising a repeating unit of the formula (Ia), (Ib), (Ic), (Id), or (Ie), especially (Ia), (Ib), (Id), or (Ie); are preferred.

Repeating unit(s) of the formula (Ia), (Ib), (Id) and (Ie); repeating unit(s) of the formula (Ia), (Ib) and (Ie) are more preferred; repeating unit(s) of the formula (Ia) and (Ie) are most preferred.

Preferably $U^1$ and $U^2$ are the same.

Preferably, $T^1$, $T^2$, $T^3$ and $T^4$ are independently of each other hydrogen, halogen, cyano, $—COOR^{103}$, $—OR^{103'}$, $—SR^{103'}$, or $C_1$-$C_{25}$alkyl. More preferably, $T^1$, $T^2$, $T^3$ and $T^4$ are independently of each other hydrogen, halogen, $—OR^{103'}$, or $C_1$-$C_{25}$alkyl. $T^1$, $T^2$, $T^3$ and $T^4$ are even more preferably hydrogen, or $C_1$-$C_{25}$alkyl, most preferred hydrogen. Preferably $T^1$ and $T^2$ are the same. Preferably $T^3$ and $T^4$ are the same.

In another embodiment the present invention is directed to polymers, comprising (repeating) unit(s) of the formula

*―⟮A⟯―* and *―⟮COM¹⟯―*, wherein A is a repeating unit of formula (I), and
—COM¹- is a repeating unit, which has the meaning of Ar¹, wherein Ar¹ are as defined above, or is a group of formula

*―⟮Ar¹⁴⟯ₛ⟮Ar¹⁵⟯ₜ⟮Ar¹⁶⟯ᵤ⟮Ar¹⁷⟯ᵥ―*, s is 1, t is 1, u is 0, or 1, v is 0, or 1, and
Ar¹⁴, Ar¹⁵, Ar¹⁶ and Ar¹⁷ are independently of each other a group of formula

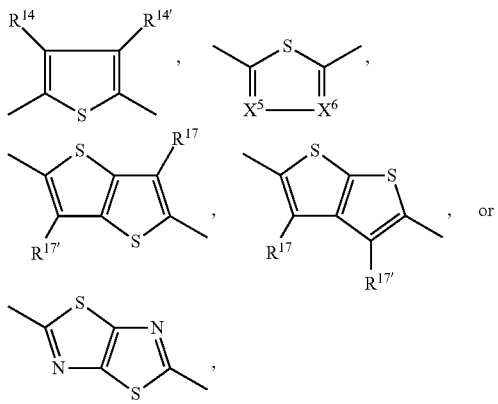

wherein one of $X^5$ and $X^6$ is N and the other is $CR^{14}$, and $R^{14}$, $R^{14'}$, $R^{17}$ and $R^{17'}$ are independently of each other H, or a $C_1$-$C_{25}$alkyl group.

Preferably Ar¹⁴, Ar¹⁵, Ar¹⁶ and Ar¹⁷ are independently of each other a group of formula

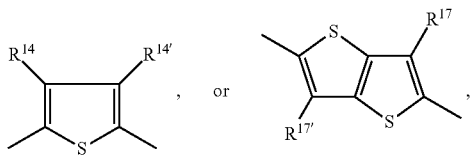

most preferably

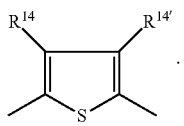

In a preferred embodiment —COM¹- is a group of formula (XIa), (XIb), (XIc), (XIe), (XIf), (XIk), (XIm), (XIn), (XIr), (XIx), (XIz), (XIIj), (XIII), such as, for example, (XIIIa), or (XIIIb); or (XIV), such as, for example, (XIVb). Preferably —COM¹- is a group of formula XIa, XIb, XIf, XIr, XIIj, or XIIIa. More preferably, —COM¹- is a group of formula XIa, XIb, XIf, or XIIj; most preferred XIa.

Examples of a group of formula

*―⟮Ar¹⁴⟯ₖ⟮Ar¹⁵⟯ₗ⟮Ar¹⁶⟯ᵣ⟮Ar¹⁷⟯_z―* are

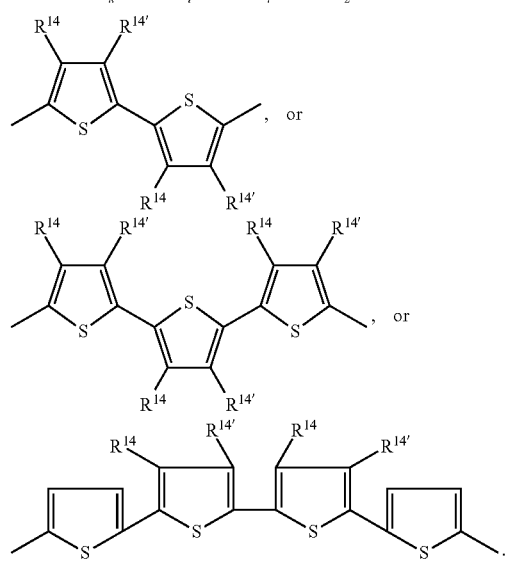

In a particularly preferred embodiment the repeating unit —COM¹- is a group of formula

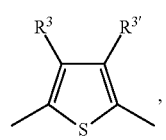
(Xa)

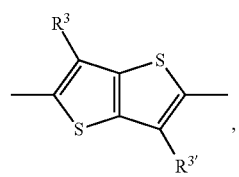
(Xf)

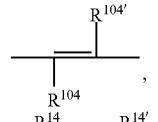
(XIIj)

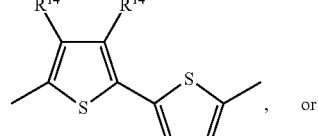

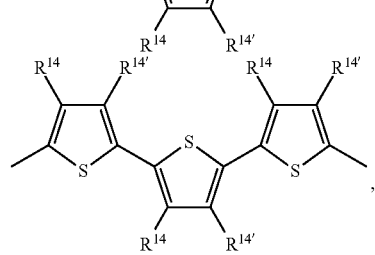

where $R^3$ and $R^{3'}$ are independently of each other hydrogen, or $C_1$-$C_{25}$alkyl, $R^{104}$ and $R^{104'}$ preferably are independently of each other hydrogen, cyano or a $C_1$-$C_{25}$alkyl group, and $R^{14}$ and $R^{14'}$ are independently of each other H, or a $C_1$-$C_{25}$alkyl group, especially a $C_6$-$C_{25}$alkyl, which may optionally be interrupted by one or more oxygen atoms.

In another preferred embodiment the repeating unit —COM¹- is a group of formula

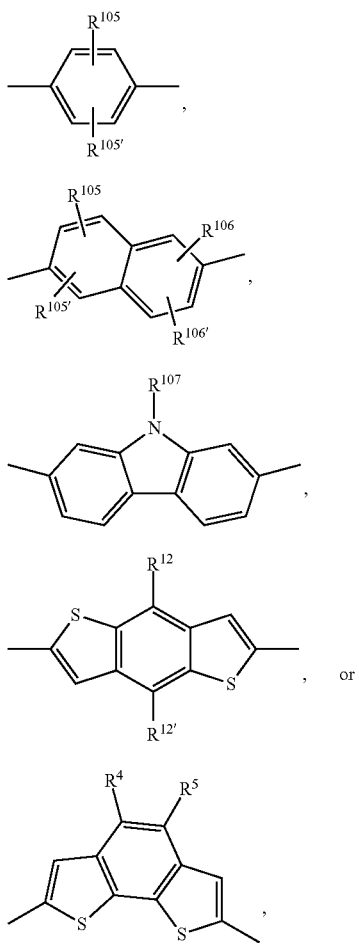

(XVa)

(XVb)

(XVIa)

(XIr)

(XIII)

wherein
$R^4$ and $R^5$ are independently of each other hydrogen, or $C_1$-$C_{25}$alkyl;
$R^{12}$ and $R^{12'}$ are H, or a $C_1$-$C_{25}$alkyl group;
$R^{105}$, $R^{105'}$, $R^{106}$ and $R^{106'}$ are independently of each other hydrogen, halogen, cyano, $C_1$-$C_{25}$alkyl or $C_1$-$C_{25}$alkoxy, especially hydrogen or $C_1$-$C_{25}$alkyl; and
$R^{107}$ is $C_1$-$C_{25}$alkyl.

In a preferred embodiment of the present invention the polymer is a copolymer, comprising repeating units of formula

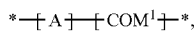

(VII)

especially a copolymer of formula

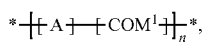

(VII')

wherein A and COM¹ are as defined above; n is number which results in a molecular weight of 4,000 to 2,000,000 Daltons, more preferably 10,000 to 1,000,000 and most preferably 10,000 to 100,000 Daltons. n is usually in the range of 4 to 1000, especially 4 to 200, very especially 5 to 150.

In a preferred embodiment the present invention is directed to polymers, wherein A is a repeating unit of formula (Ia), (Ib), (Ic), (Id), or (Ie), especially (Ia), (Ib), (Id), or (Ie), very especially (Ia), or (Ie) as defined in claim 3 and

is a group of formula

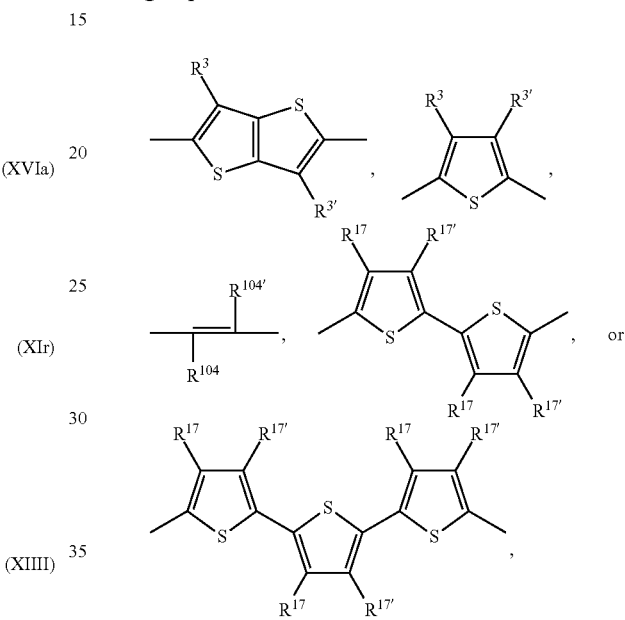

where $R^3$, $R^{3'}$, $R^{17}$ and $R^{17'}$ are independently of each other hydrogen, or $C_1$-$C_{25}$alkyl, and $R^{104}$ and $R^{104'}$ preferably are independently of each other hydrogen, cyano or a $C_1$-$C_{25}$alkyl group.

In another preferred embodiment the present invention is directed to polymers, wherein A is a repeating unit of formula (Ia), (Ib), (Ic), (Id), or (Ie), especially (Ia), (Ib), (Id), or (Ie), very especially (Ia), or (Ie) (as defined in claim 3), and

is a group of formula

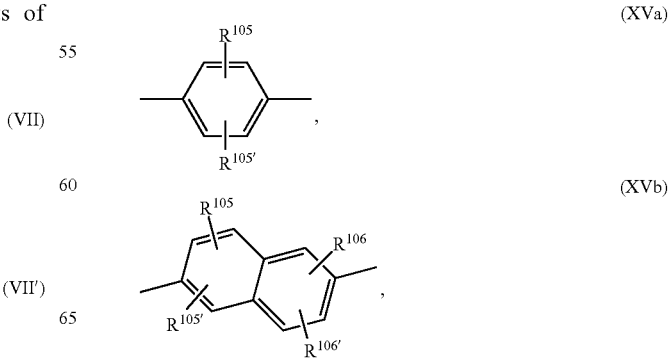

(XVa)

(XVb)

-continued

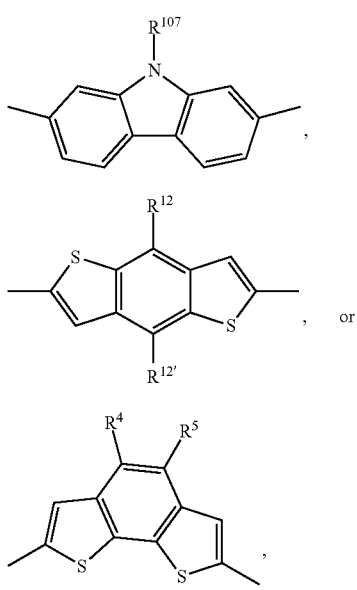

wherein
R⁴ and R⁵ are independently of each other hydrogen, or C₁-C₂₅alkyl;
R¹² and R¹²' are H, or a C₁-C₂₅alkyl group;
R¹⁰⁵, R¹⁰⁵', R¹⁰⁶ and R¹⁰⁶' are independently of each other hydrogen, halogen, cyano, C₁-C₂₅alkyl or C₁-C₂₅alkoxy, especially hydrogen or C₁-C₂₅alkyl; and
R¹⁰⁷ is C₁-C₂₅alkyl.

Among the polymers of formula I the polymers of formula (Ia-1), (Ia-2), (Ia-3), (Ia-4), (Ia-5), (Ia-6), (Ia-7), (Ia-8), (Ia-9), (Ia-10), (Ia-11), (Ia-12), (Ia-13), (Ia-14), (Ia-15), (Ia-16), (Ia-17), (Ia-18), (Ia-19), (Ia-20), (Ia-21), (Ia-22), (Ia-23), (Ia-24), (Ia-25), (Ia-26), (Ia-27), (Ia-28), (Ia-29), (Ia-30), (Ia-31), (Ia-32), (Ia-33), (Ia-34), (Ia-35), (Ia-36), (Ia-37) and (Ia-38), as defined in claim 6, are preferred.

n is 4 to 1000, especially 4 to 200, very especially 5 to 100,
R¹ is a C₁-C₃₈alkyl group, especially C₈-C₃₆alkyl group,
R³, R³'' and R³' are independently of each other hydrogen, halogen, cyano, C₁-C₂₅alkyl or C₁-C₂₅alkoxy, especially hydrogen or C₁-C₂₅alkyl;
R⁴ and R⁵ are independently of each other hydrogen, or C₁-C₂₅alkyl;
R¹² and R¹²' are H, or a C₁-C₂₅alkyl group;
R⁷ and R⁷' are independently of each other
R¹⁴ and R¹⁴' are independently of each other independently of each other hydrogen, halogen, cyano, C₁-C₂₅alkyl or C₁-C₂₅alkoxy, especially hydrogen or C₁-C₂₅alkyl;
R¹⁷ and R¹⁷' are independently of each other H, or a C₁-C₂₅alkyl group;
R¹⁰³ is C₁-C₂₅alkyl,
R¹⁰⁴ and R¹⁰⁴' are independently of each other hydrogen, cyano, COOR¹⁰³, C₁-C₂₅alkyl, especially hydrogen or cyano;
R¹⁰⁵, R¹⁰⁵', R¹⁰⁶ and R¹⁰⁶' are independently of each other hydrogen, halogen, cyano, C₁-C₂₅alkyl or C₁-C₂₅alkoxy, especially hydrogen or C₁-C₂₅alkyl; and
R¹⁰⁷ is C₁-C₂₅alkyl.

According to one embodiment of the present invention polymers of formula (Ia-1), (Ia-2), (Ia-3), (Ia-4), (Ia-5), (Ia-6), (Ia-7), (Ia-8) and (Ia-9) are preferred. According to another embodiment of the present invention polymers of formula (Ia-10), (Ia-11), (Ia-12), (Ia-13), (Ia-14), (Ia-15), (Ia-16), (Ia-17), (Ia-18), (Ia-19), (Ia-20), (Ia-21), (Ia-22), (Ia-23), (Ia-24), (Ia-25), (Ia-26), (Ia-27), and (Ia-28) are preferred. In said embodiments polymers of formula (Ia-1), (Ia-2), (Ia-3), (Ia-5), (Ia-8), (Ia-9), (Ia-10), (Ia-11), (Ia-12), (Ia-14), (Ia-16), (Ia-17), (Ia-18), (Ia-19), (Ia-20), (Ia-21), (Ia-23), (Ia-26), and (Ia-28) are more preferred.

According to another embodiment of the present invention polymers of formula (Ia29), (Ia-30), (Ia-31), (Ia-32), (Ia-33), (Ia-34), (Ia-35), (Ia-36) and (Ia-37) are preferred. The polymers of formula (Ia-1) to (Ia-38) are shown in claim 6.

Examples of particular preferred polymers are shown below:

(P-1)

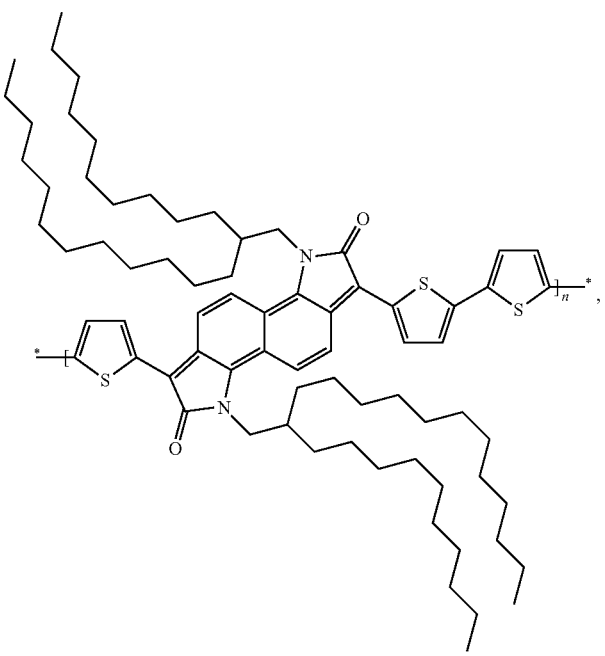

-continued
(P-2)
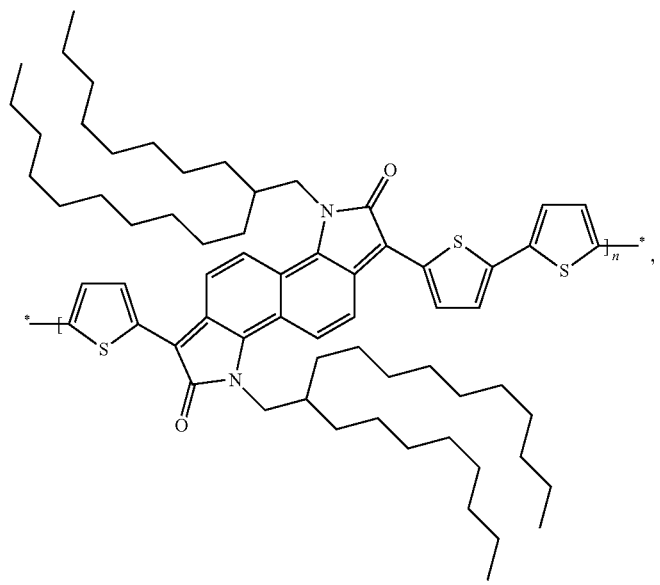
(P-3)
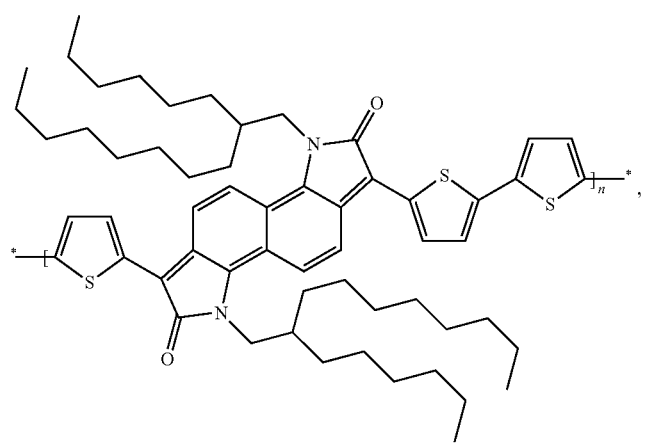
(P-4)
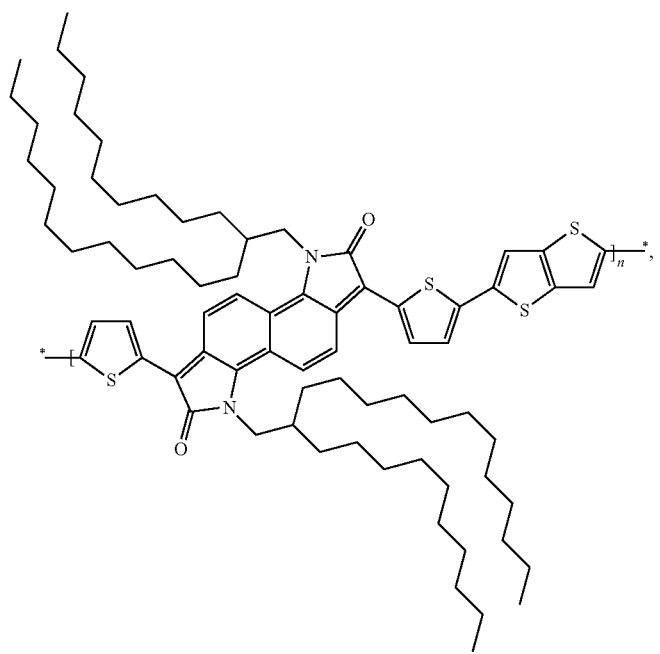

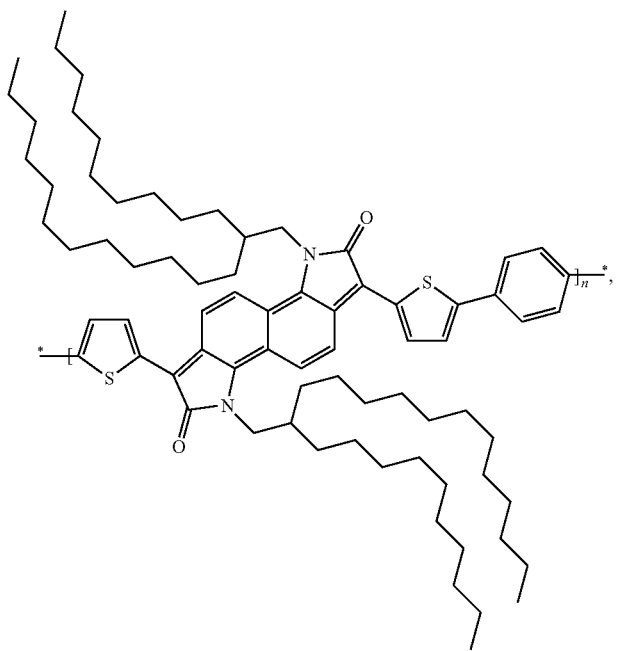
(P-5)
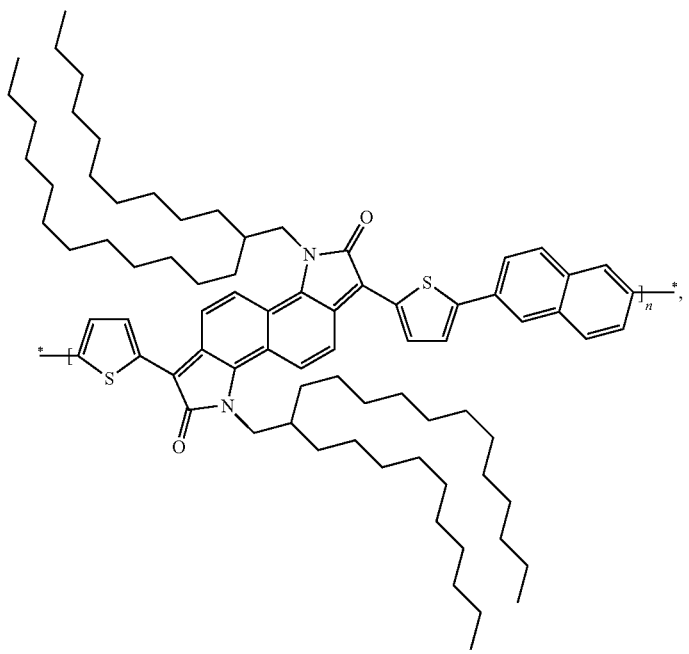
(P-6)

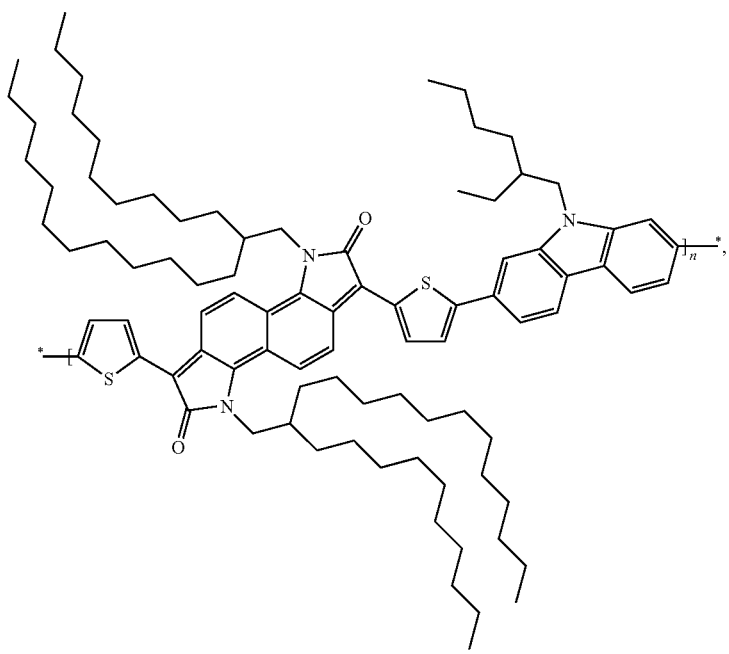
(P-7)
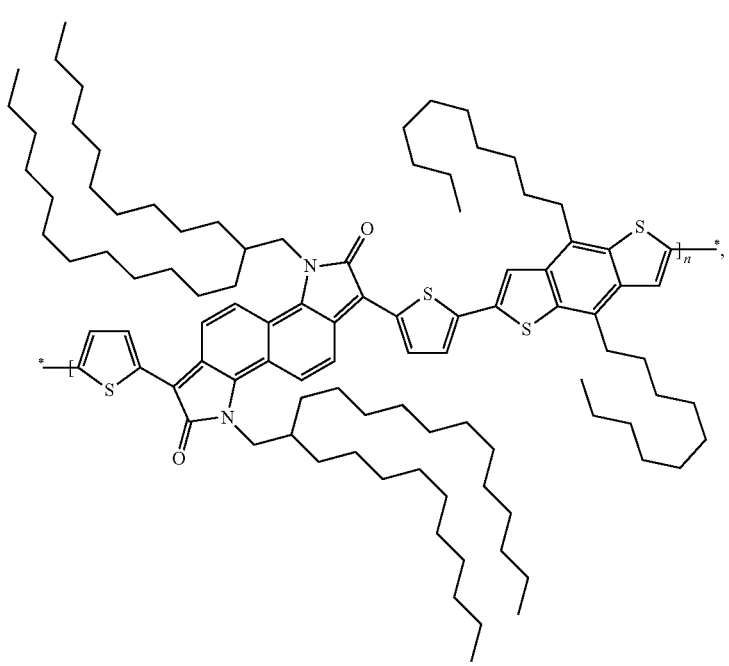
(P-8)

(P-9)
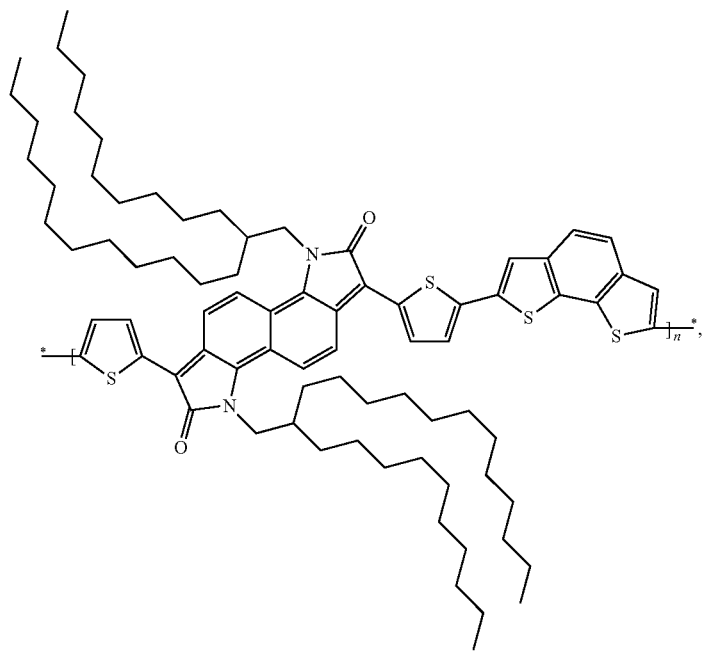
(P-10)
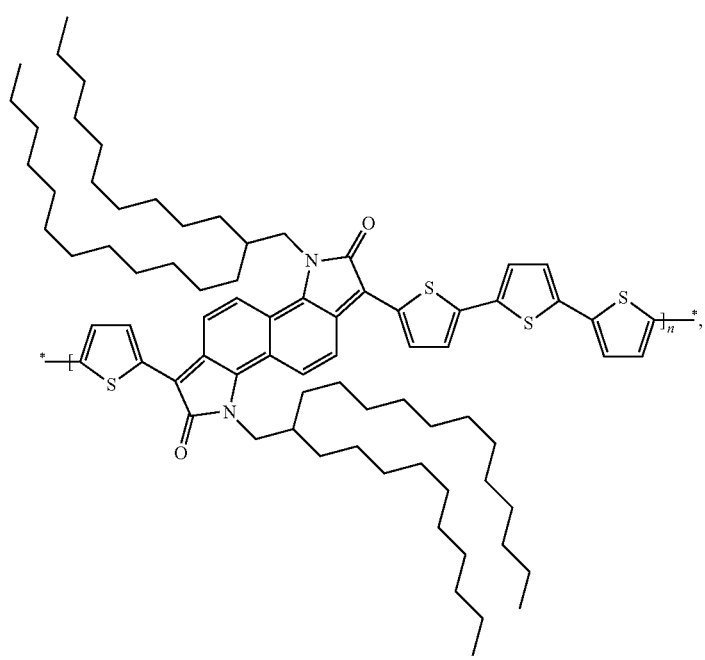

-continued
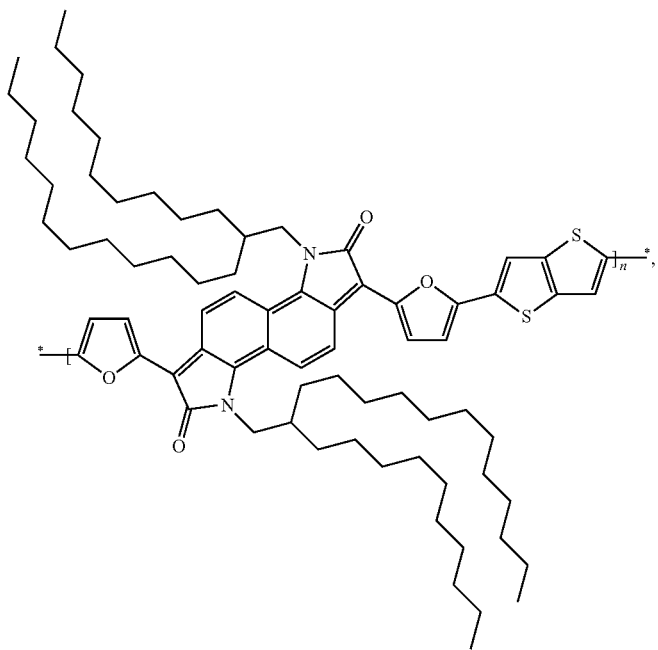
(P-11)
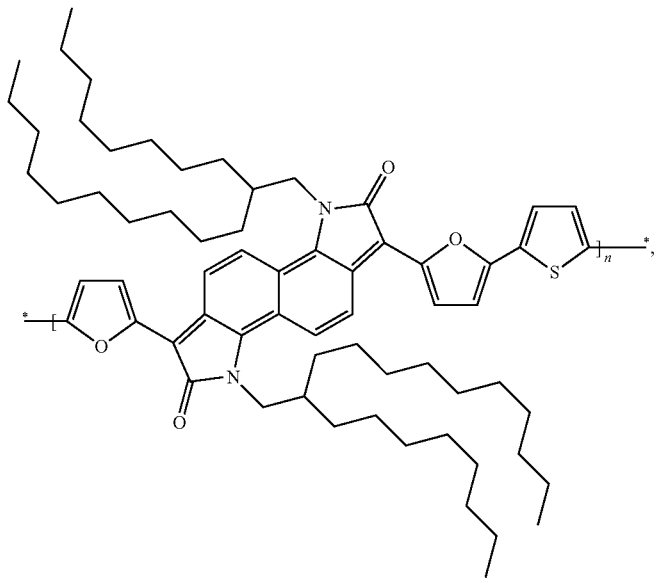
(P-12)

(P-13)
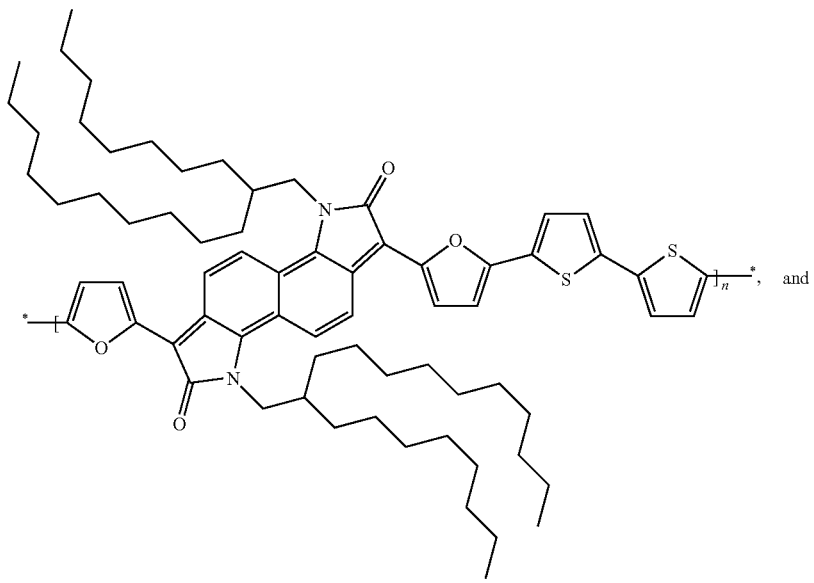
and
(P-14)
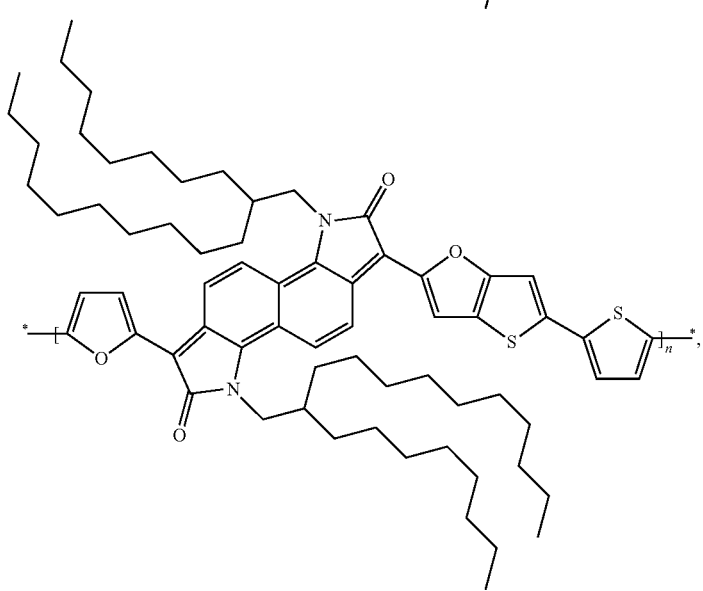
wherein
n is usually in the range of 4 to 1000, especially 4 to 200, very especially 5 to 150.
Additional polymers of the present invention are shown below:
(P-15)
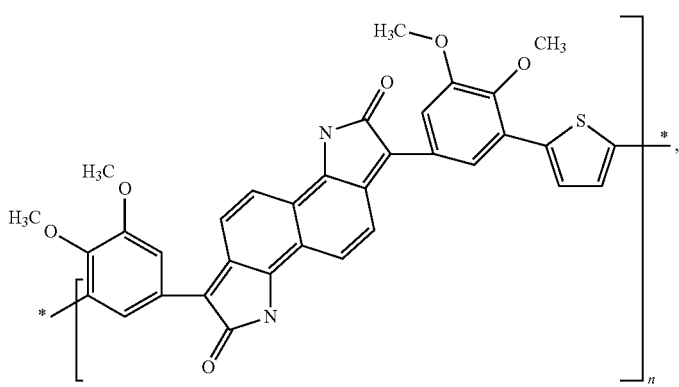

-continued
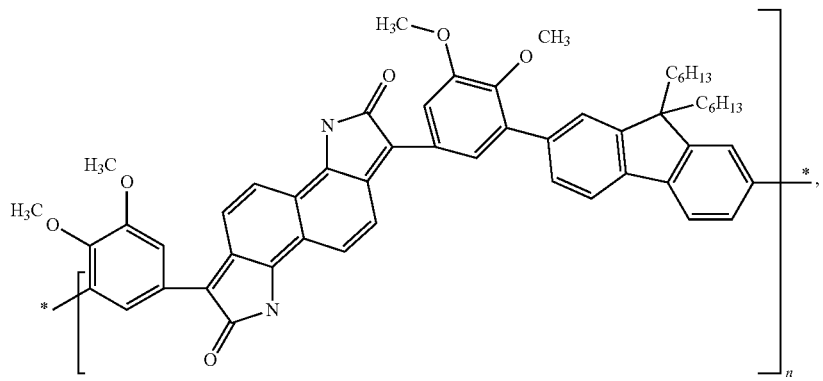
(P-16)
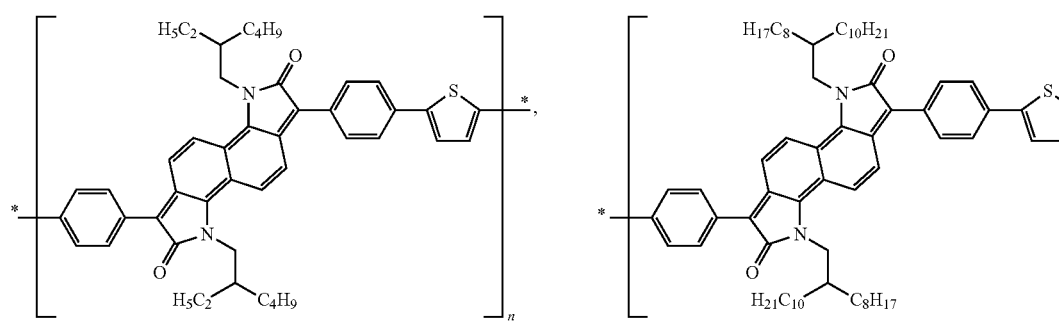
(P-17) (P-18)
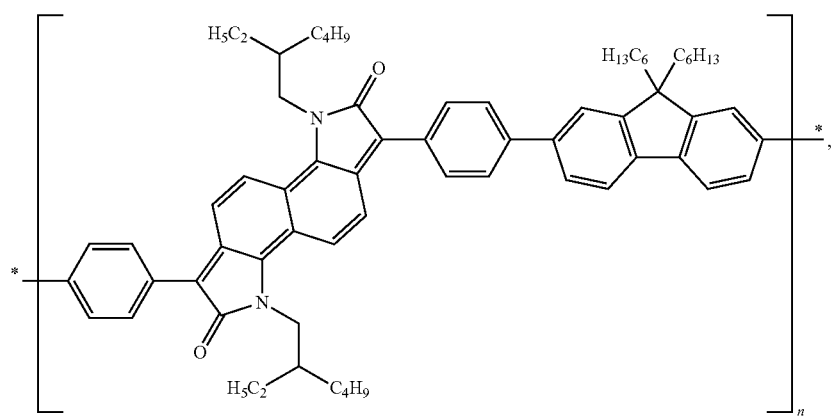
(P-19)
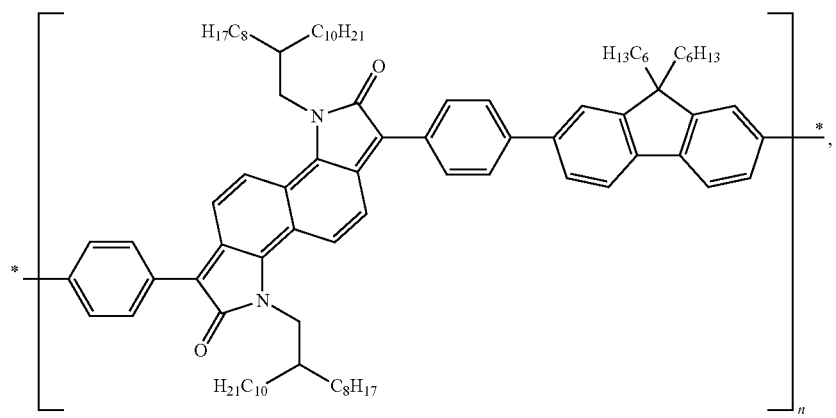
(P-20)

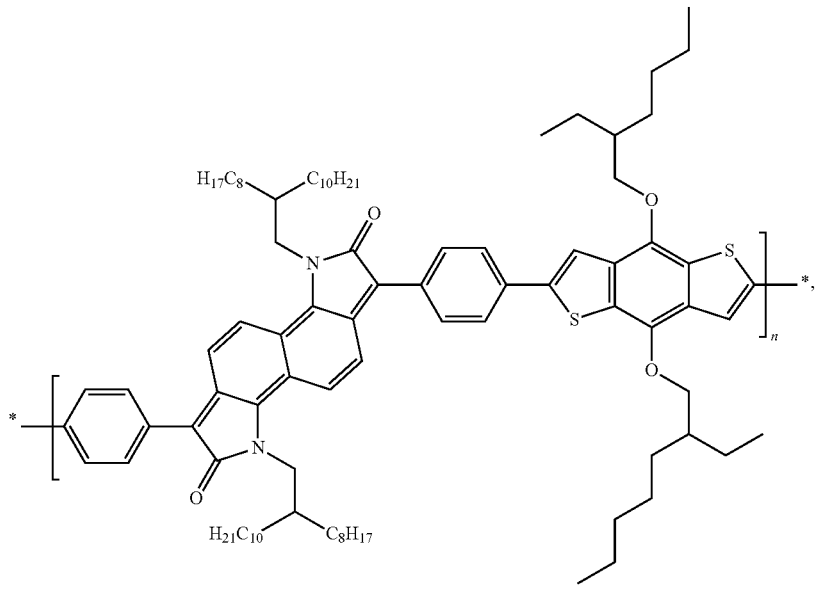
(P-21)
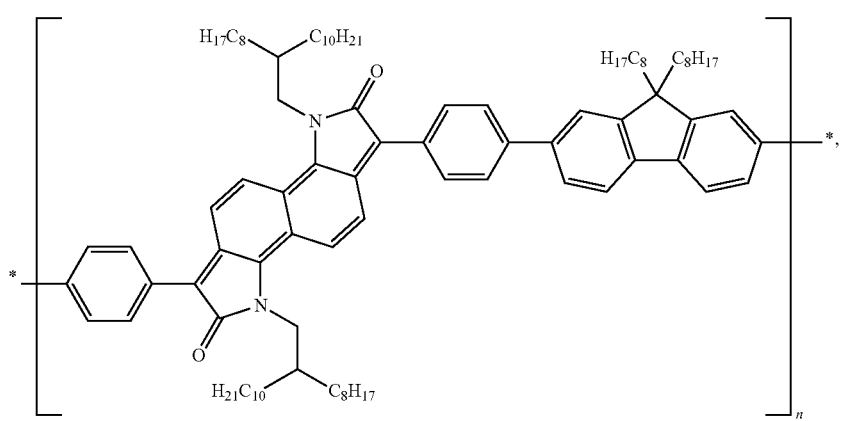
(P-22)
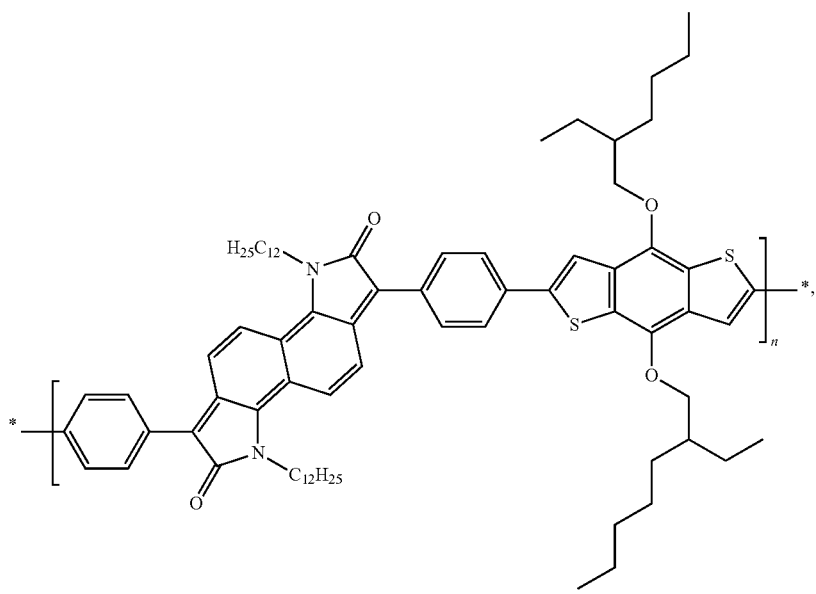
(P-23)

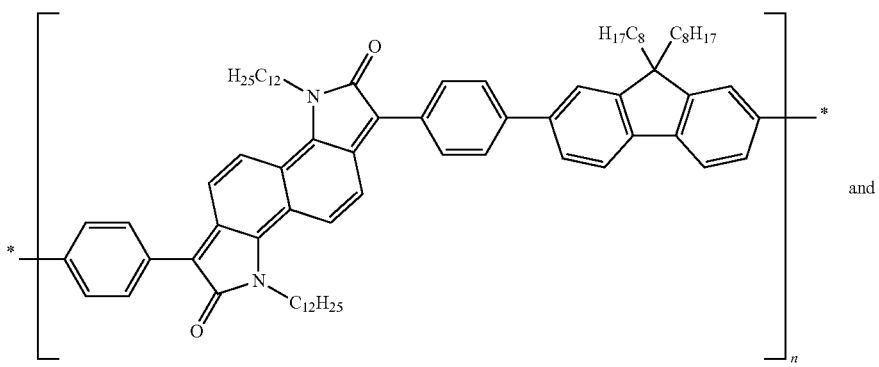

(P-24)

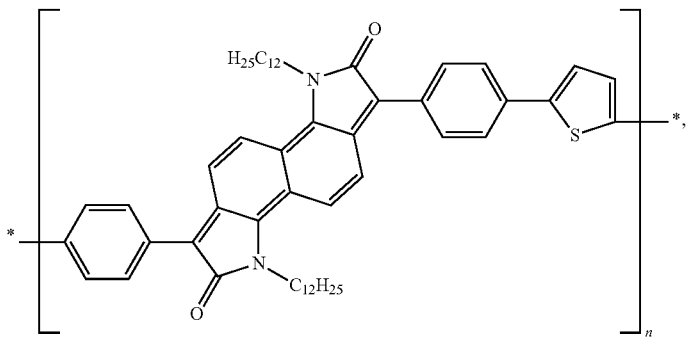

(P-25)

wherein n is usually in the range of 4 to 1000, especially 4 to 200, very especially 5 to 150.

The polymers of the present invention can comprise more than 2 different repeating units, such as, for example, repeating units A, B and D, which are different from each other. If the polymers comprise repeating units of the formula

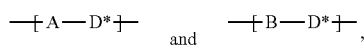

they are preferably (random) copolymers of formula

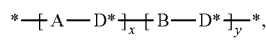

wherein x=0.995 to 0.005, y=0.005 to 0.995, especially x=0.2 to 0.8, y=0.8 to 0.2, and wherein x+y=1. A is a repeating unit of formula (I), D* is a repeating unit —COM$^1$- and B is a repeating unit —COM$^1$-, or a repeating unit of formula (I); with the proviso that A, B and D* are different from each other. For A and —COM$^1$- the same preferences apply as above.

Copolymers of formula VII can be obtained, for example, by the Suzuki reaction. The condensation reaction of an aromatic boronate and a halogenide, especially a bromide, commonly referred to as the "Suzuki reaction", is tolerant of the presence of a variety of organic functional groups as reported by N. Miyaura and A. Suzuki in Chemical Reviews, Vol. 95, pp. 457-2483 (1995). Preferred catalysts are 2-dicyclohexylphosphino-2',6'-di-alkoxybiphenyl/palladium(II) acetates, tri-alykl-phosphonium salts/palladium (0) derivatives and tri-alkylphosphine/palladium (0) derivatives. Especially preferred catalysts are 2-dicyclohexylphosphino-2',6'-di-methoxybiphenyl (sPhos)/palladium(II)acetate and, tri-tert-butylphosphonium tetrafluoroborate ((t-Bu)$_3$P* HBF$_4$)/tris(dibenzylideneacetone)dipalladium (0) (Pd$_2$(dba)$_3$) and tri-tert-butylphosphine (t-Bu)$_3$P/tris(dibenzylideneacetone)dipalladium (0) (Pd$_2$(dba)$_3$). This reaction can be applied to preparing high molecular weight polymers and copolymers.

To prepare polymers corresponding to formula VII a dihalogenide of formula X$^{10}$-A-X$^{10}$ is reacted with an (equimolar) amount of a diboronic acid or diboronate corresponding to formula X$^{11}$—COM$^1$-X$^{11}$; or a dihalogenide of formula X$^{10}$—COM$^1$-X$^{10}$ is reacted with an (equimolar) amount of a diboronic acid or diboronate corresponding to formula X$^{11}$-A-X$^{11}$, wherein X$^{10}$ is halogen, especially Br, or I; and X$^{11}$ is independently in each occurrence —B(OH)$_2$, —B(OY$^1$)$_2$,

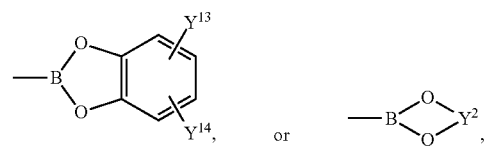

wherein Y$^1$ is independently in each occurrence a C$_1$-C$_{10}$alkyl group and Y$^2$ is independently in each occurrence a C$_2$-C$_{10}$alkylene group, such as —CY$^3$Y$^4$—CY$^5$Y$^6$—, or —CY$^7$Y$^8$—CY$^9$C$^{10}$—CY$^{11}$Y$^{12}$—, wherein Y$^3$, Y$^4$, Y$^5$, Y$^6$, Y$^7$, Y$^8$, Y$^9$, Y$^{10}$, Y$^{11}$ and Y$^{12}$ are independently of each other hydrogen, or a C$_1$-C$_{10}$alkyl group, especially —C(CH$_3$)$_2$C(CH$_3$)$_2$—, —CH$_2$C(CH$_3$)$_2$CH$_2$—, or —C(CH$_3$)$_2$CH$_2$C(CH$_3$)$_2$—, and Y$^{13}$ and Y$^{14}$ are independently of each other hydrogen, or a C$_1$-C$_{10}$alkyl group, under the catalytic action of Pd and triphenylphosphine. The reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A polymerization reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252. Control of molecular weight is possible by using either an excess of dibromide, diboronic acid, or diboronate, or a chain terminator.

According to the process described in WO2010/136352 the polymerisation is carried out in presence of
a) a catalyst/ligand system comprising a palladium catalyst and an organic phosphine or phosphonium compound,
b) a base,
c) a solvent or a mixture of solvents, characterized in that the organic phosphine is a trisubstituted phosphine of formula

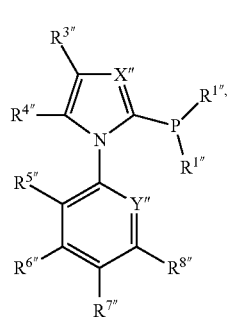

(VI)

or phosphonium salt thereof, wherein X" independently of Y" represents a nitrogen atom or a C—$R^{2''}$ group and Y" independently of X" represents a nitrogen atom or a C—$R^{9''}$ group, $R^{1''}$ for each of the two $R^{1''}$ groups independently of the other represents a radical selected from the group $C_1$-$C_{24}$-alkyl, $C_3$-$C_{20}$-cycloalkyl, which includes especially both monocyclic and also bi- and tri-cyclic cycloalkyl radicals, $C_5$-$C_{14}$-aryl, which includes especially the phenyl, naphthyl, fluorenyl radical, $C_2$-$C_{13}$-heteroaryl, wherein the number of hetero atoms, selected from the group N, O, S, may be from 1 to 2, wherein the two radicals $R^{1''}$ may also be linked to one another, and wherein the above-mentioned radicals $R^{1''}$ may themselves each be mono- or poly-substituted independently of one another by substituents selected from the group hydrogen, $C_1$-$C_{20}$-alkyl, $C_2$-$C_{20}$-alkenyl, $C_3$-$C_8$-cycloalkyl, $C_2$-$C_9$-hetero-alkyl, $C_2$-$C_9$-heteroaryl, wherein the number of hetero atoms from the group N, O, S may be from 1 to 4, $C_1$-$C_{20}$-alkoxy, hydroxy, amino of the forms NH—($C_1$-$C_{20}$-alkyl), NH—($C_5$-$C_{10}$-aryl), N($C_1$-$C_{20}$-alkyl)$_2$, N($C_1$-$C_{20}$-alkyl) ($C_5$-$C_{10}$-aryl), N($C_5$-$C_{10}$-aryl)$_2$, N($C_1$-$C_{20}$-alkyl/$C_5$-$C_{10}$-aryl)$_{3+}$, NH—CO—$C_1$-$C_{20}$-alkyl, NH—CO—$C_5$-$C_{10}$-aryl, carboxylato of the forms COOH and COOQ (wherein Q represents either a monovalent cation or $C_1$-$C_8$-alkyl), $C_1$-$C_6$-acyloxy, sulfinato, sulfonato of the forms $SO_3H$ and $SO_3Q'$ (wherein Q' represents either a monovalent cation, $C_1$-$C_{20}$-alkyl, or $C_5$-$C_{10}$-aryl), tri-$C_1$-$C_6$-alkylsilyl, wherein two of the mentioned substituents may also be bridged with one another, $R^{2''}$-$R^{9''}$ represent a hydrogen, alkyl, alkenyl, cycloalkyl, aromatic or heteroaromatic aryl, O-alkyl, NH-alkyl, N-(alkyl)$_2$, O-(aryl), NH-(aryl), N-(alkyl)(aryl), O—CO-alkyl, O—CO-aryl, F, Si(alkyl)$_3$, $CF_3$, CN, $CO_2H$, COH, $SO_3H$, $CONH_2$, CONH(alkyl), CON(alkyl)$_2$, $SO_2$(alkyl), SO(alkyl), SO(aryl), $SO_2$(aryl), $SO_3$(alkyl), $SO_3$(aryl), S-alkyl, S-aryl, NH—CO(alkyl), $CO_2$(alkyl), $CONH_2$, CO(alkyl), NHCOH, $NHCO_2$(alkyl), CO(aryl), $CO_2$(aryl) radical, wherein two or more adjacent radicals, each independently of the other (s), may also be linked to one another so that a condensed ring system is present and wherein in $R^{2''}$ to $R^{9''}$ alkyl represents a hydrocarbon radical having from 1 to 20 carbon atoms which may in each case be linear or branched, alkenyl represents a mono- or poly-unsaturated hydrocarbon radical having from 2 to 20 carbon atoms which may in each case be linear or branched, cycloalkyl represents a hydrocarbon having from 3 to 20 carbon atoms, aryl represents a 5- to 14-membered aromatic radical, wherein from one to four carbon atoms in the aryl radical may also be replaced by hetero atoms from the group nitrogen, oxygen and sulfur so that a 5- to 14-membered heteroaromatic radical is present, wherein the radicals $R^{2''}$ to $R^{9''}$ may also carry further substituents as defined for $R^{1'''}$.

The organic phosphines and their synthesis are described in WO2004101581.

Preferred organic phosphines are selected from trisubstituted phosphines of formula

| Cpd. | $R^{1''}$ | $R^{5''}$ | $R^{6''}$ | $R^{3''}$ | $R^{4''}$ |
|---|---|---|---|---|---|
| A-1 | $H_3C$—C($CH_3$)($CH_3$)— | H | H | H | H |
| A-2 | cyclohexyl | H | H | H | H |
| A-3 | phenyl | H | H | H | H |
| A-4 | adamantyl | H | H | H | H |
| A-5 | cyclohexyl | —$OCH_3$ | H | H | H |
| A-6 | cyclohexyl | 1) | 1) | H | H |
| A-7 | $H_3C$—C($CH_3$)($CH_3$)— | 1) | 1) | H | H |
| A-8 | phenyl | 1) | 1) | H | H |
| A-9 | adamantyl | 1) | 1) | H | H |
| A-10 | cyclohexyl | H | H | 2) | 2) |
| A-11 | $H_3C$—C($CH_3$)($CH_3$)— | H | H | 2) | 2) |

-continued

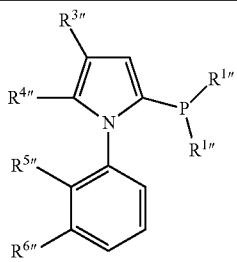

| Cpd. | R¹″ | R⁵″ | R⁶″ | R³″ | R⁴″ |
|---|---|---|---|---|---|
| A-12 | phenyl | H | H | 2) | 2) |
| A-13 | adamantyl | H | H | 2) | 2) |

1) R⁵″ and R⁶″ together form a ring 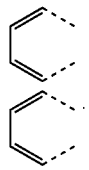

2) R³″ and R⁴″ together form a ring 

Examples of preferred catalysts include the following compounds:
palladium(II) acetylacetonate, palladium(0) dibenzylideneacetone complexes, palladium(II) propionate,
Pd₂(dba)₃: [tris(dibenzylideneacetone)dipalladium(0)],
Pd(dba)₂: [bis(dibenzylideneacetone) palladium(0)],
Pd(PR₃)₂, wherein PR₃ is a trisubstituted phosphine of formula VI,
Pd(OAc)₂: [palladium(II) acetate], palladium(II) chloride, palladium(II) bromide, lithium tetrachloropalladate(II),
PdCl₂(PR₃)₂; wherein PR₃ is a trisubstituted phosphine of formula VI; palladium(0) diallyl ether complexes, palladium(II) nitrate,
PdCl₂(PhCN)₂: [dichlorobis(benzonitrile) palladium(II)],
PdCl₂(CH₃CN): [dichlorobis(acetonitrile) palladium(II)], and
PdCl₂(COD): [dichloro(1,5-cyclooctadiene) palladium(II)].
Especially preferred are PdCl₂, Pd₂(dba)₃, Pd(dba)₂, Pd(OAc)₂, or Pd(PR₃)₂. Most preferred are Pd₂(dba)₃ and Pd(OAc)₂.

The palladium catalyst is present in the reaction mixture in catalytic amounts. The term "catalytic amount" refers to an amount that is clearly below one equivalent of the (hetero)aromatic compound(s), preferably 0.001 to 5 mol-%, most preferably 0.001 to 1 mol-%, based on the equivalents of the (hetero)aromatic compound(s) used.

The amount of phosphines or phosphonium salts in the reaction mixture is preferably from 0.001 to 10 mol-%, most preferably 0.01 to 5 mol-%, based on the equivalents of the (hetero)aromatic compound(s) used. The preferred ratio of Pd:phosphine is 1:4.

The base can be selected from all aqueous and nonaqueous bases and can be inorganic, or organic. It is preferable that at least 1.5 equivalents of said base per functional boron group is present in the reaction mixture. Suitable bases are, for example, alkali and alkaline earth metal hydroxides, carboxylates, carbonates, fluorides and phosphates such as sodium and potassium hydroxide, acetate, carbonate, fluoride and phosphate or also metal alcoholates. It is also possible to use a mixture of bases. The base is preferably a lithium salt, such as, for example, lithium alkoxides (such as, for example, lithium methoxide and lithium ethoxide), lithium hydroxide, carboxylate, carbonate, fluoride and/or phosphate.

The at present most preferred base is aqueous LiOHxH₂O (monohydrate of LiOH) and (waterfree) LiOH.

The reaction is typically conducted at about 0° C. to 180° C., preferably from 20 to 160° C., more preferably from 40 to 140° C. and most preferably from 40 to 120° C. A polymerization reaction may take 0.1, especially 0.2 to 100 hours.

In a preferred embodiment of the present invention the solvent is THF, the base is LiOH*H₂O and the reaction is conducted at reflux temperature of THF (about 65° C.).

The solvent is for example selected from toluene, xylenes, anisole, THF, 2-methyltetrahydrofuran, dioxane, chlorobenzene, fluorobenzene or solvent mixtures comprising one or more solvents like e.g. THF/toluene and optionally water. Most preferred is THF, or THF/water.

Advantageously, the polymerisation is carried out in presence of
a) palladium(II) acetate, or Pd₂(dba)₃, (tris(dibenzylideneacetone)dipalladium(0)) and an organic phosphine A-1 to A-13,
b) LiOH, or LiOHxH₂O; and
c) THF, and optionally water. If the monohydrate of LiOH is used, no water needs to be added.

Most preferred the polymerisation is carried out in presence of
a) palladium(II) acetate, or Pd₂(dba)₃ (tris(dibenzylideneacetone)dipalladium(0)) and

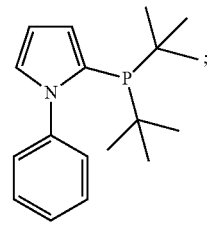 [SMILES: CC(C)(C)P(c1cccn1-c1ccccc1)C(C)(C)C]

b) LiOHxH₂O; and
c) THF. The palladium catalyst is present in an amount of preferably about 0.5 mol-%, based on the equivalents of the (hetero)aromatic compound(s) used. The amount of phosphines or phosphonium salts in the reaction mixture is preferably about 2 mol-%, based on the equivalents of the (hetero)aromatic compound(s) used. The preferred ratio of Pd:phosphine is about 1:4.

Preferably the polymerization reaction is conducted under inert conditions in the absence of oxygen. Nitrogen and more preferably argon are used as inert gases.

The process described in WO2010/136352 is suitable for large-scale applications, is readily accessible and convert starting materials to the respective polymers in high yield, with high purity and high selectivity. The process can provide polymers having weight average molecular weights of at least 10,000, more preferably at least 20,000, most preferably at least 30,000. The at present most preferred polymers have a weight average molecular weight of 30,000 to 80,000 Daltons. Molecular weights are determined according to high-temperature gel permeation chromatography (HT-GPC) using polystyrene standards. The polymers preferably have a polydispersibility of 1.01 to 10, more preferably 1.1 to 3.0, most preferred 1.5 to 2.5.

If desired, a monofunctional aryl halide or aryl boronate, such as, for example,

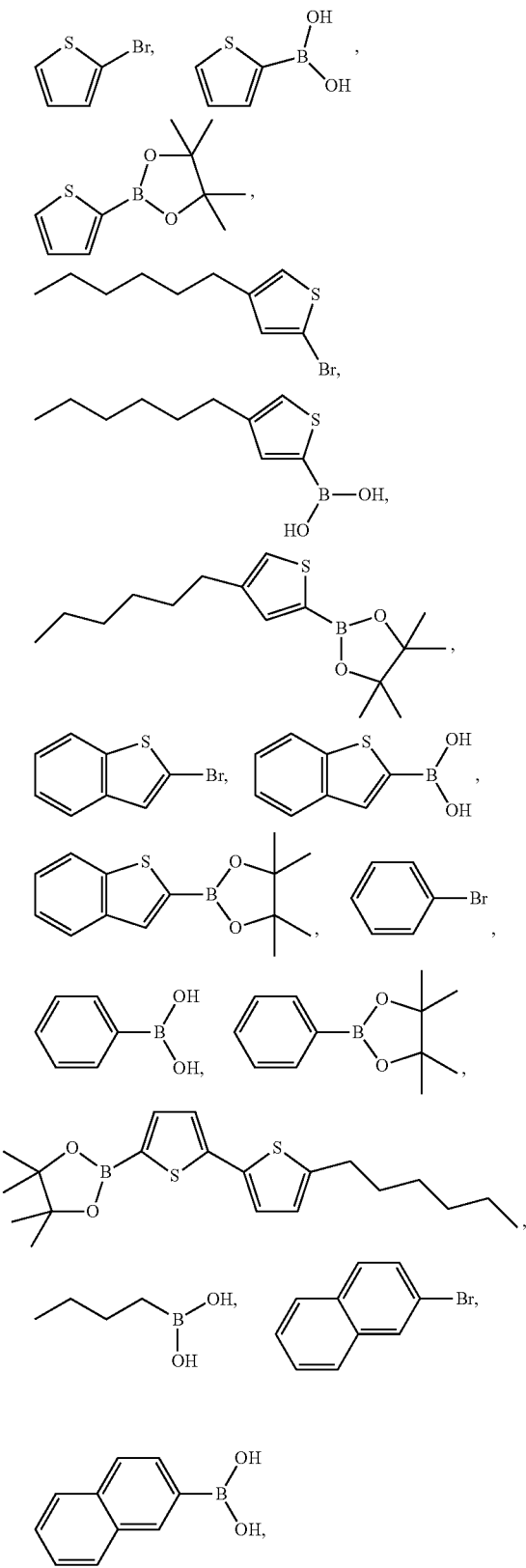

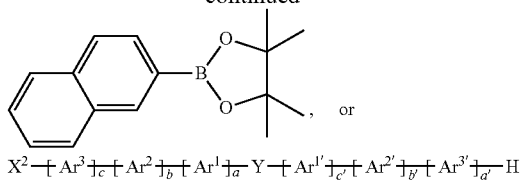

$$X^2 \!-\!\!\left[\!Ar^3\!\right]_{\!c}\!\!-\!\!\left[\!Ar^2\!\right]_{\!b}\!\!-\!\!\left[\!Ar^1\!\right]_{\!a}\!\!-\!Y\!-\!\!\left[\!Ar^{1'}\!\right]_{\!c'}\!\!-\!\!\left[\!Ar^{2'}\!\right]_{\!b'}\!\!-\!\!\left[\!Ar^{3'}\!\right]_{\!a'}\!\!-\!H$$

($X^2$ is Br, —B(OH)$_2$, —B(OY$^1$)$_2$,

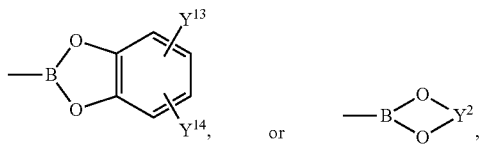

—BF$_4$Na, or —BF$_4$K) may be used as a chain-terminator in such reactions, which will result in the formation of a terminal aryl group.

It is possible to control the sequencing of the monomeric units in the resulting copolymer by controlling the order and composition of monomer feeds in the Suzuki reaction.

The polymers of the present invention can also be synthesized by the Stille coupling (see, for example, Babudri et al, J. Mater. Chem., 2004, 14, 11-34; J. K. Stille, Angew. Chemie Int. Ed. Engl. 1986, 25, 508). To prepare polymers corresponding to formula VII a dihalogenide of formula $X^{10}$-A-$X^{10}$ is reacted with a compound of formula $X^{11'}$—COM$^1$-$X^{11'}$, or a dihalogenide of formula $X^{10}$—COM$^1$-$X^{10}$ is reacted with a compound of formula $X^{11'}$-A-$X^{11'}$, wherein $X^{11'}$ is a group —SnR$^{207}$R$^{208}$R$^{209}$ and $X^{10}$ is as defined above, in an inert solvent at a temperature in range from 0° C. to 200° C. in the presence of a palladium-containing catalyst, wherein R$^{207}$, R$^{208}$ and R$^{209}$ are identical or different and are H or C$_1$-C$_6$alkyl, wherein two radicals optionally form a common ring and these radicals are optionally branched or unbranched. It must be ensured here that the totality of all monomers used has a highly balanced ratio of organotin functions to halogen functions. In addition, it may prove advantageous to remove any excess reactive groups at the end of the reaction by end-capping with monofunctional reagents. In order to carry out the process, the tin compounds and the halogen compounds are preferably introduced into one or more inert organic solvents and stirred at a temperature of from 0 to 200° C., preferably from 30 to 170° C. for a period of from 1 hour to 200 hours, preferably from 5 hours to 150 hours. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, isohexane, heptane, cyclohexane, benzene, toluene and xylene, alcohols, for example methanol, ethanol, 1-propanol, 2-propanol, ethylene glycol, 1-butanol, 2-butanol and tert-butanol, ketones, for example acetone, ethyl methyl ketone and isobutyl methyl ketone, amides, for example dimethylformamide (DMF), dimethylacetamide and N-methylpyrrolidone, nitriles, for example acetonitrile, propionitrile and butyronitrile, and mixtures thereof.

The palladium and phosphine components should be selected analogously to the description for the Suzuki variant.

Alternatively, the polymers of the present invention can also be synthesized by the Negishi reaction using a zinc reagent A-(ZnX$^{12}$)$_2$, wherein X$^{12}$ is halogen and halides, and COM$^1$-(X$^{23}$)$_2$, wherein X$^{23}$ is halogen or triflate, or using A-(X$^{23}$)$_2$ and COM$^1$-(ZnX$^{23}$)$_2$. Reference is, for example, made to E. Negishi et al., Heterocycles 18 (1982) 117-22.

Alternatively, the polymers of the present invention can also be synthesized by the Hiyama reaction using a organosilicon reagent A-(SiR$^{210}$R$^{211}$R$^{212}$)$_2$, wherein R$^{210}$, R$^{211}$ and R$^{212}$ are identical or different and are halogen, or C$_1$-C$_6$alkyl, and COM$^1$-(X$^{23}$)$_2$, wherein X$^{23}$ is halogen or triflate, or using A-(X$^{23}$)$_2$ and COM$^1$-(SiR$^{210}$R$^{211}$R$^{212}$)$_2$. Reference is, for example, made to T. Hiyama et al., Pure Appl. Chem. 66 (1994) 1471-1478 and T. Hiyama et al., Synlett (1991) 845-853.

Homopolymers of the type (A)$_n$ can be obtained via Yamamoto coupling of dihalides X$^{10}$-A-X$^{10}$, where X$^{10}$ is halogen, preferably bromide. Alternatively homopolymers of the type (A)$_n$ can be obtained via oxidative polymerization of units X$^{10}$-A-X$^{10}$, where X$^{10}$ is hydrogen, e.g. with FeCl$_3$ as oxidizing agent.

The compounds of the formula

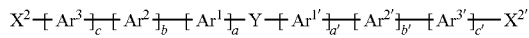

(V)

are intermediates in the production of the polymers of the present invention, are new and form a further subject of the present invention. a, a', b, b', c, c', Y, Ar$^1$, Ar$^{1'}$, Ar$^2$, Ar$^{2'}$, Ar$^3$ and Ar$^{3'}$ are as defined above, and X$^2$ and X$^{2'}$ are independently of each other halogen, especially Br, or J, ZnX$^{12}$, —SnR$^{207}$R$^{208}$R$^{209}$, wherein R$^{207}$, R$^{208}$ and R$^{209}$ are identical or different and are H or C$_1$-C$_8$alkyl, wherein two radicals optionally form a common ring and these radicals are optionally branched or unbranched; —SiR$^{210}$R$^{211}$R$^{212}$, wherein R$^{210}$, R$^{211}$ and R$^{212}$ are identical or different and are halogen, or C$_1$-C$_6$alkyl; X$^{12}$ is a halogen atom, very especially I, or Br; —OS(O)$_2$CF$_3$, —OS(O)$_2$-aryl, especially

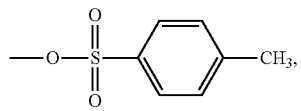

—OS(O)$_2$CH$_3$, —B(OH)$_2$, —B(OY$^1$)$_2$,

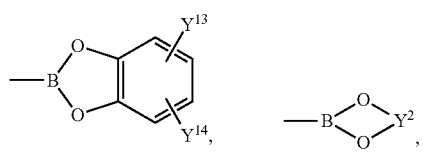

—BF$_4$Na, or —BF$_4$K, wherein Y$^1$ is independently in each occurrence a C$_1$-C$_{10}$alkyl group and Y$^2$ is independently in each occurrence a C$_2$-C$_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein Y$^3$, Y$^4$, Y$^5$, Y$^6$, Y$^7$, Y$^8$, Y$^9$, Y$^{10}$, Y$^{11}$ and Y$^{12}$ are independently of each other hydrogen, or a C$_1$-C$_{10}$alkyl group, especially —C(CH$_3$)$_2$C(CH$_3$)$_2$—, —C(CH$_3$)$_2$CH$_2$C(CH$_3$)$_2$—, or —CH$_2$C(CH$_3$)$_2$CH$_2$—, and Y$^{13}$ and Y$^{14}$ are independently of each other hydrogen, or a C$_1$-C$_{10}$alkyl group. The compounds of the formula (V) can be used in the production of polymers.

X$^2$ and X$^{2'}$ are preferably the same. U$^1$ and U$^2$ are preferably O, more preferably NR$^1$. T$^1$, T$^2$, T$^3$ and T$^4$ are preferably hydrogen. For a, a', b, b', c, c', Y, Ar$^2$, Ar$^{2'}$, Ar$^3$ and Ar$^{3'}$ the same preferences apply as in the repeating units of formula (I).

Compounds of formula

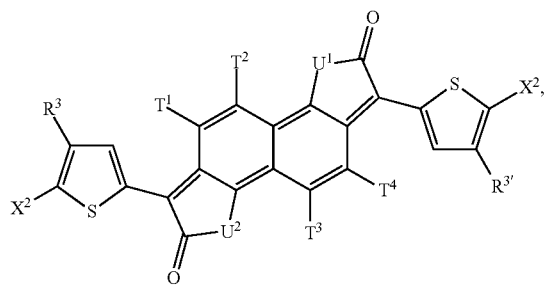

(Va)

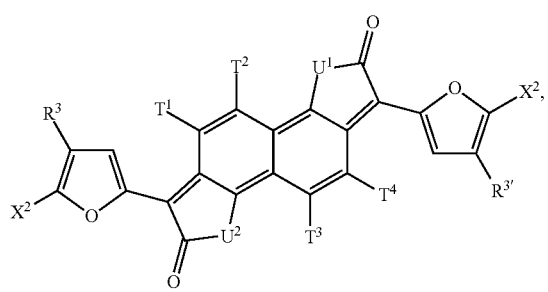

(Vb)

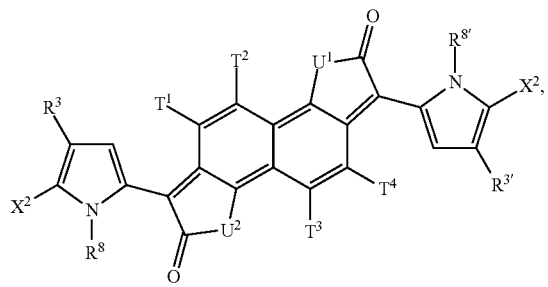

(Vc)

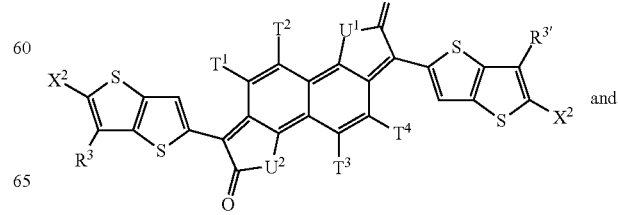

(Vd)

and

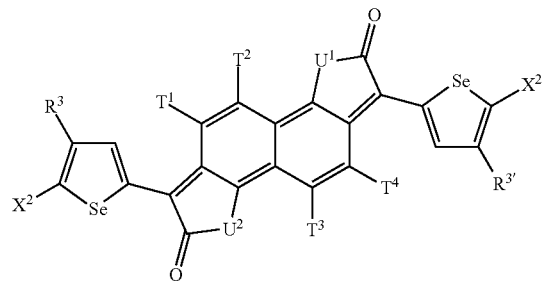

(Ve)

are preferred, wherein U¹ is O, or NR¹, especially NR¹; U² is O, or NR¹, especially NR¹;

T¹, T², T³ and T⁴ are independently of each other hydrogen, or $C_1$-$C_{25}$alkyl, especially hydrogen;

R¹ and R² are independently of each other a $C_1$-$C_{38}$alkyl group, especially $C_8$-$C_{36}$alkyl group, R³ and R³' are independently of each other hydrogen, halogen, cyano, $C_1$-$C_{25}$alkyl or $C_1$-$C_{25}$alkoxy, especially hydrogen or $C_1$-$C_{25}$alkyl;

R⁸ and R⁸' are independently of each other hydrogen or $C_1$-$C_{25}$alkyl, especially $C_1$-$C_{25}$alkyl, especially $C_1$-$C_{25}$alkyl; and X² is as defined above.

Examples of preferred compounds of formula V are shown below:

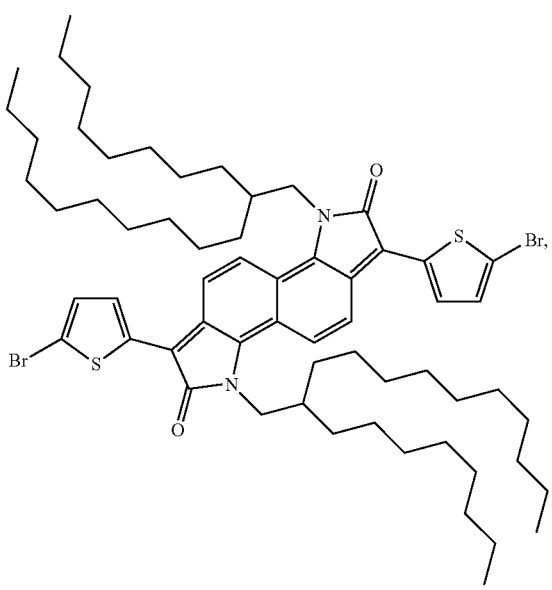

(I-1)

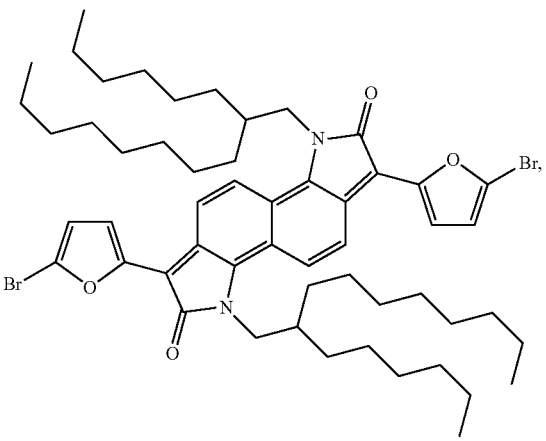

(I-2)

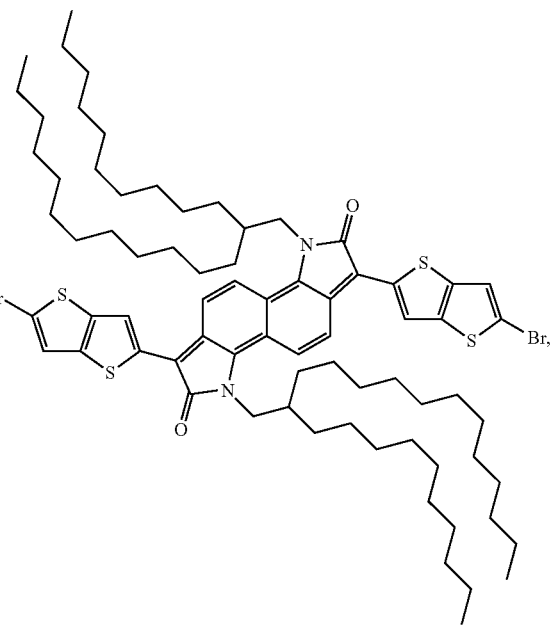

(I-3)

(I-4)
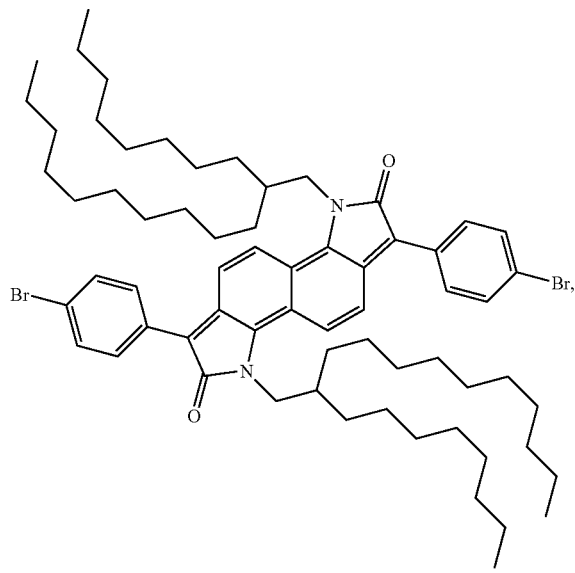
(I-5)
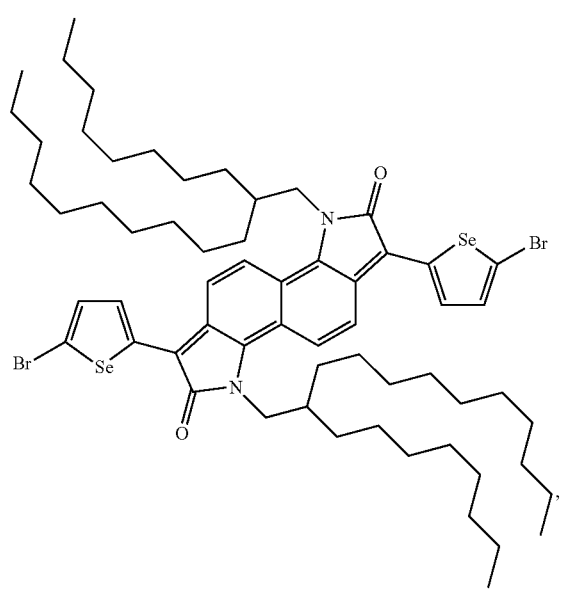
(I-6)
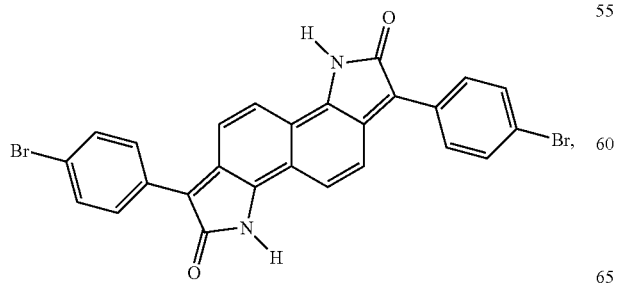
(I-7)
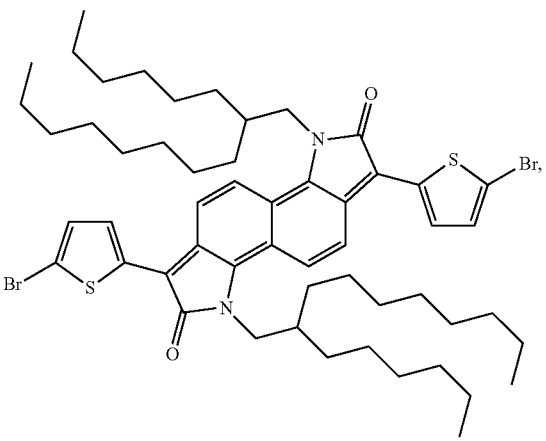
(I-8)
and
(I-9)
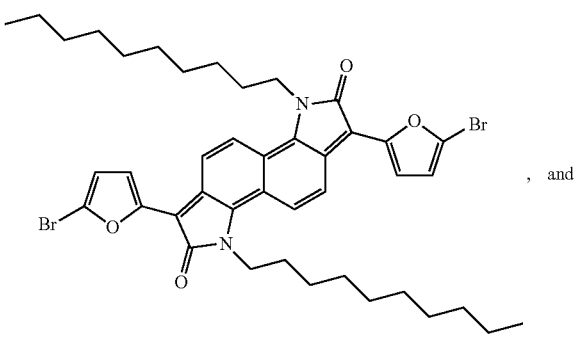
, and (I-10)

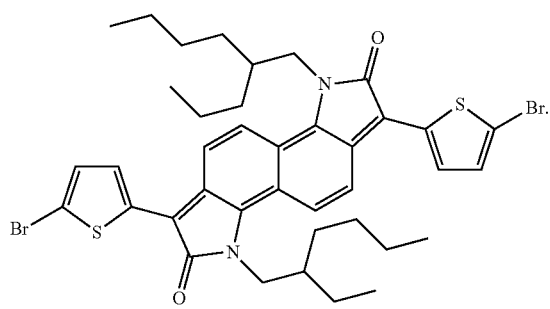

Additional examples of compounds of formula V are shown below:

(I-11)

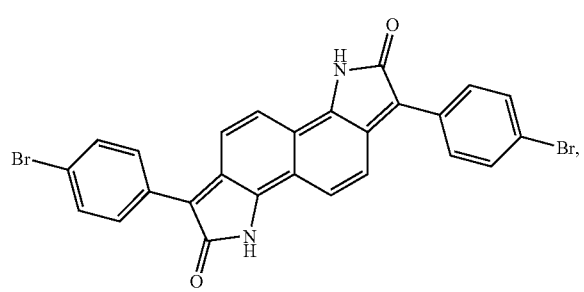

(I-12)

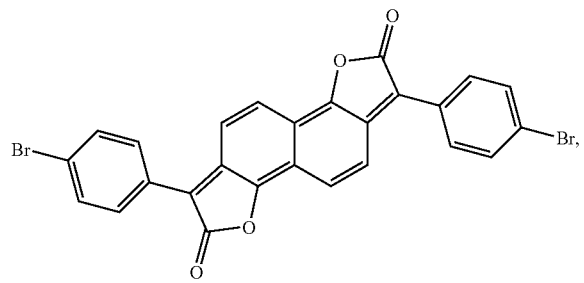

(I-13)

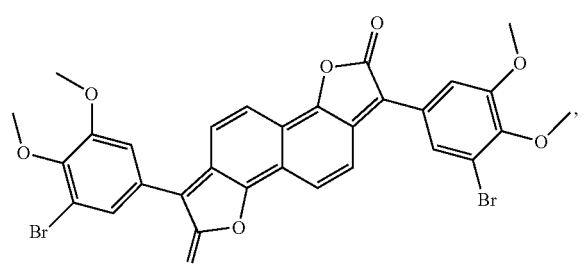

(I-13)

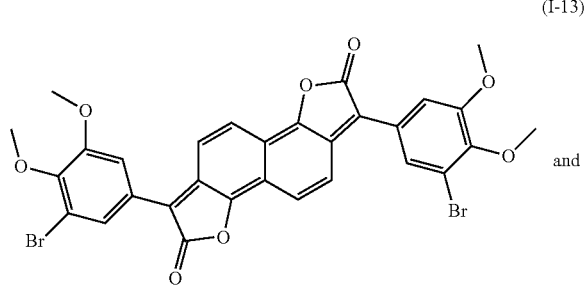

and (I-14)

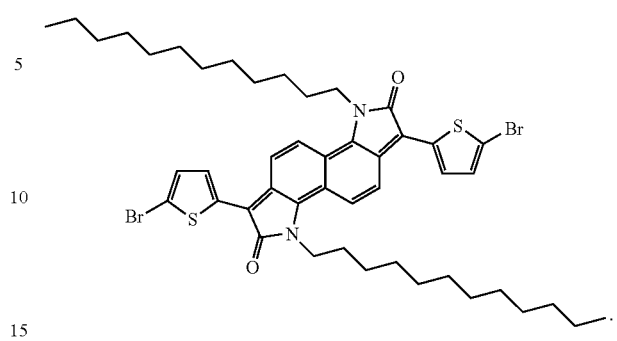

The polymers, wherein $R^1$ and/or $R^2$ are hydrogen can be obtained by using a protecting group which can be removed after polymerization. Reference is made, for example, to EP-A-0648770, EP-A-0648817, EP-A-0742255, EP-A-0761772, WO98/32802, WO98/45757, WO98/58027, WO99/01511, WO00/17275, WO00/39221, WO00/63297 and EP-A-1086984, which describe the basic procedural method. Conversion of the pigment precursor into its pigmentary form is carried out by means of fragmentation under known conditions, for example thermally, optionally in the presence of an additional catalyst, for example the catalysts described in WO00/36210.

An example of such a protecting group is group of formula

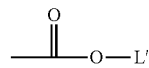

wherein L is any desired group suitable for imparting solubility.

L is preferably a group of formula

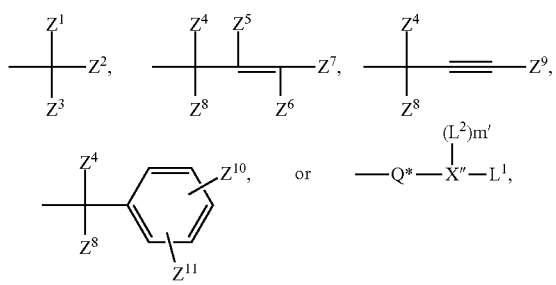

wherein $Z^1$, $Z^2$ and $Z^3$ are independently of each other $C_1$-$C_6$alkyl,
$Z^4$ and $Z^8$ are independently of each other $C_1$-$C_6$alkyl, $C_1$-$C_6$alkyl interrupted by oxygen, sulfur or $N(Z^{12})_2$, or unsubstituted or $C_1$-$C_6$alkyl-, $C_1$-$C_6$alkoxy-, halo-, cyano- or nitro-substituted phenyl or biphenyl,
$Z^5$, $Z^6$ and $Z^7$ are independently of each other hydrogen or $C_1$-$C_6$alkyl,
$Z^9$ is hydrogen, $C_1$-$C_6$alkyl or a group of formula

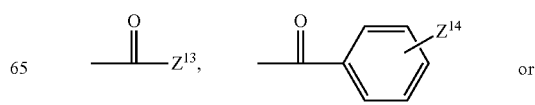

or

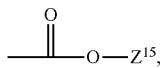

$Z^{10}$ and $Z^{11}$ are each independently of the other hydrogen, $C_1$-$C_6$alkyl, $C_1$-$C_6$alkoxy, halogen, cyano, nitro, $N(Z^{12})_2$, or unsubstituted or halo-, cyano-, nitro-, $C_1$-$C_6$alkyl- or $C_1$-$C_6$alkoxy-substituted phenyl, $Z^{12}$ and $Z^{13}$ are $C_1$-$C_6$alkyl, $Z^{14}$ is hydrogen or $C_1$-$C_6$alkyl, and $Z^{15}$ is hydrogen, $C_1$-$C_6$alkyl, or unsubstituted or $C_1$-$C_6$alkyl-substituted phenyl, Q* is p,q-$C_2$-$C_6$alkylene unsubstituted or mono- or poly-substituted by $C_1$-$C_6$alkoxy, $C_1$-$C_6$alkylthio or $C_2$-$C_{12}$dialkylamino, wherein p and q are different position numbers, X" is a hetero atom selected from the group consisting of nitrogen, oxygen and sulfur, m' being the number 0 when X" is oxygen or sulfur and m being the number 1 when X" is nitrogen, and $L^1$ and $L^2$ are independently of each other unsubstituted or mono- or poly-$C_1$-$C_{12}$alkoxy-, —$C_1$-$C_{12}$alkylthio-, —$C_2$-$C_{24}$dialkylamino-, —$C_6$-$C_{12}$aryloxy-, —$C_6$-$C_{12}$arylthio-, —$C_7$-$C_{24}$alkylarylamino- or —$C_{12}$-$C_{24}$diarylamino-substituted $C_1$-$C_6$alkyl or [-(p',q'—$C_2$-$C_6$alkylene)-Z—]$_{n'}$—$C_1$-$C_6$alkyl, n' being a number from 1 to 1000, p' and q' being different position numbers, each Z independently of any others being a hetero atom oxygen, sulfur or $C_1$-$C_{12}$alkyl-substituted nitrogen, and it being possible for $C_2$-$C_6$alkylene in the repeating [—$C_2$-$C_6$alkylene-Z—] units to be the same or different, and $L_1$ and $L_2$ may be saturated or unsaturated from one to ten times, may be uninterrupted or interrupted at any location by from 1 to 10 groups selected from the group consisting of —(C=O)— and —$C_6H_4$—, and may carry no further substituents or from 1 to 10 further substituents selected from the group consisting of halogen, cyano and nitro. Most preferred L is a group of formula

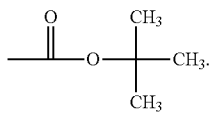

The synthesis of the compounds of formula H-A-H can be done in analogy to the methods described in C. Greenhalgh et al., Dyes and Pigments 1 (1980) 103-120 and G Hallas et al. Dyes and Pigments 48 (2001) 121-132.

In the context of the present invention, the terms halogen, $C_1$-$C_{25}$alkyl ($C_1$-$C_{18}$alkyl), $C_2$-$C_{25}$alkenyl ($C_2$-$C_{18}$alkenyl), $C_2$-$C_{25}$alkynyl ($C_2$-$C_{18}$alkynyl), aliphatic groups, aliphatic hydrocarbon groups, alkylene, alkenylene, cycloaliphatic hydrocarbon groups, cycloalkyl, cycloalkenyl groups, $C_1$-$C_{25}$alkoxy ($C_1$-$C_{18}$alkoxy), $C_1$-$C_{18}$perfluoroalkyl, carbamoyl groups, $C_6$-$C_{24}$aryl ($C_6$-$C_{18}$aryl), $C_7$-$C_{25}$aralkyl and heteroaryl are each defined as follows—unless stated otherwise:

Halogen is fluorine, chlorine, bromine and iodine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, 1-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_2$-$C_{25}$alkenyl ($C_2$-$C_{18}$alkenyl) groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-25}$alkynyl ($C_{2-18}$alkynyl) is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

An aliphatic hydrocarbon group having up to 25 carbon atoms is a linear or branched alkyl, alkenyl or alkynyl (also spelled alkinyl) group having up to 25 carbon atoms as exemplified above.

Alkylene is bivalent alkyl, i.e. alkyl having two (instead of one) free valencies, e.g. trimethylene or tetramethylene.

Alkenylene is bivalent alkenyl, i.e. alkenyl having two (instead of one) free valencies, e.g. —$CH_2$—CH=CH—$CH_2$—.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

A cycloaliphatic hydrocarbon group is a cycloalkyl or cycloalkenyl group which may be substituted by one or more aliphatic and/or cycloaliphatic hydrocarbon groups.

A cycloaliphatic-aliphatic group is an aliphatic group substituted by a cycloaliphatic group, wherein the terms "cycloaliphatic" and "aliphatic" have the meanings given herein and wherein the free valency extends from the aliphatic moiety. Hence, a cycloaliphatic-aliphatic group is for example a cycloalkyl-alkyl group.

A cycloalkyl-alkyl group is an alkyl group substituted by a cycloalkyl group, e.g. cyclohexyl-methyl.

A "cycloalkenyl group" means an unsaturated alicyclic hydrocarbon group containing one or more double bonds, such as cyclopentenyl, cyclopentadienyl, cyclohexenyl and the like, which may be unsubstituted or substituted by one or more aliphatic and/or cycloaliphatic hydrocarbon groups and/or condensed with phenyl groups.

For example, a cycloalkyl or cycloalkenyl group, in particular a cyclohexyl group, can be condensed one or two times with phenyl which can be substituted one to three times with $C_1$-$C_4$-alkyl. Examples of such condensed cyclohexyl groups are groups of the formulae:

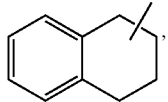
(XXIa)

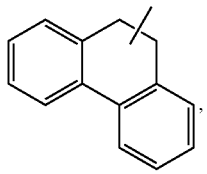
(XXIb)

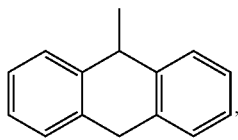
(XXII)

in particular

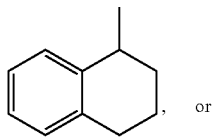
(XXIII)

or

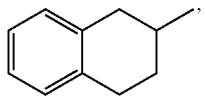
(XXIV)

which can be substituted in the phenyl moieties one to three times with $C_1$-$C_4$-alkyl.

A bivalent group of the formula XII wherein $R^{28}$ and $R^{27}$ together represent alkylene or alkenylene which may be both bonded via oxygen and/or sulfur to the thienyl residue and which may both have up to 25 carbon atoms, is e.g. a group of the formula

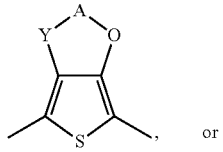
(XXIX)

or

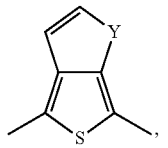
(XXX)

wherein A represents linear or branched alkylene having up to 25 carbon atoms, preferably ethylene or propylene which may be substituted by one or more alkyl groups, and Y represents oxygen or sulphur. For example, the bivalent group of the formula —Y-A-O— represents —O—$CH_2$—$CH_2$—O— or —O—$CH_2$—$CH_2$—$CH_2$—O—.

A group of the formula XI wherein two groups $R^{22}$ to $R^{26}$ which are in the neighborhood of each other, together represent alkylene or alkenylene having up to 8 carbon atoms, thereby forming a ring, is e.g. a group of the formula

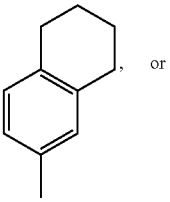
(XXXII)

, or

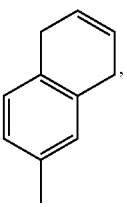
(XXXIII)

wherein in the group of the formula XXXII $R^{23}$ and $R^{24}$ together represent 1,4-butylene and in the group of the formula XXXIII $R^{23}$ and $R^{24}$ together represent 1,4-but-2-en-ylene.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

The term "carbamoyl group" is typically a $C_{1-18}$carbamoyl radical, preferably $C_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

A cycloalkyl group is typically $C_3$-$C_{12}$cycloalkyl, such as, for example, cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

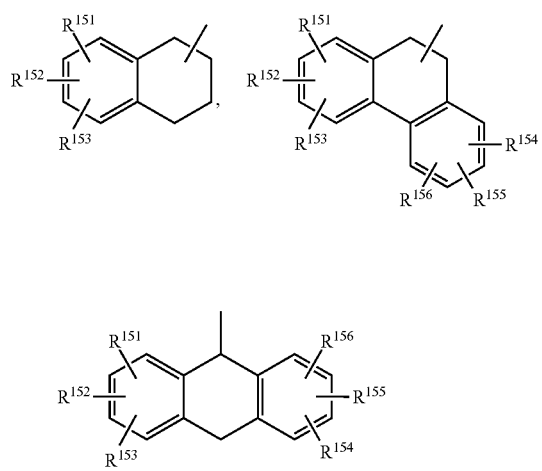

in particular

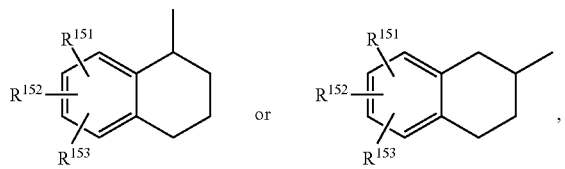

wherein $R^{151}$, $R^{152}$, $R^{153}$, $R^{154}$, $R^{155}$ and $R^{156}$ are independently of each other $C_1$-$C_8$-alkyl, $C_1$-$C_8$-alkoxy, halogen and cyano, in particular hydrogen.

$C_6$-$C_{24}$aryl ($C_6$-$C_{18}$aryl) is typically phenyl, indenyl, azulenyl, naphthyl, biphenyl, as-indacenyl, s-indacenyl, acenaphthylenyl, fluorenyl, phenanthryl, fluoranthenyl, triphenylenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of $C_6$-$C_{12}$aryl are phenyl, 1-naphthyl, 2-naphthyl, 3- or 4-biphenyl, 2- or 9-fluorenyl or 9-phenanthryl, which may be unsubstituted or substituted.

$C_7$-$C_{25}$aralkyl is typically benzyl, 2-benzyl-2-propyl, β-phenyl-ethyl, α,α-dimethylbenzyl, ω-phenyl-butyl, ω,ω-dimethyl-co-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

Heteroaryl is typically $C_2$-$C_{20}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, thienothienyl, furazanyl or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, a carbamoyl group, a nitro group or a silyl group, especially $C_1$-$C_8$alkyl, $C_1$-$C_8$alkoxy, $C_1$-$C_8$alkylthio, halogen, halo-$C_1$-$C_8$alkyl, or a cyano group.

$C_1$-$C_{18}$alkyl interrupted by one or more O is, for example, $(CH_2CH_2O)_{1-9}$—$R^x$, where $R^x$ is H or $C_1$-$C_{10}$alkyl, $CH_2$—$CH(OR^{y'})$—$CH_2$—O—$R^y$, where $R^y$ is $C_1$-$C_{18}$alkyl, and $R^{y'}$ embraces the same definitions as $R^y$ or is H. If a substituent, such as, for example $R^3$, occurs more than one time in a group, it can be different in each occurrence.

A mixture containing a polymer of the present invention results in a semi-conducting layer comprising a polymer of the present invention (typically 5% to 99.9999% by weight, especially 20 to 85% by weight) and at least another material. The other material can be, but is not restricted to a fraction of the same polymer of the present invention with different molecular weight, another polymer of the present invention, a semi-conducting polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.). The polymers of the present invention can be blended with compounds of formula III according to the present invention, or small molecules described, for example, in WO2009/047104, WO2010108873 (PCT/EP2010/053655), WO09/047104, U.S. Pat. No. 6,690,029, WO2007082584, and WO2008107089:

WO2007082584:

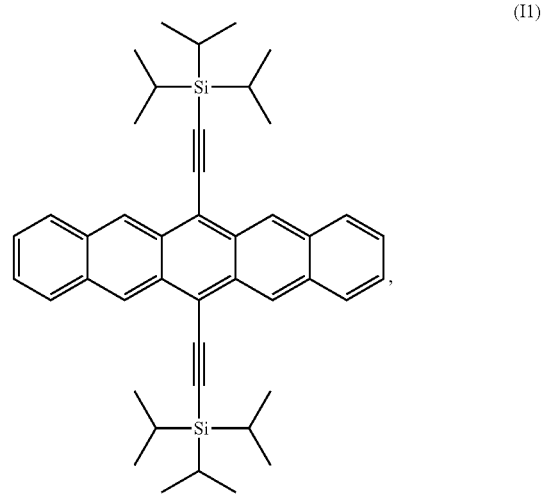

(II)

-continued
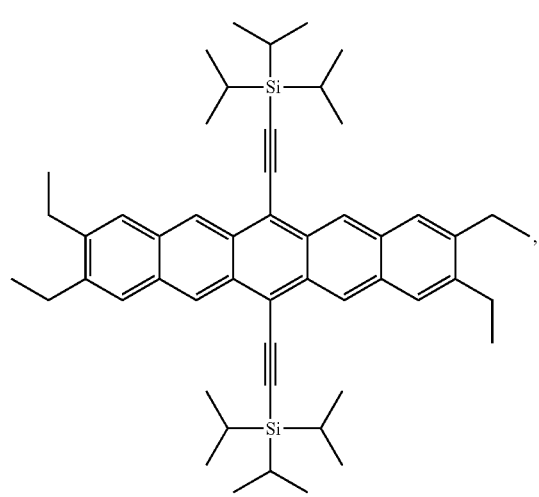
(I2)
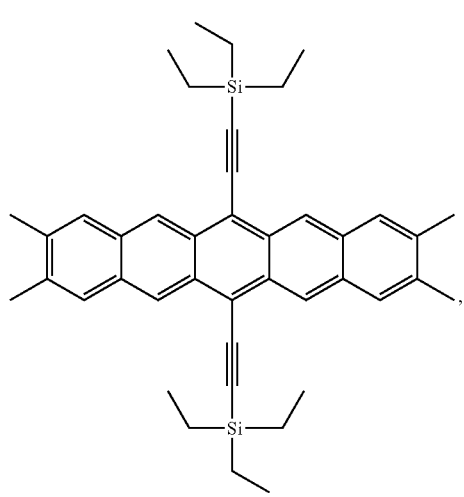
(I3)
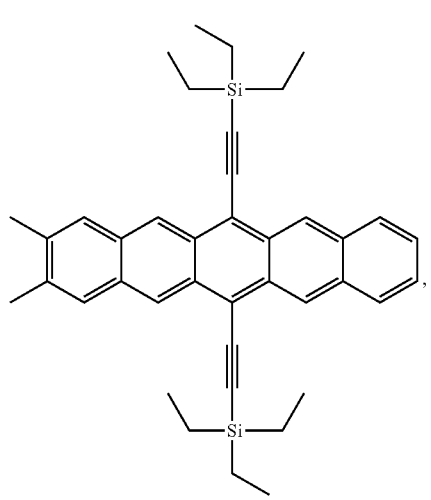
(I4)
-continued
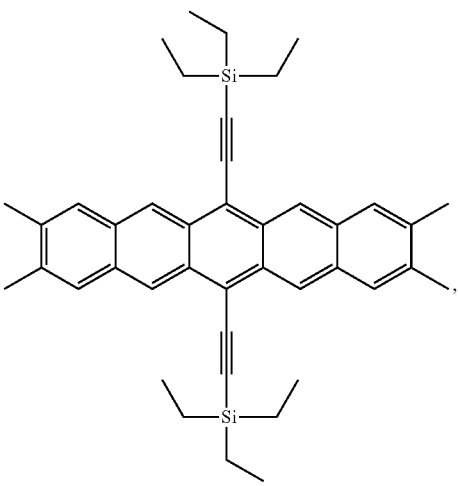
(I5)
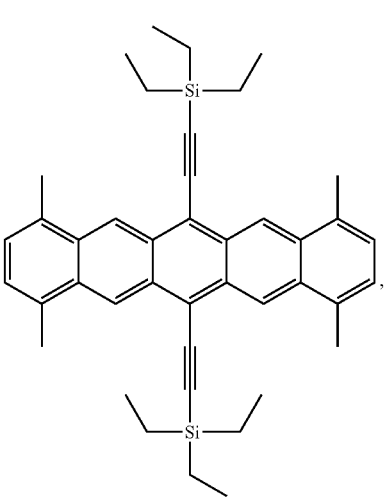
(I6)
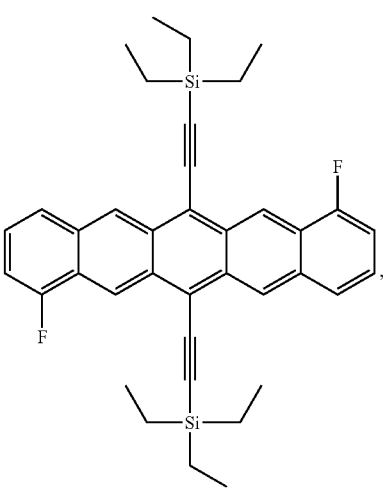
(I7)

-continued

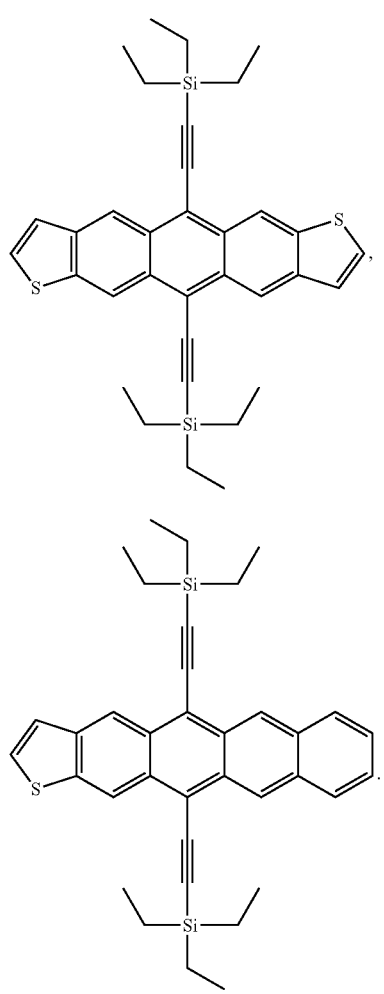

WO2008107089:

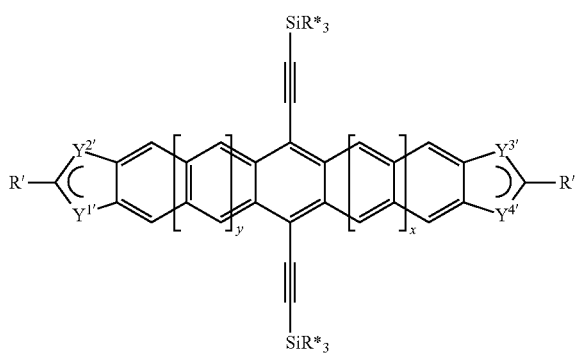

wherein one of $Y^{1'}$ and $Y^{2'}$ denotes —CH= or =CH— and the other denotes —X*—,
one of $Y^{3'}$ and $Y^{4'}$ denotes —CH= or =CH— and the other denotes —X*—,
X* is —O—, —S—, —Se— or —NR'''—,
R* is cyclic, straight-chain or branched alkyl or alkoxy having 1 to 20 C-atoms, or aryl having 2-30 C-atoms, all of which are optionally fluorinated or perfluorinated,
R' is H, F, Cl, Br, I, CN, straight-chain or branched alkyl or alkoxy having 1 to 20 C-atoms and optionally being fluorinated or perfluorinated, optionally fluorinated or perfluorinated aryl having 6 to 30 C-atoms, or $CO_2R''$, with R'' being H, optionally fluorinated alkyl having 1 to 20 C-atoms, or optionally fluorinated aryl having 2 to 30 C-atoms,
R''' is H or cyclic, straight-chain or branched alkyl with 1 to 10 C-atoms, y is 0, or 1, x is 0, or 1.

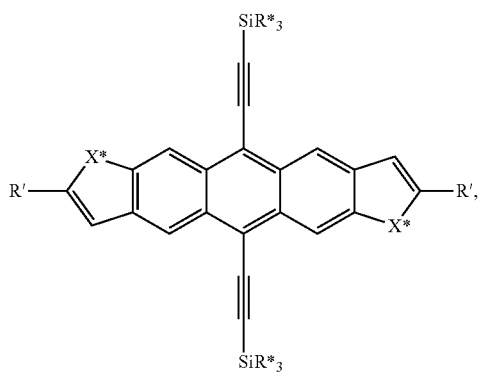

A1

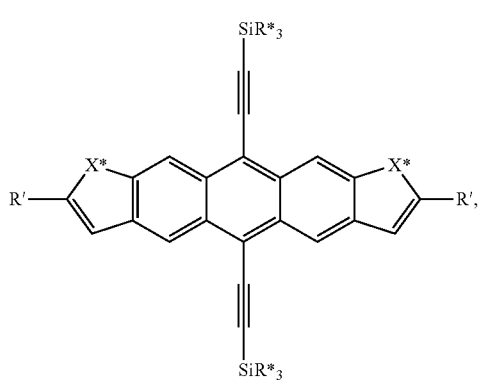

A2

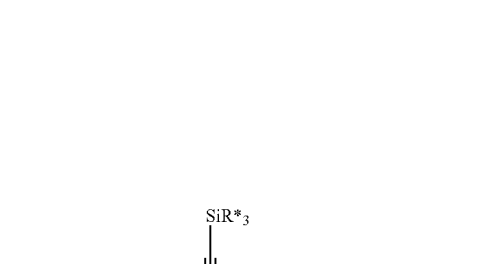

B1

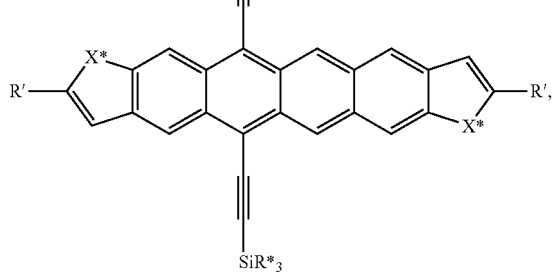

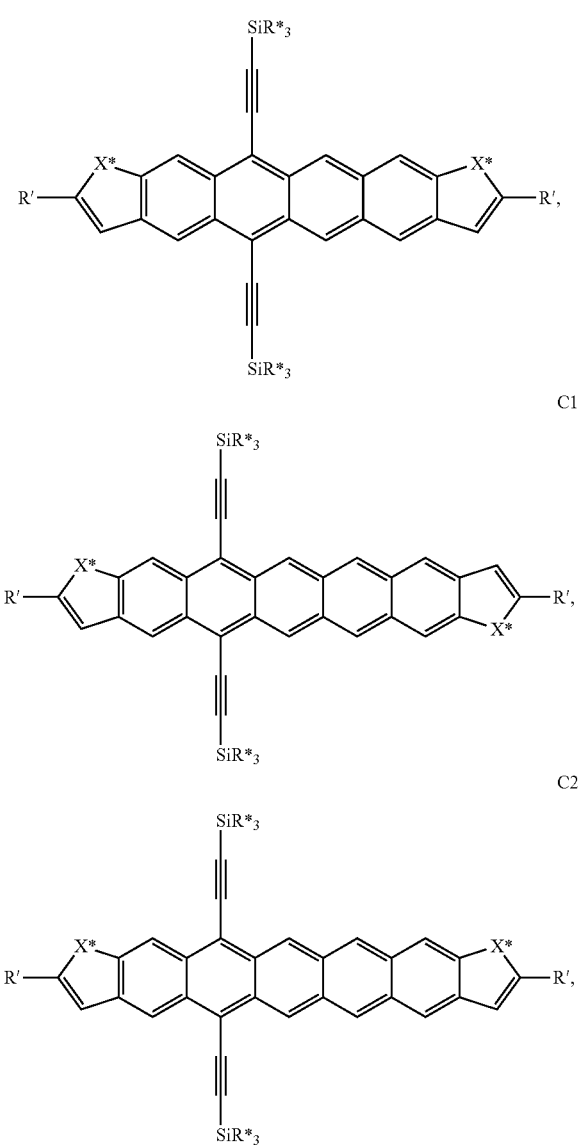

The polymer can contain a small molecule, or a mixture of two, or more small molecule compounds.

Accordingly, the present invention also relates to an organic semiconductor material, layer or component, comprising a polymer according to the present invention.

The polymers of the invention can be used as the semiconductor layer in semiconductor devices. Accordingly, the present invention also relates to semiconductor devices, comprising a polymer of the present invention, or an organic semiconductor material, layer or component. The semiconductor device is especially an organic photovoltaic (PV) device (solar cell), a photodiode, or an organic field effect transistor.

The polymers of the invention can be used alone or in combination as the organic semiconductor layer of the semiconductor device. The layer can be provided by any useful means, such as, for example, vapor deposition (for materials with relatively low molecular weight) and printing techniques. The compounds of the invention may be sufficiently soluble in organic solvents and can be solution deposited and patterned (for example, by spin coating, dip coating, slot die coating, ink jet printing, gravure printing, flexo printing, offset printing, screen printing, microcontact (wave)-printing, drop or zone casting, or other known techniques).

The polymers of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like.

A further aspect of the present invention is an organic semiconductor material, layer or component comprising one or more polymers, or compounds of the present invention. A further aspect is the use of the polymers or materials of the present invention in an organic photovoltaic (PV) device (solar cell), a photodiode, or an organic field effect transistor (OFET). A further aspect is an organic photovoltaic (PV) device (solar cell), a photodiode, or an organic field effect transistor (OFET) comprising a polymer or material of the present invention.

The polymers of the present invention are typically used as organic semiconductors in form of thin organic layers or films, preferably less than 30 microns thick. Typically the semiconducting layer of the present invention is at most 1 micron (=1 μm) thick, although it may be thicker if required. For various electronic device applications, the thickness may also be less than about 1 micron thick. For example, for use in an OFET the layer thickness may typically be 100 nm or less. The exact thickness of the layer will depend, for example, upon the requirements of the electronic device in which the layer is used.

For example, the active semiconductor channel between the drain and source in an OFET may comprise a layer of the present invention.

An OFET device according to the present invention preferably comprises:
a source electrode,
a drain electrode,
a gate electrode,
a semiconducting layer,
one or more gate insulator layers, and
optionally a substrate, wherein the semiconductor layer comprises one or more polymers of the present invention.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a polymer of the present invention located on the second side of the insulator, and a drain electrode and a source electrode located on the polymer layer.

The OFET device can be a top gate device or a bottom gate device.

Suitable structures and manufacturing methods of an OFET device are known to the person skilled in the art and are described in the literature, for example in WO03/052841.

The gate insulator layer may comprise for example a fluoropolymer, like e.g. the commercially available Cytop 809M®, or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont), or Fluoropel® (from Cytonix) or the perfluorosolvent FC 43® (Acros, No. 12377).

The semiconducting layer comprising a polymer of the present invention may additionally comprise at least another material. The other material can be, but is not restricted to another polymer of the present invention, a semi-conducting polymer, a polymeric binder, organic small molecules different from a polymer of the present invention, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.). As stated above, the semiconductive layer can also be composed of a mixture of one or more polymers of the present invention and a polymeric binder. The ratio of the polymers of the present invention to the polymeric binder can vary from 5 to 95 percent. Preferably, the polymeric binder is a semicrystalline polymer such as polystyrene (PS), high-density polyethylene (HDPE), polypropylene (PP) and polymethylmethacrylate (PMMA). With this technique, a degradation of the electrical performance can be avoided (cf. WO2008/001123A1).

The polymers of the present invention are advantageously used in organic photovoltaic (PV) devices (solar cells). Accordingly, the invention provides PV devices comprising a polymer according to the present invention. A device of this construction will also have rectifying properties so may also be termed a photodiode. Photoresponsive devices have application as solar cells which generate electricity from light and as photodetectors which measure or detect light.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the polymers of the present invention. Preferably, the photoactive layer is made of a conjugated polymer of the present invention, as an electron donor and an acceptor material, like a fullerene, particularly a functionalized fullerene PCBM, as an electron acceptor. As stated above, the photoactive layer may also contain a polymeric binder. The ratio of the polymers of formula I to the polymeric binder can vary from 5 to 95 percent. Preferably, the polymeric binder is a semicrystalline polymer such as polystyrene (PS), high-density polyethylene (HDPE), polypropylene (PP) and polymethylmethacrylate (PMMA).

For heterojunction solar cells the active layer comprises preferably a mixture of a polymer of the present invention and a fullerene, such as [60]PCBM (=6,6-phenyl-$C_{61}$-butyric acid methyl ester), or [70]PCBM, in a weight ratio of 1:1 to 1:3. The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of any semi-conducting polymer, such as, for example, a polymer of the present invention, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a polymer of the present invention as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the polymers of the present invention can also be used alone or together with other materials in or as alignment layers in LCD or OLED devices, as described for example in US2003/0021913.

It is another object of the present invention to provide compounds, which show high efficiency of energy conversion, excellent field-effect mobility, good on/off current ratios and/or excellent stability, when used in organic field effect transistors, organic photovoltaics (solar cells) and photodiodes.

In a further embodiment the present invention relates to compounds of the formula

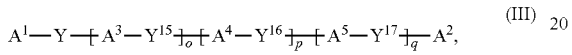
(III)

wherein Y, $Y^{15}$, $Y^{16}$ and $Y^{17}$ are independently of each other a group of formula

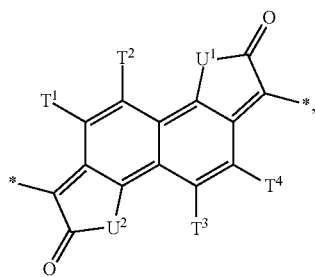

o is 0, or 1, p is 0, or 1, q is 0, or 1;
$A^1$ and $A^2$ are independently of each other a group of formula

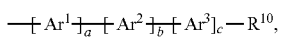

$A^3$, $A^4$ and $A^5$ are independently of each other a group of formula

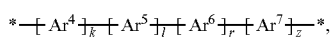

k is 1, 2, or 3; l is 0, 1, 2, or 3; r is 0, 1, 2, or 3; z is 0, 1, 2, or 3;
$R^{10}$ is hydrogen, halogen, cyano, $C_1$-$C_{25}$alkyl, $C_1$-$C_{25}$alkyl which is substituted one or more times by E and/or interrupted one or more times by D,

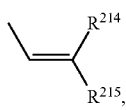

COO—$C_1$-$C_{18}$alkyl, $C_4$-$C_{18}$cycloalkyl group, $C_4$-$C_{18}$cycloalkyl group, which is substituted by G, $C_2$-$C_{18}$alkenyl, $C_2$-$C_{18}$alkynyl, $C_1$-$C_{18}$thioalkoxy, $C_1$-$C_{18}$alkoxy, $C_1$-$C_{18}$alkoxy which is substituted by E and/or interrupted by D, $C_7$-$C_{25}$aralkyl, $C_7$-$C_{25}$aralkyl, which is substituted by G, or a group of formulae IVa to IVm,

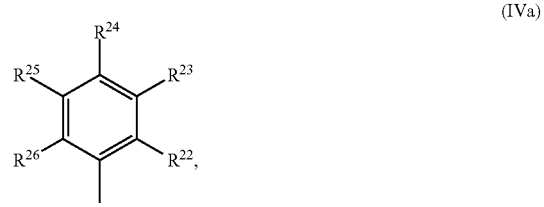
(IVa)

(IVb)

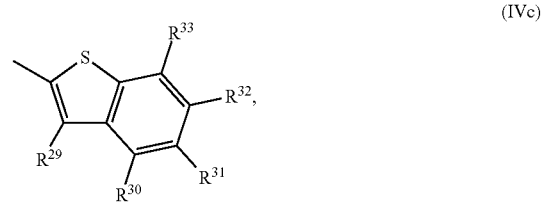
(IVc)

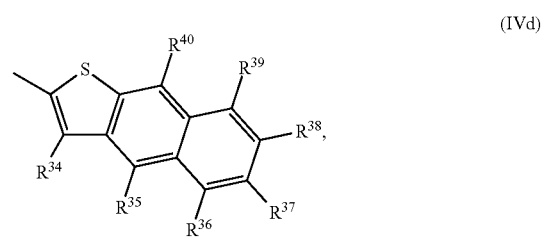
(IVd)

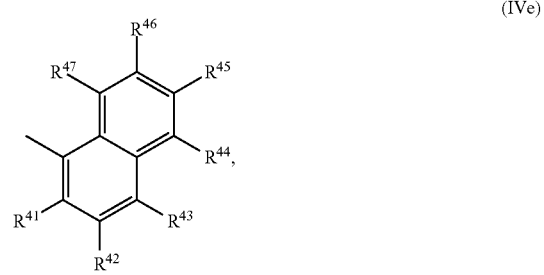
(IVe)

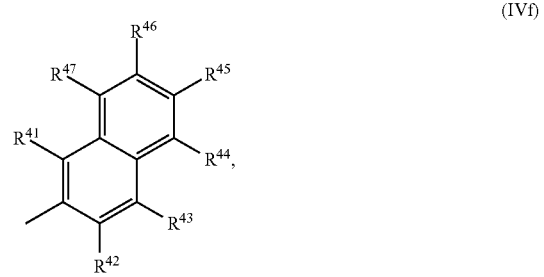
(IVf)

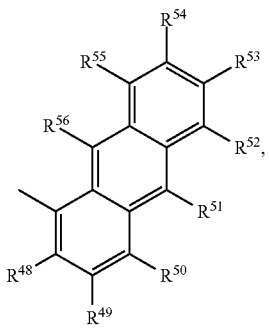 (IVg)

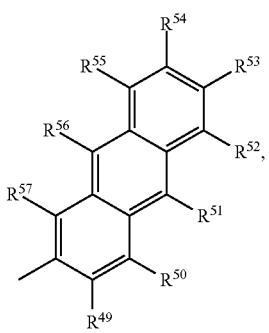 (IVh)

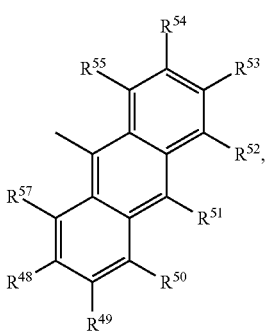 (IVi)

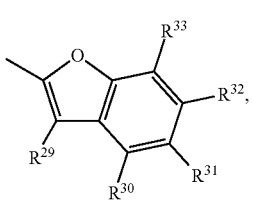 (IVj)

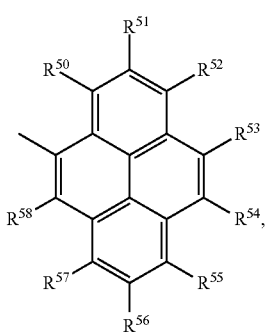 (IVk)

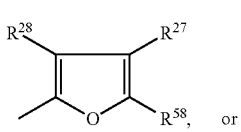 (IVl)

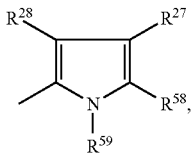 (IVm)

wherein $R^{22}$ to $R^{26}$ and $R^{29}$ to $R^{58}$ represent independently of each other H, halogen, cyano, $C_1$-$C_{25}$alkyl, $C_1$-$C_{25}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, a $C_4$-$C_{18}$cycloalkyl group, a $C_4$-$C_{18}$cycloalkyl group, which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or $C_7$-$C_{25}$aralkyl, which is substituted by G, $R^{27}$ and $R^{28}$ are independently of each other hydrogen, $C_1$-$C_{25}$alkyl, halogen, cyano or $C_7$-$C_{25}$aralkyl, or $R^{27}$ and $R^{28}$ together represent alkylene or alkenylene which may be both bonded via oxygen and/or sulfur to the thienyl residue and which may both have up to 25 carbon atoms, $R^{59}$ is hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_3$-$C_{25}$alkyl, which may optionally be interrupted by one or more oxygen or sulphur atoms; or $C_7$-$C_{25}$arylalkyl, D is —CO—, —COO—, —S—, —O—, or —$NR^{112}$—, E is $C_1$-$C_8$thioalkoxy, $C_1$-$C_8$alkoxy, CN, —$NR^{112}R^{113}$, —$CONR^{112}R^{113}$, or halogen, G is E, or $C_1$-$C_{18}$alkyl, and $R^{112}$ and $R^{113}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{214}$ and $R^{215}$ are independently of each other hydrogen, $C_1$-$C_{18}$alkyl, $C_6$-$C_{24}$aryl, $C_2$-$C_{20}$heteroaryl, —CN or $COOR^{216}$;

$R^{216}$ is $C_1$-$C_{25}$alkyl, $C_1$-$C_{25}$haloalkyl, $C_7$-$C_{25}$arylalkyl, $C_6$-$C_{24}$aryl or $C_2$-$C_{20}$heteroaryl;

$Ar^4$, $Ar^5$, $Ar^6$ and $Ar^7$ have independently of each other the meaning of $Ar^1$, and a, b, c, $Ar^1$, $Ar^2$, $Ar^3$, $T^1$, $T^2$, $U^1$ and $U^2$ are as defined above, with the proviso that, if o is 0, p is 0, q is 0, and $U^1$ is O and $U^2$ is O, $T^1$, $T^2$, $T^3$ and $T^4$ are each hydrogen, halogen, alkyl, or alkoxy; then the sum of a, b and c is equal, or greater than 2; and the further proviso that, if o is 0, p is 0, q is 0, a is 1, b is 0, c is 0, $T^1$, $T^2$, $T^3$ and $T^4$ are hydrogen, $U^1$ is O, $U^2$ is NH and $Ar^1$ is a group of formula

then $R^{10}$ is different from $OCH_3$, $OC_2H_5$, $O(CH_2)_2CH_3$, $OCH(CH_3)_2$ and $O(CH_2)_3CH_3$.

$U^1$ is preferably O, more preferably $NR^1$. $U^2$ is preferably O, more preferably $NR^2$. $T^1$, $T^2$, $T^3$ and $T^4$ are preferably hydrogen. Preferably, $U^1$ is $NR^1$ and $U^2$ is $NR^2$. More preferably, $U^1$ and $U^2$ are the same and are $NR^1$.

Among the compounds of the formula III compounds of formula

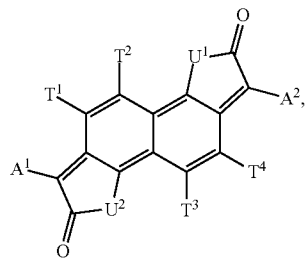
(IIIa)
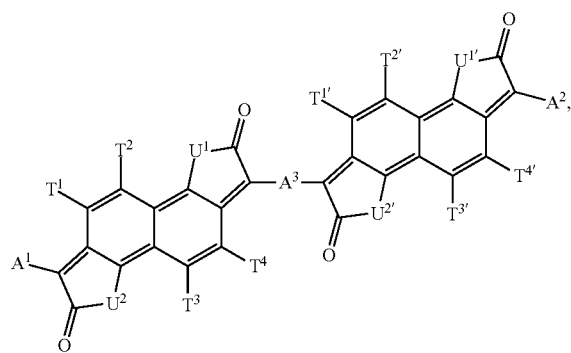
(IIIb)
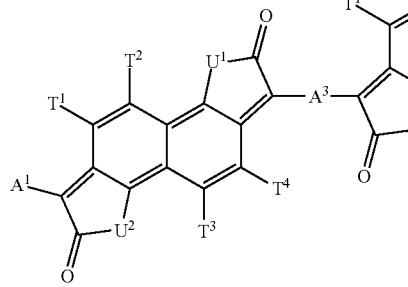
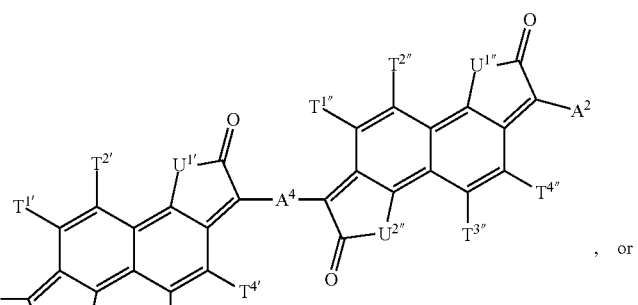
(IIIc)
, or
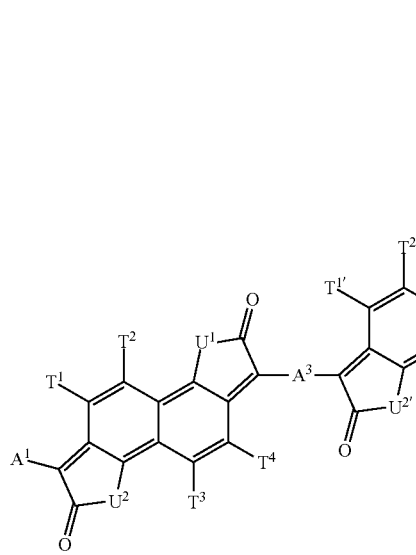
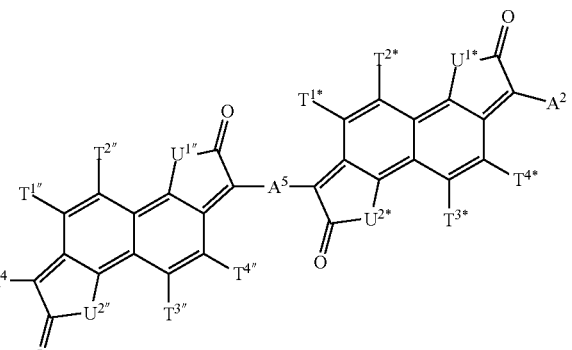
(IIId)

are more preferred, wherein
$A^1, A^2, A^3, A^4, A^5, T^1, T^2, T^3, T^4, U^1$ and $U^2$ are as defined above,
$T^{1'}, T^{2'}, T^{3'}, T^{4'}, T^{1''}, T^{2''}, T^{3''}, T^{4''}, T^{1*}, T^{2*}, T^{3*}$ and $T^{4*}$ independently of each other have the meaning of $T^1$, and $U^{1'}, U^{2'}, U^{1''}, U^{2''}, U^{1*}$ and $U^{2*}$ independently of each other have the meaning of $U^1$.

More preferred are compounds of the formula IIIa, IIIb and IIIc, even more preferred are compounds of the formula IIIa and IIIb, and most preferred are compounds of the formula IIIa.

Compounds of the formula

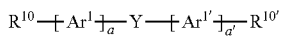   (III')

are more preferred, wherein
Y is a group of formula

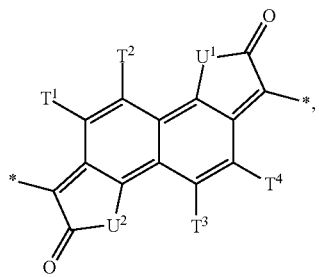

$U^1$ is O, S, or $NR^1$;
$U^2$ is O, S, or $NR^2$;
a is 1, 2, or 3, a' is 1, 2, or 3; wherein $R^{10'}$ has the meaning of $R^{10}$, $R^{10}$, $T^1$, $T^2$, $T^3$, $T^4$, $R^1$, $R^2$, $Ar^1$ and $Ar^{1'}$ are as defined above.

For $R^{10'}$ the same preferences apply as for $R^{10}$. For $T^1$, $T^2$, $T^3$, $T^4$, $R^1$, $R^2$, $Ar^1$ and $Ar^{1'}$ the same preferences apply as in case of the polymers according to the present invention.

$U^1$ and $U^2$ may be different, but are preferably the same. $U^1$ is preferably O, or $NR^1$; more preferably $NR^1$. $U^2$ is preferably O, or $NR^1$; more preferably $NR^1$.

$T^1$, $T^2$, $T^3$ and $T^4$ may be different, but are preferably the same. $T^1$, $T^2$, $T^3$ and $T^4$ are preferably independently of each other hydrogen, halogen, cyano, —COOR$^{103}$, —OCOR$^{103}$, —OR$^{103}$, —SR$^{103}$, $C_1$-$C_{25}$alkyl, which may be substituted by E and/or interrupted by D; more preferably hydrogen, halogen, cyano, —OR$^{103}$, or $C_1$-$C_{25}$alkyl; most preferred hydrogen, or $C_1$-$C_{25}$alkyl, especially hydrogen.

$R^1$ and $R^2$ may be different, but are preferably the same. More preferably $R^1$ and $R^2$ are selected from hydrogen, $C_1$-$C_{50}$alkyl, $C_1$-$C_{50}$haloalkyl, $C_7$-$C_{25}$arylalkyl, $C_2$-$C_{50}$alkenyl, $C_2$-$C_{50}$haloalkenyl, allyl, $C_5$-$C_{12}$cycloalkyl, phenyl, or naphthyl which can optionally be substituted one or more times with $C_1$-$C_{12}$alkyl or $C_1$-$C_{12}$alkoxy, —CO—$C_5$-$C_{12}$cycloalkyl and —COO—$C_1$-$C_{18}$alkyl. More preferably $R^1$ and $R^2$ are $C_1$-$C_{50}$alkyl group. Most preferred $R^1$ and $R^2$ are a $C_1$-$C_{38}$alkyl group.

a and a' may be different, but are preferably the same. a is 1, 2, or 3, a' is 1, 2, or 3.

In a preferred embodiment $Ar^1$ and $Ar^{1'}$ are independently of each other a group of formula (XIa), (XIb), (XIc), (XIe), (XIf), (XIk), (XIm), (XIn), (XIq), (XIr), (XIu), (XIw), (XIx), (XIII), such as, for example, (XIIIa) and (XIIIb); or (XIV), such as, for example, (XIVb). Preferably, $Ar^1$ and $Ar^{1'}$ are independently of each other a group of formula XIa, XIb, XIe, XIf, XIr, or XIIIa. More preferably, $Ar^1$ and $Ar^{1'}$ are independently of each other a group of formula XIa, XIb, or XIf, most preferred a group of formula XIa.

In another preferred embodiment of the present invention $Ar^1$ and $Ar^{1'}$ are independently of each other a group of formula XVa' or XVa".

Among the compounds of formula IIIa compounds of formula

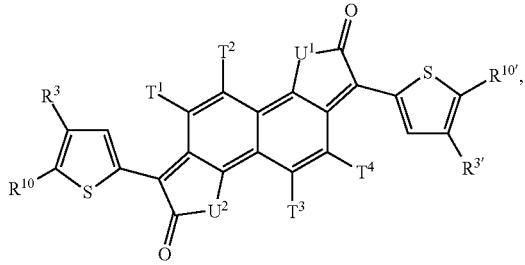   (IIIa1)

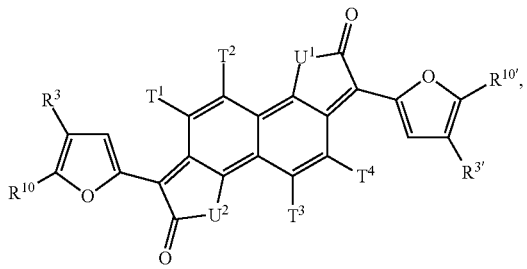   (IIIa2)

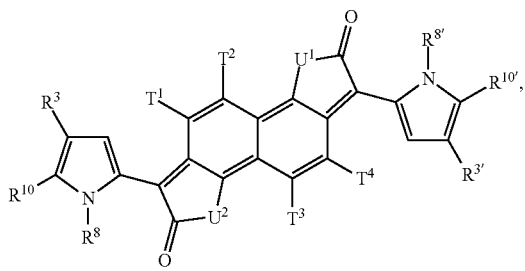   (IIIa3)

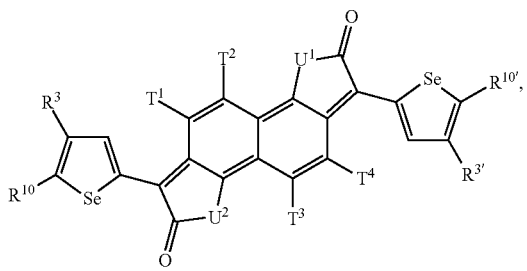   (IIIa4)

-continued
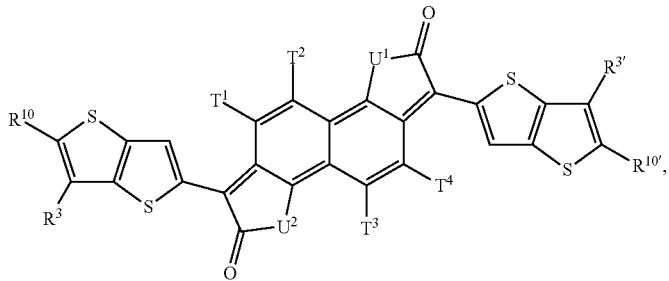
(IIIa5)
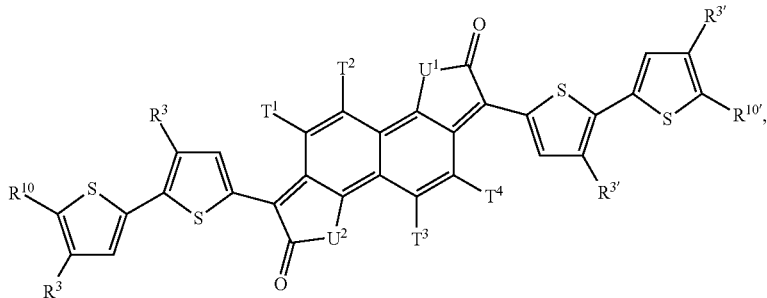
(IIIa6)
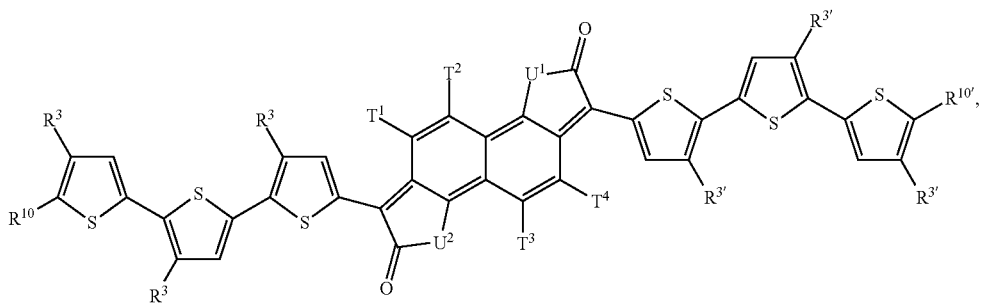
(IIIa7)
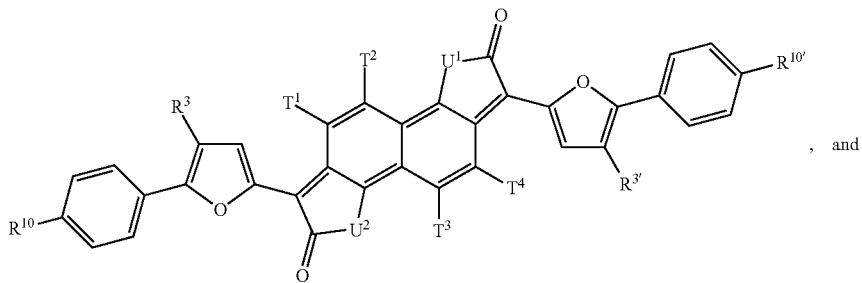
, and
(IIIa8)
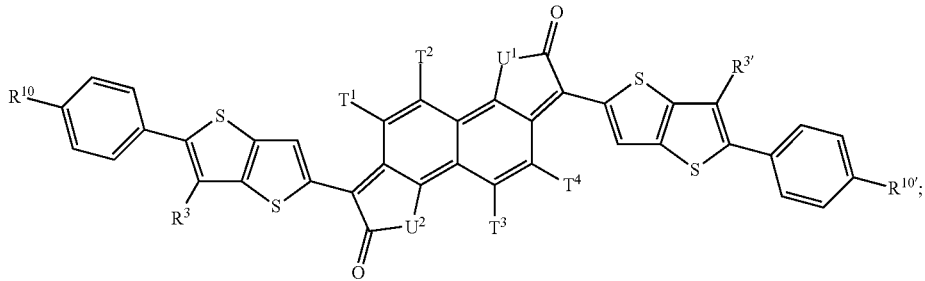
(IIIa9)

are more preferred, wherein $R^{10}$ and $R^{10'}$ are as defined above, and are preferably hydrogen, cyano, or $C_1$-$C_{25}$alkyl, $U^1$ is O, or $NR^1$, preferably $NR^1$; $U^2$ is O, or $NR^2$, preferably $NR^2$;

$T^1$, $T^2$, $T^3$ and $T^4$ are independently of each other hydrogen, or $C_1$-$C_{25}$alkyl, especially hydrogen;

$R^1$ and $R^2$ may be the same or different and are selected from a $C_1$-$C_{38}$alkyl group, especially a $C_8$-$C_{36}$alkyl group;

$R^3$ and $R^{3'}$ are independently of each other hydrogen, halogen, cyano or $C_1$-$C_{25}$alkyl, especially hydrogen or $C_1$-$C_{25}$alkyl; and $R^8$ and $R^{8'}$ are independently of each other hydrogen or $C_1$-$C_{25}$alkyl, especially $C_1$-$C_{25}$alkyl.

In said embodiment compounds of the formula (IIIa1), (IIIa2), (IIIa4), (IIIa5), (IIIa6) and (IIIa7) are even more preferred.

Examples of preferred compounds are shown below:

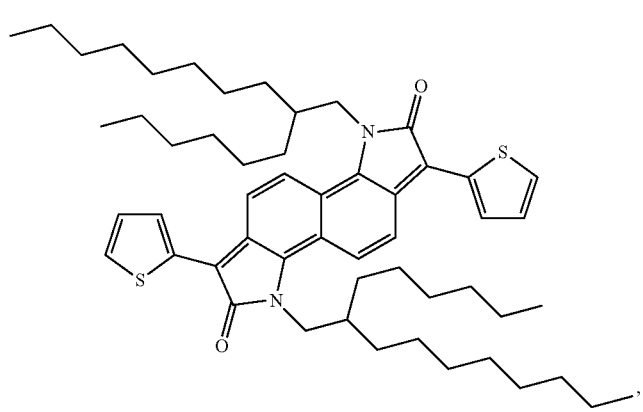

(B-1)

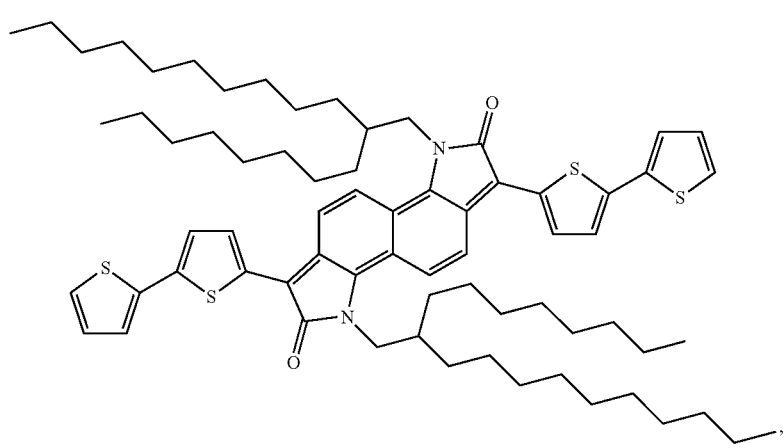

(B-2)

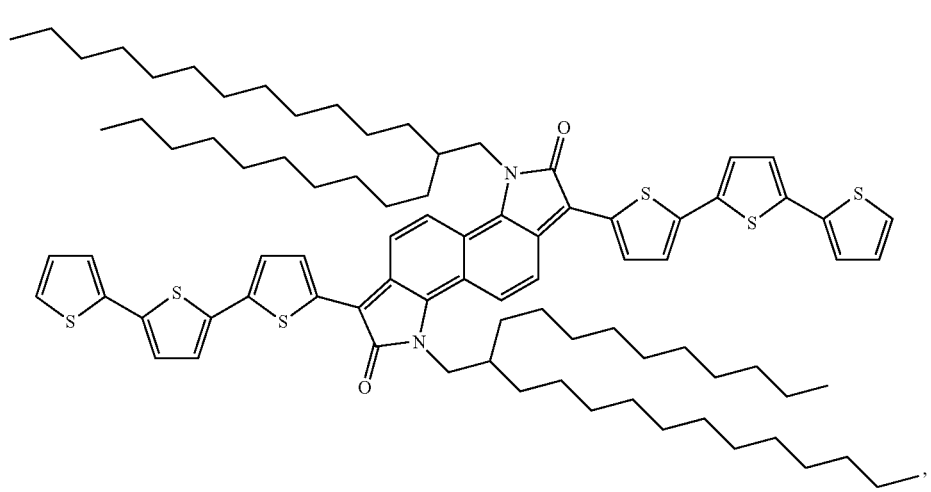

(B-3)

(B-4)
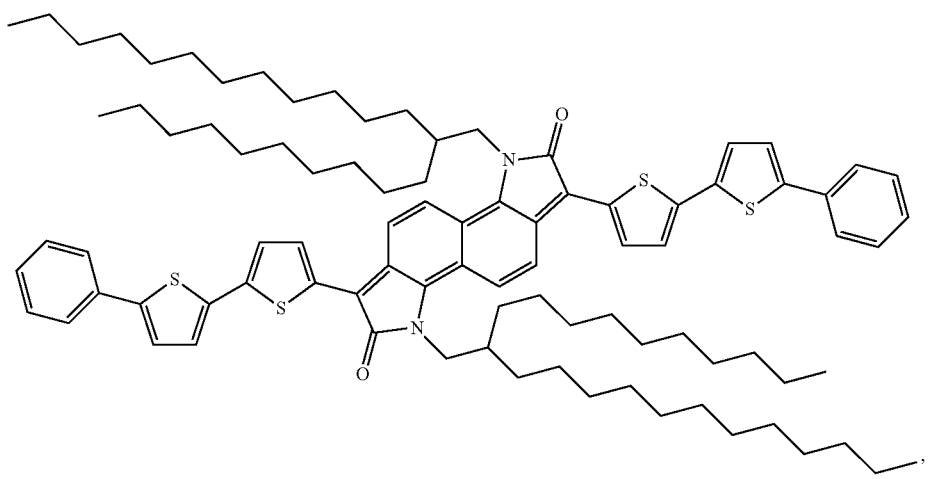
(B-5) (B-6)
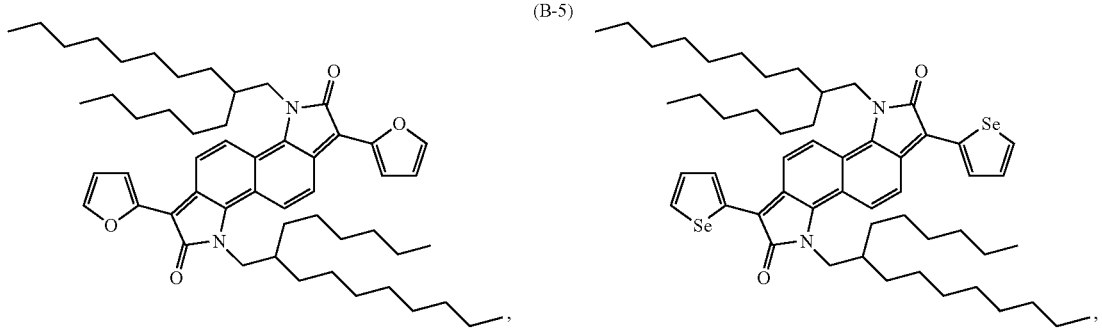
(B-7) (B-8)
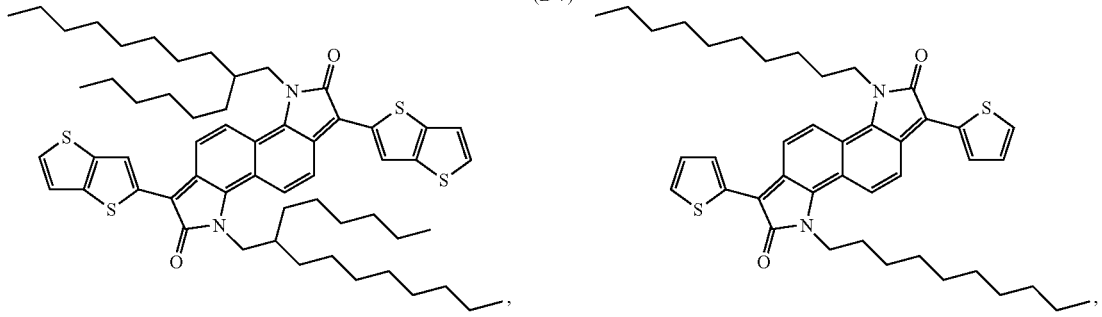
(B-9) (B-10)
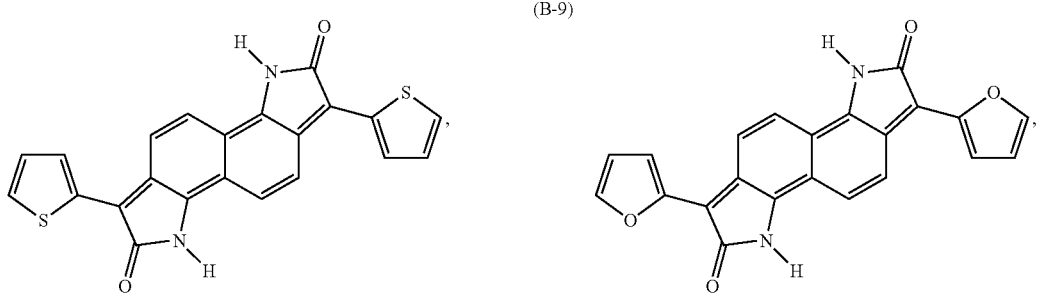

(B-11) 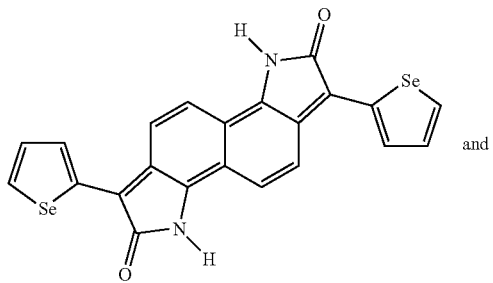 and
(B-12) 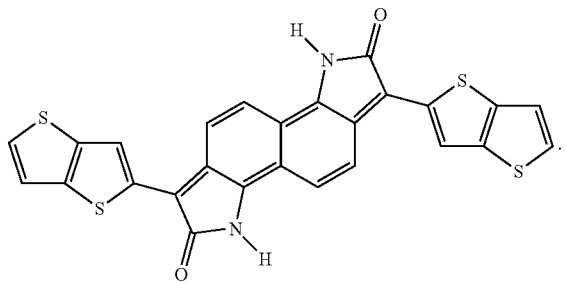.
Additional examples of compounds of formula (III) are shown below:
(B-13) 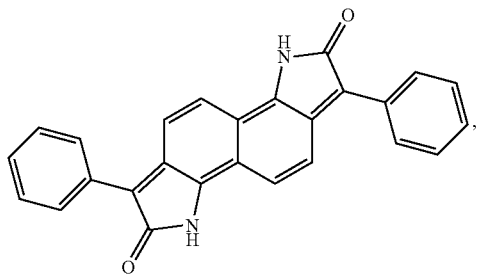,
(IIIb) 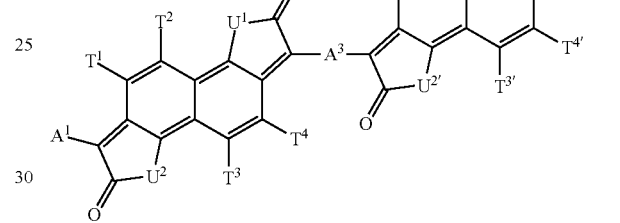
wherein
$A^1$ and $A^2$ are independently of each other a group of formula
(B-14) 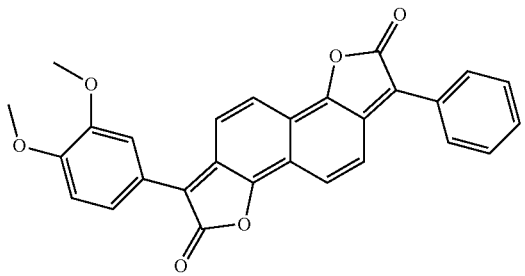
and
(B-15) 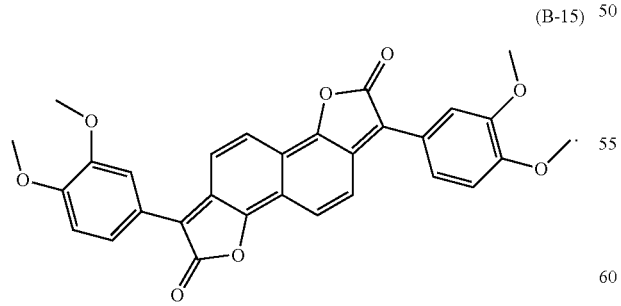.
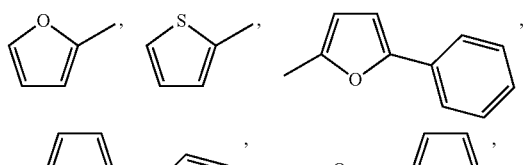
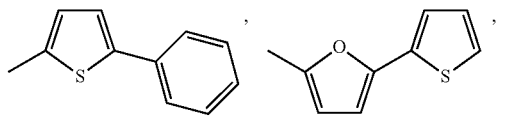
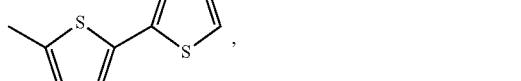
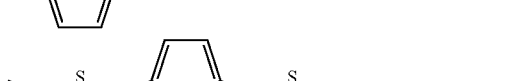
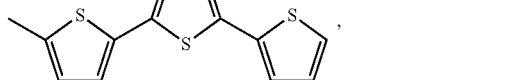
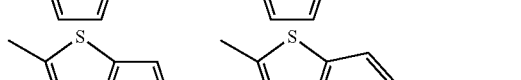
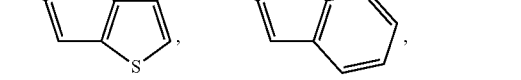
, or
In another preferred embodiment the present invention is directed to compounds of formula $A^3$ is a group of formula
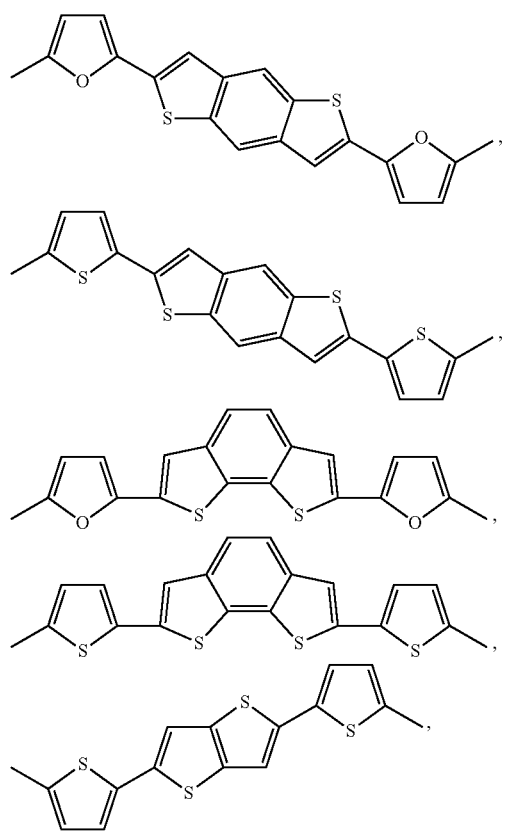
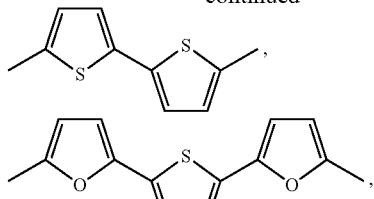
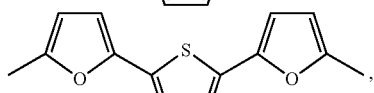
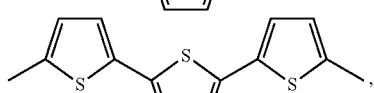
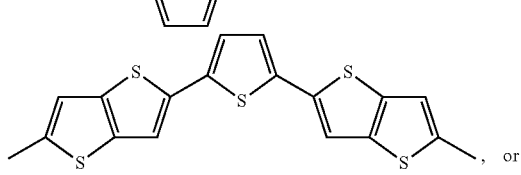, or
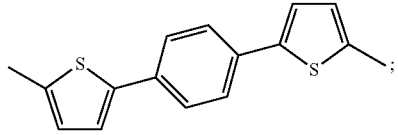;
and
$U^1$, $U^2$, $U^{1'}$ and $U^{2'}$ independently of each other $NR^1$, wherein $R^1$ is a $C_1$-$C_{38}$alkyl group, especially a $C_8$-$C_{36}$alkyl group.
$T^1$, $T^2$, $T^3$, $T^4$, $T^{2'}$, $T^{3'}$ and $T^{4'}$ are independently of each other hydrogen, or $C_1$-$C_{25}$alkyl, especially hydrogen.
An example of a compound of formula IIIb is shown below:
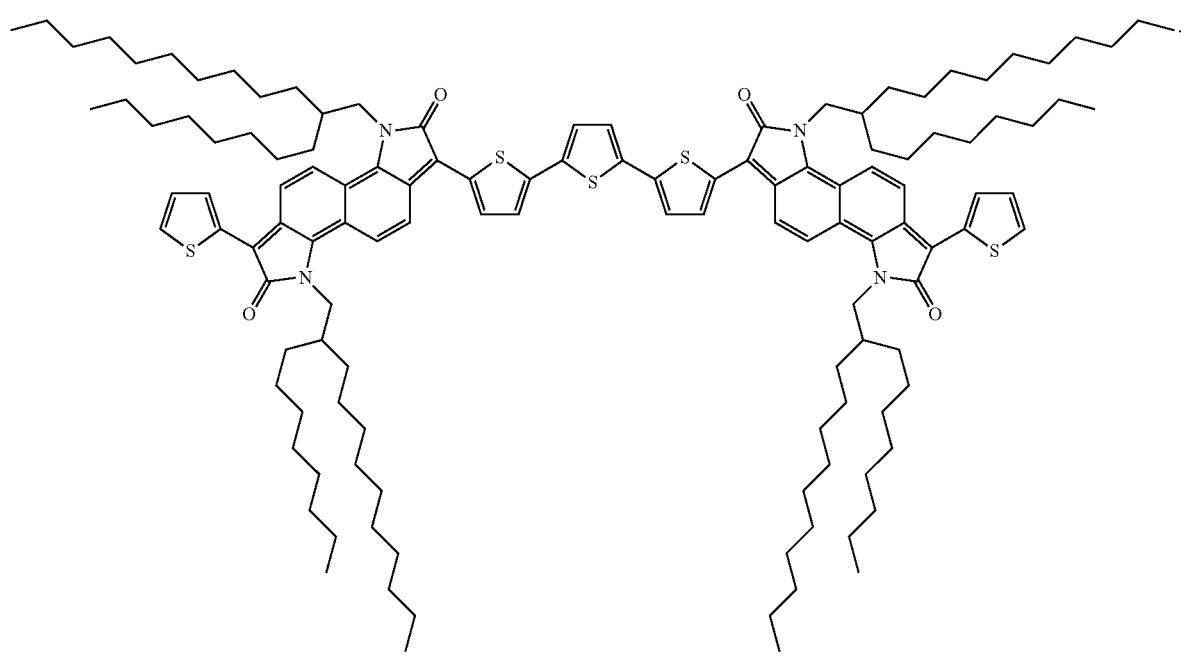
(C-1)

A process for the preparation of a compound of formula

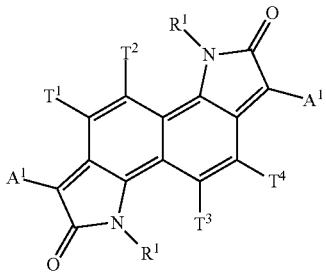

(IIIa') comprises reacting a 1,5-diaminonaphtlalene with two equivalents of a (hetero)aryl-hydroxy-acetic-acid to an intermediate amide of formula (VIIIa):

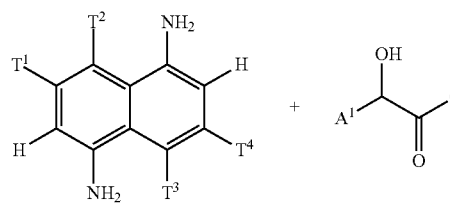 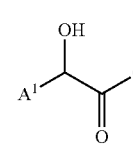

(VIIIa)

Intermediate (VIIIa) is then treated with an acid such as e.g. sulfuric acid to induce the intramolecular ring closure to intermediate (VIIIb):

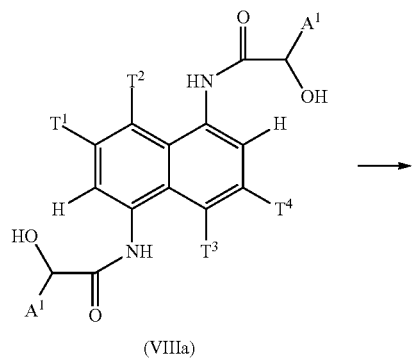

(VIIIa)

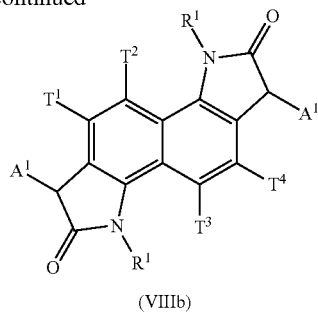

(VIIIb)

Intermediate (VIIIb) is then oxidized to compound (IIIa') with a suitable oxidant, such as, for example, a persulfate:

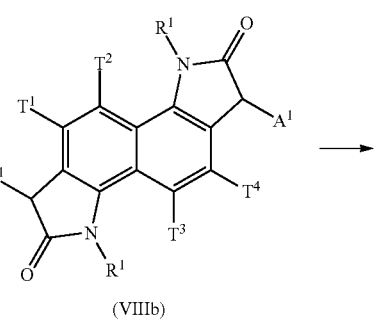

(VIIIb)

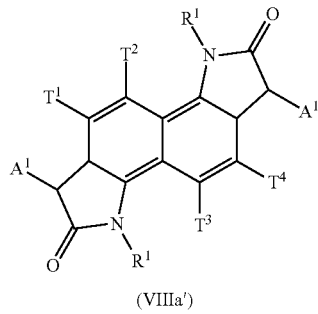

(VIIIa')

Another process for the preparation of a compound of formula

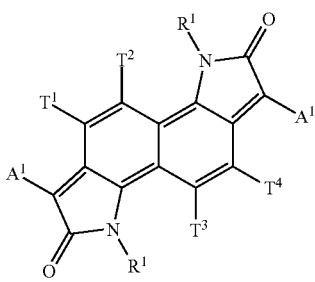

(IIIa')

may be based on a reaction sequence described in I. McCulloch et al., Chem. Commun. 49 (2013) 4465 for benzodipyrrolidone based compounds and comprises reacting a 1,5-diaminonaphtlalene with two equivalents of an acyl chloride of formula $R^{401}$—COCl, wherein $R^{401}$ is, for example, $C_1$-$C_{38}$alkyl which can optionally be interrupted by oxygen, preferably in the presence of a base, such as, for example, $K_2CO_3$, $Na_2CO_3$, triethylamine and tributylamine, at, for example, room temperature in a solvent, such as, for example, methylene chloride, to form an amide of formula (VIIId):

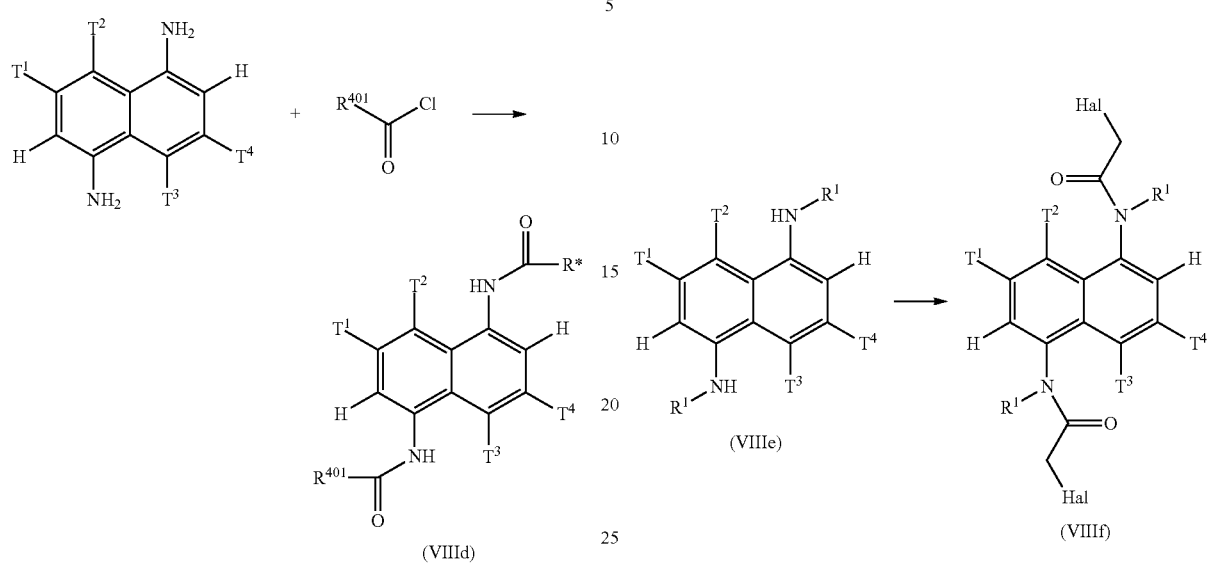

(VIIId)

Compound (VIIId) is reduced to an amine (VIIIe) in the presence of a reducing agent as, for example, LiAlH₄ or BH₃-tetrahydrofurane complex, preferably in an ether, such as, for example, tetrahydrofurane (THF); at reflux temperature.

(VIIId)

(VIIIe)

The amine (VIIIe) is reacted with Hal-acetylchloride (Hal is fluoro, chloro, bromo or iodo, preferably chloro or bromo, most preferred chloro) preferably in the presence of a base, such as, for example, K₂CO₃, Na₂CO₃, triethylamine, or tributylamine, at, for example, room temperature in a solvent, such as, for example, methylene chloride, to compound (VIIIf):

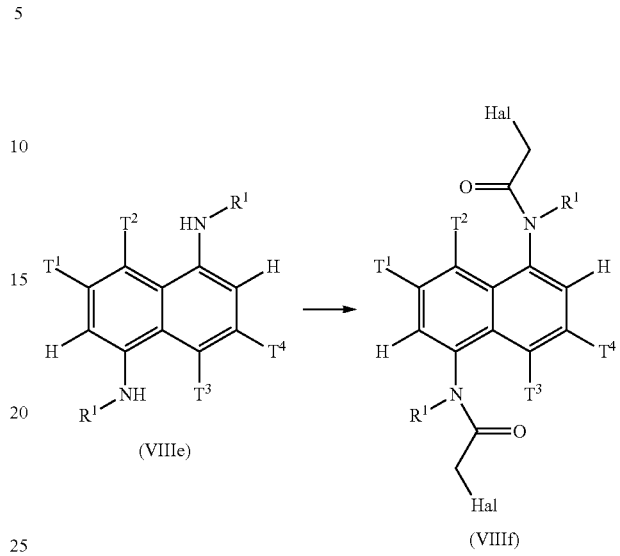

(VIIIe)

(VIIIf)

Compound (VIIIf) is hydrolyzed to compound (VIIIg) by stirring compound (VIIIf) together with a base, such as, for example, K₂CO₃, KOH, or NaOH, in a solvent, such as, for example, methanol, or THF between 0° C. and 100° C., preferably at room temperature.

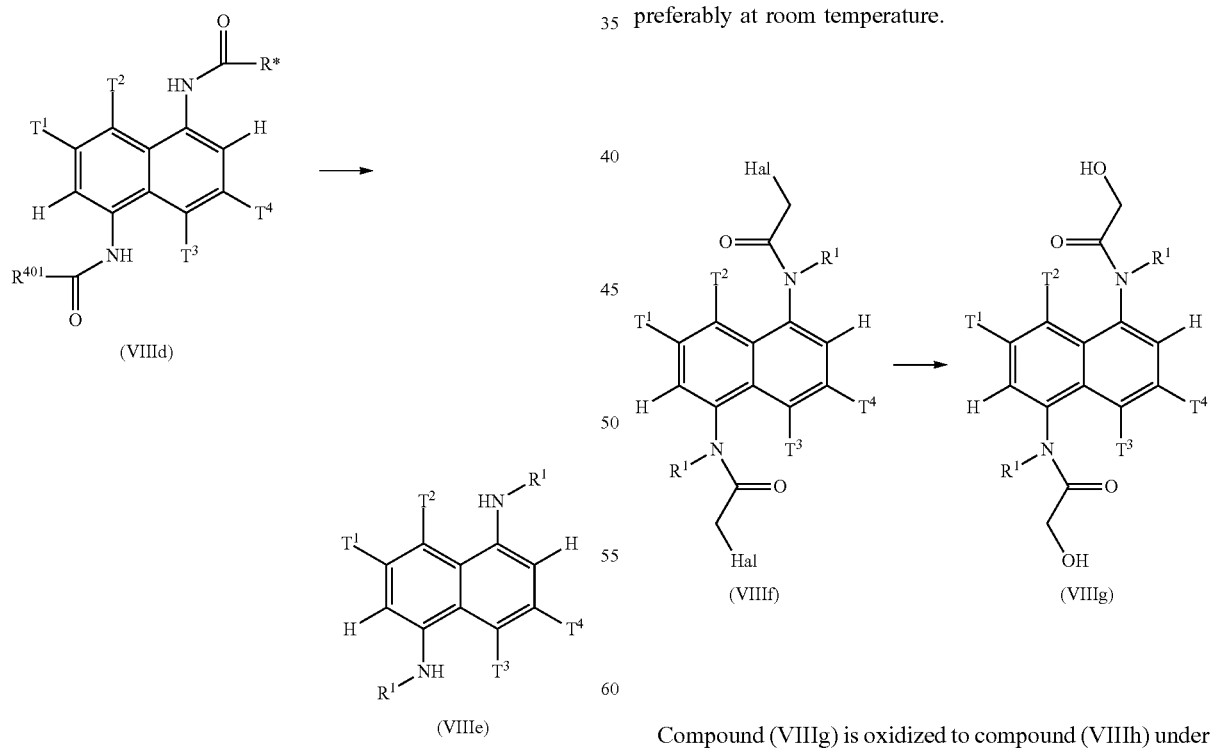

(VIIIf)

(VIIIg)

Compound (VIIIg) is oxidized to compound (VIIIh) under so-called Swern conditions: A solution of dimethylsulfoxide and then compound (VIIIg) is added to a solution of oxalylchloride in methylenechloride at −78° C. Then triethylamine is added and the mixture is allowed to warm up to room temperature.

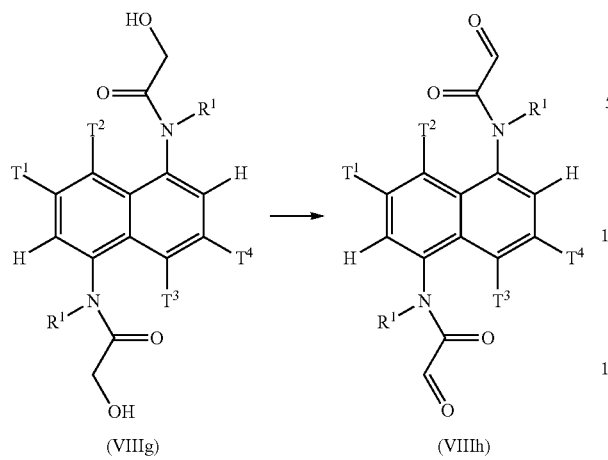

(VIIIg) → (VIIIh)

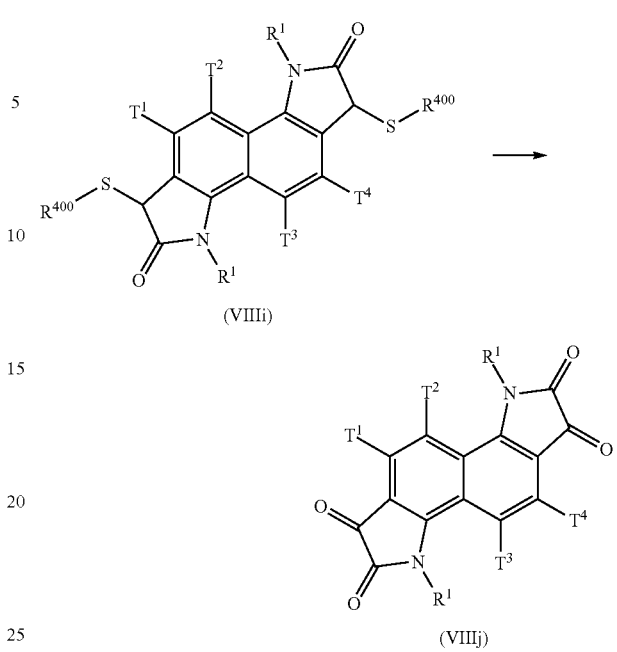

(VIIIi)

(VIIIj)

Compound (VIIIh) is reacted with a mercaptane, $R^{400}$—SH ($R^{400}$ is $C_1$-$C_{25}$alkyl, which may optionally be interrupted by one, or more oxygen, or sulphur atoms; or is $C_4$-$C_{12}$ (hetero)aryl, which can optionally be substituted one or more times with $C_1$-$C_{12}$alkyl or $C_1$-$C_{12}$alkoxy, preferably phenyl, or $C_1$-$C_{25}$ alkyl, most preferred phenyl), in methylene chloride to form a compound (VIIIi). TFAA and then $BF_3.OEt_2$ are added to this mixture. After quenching with an aqueous $NaHCO_3$ solution compound (VIIIi) is obtained.

Compound (VIIIj) is reacted with an organometallic compound, H—$Ar^1$—Li, or H—$Ar^1$—Mg—Br, such as, for example,

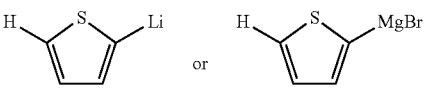

to form a compound (VIIIk):

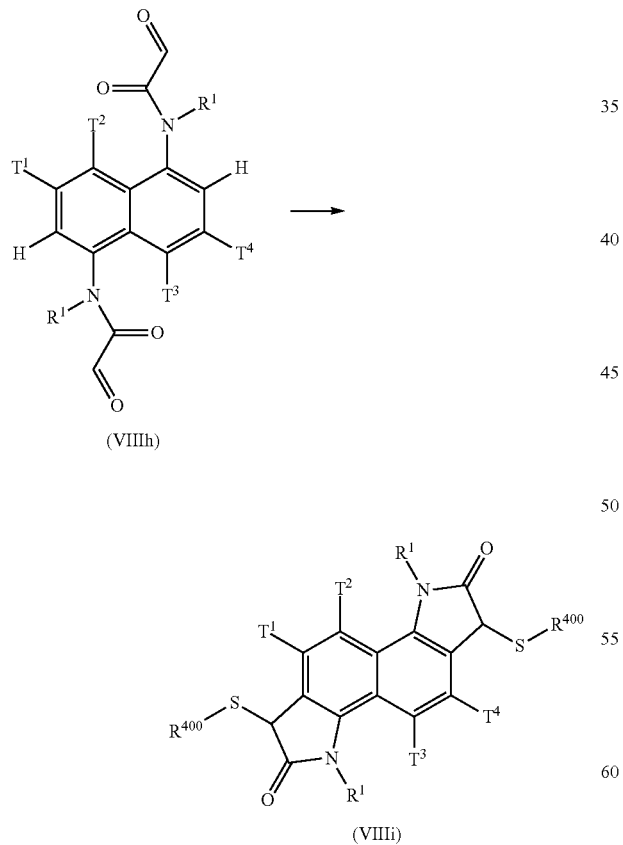

(VIIIh) → (VIIIi)

(VIIIj)

Compound (VIIIi) is reacted to compound (VIIIj) via a CAN (cerium (IV) ammonium nitrate) mediated oxidation in a mixture of THF-water at room temperature.

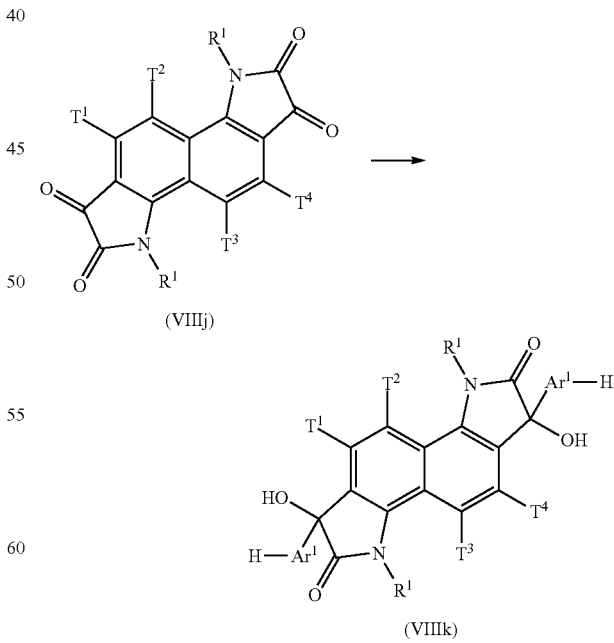

(VIIIk)

Compound (VIIIk) is reduced to compound (VIIIl) using, for example, $NaH_2PO_2/NaI/CH_3COOH$:

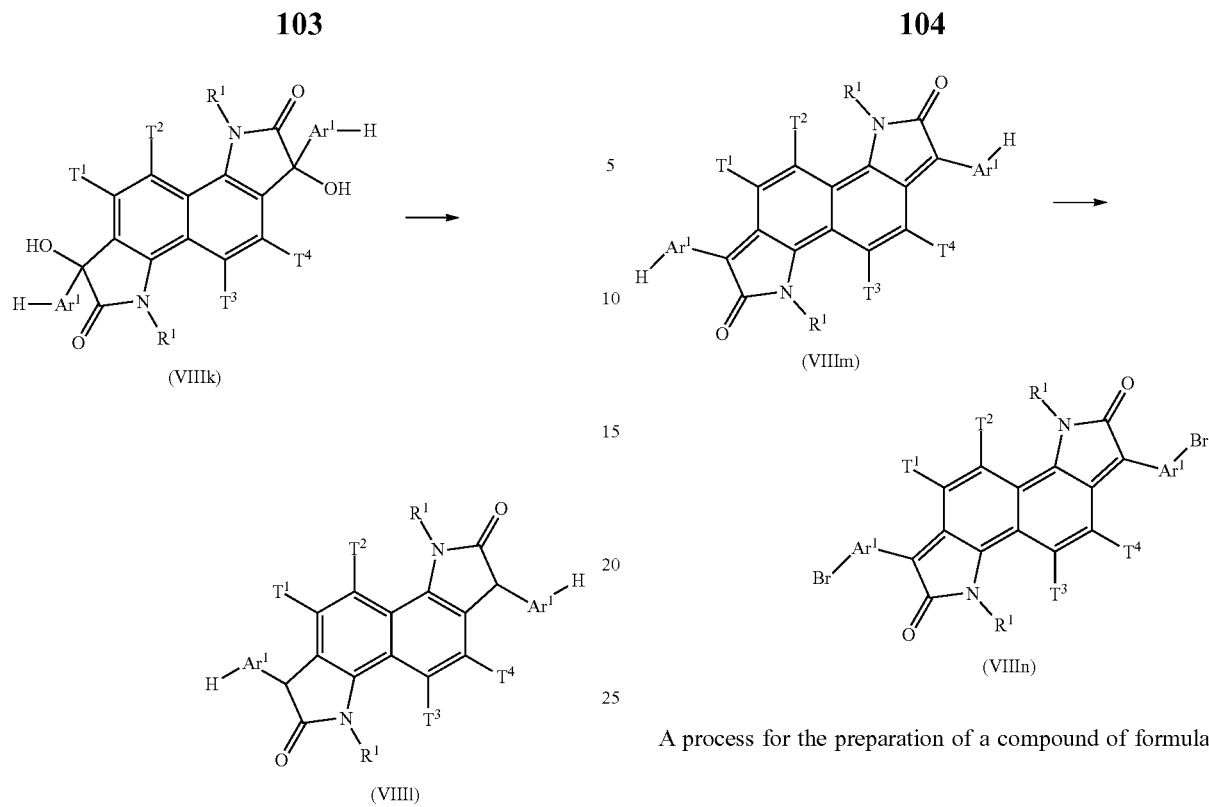

Compound (VIIIl) is oxidized to compound (VIIIm), using, for example, 2,3-dichloro-5,6-dicyanobenzoquinone (DDQ) in CH$_2$Cl$_2$.

Compound (VIIIm) can optionally be brominated to form compound (VIIIn), using, for example, N-bromosuccinimide (NBS) in THF.

A process for the preparation of a compound of formula

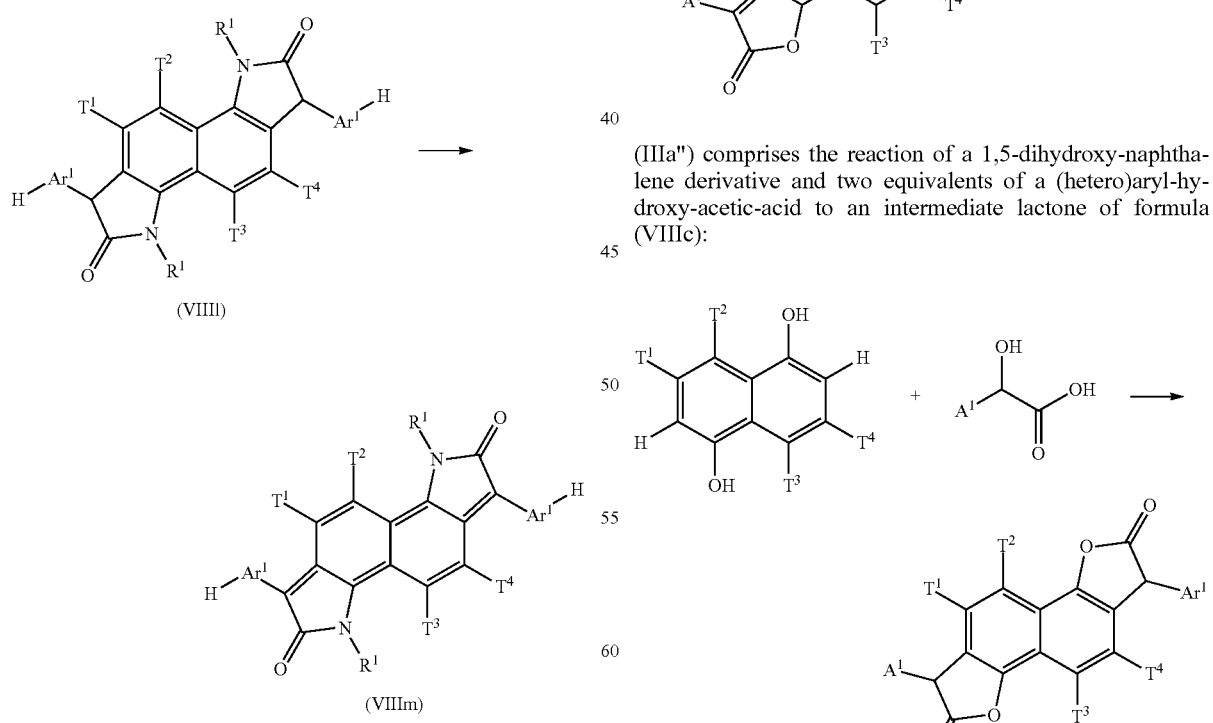

(IIIa'') comprises the reaction of a 1,5-dihydroxy-naphthalene derivative and two equivalents of a (hetero)aryl-hydroxy-acetic-acid to an intermediate lactone of formula (VIIIc):

Intermediate (VIIIc) is then oxidized to compound (IIIa''') with a suitable oxidant such as, for example, nitrobenzene:

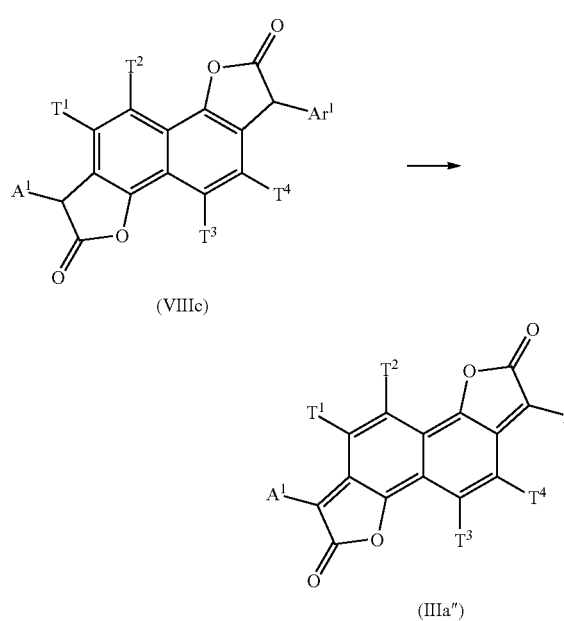

(VIIIc)

(IIIa''')

Compounds of the formula

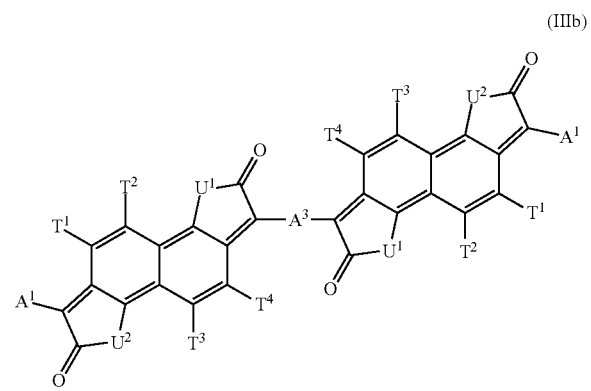

(IIIb)

($U^1=U^2=NR^1$, $A^3$ is a group of formula

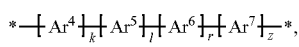

$Ar^4$ is $Ar^7$, k is 1, or 2, z is 1, or 2) may be prepared by reacting a compound of formula

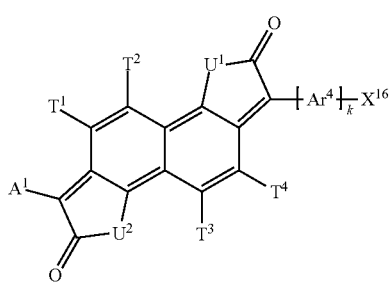

with a compound of formula

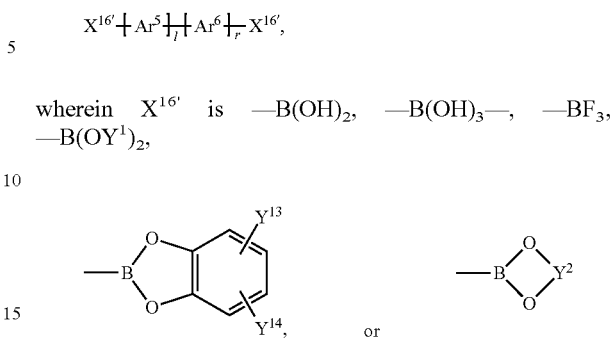

wherein $X^{16'}$ is $-B(OH)_2$, $-B(OH)_3-$, $-BF_3$, $-B(OY^1)_2$, and $X^{16}$ is halogen, such as, for example, Br, or I.

The Suzuki reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A condensation reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252.

In the above Suzuki coupling reactions the halogen $X^{16}$ on the halogenated reaction partner can be replaced with the $X^{16'}$ moiety and at the same time the $X^{16'}$ moiety of the other reaction partner is replaced by $X^{16}$.

In an additional embodiment the present invention is directed to compounds of formula

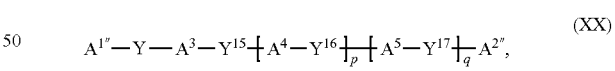

(XX)

wherein $A^{1'''}$ and $A^{2'''}$ are independently of each other a group of formula

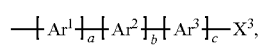

$X^3$ is independently in each occurrence halogen, very especially I, or Br; $ZnX^{12}$, $-SnR^{207}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched and $X^{12}$ is a halogen atom, very especially I, or Br; $-OS(O)_2CF_3$, $-OS(O)_2$-aryl, especially

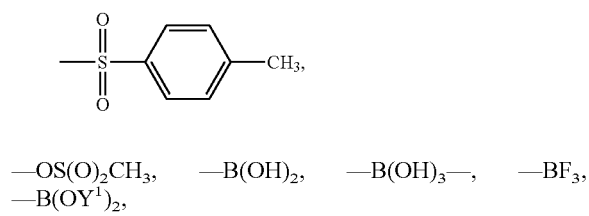

wherein $Y^1$ is independently in each occurrence a $C_1$-$C_{12}$alkyl group and $Y^2$ is independently in each occurrence a $C_2$, $C_{10}$alkylene group, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y_6$, $Y_7$, $Y^8$, $Y^9$, $Y^{10}$, $Y^{11}$ and $Y^{12}$ are independently of each other hydrogen, or a $C_1$-$C_{12}$alkyl group, especially —$C(CH_3)_2C(CH_3)_2$—, or —$C(CH_3)_2CH_2C(CH_3)_2$—, —$CH_2C(CH_3)_2$ $CH_2$—, and $Y^{13}$ and $Y^{14}$ are independently of each other hydrogen, or a $C_1$-$C_{12}$alkyl group; a, b, c, p, q, $Ar^1$, $Ar^2$, $Ar^3$, Y, $Y^{15}$, $Y^{16}$, $Y^{17}$, $A^3$, $A^4$ and $A^5$ are as defined above.

The compound of formula (XX) is preferably a compound of formula $A^{1''}$-Y-$A^3$-$Y^{15}$-$A^{2''}$ (XXa). The compounds of the formula (XX), especially (XXa) are intermediates in the production of polymers, i.e the compounds of the formula (XX) can be used in the production of the polymers, comprising repeating units of formula (X).

Accordingly, the present invention is also directed to polymers comprising repeating units of formula (X)

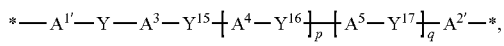

wherein $A^{1'}$ and $A^{2'}$ are independently of each other a group of formula

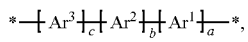

wherein a, b, c, p, q, $Ar^1$, $Ar^2$, $Ar^3$, Y, $Y^{15}$, $Y^{16}$, $Y^{17}$, $A^3$, $A^4$ and $A^5$ are as defined above. The polymers comprising repeating units of formula (X) may be used in the production of semiconductor devices. Accordingly, the present invention is also directed to semiconductor devices comprising polymers comprising repeating units of formula (X).

Advantageously, the compound of formula III, or an organic semiconductor material, layer or component, comprising the compound of formula III can be used in organic photovoltaics (solar cells) and photodiodes, or in an organic field effect transistor (OFET).

A mixture containing the compound of formula III results in a semi-conducting layer comprising the compound of formula III (typically 0.1% to 99.9999% by weight, more specifically 1% to 99.9999% by weight, even more specifically 5% to 99.9999% by weight, especially 20 to 85% by weight) and at least another material. The other material can be, but is not restricted to another compound of formula III, a polymer of the present invention, a semi-conducting polymer, a non-conductive polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.).

Accordingly, the present invention also relates to an organic semiconductor material, layer or component, comprising a compound of formula III and to a semiconductor device, comprising a compound of formula III and/or an organic semiconductor material, layer or component.

The semiconductor is preferably an organic photovoltaic (PV) device (solar cell), a photodiode, or an organic field effect transistor. The structure and the components of the OFET device has been described in more detail above.

Accordingly, the invention provides organic photovoltaic (PV) devices (solar cells) comprising a compound of the formula III.

The structure of organic photovoltaic devices (solar cells) is, for example, described in C. Deibel et al. Rep. Prog. Phys. 73 (2010) 096401 and Christoph Brabec, Energy Environ. Sci 2. (2009) 347-303.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the compounds of the formula III. Preferably, the photoactive layer is made of a compound of the formula III, as an electron donor and an acceptor material, like a fullerene, particularly a functionalized fullerene PCBM, as an electron acceptor. As stated above, the photoactive layer may also contain a polymeric binder. The ratio of the small molecules of formula III to the polymeric binder can vary from 5 to 95 percent. Preferably, the polymeric binder is a semicrystalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another compounds of formula III, or any semi-conducting polymer, such as, for example, a polymer of formula I, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a compound of the formula III, as an electron donor and a fullerene, particularly functionalized fullerene PCBM, as an electron acceptor.

These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the compounds of the formula III can also be used alone or together with other materials in or as alignment layers in LCD or OLED devices, as described for example in US2003/0021913.

An OFET device according to the present invention preferably comprises:
a source electrode,
a drain electrode,
a gate electrode,
a semiconducting layer,
one or more gate insulator layers, and
optionally a substrate, wherein the semiconductor layer comprises a compound of formula III.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a compound of formula III located on the second side of the insulator, and a drain electrode and a source electrode located on the polymer layer.

In a preferred embodiment, the deposition of at least one compound of the general formula III (and if appropriate further semiconductor materials) is carried out by a gas phase deposition process (physical vapor deposition, PVD). PVD processes are performed under high-vacuum conditions and comprise the following steps: evaporation, transport, deposition. It has been found that, surprisingly, the compounds of the general formula III are suitable particularly advantageously for use in a PVD process, since they essentially do not decompose and/or form undesired by-products. The material deposited is obtained in high purity. In a specific embodiment, the deposited material is obtained in the form of crystals or comprises a high crystalline content. In general, for the PVD, at least one compound of the general formula III is heated to a temperature above its evaporation temperature and deposited on a substrate by cooling below the crystallization temperature. The temperature of the substrate in the deposition is preferably within a range from about 20 to 250° C., more preferably from 50 to 200° C.

The resulting semiconductor layers generally have a thickness which is sufficient for ohmic contact between source and drain electrodes. The deposition can be effected under an inert atmosphere, for example under nitrogen, argon or helium. The deposition is effected typically at ambient pressure or under reduced pressure. A suitable pressure range is from about $10^{-7}$ to 1.5 bar.

The compound of the formula III is preferably deposited on the substrate in a thickness of from 10 to 1000 nm, more preferably from 15 to 250 nm. In a specific embodiment, the compound of the formula III is deposited at least partly in crystalline form. For this purpose, especially the above-described PVD process is suitable. Moreover, it is possible to use previously prepared organic semiconductor crystals. Suitable processes for obtaining such crystals are described by R. A. Laudise et al. in "Physical Vapor Growth of Organic Semi-Conductors", Journal of Crystal Growth 187 (1998), pages 449-454, and in "Physical Vapor Growth of Centimeter-sized Crystals of α-Hexathiophene", Journal of Crystal Growth 1982 (1997), pages 416-427, which are incorporated here by reference.

In addition, the polymers and compounds of the present invention may be used as IR absorbers.

Accordingly, the polymers and compounds of the present invention can be used inter alia for security printing, invisible and/or IR readable bar codes, the laser-welding of plastics, the curing of surface-coatings using IR radiators, the drying and curing of print, the fixing of toners on paper or plastics, optical filters for plasma display panels, laser marking of paper or plastics, the heating of plastics preforms, and for heat shielding applications.

In a further aspect, the invention provides a printing ink formulation for security printing, comprising at least one polymer, or compound of the present invention, such as, for example, a polymer P-1, or P-2.

In a further aspect, the invention provides a security document, comprising a substrate and at least at least one polymer, or compound of the present invention. The security document may be a bank note, a passport, a check, a voucher, an ID- or transaction card, a stamp and a tax label.

In a further aspect, the invention provides a security document, obtainable by a printing process, wherein a printing ink formulation is employed that comprises at least one polymer, or compound of the present invention.

Advantageously, the polymers, or compounds of the present invention, such as, for example, polymer P-1, or P-2, may be used in a printing ink formulation for security printing.

In security printing, the polymers, or compounds of the present invention are added to a printing ink formulation. Suitable printing inks are water-based, oil-based or solvent-based printing inks, based on pigment or dye, for inkjet printing, flexographic printing, screen printing, intaglio printing, offset printing, laser printing or letterpress printing and for use in electrophotography. Printing inks for these printing processes usually comprise solvents, binders, and also various additives, such as plasticizers, antistatic agents or waxes. Printing inks for offset printing and letterpress printing are usually formulated as high-viscosity paste printing inks, whereas printing inks for flexographic printing and intaglio printing are usually formulated as liquid printing inks with comparatively low viscosity.

The printing ink formulation, especially for security printing, according to the invention preferably comprises
 a) at least one polymer, or compound of the present invention, such as, for example, a polymer P-1, or P-2,
 b) a polymeric binder,
 c) a solvent,
 d) optionally at least one colorant, and
 e) optionally at least one further additive.

Suitable components of printing inks are conventional and are well known to those skilled in the art. Examples of such components are described in "Printing Ink Manual", fourth edition, Leach R. H. et al. (eds.), Van Nostrand Reinhold, Wokingham, (1988). Details of printing inks and their formulation are also disclosed in "Printing Inks"—Ullmann's Encyclopedia of Industrial Chemistry, Sixth Edition, 1999 Electronic Release. A formulation of an IR-absorbing intaglio ink formulation is described in US 20080241492 A1. The disclosure of the afore-mentioned documents is incorporated herein by reference.

The printing ink formulation according to the invention contains in general from 0.0001 to 25% by weight, preferably from 0.001 to 15% by weight, in particular from 0.01 to 5% by weight, based on the total weight of the printing ink formulation, of component a).

The printing ink formulation according to the invention contains in general from 5 to 74% by weight, preferably from 10 to 60% by weight, more preferably from 15 to 40% by weight, based on the total weight of the printing ink formulation, of component b).

Suitable polymeric binders b) for the printing ink formulation according to the invention are for example selected from natural resins, phenol resin, phenol-modified resins, alkyd resins, polystyrene homo- and copolymers, terpene resins, silicone resins, polyurethane resins, urea-formaldehyde resins, melamine resins, polyamide resins, polyacrylates, polymethacrylates, chlorinated rubber, vinyl ester resins, acrylic resins, epoxy resins, nitrocellulose, hydrocarbon resins, cellulose acetate, and mixtures thereof.

The printing ink formulation according to the invention can also comprise components that form a polymeric binder by a curing process. Thus, the printing ink formulation according to the invention can also be formulated to be energy-curable, e.g. able to be cured by UV light or EB (electron beam) radiation. In this embodiment, the binder comprises one or more curable monomers and/oligomers. Corresponding formulations are known in the art and can be found in standard textbooks such as the series "Chemistry & Technology of UV & EB Formulation for Coatings, Inks & Paints", published in 7 volumes in 1997-1998 by John Wiley & Sons in association with SITA Technology Limited.

Suitable monomers and oligomers (also referred to as prepolymers) include epoxy acrylates, acrylated oils, urethane acrylates, polyester acrylates, silicone acrylates, acrylated amines, and acrylic saturated resins. Further details and examples are given in "Chemistry & Technology of UV & EB Formulation for Coatings, Inks & Paints", Volume II: Prepolymers & Reactive Diluents, edited by G Webster.

If a curable polymeric binder is employed, it may contain reactive diluents, i.e. monomers which act as a solvent and which upon curing are incorporated into the polymeric binder. Reactive monomers are typically chosen from acrylates or methacrylates, and can be monofunctional or multifunctional. Examples of multifunctional monomers include polyester acrylates or methacrylates, polyol acrylates or methacrylates, and polyether acrylates or methacrylates.

In the case of printing ink formulations to be cured by UV radiation, it is usually necessary to include at least one photoinitiator to initiate the curing reaction of the monomers upon exposure to UV radiation. Examples of useful photoinitiators can be found in standard textbooks such as "Chemistry & Technology of UV & EB Formulation for Coatings, Inks & Paints", Volume III, "Photoinitiators for Free Radical Cationic and Anionic Polymerisation", 2nd edition, by J. V. Crivello & K. Dietliker, edited by G. Bradley and published in 1998 by John Wiley & Sons in association with SITA Technology Limited. It may also be advantageous to include a sensitizer in conjunction with the photoinitiator in order to achieve efficient curing.

The printing ink formulation according to the invention contains in general from 1 to 94.9999% by weight, preferably from 5 to 90% by weight, in particular from 10 to 85% by weight, based on the total weight of the printing ink formulation, of a solvent c).

Suitable solvents are selected from water, organic solvents and mixtures thereof. For the purpose of the invention, reactive monomers which also act as solvents are regarded as part of the afore-mentioned binder component b).

Examples of solvents comprise water; alcohols, e.g. ethanol, 1-propanol, 2-propanol, ethylene glycol, propylene glycol, diethylene glycol and ethoxy propanol; esters, e.g. ethyl acetate, isopropyl acetate, n-propyl acetate and n-butyl acetate; hydrocarbons, e.g. toluene, xylene, mineral oils and vegetable oils, and mixtures thereof.

The printing ink formulation according to the invention may contain an additional colorant d). Preferably, the printing ink formulation contains from 0 to 25% by weight, more preferably from 0.1 to 20% by weight, in particular from 1 to 15% by weight, based on the total weight of the printing ink formulation, of a colorant d).

Suitable colorants d) are selected conventional dyes and in particular conventional pigments. The term "pigment" is used in the context of this invention comprehensively to identify all pigments and fillers, examples being colour pigments, white pigments, and inorganic fillers. These include inorganic white pigments, such as titanium dioxide, preferably in the rutile form, barium sulfate, zinc oxide, zinc sulfide, basic lead carbonate, antimony trioxide, lithopones (zinc sulfide+barium sulfate), or coloured pigments, examples being iron oxides, carbon black, graphite, zinc yellow, zinc green, ultramarine, manganese black, antimony black, manganese violet, Paris blue or Schweinfurt green. Besides the inorganic pigments the printing ink formulation of the invention may also comprise organic colour pigments, examples being sepia, gamboge, Cassel brown, toluidine red, para red, Hansa yellow, indigo, azo dyes, anthraquinonoid and indigoid dyes, and also dioxazine, quinacridone, phthalocyanine, isoindolinone, and metal complex pigments. Also suitable are synthetic white pigments with air inclusions to increase the light scattering, such as the Rhopaque® dispersions. Suitable fillers are, for example, aluminosilicates, such as feldspars, silicates, such as kaolin, talc, mica, magnesite, alkaline earth metal carbonates, such as calcium carbonate, in the form for example of calcite or chalk, magnesium carbonate, dolomite, alkaline earth metal sulfates, such as calcium sulfate, silicon dioxide, etc.

The printing ink formulation according to the invention may contain at least one additive e). Preferably, the printing ink formulation contains from 0 to 25% by weight, more preferably from 0.1 to 20% by weight, in particular from 1 to 15% by weight, based on the total weight of the printing ink formulation, of at least one component e).

Suitable additives (component e)) are selected from plasticizers, waxes, siccatives, antistatic agents, chelators, antioxidants, stabilizers, adhesion promoters, surfactants, flow control agents, defoamers, biocides, thickeners, etc. and combinations thereof. These additives serve in particular for fine adjustment of the application-related properties of the printing ink, examples being adhesion, abrasion resistance, drying rate, or slip.

In particular, the printing ink formulation for security printing according to the invention preferably contains
a) 0.0001 to 25% by weight of at least one polymer, or compound of the present invention, such as, for example, a polymer P-1, or P-2,
b) 5 to 74% by weight of at least one polymeric binder,
c) 1 to 94.9999% by weight of at least one a solvent,
d) 0 to 25% by weight of at least one colorant, and
e) 0 to 25% by weight of at least one further additive, wherein the sum of components a) to e) adds up to 100%.

The printing ink formulations according to the invention are advantageously prepared in a conventional manner, for example by mixing the individual components.

Primers can be applied prior to the printing ink formulation according to the invention. By way of example, the primers are applied in order to improve adhesion to the substrate. It is also possible to apply additional printing lacquers, e.g. in the form of a covering to protect the printed image.

The following examples are included for illustrative purposes only and do not limit the scope of the claims. Unless otherwise stated, all parts and percentages are by weight. Weight-average molecular weight (Mw) and polydispersity (Mw/Mn=PD) are determined by Heat Temperature Gel Permeation Chromatography (HT-GPC) [Apparatus: GPC PL 220 from Polymer laboratories (Church Stretton, UK; now Varian) yielding the responses from refractive index (RI), Chromatographic conditions: Column: 3 "PLgel Olexis" column from Polymer Laboratories (Church Stretton, UK); with an average particle size of 13 im (dimensions 300×8 mm I.D.) Mobile phase: 1,2,4-trichlorobenzene purified by vacuum distillation and stabilised by butylhydroxytoluene (BHT, 200 mg/l), Chromatographic temperature: 150° C.; Mobile phase flow: 1 ml/min; Solute concentration: about 1 mg/ml; Injection volume: 200 il; Detection: RI, Procedure of molecular weight calibration: Relative calibration is done by use of a set of 10 polystyrene calibration standards obtained from Polymer Laboratories (Church Stretton, UK) spanning the molecular weight range from 1'930'000 Da-5'050 Da, i.e., PS 1'930'000, PS 1'460'000, PS 1'075'000, PS 560'000, PS 330'000, PS 96'000, PS 52'000, PS 30'300, PS 10'100, PS 5'050 Da. A polynomic calibration is used to calculate the molecular weight.

All polymer structures given in the examples below are idealized representations of the polymer products obtained via the polymerization procedures described. If more than two components are copolymerized with each other sequences in the polymers can be either alternating or random depending on the polymerisation conditions.

EXAMPLES

Example 1

Synthesis of Compound 3 a)
1,5-Bis(α-hydroxyphenylacetylamino)naphthalene
(1)

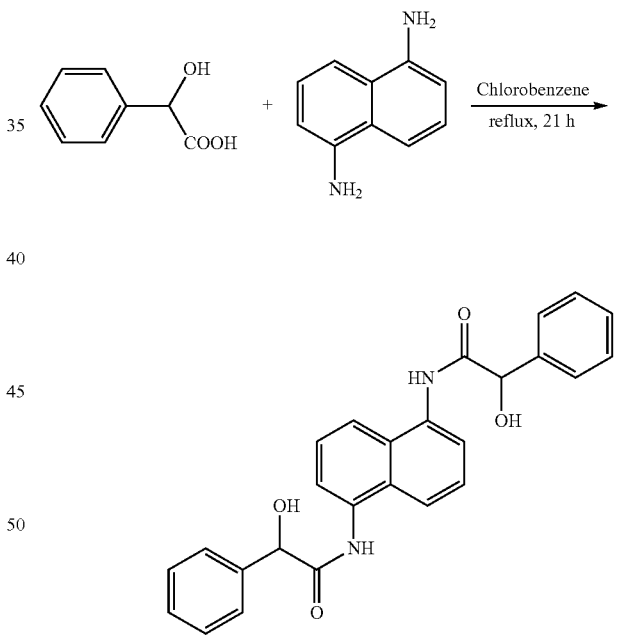

A mixture of 1,5-diaminonaphthalene (1.58 g, 10 mmol) and DL-mandelic acid (4.56 g, 30 mmol) in chlorobenzene (40 ml) is heated at 135° C. for 21 hours. On cooling to room temperature, the precipitate is filtered, washed with ethanol and dried in vacuo to yield the product (2.27 g, yield: 55%). NMR (1H, 300 MHz, DMSO): δ ppm 10.10 (s, 2H), 7.74 (d, J=8.4 Hz, 2H), 7.59-7.61 (m, 6H), 7.48 (t, J=8.1 Hz, 2H), 7.40 (t, J=7.2 Hz, 4H), 7.34 (t, J=7.2 Hz, 2H), 6.56 (d, t=4.5 Hz, 2H), 5.27 (d, t=4.5 Hz, 2H).

b) 3,8-Diphenyl-2,7-dioxo-1,2,3,6,7,8-hexahydronaphtho[1,2-b:5,6-b']dipyrrole (2)

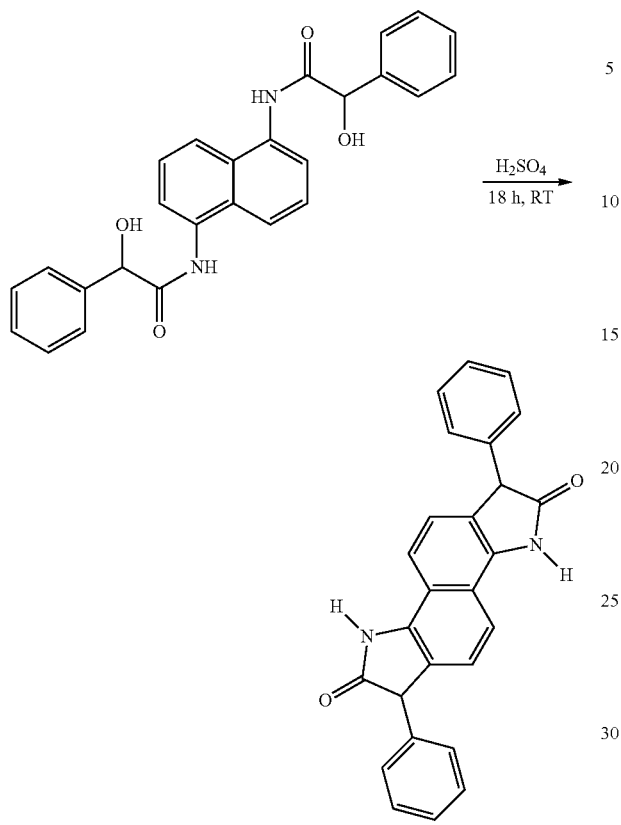

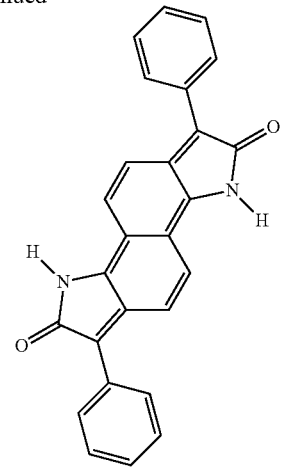

1,5-Bis(a-hydroxyphenylacetylamino)naphthalene (2.27 g, 5.5 mmol) is added to sulfuric acid (20 ml). After stirring at room temperature for 20 hours, the mixture is poured into ice water. The precipitate is filtered, washed with water and dried to yield the product (1.98 g, yield: 92%). NMR (1H, 300 MHz, DMSO): δ ppm 11.26-11.54 (m, 2H), 7.82-7.86 (m, 2H), 7.31-7.62 (m, 8H), 7.18-7.31 (m, 4H), 4.94-5.0 (m, 2H).

c) 3,8-Diphenyl-2,7-dioxo-1,2,6,7-tetrahydronaphtho[1,2-b:5,6-b']dipyrrole (3)

(B-13)

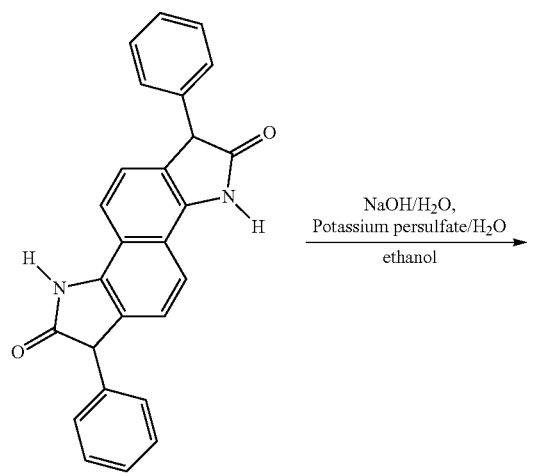

An aqueous sodium hydroxide solution (1.84 ml, 5 N) is dropwisely added to a suspension of 3,8-diphenyl-2,7-dioxo-1,2,3,6,7,8-hexahydronaphtho[1,2-b:5,6-b']-dipyrrole (1.98 g, 5.06 mmol) in ethanol (16 ml). Then potassium persulfate (3.68 g, 13.63 mmol) in water (12 ml) is added. The resulting mixture is heated at reflux for 3 hours. The precipitate in the mixture is filtered, washed with water and ethanol, and dried to yield the product (1.75 g, yield: 89%). NMR (1H, 500 MHz, DMSO): δ ppm 10.41 (s, 2H), 7.84 (d, J=6 Hz, 2H), 7.51 (t, J=6 Hz, 4H), 7.44 (t, J=8 Hz, 4H), 7.34 (d, J=7.5 Hz, 2H). UV/Vis (DMF, $\lambda_{max}$): 557 nm.

Example 2

Synthesis of Compound 6 a) 1,4-Bis(α-hydroxy(4-bromophenyl)acetylamino)naphthalene (4)

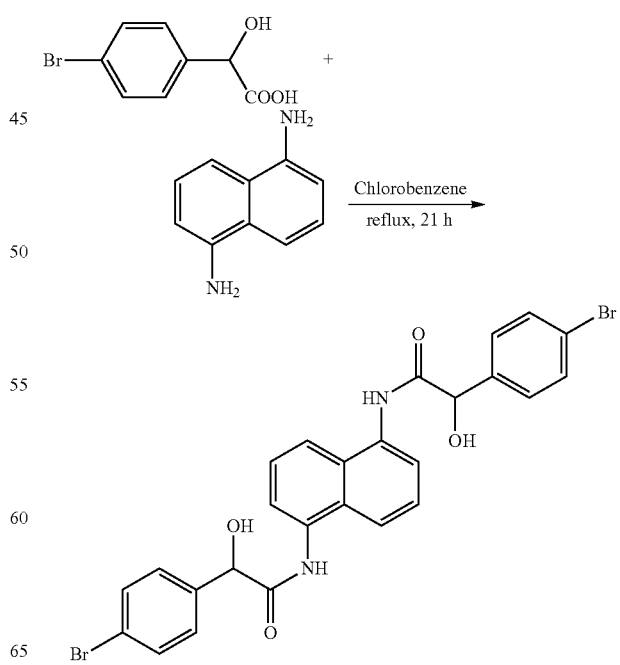

A mixture of 1,5-diaminonaphthalene (1.582 g, 10 mmol) and 4-bromo-mandelic acid (6.93 g, 30 mmol) in chlorobenzene (40 ml) is heated at 135° C. for 21 hours. On cooling to room temperature, the precipitate is filtered, washed with ethanol and dried in vacuo to yield the crude product (3.56 g, yield: 61%). The crude product is suspended in chlorobenzene (20 ml), heated to 135° C. stirring for 20 minutes, and is then cooled to room temperature. The precipitated product is filtered off and washed with methanol. The product is dried in air giving a white solid (2.82 g, yield: 48%). NMR (1H, 300 MHz, DMSO): δ ppm 10.13 (s, 2H), 7.74 (d, J=8.1 Hz, 2H), 7.60 (d, J=8.4 Hz, 4H), 7.55 (d, J=8.4 Hz, 4H), 7.49 (t, J=8.0 Hz, 2H), 6.67 (d, J=4.8 Hz, 2H), 5.27 (d, J=4.5 Hz, 2H).

b) 3,8-Di(4-bromophenyl)-2,7-dioxo-1,2,3,6,7,8-hexahydronaphtho[1,2-b:5,6-b']dipyrrole (5)

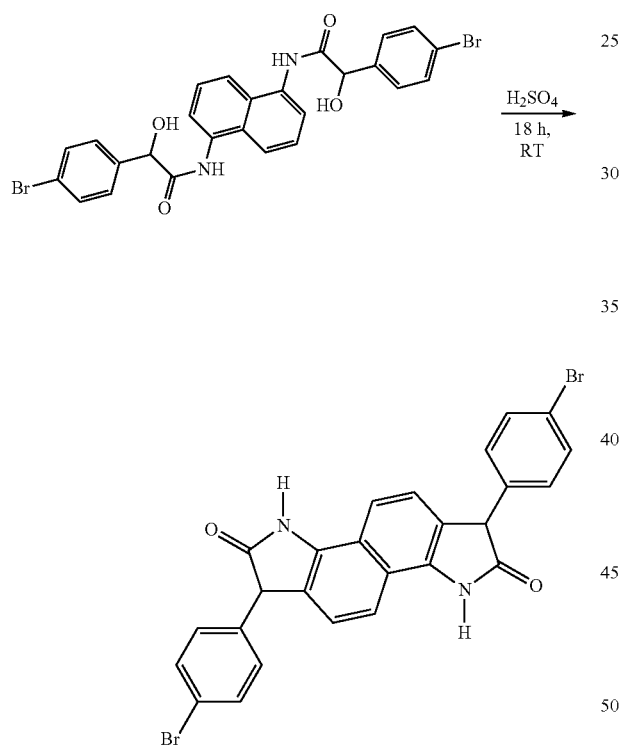

1,4-Bis(α-hydroxy(4-bromophenyl)acetylamino)naphthalene (3.56 g, 6.1 mmol) is added to sulfuric acid (20 ml). After stirring at room temperature for 18 hours, the mixture is poured into ice water. The precipitate is filtered, washed with water and dried to yield the product (3.16 g, yield: 95%). NMR (1H, 300 MHz, DMSO): δ ppm 11.27-11.58 (m, 2H), 7.74-7.88 (m, 2H), 7.55-7.57 (m, 6H), 7.15-7.29 (m, 4H), 5.0 (m, 2H).

c) 3,8-Di(4-bromophenyl)-2,7-dioxo-1,2,6,7-tetrahydronaphtho[1,2-b:5,6-b']dipyrrole (6) (=I-10)

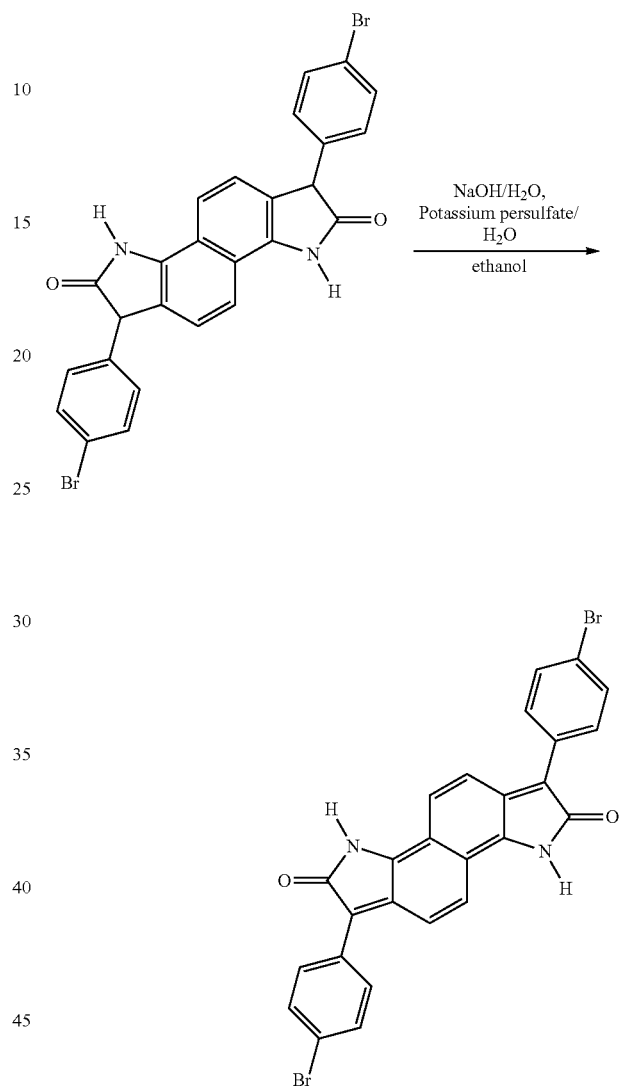

An aqueous sodium hydroxide solution (2.11 ml, 5 N) is dropwisely added to a suspension of 3,8-di(4-bromophenyl)-2,7-dioxo-1,2,3,6,7,8-hexahydronaphtho[1,2-b:5,6-b']dipyrrole (3.16 g, 5.8 mmol) in ethanol (18 ml). Then potassium persulfate (4.22 g, 15.7 mmol) in water (14 ml) is added. The resulting mixture is heated at reflux for 3 hours. The precipitate in the mixture is filtered, washed with water and ethanol, and dried to yield the product (2.88 g, yield: 91%). Microanalysis found C, 58.01%; H, 2.98%, N, 9.89% (C, 57.17%, H, 2.58%, N, 5.13%). UV/Vis (DMF, $\lambda_{max}$): 567 nm.

Example 3

Synthesis of Compound 7

3,8-Bis(4-bromophenyl)naphtho[1,2-b:5,6-b']difuran-2,7-dione (7)

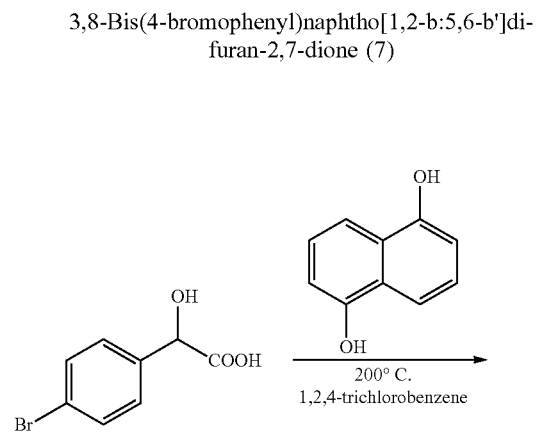

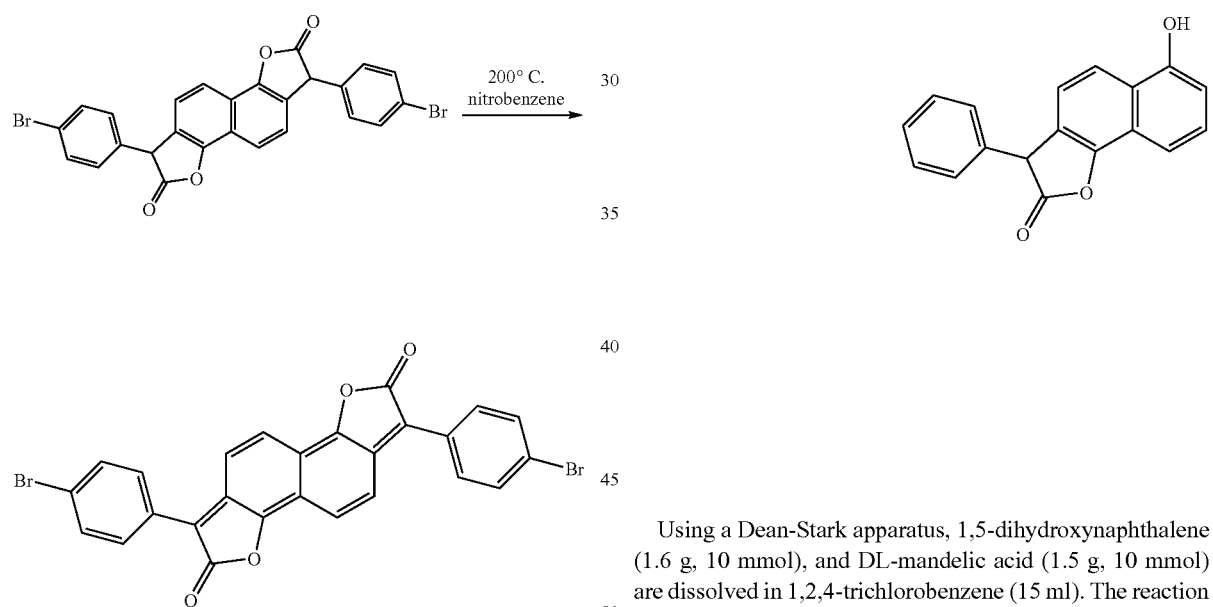

Using a Dean-Stark apparatus, 1,5-dihydroxynaphthalene (0.8 g, 5 mmol), and 4-bromo-mandelic acid (2.31 g, 10 mmol) are dissolved in 1,2,4-trichlorobenzene (10 ml). The reaction mixture is stirred for 4 hours at 200° C. allowing formed water to distil off, before it is cooled to room temperature. Then nitrobenzene (0.67 g, 5 mmol) is added. The mixture is stirred for another half an hour at 200° C. and allowed to cool. A precipitate is formed, which is filtered off, and washed with methanol. The crude product is dissolved in 1,2,4-trichlorobenzene at 200° C., precipitated at room temperature, and digested in hot acetic acid. The product obtained is refluxed in methanol giving a deep purple solid (1.69 g, yield: 62%). Microanalysis found C, 56.93%, H, 2.59% (C, 56.97%; H, 2.21%). UV/Vis (DMF, $\lambda_{max}$): 560 nm.

Example 4

Synthesis of Compound 9 a) 6-Hydroxy-2-oxo-3-phenyl-2,3-dihydronaphtho[1,2-b]furan (8)

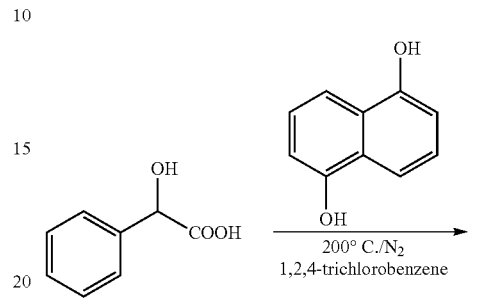

Using a Dean-Stark apparatus, 1,5-dihydroxynaphthalene (1.6 g, 10 mmol), and DL-mandelic acid (1.5 g, 10 mmol) are dissolved in 1,2,4-trichlorobenzene (15 ml). The reaction mixture is stirred for 1.5 hours at 200° C. During the heating, nitrogen gas is used in order to remove water and to prevent contact with air. The mixture is allowed to cool to room temperature. A precipitate is formed, which is filtered off, washed with a small amount of toluene and hexane, respectively. The crude product is suspended in 1,2,4-trichlorobenzene, heated to 200° C. to dissolve, and is then cooled to room temperature. The precipitated product is filtered off and washed with toluene. The product is dried in air. The dried product is dissolved in DMF and precipitated by adding water. The product is dried in air giving a white solid (1.02 g, yield: 37%). NMR (1H, 300 MHz, DMSO): δ ppm 10.46 (s, 1H), 7.98 (d, J=8.4 Hz, 2H), 7.48 (d, J=8.1 Hz, 1H), 7.45 (s, 1H), 7.41 (s, 1H), 7.37 (d, J=7.5 Hz, 2H), 7.25 (d, J=8.1 Hz, 3H), 5.57 (s, 1H). Microanalysis found C, 79.19%; H, 3.70% (C, 80.0%; H, 3.6%).

b) 3-Phenyl-8-(3,4-dimethoxy-phenyl)naphtho[1,2-b:5,6-b']difuran-2,7-dione (9)

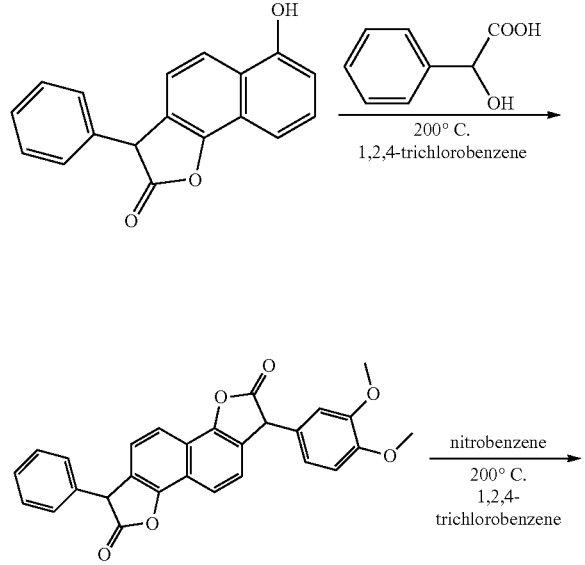

(B-14)

Example 5

Synthesis of Compound 10

3,8-Bis(3,4-dimethoxyphenyl)naphtho[1,2-b:5,6-b']difuran-2,7-dione (10)

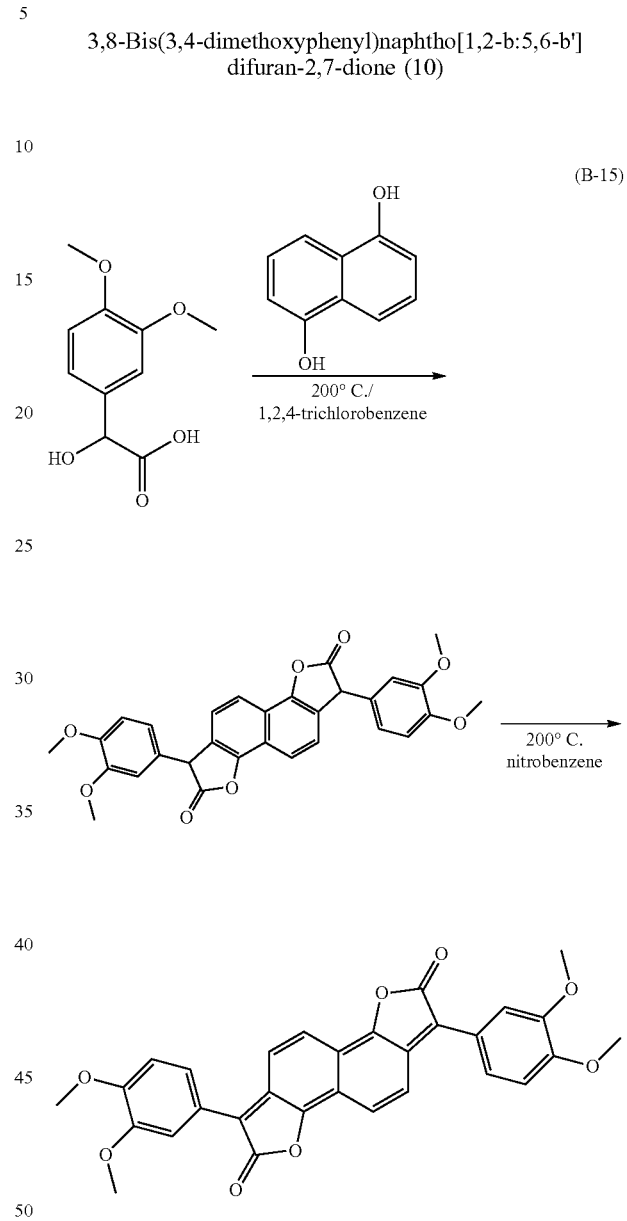

(B-15)

Using a Dean-Stark apparatus, 6-hydroxy-2-oxo-3-phenyl-2,3-dihydronaphtho[1,2-b]furan (1.02 g, 3.7 mmol) and 3,4-dimethoxy-mandelic acid (1.13 g, 7.4 mmol) are dissolved in 1,2,4-trichlorobenzene (15 ml). The reaction mixture is stirred for 4 hours at 200° C. allowing formed water to evaporate and then it is cooled to room temperature. Nitrobenzene (0.91 g, 7.4 mmol) is added and the mixture is stirred for another hour at 200° C. After cooling to room temperature, 40 ml methanol are added. A precipitate is formed, which is filtered off, and washed with methanol. The crude product is dissolved in 1,2,4-trichlorobenzene at 200° C., precipitated at room temperature, and digested in hot acetic acid. The product obtained is refluxed in methanol, giving a dark solid (0.63 g, yield: 38%). Microanalysis found C, 74.01%; H, 3.90% (C, 74.66%, H, 4.03%). UV/Vis (DCM, $\lambda_{max}$): 572 nm. ∈ (572)/L mol$^{-1}$ cm$^{-1}$: 39222.

Using a Dean-Stark apparatus, 1,5-dihydroxynaphthalene (0.8 g, 5 mmol) and 3,4-dimethoxy-mandelic acid (2.12 g, 10 mmol) are dissolved in 1,2,4-trichlorobenzene (10 ml). The reaction mixture is stirred for 4 hours at 200° C. allowing formed water to distil off, before it is cooled to room temperature again. Nitrobenzene (1.23 g, 10 mmol) is added and the mixture is stirred for another hour at 200° C. After cooling to room temperature, 50 ml methanol are added. A precipitate is formed, which is filtered off, and washed with methanol. The crude product is dissolved in 1,2,4-trichlorobenzene at 200° C., precipitated at room temperature, and digested in hot acetic acid. The product obtained is refluxed in methanol giving a dark solid (1.07 g, yield: 42%). Microanalysis found C, 70.31%; H, 4.37% (C, 70.58%; H, 4.37%). UV/Vis (DCM, $\lambda_{max}$): 635 nm. ∈ (635)/L mol$^{-1}$ cm$^{-1}$: 102626.

Example 6

Synthesis of Compound 11

3,8-Bis(3-bromo-4,5-dimethoxyphenyl)naphtho[1,2-b:5,6-b']difuran-2,7-dione (11)

(I-12)

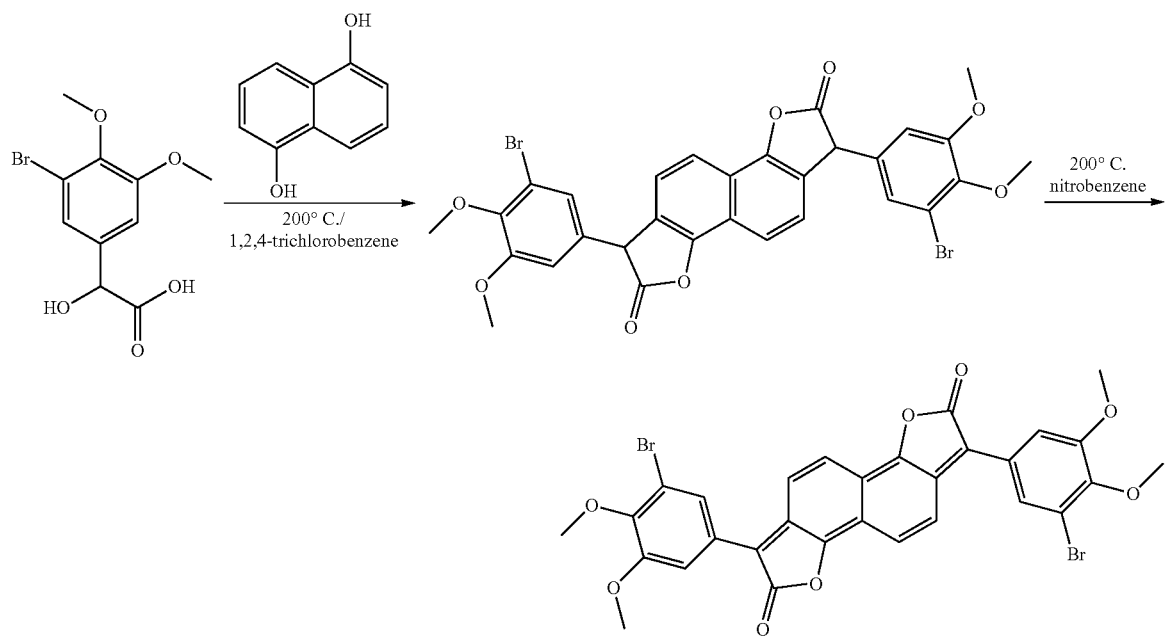

Using a Dean-Stark apparatus, 1,5-dihydroxynaphthalene (0.8 g, 5 mmol) and 3-bromo-4,5-dimethoxy-mandelic acid (2.92 g, 10 mmol) are dissolved in 1,2,4-trichlorobenzene (10 ml). The reaction mixture is stirred for 4 hours at 200° C. allowing formed water to distil off, before it is cooled to room temperature. Nitrobenzene (1.23 g, 10 mmol) is added and the mixture is stirred for another hour at 200° C. After cooling to room temperature, 50 ml methanol are added. A precipitate is formed, which is filtered off, and washed with methanol. The crude product is dissolved in 1,2,4-trichlorobenzene at 200° C., precipitated at room temperature, and digested in hot acetic acid. The product obtained is refluxed in methanol giving a dark solid (1.57 g, yield: 47%). Microanalysis found C, 52.01%; H, 3.98% (C, 53.92%; H, 3.02%). UV/Vis (DCM, $\lambda_{max}$): 588 nm. $\in$ (588)/L mol$^{-1}$ cm$^{-1}$: 26208.

Example 7

Polymer P-15

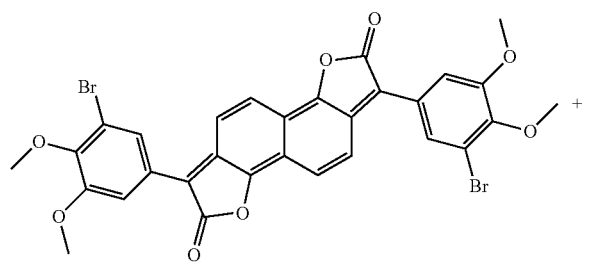

+

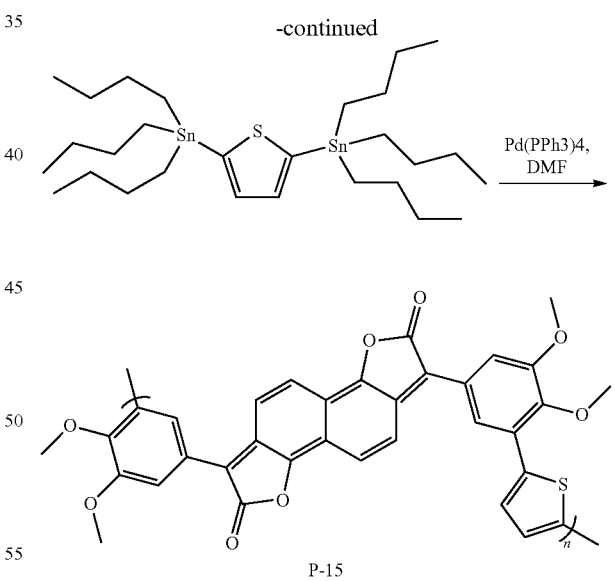

In a Schlenk flask, 3,8-bis(3-bromo-4,5-dimethoxyphenyl)naphtho[1,2-b:5,6-b']-difuran-2,7-dione (200.0 mg, 0.30 mmol), 2,5-bis(tributylstannyl)thiophene (198.8 mg, 0.30 mmol) and tetrakis(triphenylphosphine)palladium(0) (17.3 mg, 0.015 mmol), are dissolved in dry DMF (10 ml). Then the mixture is heated and kept at 90° C. under nitrogen for 18 hours. After cooling to room temperature, methanol is added and a precipitate is formed. The precipitate is collected by filtration. Then the product is purified upon Soxhlet extraction with methanol and hexane. A dark solid is obtained. (123 mg, yield: 45%). UV/Vis (1,2,4-trichlorobenzene, $\lambda_{max}$ of red shifted absorption band): 644 nm. Molecular weight: 4000 Da.

Example 8

Polymer P-16

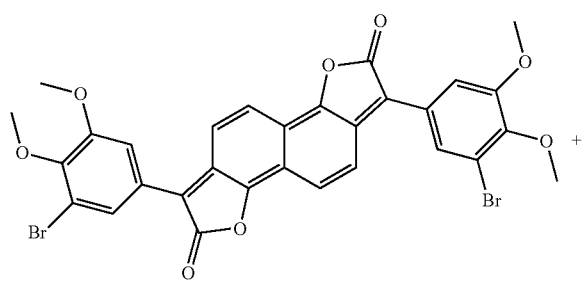

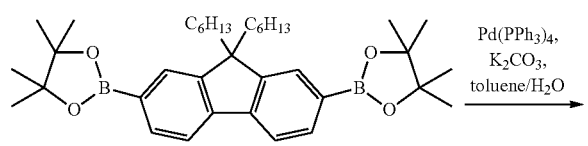

P-16

In a Schlenk flask, 3,8-bis(3-bromo-4,5-dimethoxyphenyl)naphtho[1,2-b:5,6-b']difuran-2,7-dione (200.0 mg, 0.30 mmol), 2,2'-(9,9-dihexyl-9H-fluorene-2,7-diyl)-bis(4,4-5,5-tetramethyl-1,3,2-dioxaborolane) (176 mg, 0.3 mmol) and tetrakis-(triphenyl-phosphine)palladium(0) (17.3 mg, 0.015 mmol) are dissolved in dry toluene (15 ml) under nitrogen. The reaction is degassed and heated to 50° C. A degassed solution of potassium carbonate (137.8 mg, 1.3 mmol) in water (5 ml) is added. The mixture is stirred at 90° C. for 24 hours. After cooling to room temperature, the dark solution is diluted with DCM, washed three times with water and once with brine. Then the organic layer is dried over anhydrous magnesium sulfate and the solvent is removed by reduced pressure. After that, the crude product is dissolved in a minimal amount of DCM and precipitated in methanol. The product is obtained as a dark solid (43.6 mg, yield: 17%). UV/Vis (DCM, $\lambda_{max}$ of red shifted absorption band): 618 nm. Molecular weight: 2100 Da.

Example 9

Synthesis of Compound 12 (=I-10)

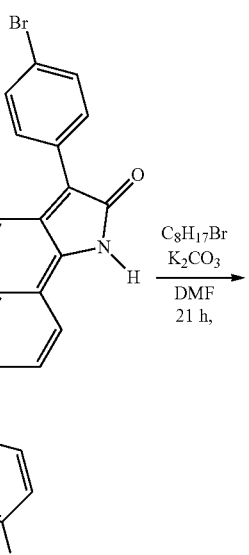

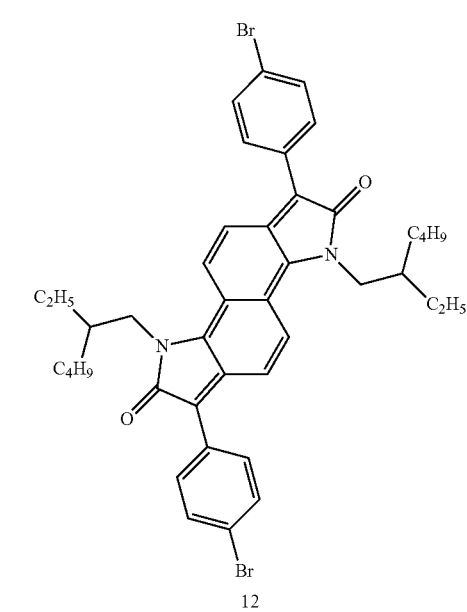

12

500 mg of compound 6 are dissolved in 10 ml of dry dimethylformamide. Then 2.2 equivalents of $K_2CO_3$ are added, followed by 2.2 equivalents of ethylhexylbromide [18908-66-2]. The reaction mixture is then heated for 21 h at 90° C. The mixture is poured on water and the product is extracted with methylenechloride. The organic phase is dried and evaporated. The product is then purified by column chromatography over silica gel to give compound 12.

Example 10

Synthesis of Polymer P-17

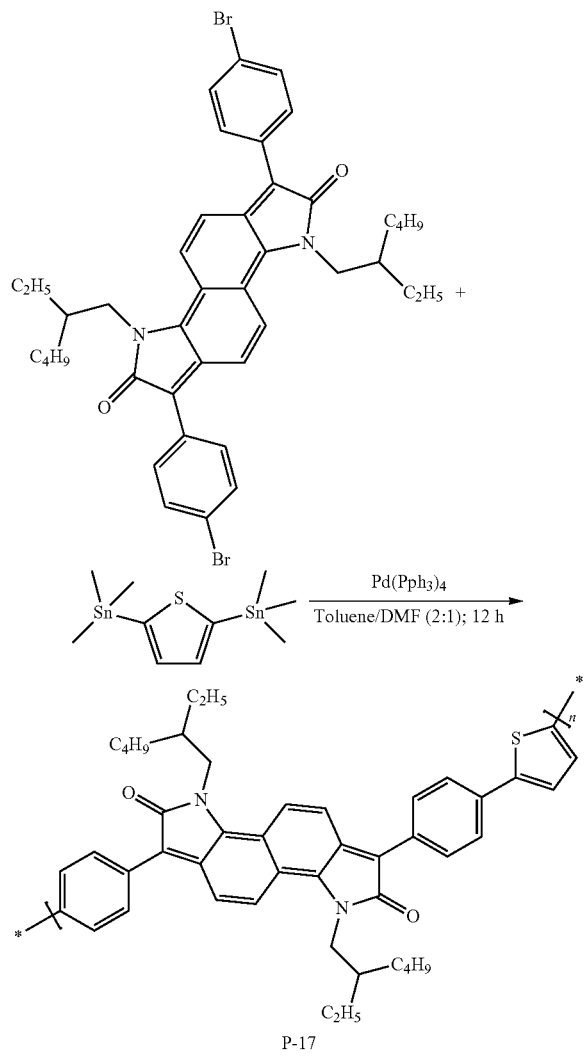

The polymer P-17 is obtained according to example 7 starting from compounds 12 and 2,5-bis-trimethylstannyl-thiophene [86134-26-1] in a 1:1 ratio.

Example 11

Synthesis of Compound 13 (I-1)

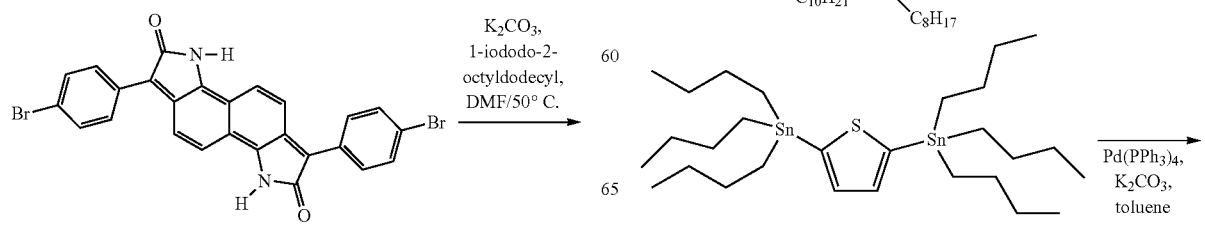

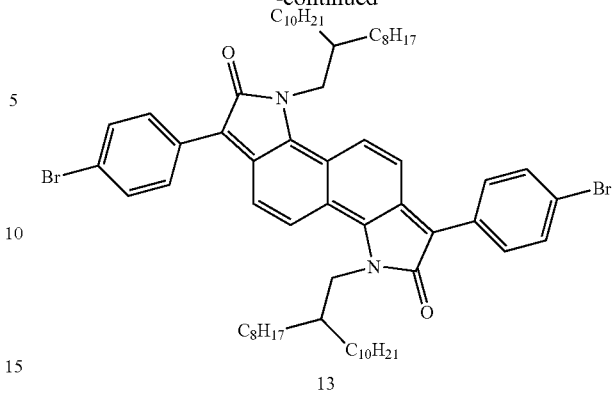

3,8-Di(4-bromophenyl)-2,7-dioxo-1,2,6,7-tetrahydronaphtho[1,2-b:5,6-b']dipyrrole (1.5 g, 2.75 mmol) is dissolved in anhydrous dimethylformamide (40 ml) and then potassium carbonate (2.66 g, 19.25 mmol) and 1-iodo-2-octyldodecane (4.49 g, 10.98 mmol) are added. After stirring for 12 hours at 50° C., the mixture is poured into water and extracted with DCM. The organic layer is washed with brine and dried over anhydrous MgSO$_4$. On removal of the solvent, the crude solid product is obtained. Then the crude product is dissolved in a minimal amount of DCM and precipitated in methanol. The crude product is obtained as a dark solid (1.46 g, yield: 48%). The crude product is purified by column chromatography over silica gel with hexane: DCM=1:2 as eluent to yield the product 13 (0.55 g, 18%). $^1$H NMR (300 MHz, DMSO): δ ppm 7.65 (d, J=8.7 Hz, 4 H), 7.60 (d, J=8.7 Hz, 4 H), 7.40 (d, J=9.6 Hz, 2H), 7.15 (d, J=9.6 Hz, 2H), 4.07 (d, J=7.2 Hz, 4 H), 1.93 (s, 2H), 1.15-1.35 (br, 64 H), 0.87-0.91 (t, 12 H). Microanalysis found C, 72.05%; H, 4.68%, N, 2.68% (C, 71.59%, H, 4.56%, N, 2.53%). UV/Vis (DCM): 571 nm. ∈ (571)/L mol$^{-1}$ cm$^{-1}$: 4.9*10$^4$.

Example 12

Synthesis of Polymer P-18

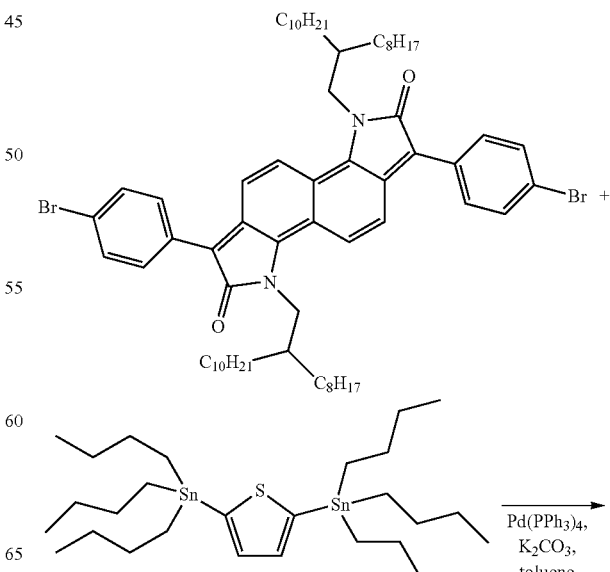

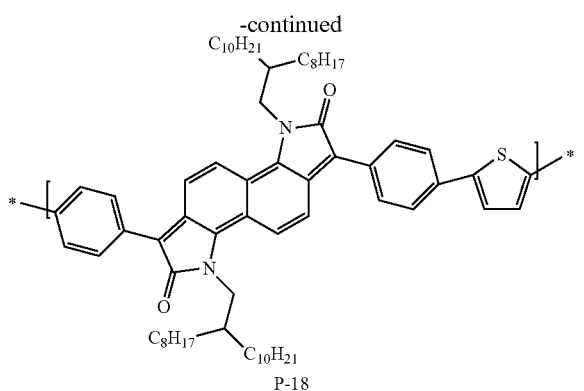
P-18

In a Schlenk flask, 3,8-di(4-bromophenyl)-1.6-bis-(2-octyl-dodecyl)-2,7-dioxo-1,2,6,7-tetrahydronaphtho[1,2-b:5,6-b']dipyrrole (200.0 mg, 0.18), 2,5-bis(tributylstannyl)thiophene (119.0 mg, 0.18 mmol) and tetrakis(triphenylphosphine)palladium(0) (10.4 mg, 0.009 mmol) are dissolved in dry DMF (10 ml). Then the mixture is heated and kept under nitrogen at 90° C. for 18 hours. After cooling to room temperature, methanol is added and a precipitate is formed. The precipitate is collected by filtration. Then the product is purified upon Soxhlet extraction with methanol and hexane. A dark solid is obtained. (96.3 mg, yield: 52%). NMR ($^1$H, 300 MHz, d$^1$-CHCl$_3$): δ ppm 7.82-7.91 (br, 4 H), 7.73-7.79 (br, 4 H), 7.76-7.72 (br, 2 H), 7.38-7.45 (br, 4 H), 4.08-4.12 (br, 2 H), 1.95-2.08 (br, 4 H), 1.19-1.38 (br, 64 H), 0.87-0.99 (br, 12 H). UV/Vis (DCM): 601 nm. Molecular weight: 3.8 kDa.

Example 13

Synthesis of Polymer P-19

400 mg of compound 12 together with an equimolar amount of the diboronic acid pinacol ester [254755-24-3] are dissolved in 10 ml toluene. The solution is degassed with argon. Then 0.05 equivalents Pd(PPh$_3$)$_4$ are added. In a separate flask 3 equivalents of K$_2$CO$_3$ are dissolved in water and degassed with argon. The first solution is heated to 80° C. and then the second solution is added. The reaction mixture is then heated to reflux over night to give polymer P-19.

Example 14

Synthesis of Polymer P-20

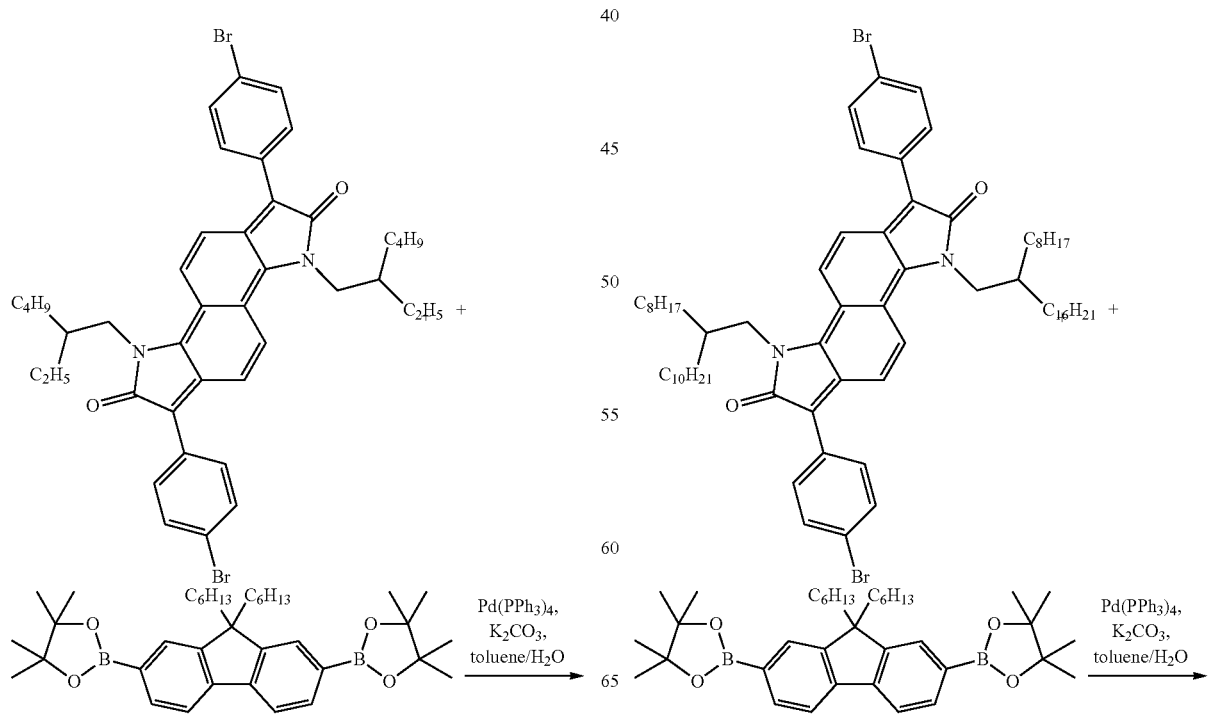

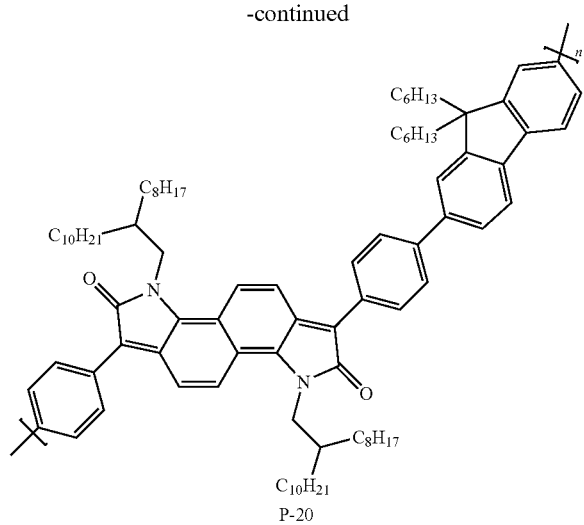

P-20

In a Schlenk flask, 3,8-di(4-bromophenyl)-1,6-bis-(2-octyl-dodecyl)-2,7-dioxo-1,2,6,7-tetrahydronaphtho[1,2-b:5,6-b']dipyrrole (200.0 mg, 0.18 mmol), 2,2'-(9,9-dihexyl-9H-fluorene-2,7-diyl)-bis(4,4-5,5-tetramethyl-1,3,2-dioxaborolane) (105.6 mg, 0.18 mmol) and tetrakis-(triphenyl-phosphine)palladium(0) (10.4 mg, 0.009 mmol) are dissolved in dry toluene (15 ml) under nitrogen. The reaction is degassed and heated to 50° C. A degassed solution of potassium carbonate (87.1 mg, 0.63 mmol) in water (5 ml) is added. The mixture is stirred at 90° C. for 24 hours. After cooling to room temperature, the dark solution is diluted with dichloromethane (DCM), washed three times with water and once with brine. Then the organic layer is dried over anhydrous magnesium sulfate and the solvent is removed by reduced pressure. After that, the crude product is dissolved in a minimal amount of DCM and precipitated in methanol. The product is obtained as a dark solid (173 mg, yield: 75%). NMR ($^1$H, 300 MHz, $d_1$-CHCl$_3$): δ ppm 7.93-7.96 (br, 4 H), 7.67-7.83 (br, 4 H), 7.93-7.96 (br, 6 H), 7.64-7.67 (br, 4 H), 7.43-7.50 (br, 2 H), 7.18-7.20 (br, 2 H), 3.73-3.76 (m, 2 H), 1.95-2.08 (br, 4 H), 1.56 (s, 4 H), 1.15-1.28 (br, 80 H), 0.65-0.91 (br, 18 H). UV/Vis (DCM): 603 nm. Molecular weight: 11.0 kDa.

Example 15

Synthesis of Polymer P-21

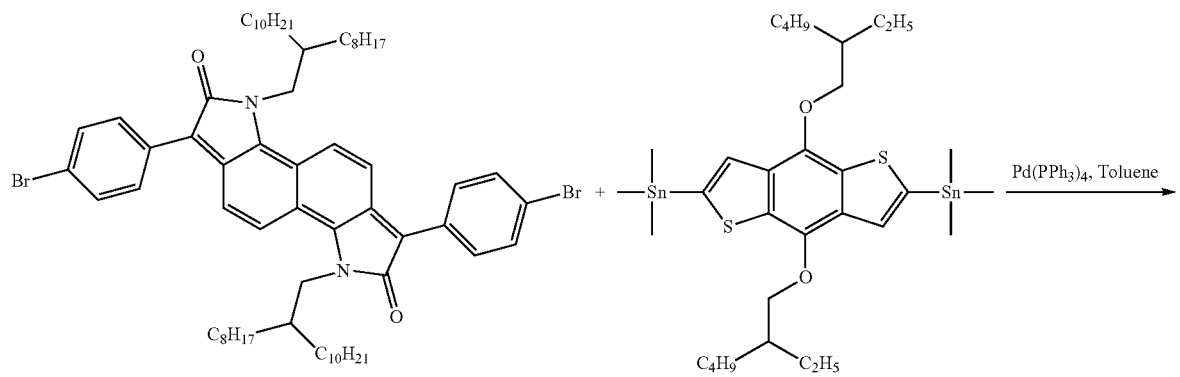

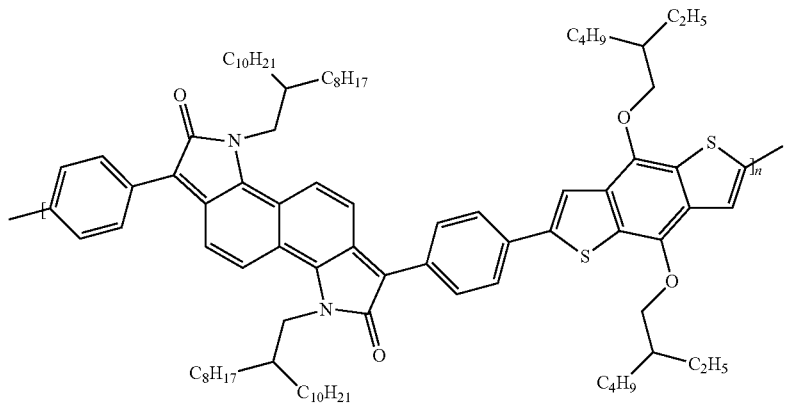

P-21

In a Schlenk flask 3,8-di(4-bromophenyl)-1.6-bis-2-octyl-dodecyl-2,7-dioxo-1,2,6,7-tetrahydro-naphtho[1,2-b:5,6-b']dipyrrole 13 (200.0 mg, 0.18), (4,8-bis(2-ethylhexyloxy)benzo[1,2-b:4,5-b]dithiophene-2,6-diyl)bis(trimethylstannane) (139.5 mg, 0.18 mmol) and tetrakis(triphenylphosphine)palladium(0) (8.2 mg, 0.007 mmol) are dissolved in dry toluene (10 ml). Then the mixture is heated and kept under nitrogen at 100° C. for 18 hours. After cooling to room temperature, methanol is added and a precipitate is formed. The precipitate is collected by filtration. Then the product is purified upon Soxhlet extraction with methanol and hexane. A dark solid is obtained (148.5 mg, yield: 58%). UV/Vis (DCM): 659 nm. UV/Vis (thin film): 684 nm. ∈ (659)/L mol$^{-1}$ cm$^{-1}$: 4.5*10$^4$. Molecular weight: 21.6 kDa.

In a Schlenk flask 3,8-di(4-bromophenyl)-1.6-bis-2-octyl-dodecyl-2,7-dioxo-1,2,6,7-tetrahydro-naphtho[1,2-b:5,6-b']dipyrrole 13 (200.0 mg, 0.18 mmol), 2,2-(9,9-dioctyl-9H-fluoren-2,7-diyl)bis(4,4,5,5-tetramethyl-1,3,2-dioxaborolane) (105.5 mg, 0.18 mmol) and tetrakis(triphenyl-phosphine)palladium(0) (8.2 mg, 0.007 mmol) are dissolved in dry toluene (10 ml) under nitrogen. The reaction is degassed and heated to 50° C. A degassed solution of potassium carbonate (82.68 mg, 0.78 mmol) in water (3 ml) is added. The mixture is stirred at 90° C. for 24 hours. After cooling to room temperature, the dark solution is diluted with DCM, washed three times with water and once with brine. Then the organic layer is dried over anhydrous magnesium sulfate and the solvent is removed at reduced pressure. After that the crude product is dissolved in a minimal amount of DCM and precipitated in methanol. The product is obtained as a dark solid (43.6 mg, yield: 17%). UV/Vis (DCM): 612 nm. UV/Vis (thin film): 639 nm. ∈ (612)/L mol$^{-1}$ cm$^{-1}$: 8.8*10$^4$. Molecular weight: 25.6 kDa.

Example 16

Synthesis of Polymer P-22

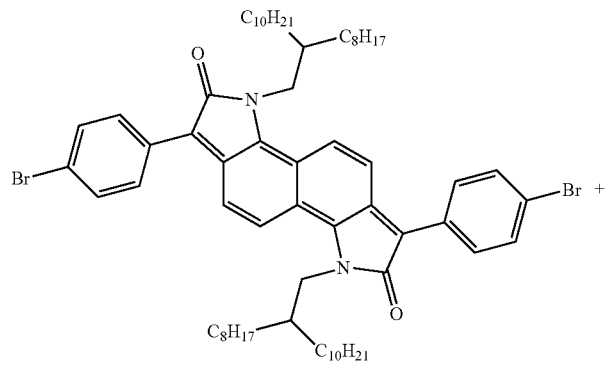

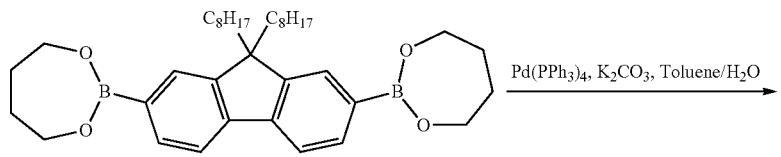

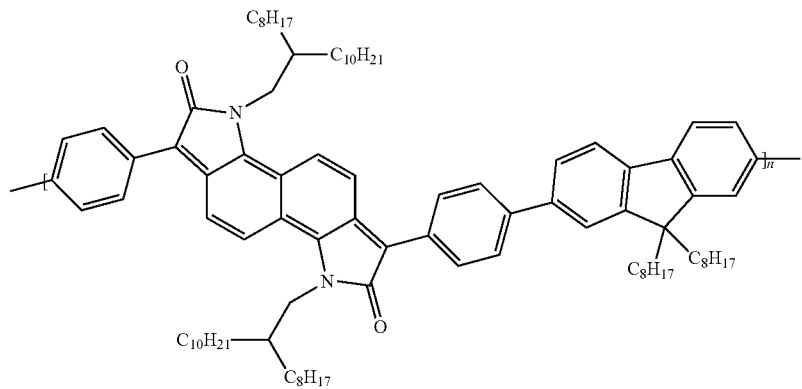

P-22

Example 17

Synthesis of Compound 14

3,8-Di(4-bromophenyl)-1,6-bis-dodecyl-2,7-dioxo-1,2,6,7-tetrahydro-naphtho[1,2-b:5,6-b']dipyrrole

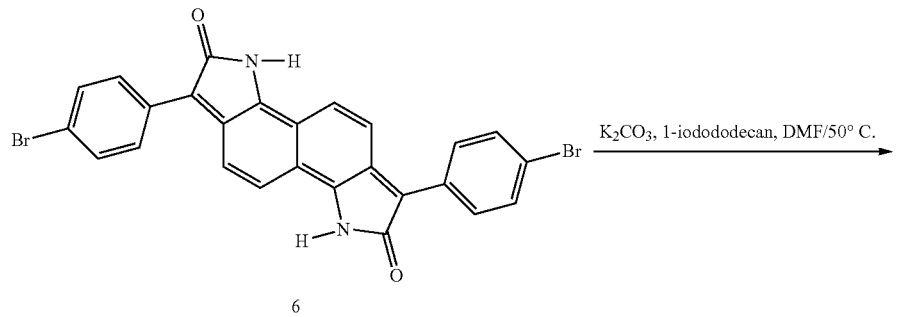

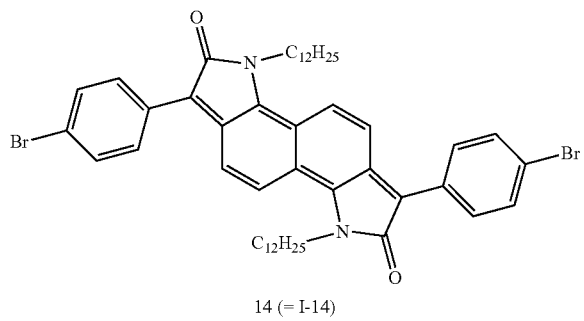

14 (= I-14)

3,8-Di(4-bromophenyl)-2,7-dioxo-1,2,6,7-tetrahydronaphtho[1,2-b:5,6-b']dipyrrole (1.5 g, 2.75 mmol) is dissolved in anhydrous dimethylformamide (40 ml), and then potassium carbonate (2.66 g, 19.25 mmol) and n-dodecyl iodide (3.39 g, 10.98 mmol) are added. After stirring for 12 hours at 50° C., the mixture is poured into water and extracted with DCM. The organic layer is washed with brine and dried over anhydrous $MgSO_4$. On removal of the solvent, the crude solid product is obtained. Then the crude product is dissolved in a minimal amount of DCM and precipitated in methanol. The crude product is obtained as a dark solid (1.41 g, yield: 52%). The crude product is purified by column chromatography over silica gel with hexane:DCM=1:2 as eluent to yield the product (0.54 g, 20%). $^1$H NMR (300 MHz, DMSO): δ ppm 7.65 (d, J=8.7 Hz, 4 H), 7.60 (d, J=8.7 Hz, 4 H), 7.40 (d, J=9.6 Hz, 2H), 7.15 (d, J=9.6 Hz, 2H), 4.07 (t, 4H), 1.77 (m, 4H), 1.15-1.35 (br, 36 H), 0.87-0.91 (t, 6 H). Microanalysis found C, 67.95%; H, 7.12%, N, 3.19% (C, 68.02%, H, 7.08%, N, 3.17%). UV/Vis (DCM): 571 nm. ∈ (571)/L mol$^{-1}$ cm$^{-1}$: 4.6*10$^4$.

Example 18

Synthesis of Polymer P-23

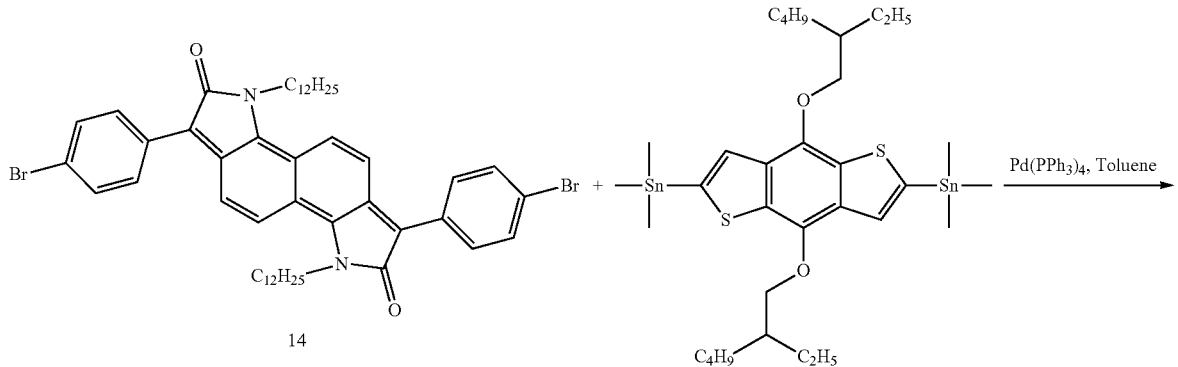

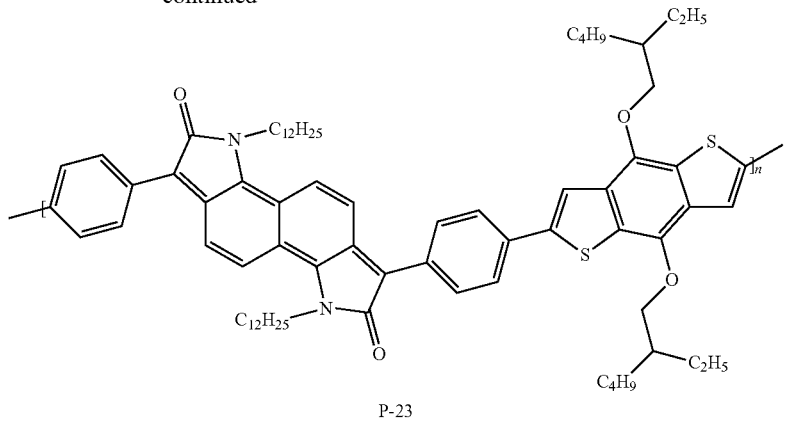

P-23

In a Schlenk flask 3,8-di(4-bromophenyl)-1.6-bis-dodecyl-2,7-dioxo-1,2,6,7-tetrahydro-naphtho[1,2-b:5,6-b']dipyrrole 14 (200.0 mg, 0.23), (4,8-bis(2-ethylhexyloxy)benzo[1,2-b:4,5-b]dithiophene-2,6-diyl)bis(trimethylstannane) (174.9 mg, 0.23 mmol) and tetrakis(triphenylphosphine)palladium(0) (10.4 mg, 0.009 mmol) are dissolved in dry toluene (10 ml). Then the mixture is heated and kept under nitrogen at 100° C. for 18 hours. After cooling to room temperature methanol is added and a precipitate is formed. The precipitate is collected by filtration. Then the product is purified upon Soxhlet extraction with methanol and hexane. A dark solid is obtained (173.5 mg, yield: 63%). UV/Vis (DCM): 666 nm. UV/Vis (thin film): 696 nm. ∈ (666)/L mol$^{-1}$ cm$^{-1}$: 4.3*10$^4$. Molecular weight: 14.2 kDa.

Example 19

Synthesis of Polymer P-24

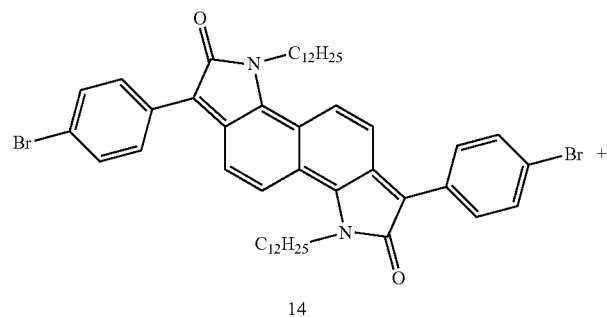

14

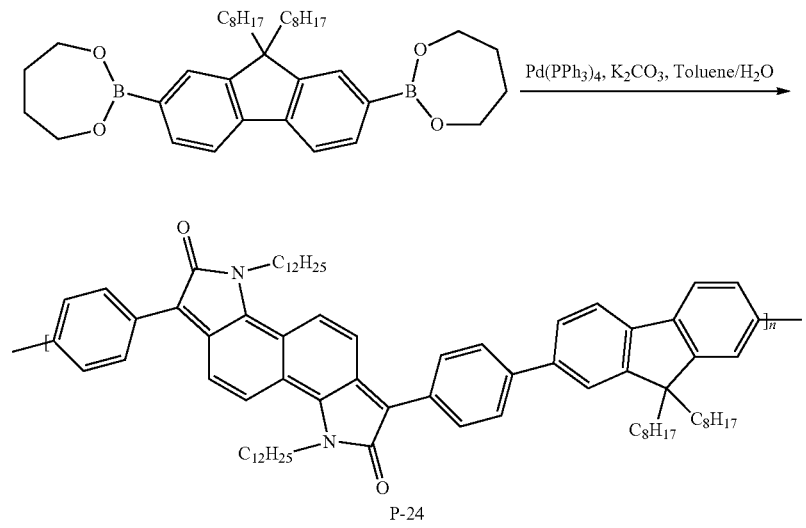

P-24

In a Schlenk flask, 3,8-di(4-bromophenyl)-1,6-bis-dodecyl-2,7-dioxo-1,2,6,7-tetrahydro-naphtho[1,2-b:5,6-b']dipyrrole 14 (200.0 mg, 0.23 mmol), 2,2-(9,9-dioctyl-9H-fluoren-2,7-diyl)bis(4,4,5,5-tetramethyl-1,3,2-dioxaborolane) (132.8 mg, 0.23 mmol) and tetrakis(triphenyl-phosphine)palladium(0) (10.4 mg, 0.009 mmol) are dissolved in dry toluene (10 ml) under nitrogen. The reaction is degassed and heated to 50° C. A degassed solution of potassium carbonate (105.6 mg, 1.0 mmol) in water (3.5 ml) is added. The mixture is stirred at 90° C. for 24 hours. After cooling to room temperature, the dark solution is diluted with DCM, washed three times with water and once with brine. Then the organic layer is dried over anhydrous magnesium sulfate and the solvent is removed at reduced pressure. After that the crude product is dissolved in a minimal amount of DCM and precipitated in methanol. The product is obtained as a dark solid (128.6 mg, yield: 49%). UV/Vis (DCM): 603 nm. UV/Vis (thin film): 624 nm. ∈ (603)/L mol$^{-1}$ cm$^{-1}$: 8.6*10$^4$. Molecular weight: 14.8 kDa Example 20

Synthesis of Polymer P-25

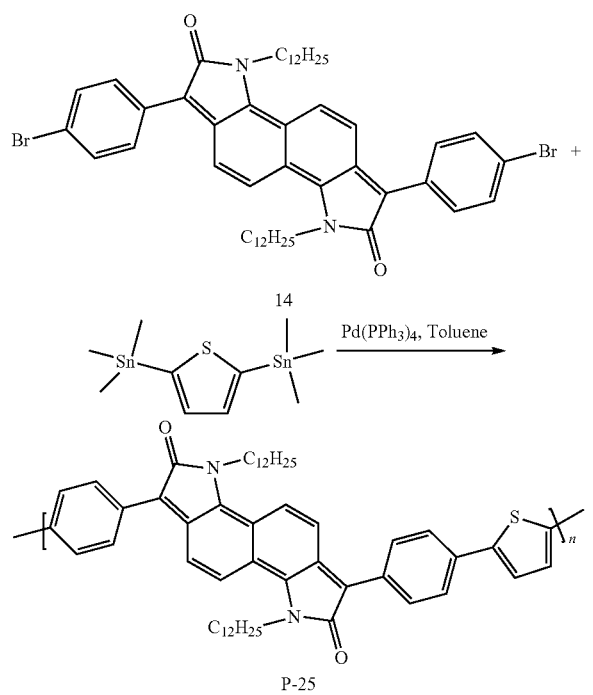

In a Schlenk flask 3,8-di(4-bromophenyl)-1,6-bis-dodecyl-2,7-dioxo-1,2,6,7-tetrahydro-naphtho[1,2-b:5,6-b']dipyrrole 14 (200.0 mg, 0.23), 2,5-bis(trimethylstannane)thiophene (92.8 mg, 0.23 mmol) and tetrakis-(triphenylphosphine)palladium(0) (10.4 mg, 0.009 mmol) are dissolved in dry DMF (10 ml). Then the mixture is heated and kept under nitrogen at 100° C. for 18 hours. After cooling to room temperature, methanol is added and a precipitate is formed. The precipitate is collected by filtration. Then the product is purified upon Soxhlet extraction with methanol and hexane. A dark solid is obtained. (96.3 mg, yield: 52%). UV/Vis (DCM): 615 nm. UV/Vis (thin film): 678 nm. ∈ (615)/L mol$^{-1}$ cm$^{-1}$: 2.8*10$^4$. Molecular weight: 14.9 kDa.

Application Example 1

UV/Vis Absorption Spectra

UV/Vis absorption spectra of polymer 20 are recorded on an Agilent 8453 spectrometer. The $^{max}\lambda_{abs}$ in trichloroethylene (TCE) solution and as film are shown in Table 1. Band Gap (BG) is calculated as onset of absorption spectrum.

TABLE 1

| Polymer | Solvent | $^{max}\lambda_{abs}$ [nm] |
|---|---|---|
| P-20 | CHCl=CCl$_2$ | 330, 600 |
| P-20 | Film | 335, 610 |

Application Example 2

Cyclic Voltammograms (CVs)

CVs of the films are recorded on a Autolab PGSTAT302 potentiostat in acetonitrile containing tetrabutylammonium-tetrafluoroborate (Bu$_4$NBF$_4$, 0.1M) as supporting electrolyte at scan rate 100 mV/s. Counter and working electrodes are made of Pt and the reference electrode is Ag/AgCl. Films are drop casted on the Pt disc working electrode. All the potentials are calibrated vs. Ferrocene/Ferrocenium redox couple and HOMO/LUMO values are calculated as follows:

$$HOMO(CV) = -4.8 - E^{ox}_{onset} \quad LUMO(CV) = -4.8 - E^{red}_{onset}$$

All values are shown in Table 2.

TABLE 2

| Polymer | Onset UV, nm | BG, eV | HOMO (CV), eV | LUMO (CV), eV |
|---|---|---|---|---|
| P-20 | 738 | 1.68 | −5.4 | not determined |

The invention claimed is:
1. A polymer, comprising a unit of formula (I):

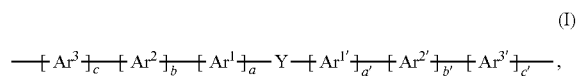

wherein
Y is a group of formula

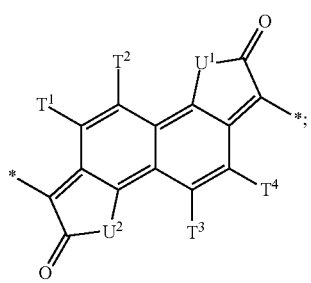

a is 1, 2, or 3;
a' is 1, 2, or 3;
b is 0, 1, 2, or 3;
b' is 0, 1, 2, or 3;

c is 0, 1, 2, or 3;
c' is 0, 1, 2, or 3;
$U^1$ is O, S, or $NR^1$;
$U^2$ is O, S, or $NR^2$;
$T^1$, $T^2$, $T^3$ and $T^4$ are independently hydrogen, halogen, hydroxyl, cyano, —$COOR^{103}$, —$OCOR^{103}$, —$NR^{112}COR^{103}$, —$CONR^{112}R^{113}$, —$OR^{103}$, —$SR^{103}$, —$SOR^{103}$, —$SO_2R^{103}$, —$NR^{112}SO_2R^{103}$, —$NR^{112}R^{113}$, $C_1$-$C_{25}$alkyl, which is optionally substituted by E and/or interrupted by D, $C_5$-$C_{12}$ cycloalkyl, which is optionally substituted one to three times with $C_1$-$C_8$ alkyl and/or $C_1$-$C_8$ alkoxy; $C_7$-$C_{25}$ arylalkyl, $C_6$-$C_{24}$ aryl, $C_6$-$C_{24}$ aryl which is substituted by G, $C_2$-$C_{20}$ heteroaryl, or $C_2$-$C_{20}$ heteroaryl which is substituted by G;
$R^1$ and $R^2$ are independently selected from the group consisting of hydrogen, a $C_1$-$C_{100}$alkyl group which is optionally substituted one or more times with $C_1$-$C_{12}$ alkyl, $C_1$-$C_{12}$ alkoxy, halogen, $C_5$-$C_{12}$ cycloalkyl, nitro, cyano, vinyl, allyl, $C_6$-$C_{24}$aryl, $C_2$-$C_{20}$ heteroaryl, a silyl group, or a siloxanyl group; and/or is optionally interrupted by —O—, —S—, —$NR^{39}$—, $CONR^{39}$—, $NR^{39}CO$—, —COO—, —CO— or —OCO—,
a $C_2$-$C_{100}$ alkenyl group which is optionally substituted one or more times with $C_1$-$C_{12}$ alkyl, $C_1$-$C_{12}$ alkoxy, halogen, $C_5$-$C_{12}$ cycloalkyl, nitro, cyano, vinyl, allyl, $C_6$-$C_{24}$ aryl, $C_2$-$C_{20}$ heteroaryl, a silyl group, or a siloxanyl group; and/or is optionally interrupted by —O—, —S—, —$NR^{39}$—, $CONR^{39}$—, $NR^{39}CO$—, —COO—, —CO— or —OCO—,
a $C_3$-$C_{100}$ alkinyl group which is optionally substituted one or more times with $C_1$-$C_{12}$ alkyl, $C_1$-$C_{12}$ alkoxy, halogen, $C_5$-$C_{12}$ cycloalkyl, nitro, cyano, vinyl, allyl, $C_6$-$C_{24}$ aryl, $C_2$-$C_{20}$ heteroaryl, a silyl group, or a siloxanyl group; and/or is optionally interrupted by —O—, —S—, —$NR^{39}$—, $CONR^{39}$—, $NR^{39}CO$—, —COO—, —CO— or —OCO—,
a $C_3$-$C_{12}$ cycloalkyl group which is optionally substituted one or more times with $C_1$-$C_{12}$ alkyl, $C_1$-$C_{12}$ alkoxy, halogen, $C_5$-$C_{12}$ cycloalkyl, nitro, cyano, vinyl, allyl, $C_6$-$C_{24}$ aryl, $C_2$-$C_{20}$ heteroaryl, a silyl group, or a siloxanyl group; and/or is optionally interrupted by —O—, —S—, —$NR^{39}$—, $CONR^{39}$—, $NR^{39}CO$—, —COO—, —CO— or —OCO—,
a $C_6$-$C_{24}$ aryl group which is optionally substituted one or more times with $C_1$-$C_{12}$ alkyl, $C_1$-$C_{12}$ alkoxy, halogen, $C_5$-$C_{12}$ cycloalkyl, nitro, cyano, vinyl, allyl, $C_6$-$C_{24}$ aryl, $C_2$-$C_{20}$ heteroaryl, a silyl group, or a siloxanyl group;
a $C_2$-$C_{20}$ heteroaryl group which is optionally substituted one or more times with $C_1$-$C_{12}$ alkyl, $C_1$-$C_{12}$ alkoxy, halogen, $C_5$-$C_{12}$ cycloalkyl, nitro, cyano, vinyl, allyl, $C_6$-$C_{24}$ aryl, $C_2$-$C_{20}$ heteroaryl, a silyl group, or a siloxanyl group;
a —CO—$C_1$-$C_{18}$ alkyl group, a —CO—$C_5$-$C_{12}$ cycloalkyl group, or —COO—$C_1$-$C_{18}$ alkyl group;
$R^{39}$ is hydrogen, $C_1$-$C_{18}$ alkyl, $C_1$-$C_{18}$ haloalkyl, $C_7$-$C_{25}$ arylalkyl, or $C_1$-$C_{18}$ alkanoyl,
$Ar^1$, $Ar^{1'}$, $Ar^2$, $Ar^{2'}$, $Ar^3$ and $Ar^{3'}$ are independently

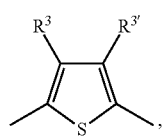

(XIa)

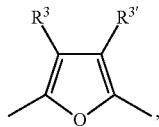

(XIb)

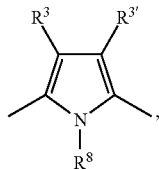

(XIc)

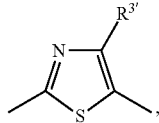

(XId)

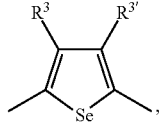

(XIe)

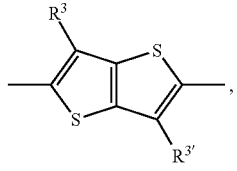

(XIf)

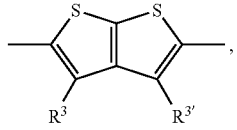

(XIg)

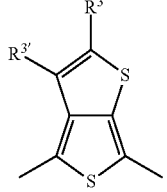

(XIh)

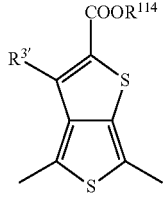

(XIi)

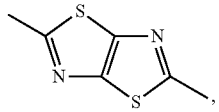

(XIj)

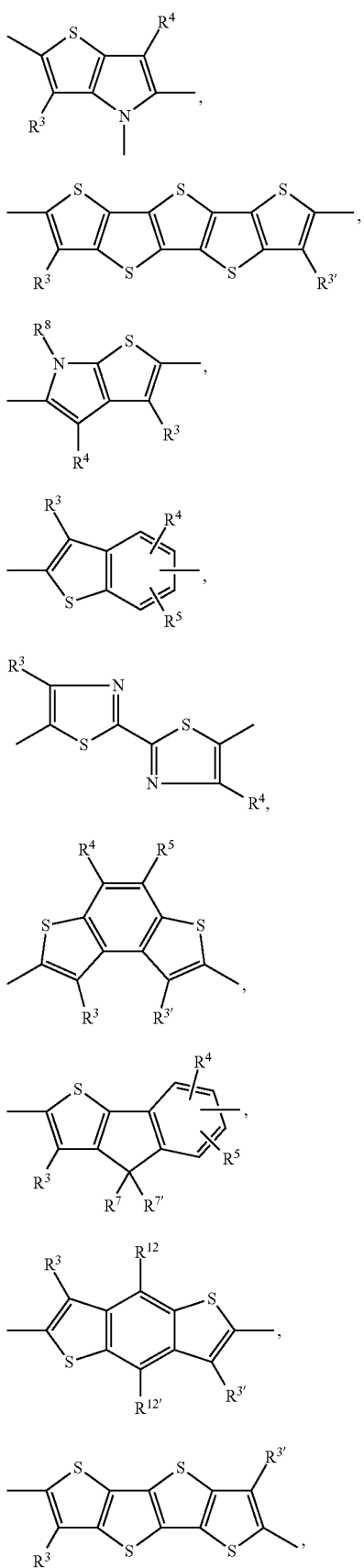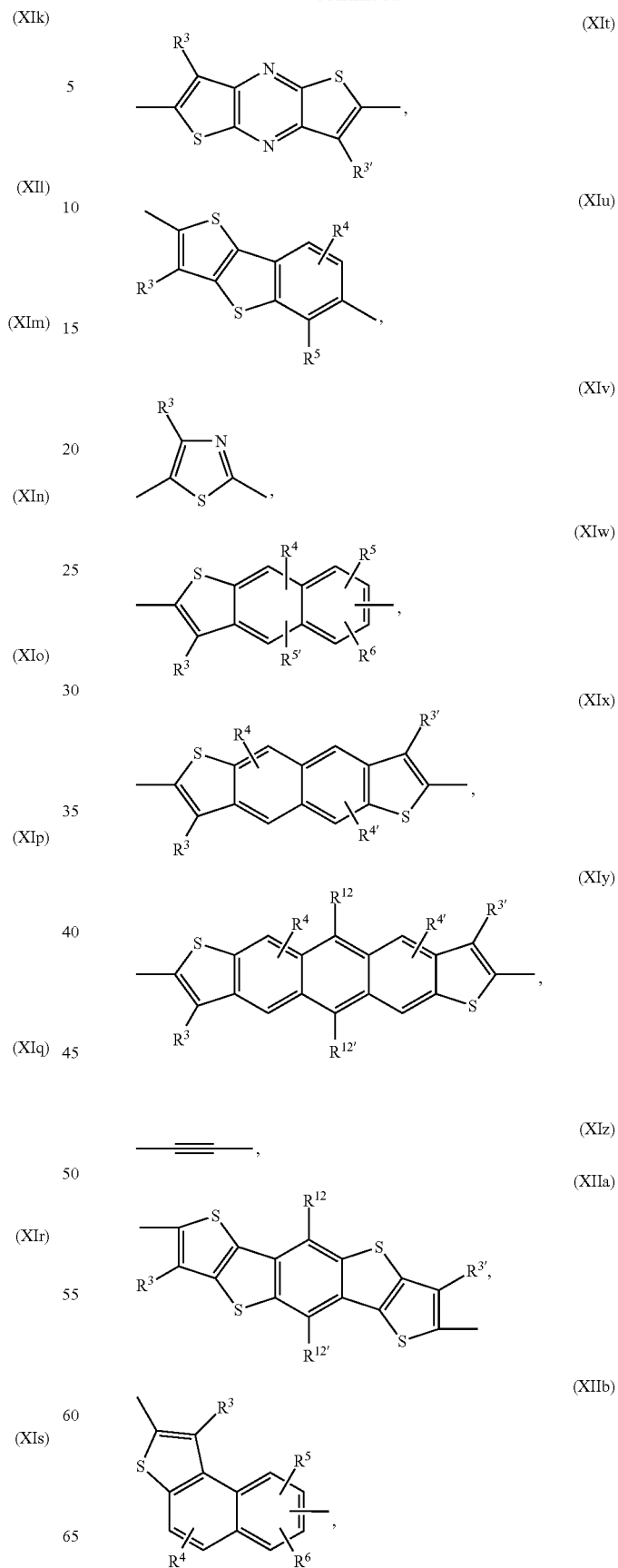

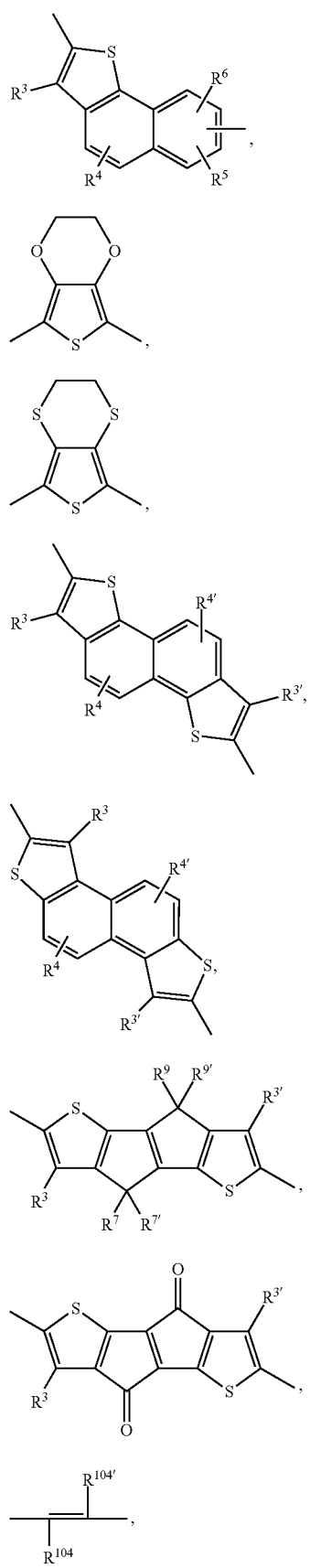

-continued
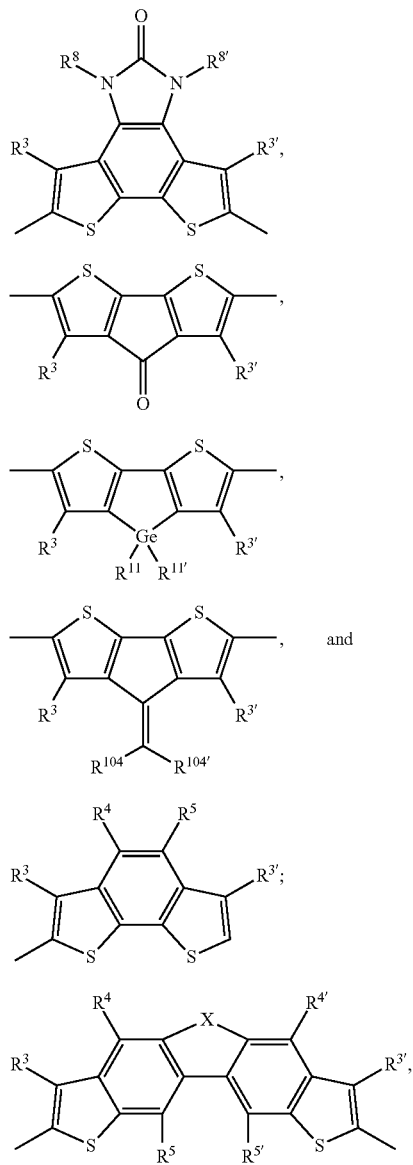
which optionally is
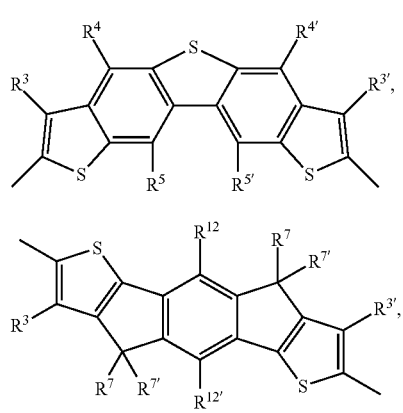
-continued
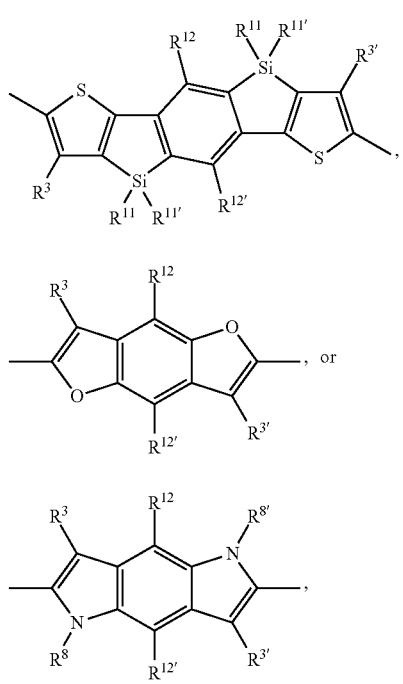
wherein
X is —O—, —S—, —NR$^8$—, —Si(R$^{11}$)(R$^{11'}$)—, —Ge(R$^{11}$)(R$^{11'}$)—, —C(R$^7$)(R$^{7'}$)—, —C(=O)—, —C(=CR$^{104}$R$^{104'}$)—,
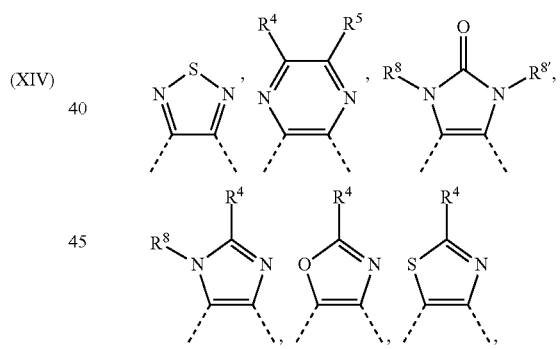
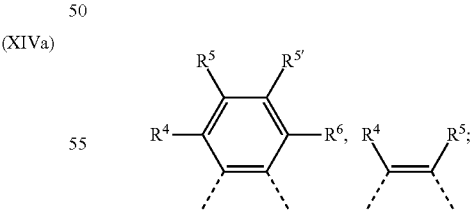
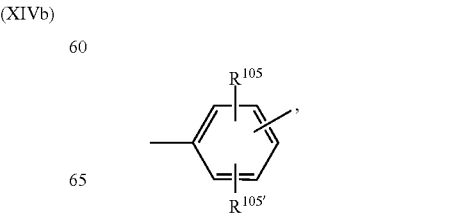

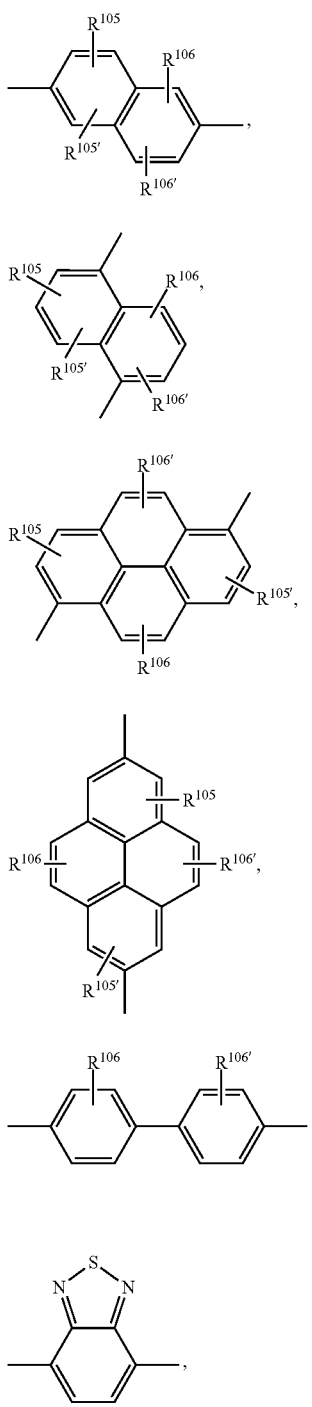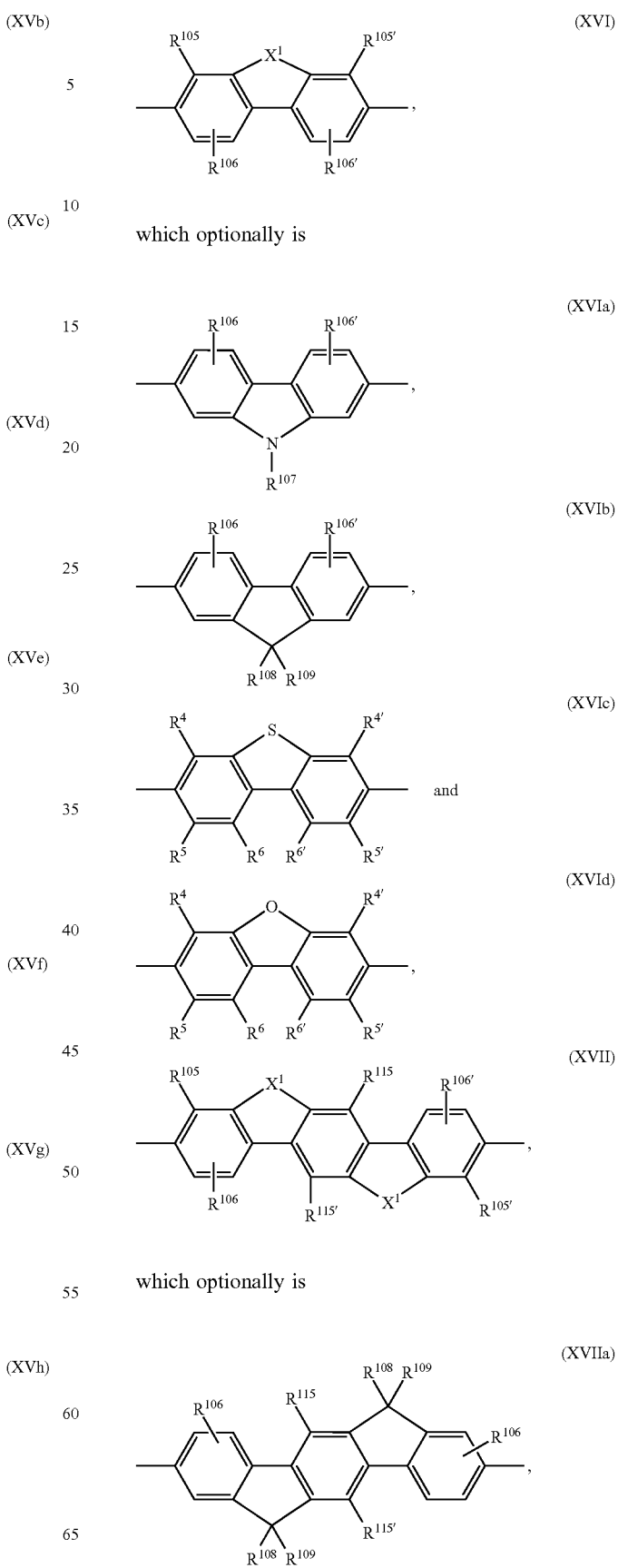
which optionally is
which optionally is

-continued

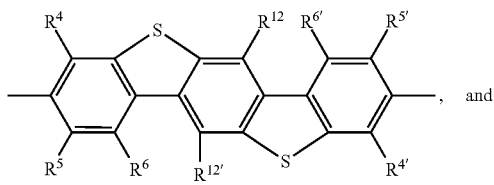

(XVIIb)

and

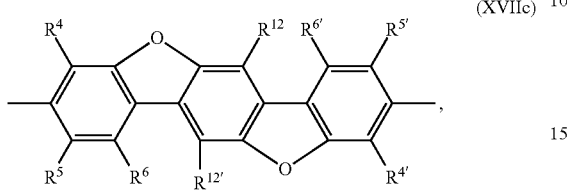

(XVIIc)

wherein
X$^1$ is S, O, NR$^{107}$—, —Si(R$^{117}$)(R$^{117'}$)—, —Ge(R$^{117}$)(R$^{117'}$)—, —C(R$^{106}$)(R$^{109}$)—, —C(=O)—, —C(=CR$^{104}$R$^{104'}$)—,

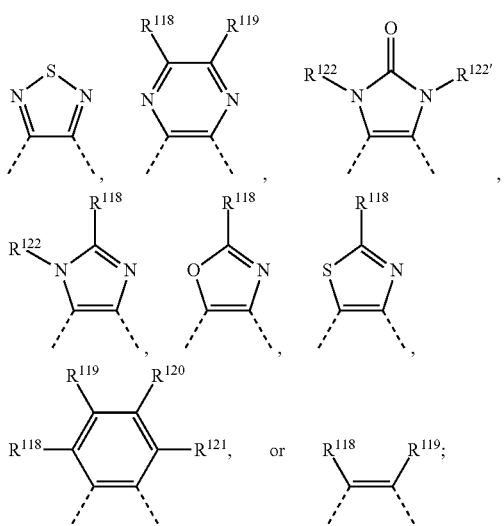

R$^3$ and R$^{3'}$ are independently hydrogen, halogen, halogenated C$_1$-C$_{25}$ alkyl, cyano, C$_1$-C$_{25}$ alkyl, which is optionally interrupted by one or more oxygen or sulphur atoms; C$_7$-C$_{25}$ arylalkyl, or C$_1$-C$_{25}$ alkoxy;

R$^4$, R$^{4'}$, R$^5$, R$^{5'}$, R$^6$, and R$^{6'}$ are independently hydrogen, halogen, halogenated C$_1$-C$_{25}$ alkyl, cyano, C$_1$-C$_{25}$ alkyl, which is optionally interrupted by one or more oxygen or sulphur atoms; C$_7$-C$_{25}$ arylalkyl, or C$_1$-C$_{25}$ alkoxy;

R$^7$, R$^{7'}$, R$^9$ and R$^{9'}$ are independently hydrogen, C$_1$-C$_{25}$ alkyl, which is optionally interrupted by one, or more oxygen, or sulphur atoms; or C$_7$-C$_{25}$ arylalkyl, R$^8$ and R$^{8'}$ are independently hydrogen, C$_6$-C$_{18}$ aryl; C$_6$-C$_{18}$ aryl which is substituted by C$_1$-C$_{18}$ alkyl, or C$_1$-C$_{18}$ alkoxy; or C$_1$-C$_{25}$ alkyl, which is optionally interrupted by one or more oxygen or sulphur atoms; or C$_7$-C$_{25}$ arylalkyl, R$^{11}$ and R$^{11'}$ are independently C$_1$-C$_{25}$ alkyl group, C$_7$-C$_{25}$ arylalkyl, or a phenyl group, which is optionally substituted one to three times with C$_1$-C$_8$ alkyl and/or C$_1$-C$_8$ alkoxy;

R$^{12}$ and R$^{12'}$ are independently hydrogen, halogen, cyano, C$_1$-C$_{25}$ alkyl, which is optionally interrupted by one, or more oxygen, or sulphur atoms, C$_1$-C$_{25}$ alkoxy, C$_7$-C$_{25}$ arylalkyl, or

wherein R$^{13}$ is a C$_1$-C$_{10}$ alkyl group, or a tri(C$_1$-C$_8$ alkyl)silyl group;

R$^{103}$ and R$^{103'}$ are independently C$_1$-C$_{100}$ alkyl, C$_1$-C$_{25}$ alkyl substituted by E and/or interrupted with D, C$_7$-C$_{25}$ arylalkyl, C$_6$-C$_{24}$ aryl, C$_6$-C$_{24}$ aryl which is substituted by G, C$_2$-C$_{20}$ heteroaryl, or C$_2$-C$_{20}$ heteroaryl which is substituted by G, R$^{104}$ and R$^{104'}$ are independently hydrogen, C$_1$-C$_{18}$ alkyl, cyano, COOR$^{103}$, C$_6$-C$_{10}$ aryl, which is optionally substituted by G, or C$_2$-C$_8$ heteroaryl, which is optionally substituted by G, R$^{105}$, R$^{105'}$, R$^{106}$ and R$^{106'}$ are independently hydrogen, halogen, cyano, C$_1$-C$_{25}$ alkyl, which is optionally interrupted by one or more oxygen or sulphur atoms; C$_7$-C$_{25}$ arylalkyl, or C$_1$-C$_{18}$ alkoxy, R$^{107}$ is hydrogen, C$_7$-C$_{25}$ arylalkyl, C$_6$-C$_{18}$ aryl; C$_6$-C$_{18}$ aryl which is substituted by C$_1$-C$_{18}$ alkyl, or C$_1$-C$_{18}$ alkoxy; C$_1$-C$_{18}$ perfluoroalkyl; C$_1$-C$_{25}$ alkyl; which is optionally interrupted by —O—, or —S—; or —COOR$^{103}$;

R$^{108}$ and R$^{109}$ are independently H, C$_1$-C$_{25}$ alkyl, C$_1$-C$_{25}$ alkyl which is substituted by E and/or interrupted by D, C$_7$-C$_{25}$ arylalkyl, C$_6$-C$_{24}$ aryl, C$_6$-C$_{24}$ aryl which is substituted by G, C$_2$-C$_{20}$ heteroaryl, C$_2$-C$_{20}$ heteroaryl which is substituted by G, C$_2$-C$_{18}$ alkenyl, C$_2$-C$_{18}$ alkynyl, C$_1$-C$_{18}$ alkoxy, C$_1$-C$_{18}$ alkoxy which is substituted by E and/or interrupted by D, or C$_7$-C$_{25}$ aralkyl, or R$^{108}$ and R$^{109}$ together form a group of formula =CR$^{110}$R$^{111}$, wherein R$^{110}$ and R$^{111}$ are independently H, C$_1$-C$_{18}$ alkyl, C$_1$-C$_{18}$ alkyl which is substituted by E and/or interrupted by D, C$_6$-C$_{24}$ aryl, C$_6$-C$_{24}$ aryl which is substituted by G, or C$_2$-C$_{20}$ heteroaryl, or C$_2$-C$_{20}$ heteroaryl which is substituted by G, or R$^{108}$ and R$^{109}$ together form a five or six membered ring, which is optionally substituted by C$_1$-C$_{18}$ alkyl, C$_1$-C$_{18}$ alkyl which is substituted by E and/or interrupted by D, C$_6$-C$_{24}$ aryl, C$_6$-C$_{24}$ aryl which is substituted by G, C$_2$-C$_{20}$ heteroaryl, C$_2$-C$_{20}$ heteroaryl which is substituted by G, C$_2$-C$_{18}$ alkenyl, C$_2$-C$_{18}$ alkynyl, C$_1$-C$_{18}$ alkoxy, C$_1$-C$_{18}$ alkoxy which is substituted by E and/or interrupted by D, or C$_7$-C$_{25}$ aralkyl, D is —CO—, —COO—, —S—, —O—, or —NR$^{112}$—, E is C$_1$-C$_8$ thioalkoxy, C$_1$-C$_8$ alkoxy, CN, —NR$^{112}$R$^{113}$, —CONR$^{112}$R$^{113}$, or halogen, G is E, or C$_1$-C$_{18}$ alkyl, and R$^{112}$ and R$^{113}$ are independently H; C$_6$-C$_{18}$ aryl; C$_6$-C$_{18}$ aryl which is substituted by C$_1$-C$_{18}$ alkyl, or C$_1$-C$_{18}$ alkoxy; C$_1$-C$_{18}$ alkyl; or C$_1$-C$_{18}$ alkyl which is interrupted by —O—, R$^{114}$ is C$_1$-C$_{25}$ alkyl, which is optionally interrupted by one, or more oxygen, or sulphur atoms, R$^{115}$ and R$^{115'}$ are independently hydrogen, halogen, cyano, C$_1$-C$_{25}$ alkyl, which is optionally interrupted by one, or more oxygen, or sulphur atoms, C$_1$-C$_{25}$ alkoxy, C$_7$-C$_{25}$ arylalkyl, or

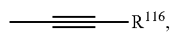—R[116], wherein R[116] is a $C_1$-$C_{10}$ alkyl group, or a tri($C_1$-$C_8$alkyl)silyl group;

R[117] and R[117'] are independently $C_1$-$C_{25}$ alkyl group, $C_7$-$C_{25}$ arylalkyl, or a phenyl group, which is optionally substituted one to three times with $C_1$-$C_8$ alkyl and/or $C_1$-$C_8$ alkoxy;

R[118], R[119], R[120] and R[121] are independently hydrogen, halogen, halogenated $C_1$-$C_{25}$ alkyl, cyano, $C_1$-$C_{25}$ alkyl, which is optionally interrupted by one or more oxygen or sulphur atoms; $C_7$-$C_{25}$ arylalkyl, or $C_1$-$C_{25}$ alkoxy;

R[122] and R[122'] are independently hydrogen, $C_6$-$C_{18}$ aryl; $C_6$-$C_{18}$ aryl which is substituted by $C_1$-$C_{18}$ alkyl, or $C_1$-$C_{18}$ alkoxy; or $C_1$-$C_{25}$ alkyl, which is optionally interrupted by one or more oxygen or sulfur atoms; or $C_7$-$C_{25}$ arylalkyl.

2. The polymer according to claim 1, comprising a unit of formula (I'):

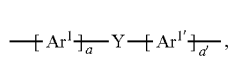

wherein
Y is a group of formula

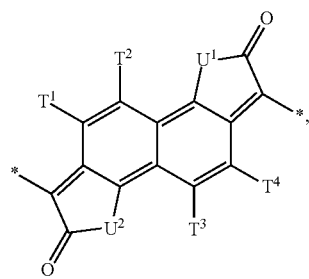

$U^1$ is O, S, or NR[1];
$U^2$ is O, S, or NR[2];
$T^1$, $T^2$, $T^3$ and $T^4$ are independently hydrogen, halogen, cyano, —COOR[103], —OCOR[103], —OR[103'], $C_1$-$C_{25}$ alkyl, which is optionally substituted by E and/or interrupted by D, $C_6$-$C_{24}$ aryl, $C_6$-$C_{24}$ aryl which is substituted by G, $C_2$-$C_{20}$ heteroaryl, or $C_2$-$C_{20}$ heteroaryl which is substituted by G;
R[1] and R[2] are independently selected from the group consisting of hydrogen, $C_1$-$C_{50}$ alkyl, $C_1$-$C_{50}$ haloalkyl, $C_7$-$C_{25}$ arylalkyl, $C_2$-$C_{50}$ alkenyl, $C_2$-$C_{50}$ haloalkenyl, allyl, $C_5$-$C_{12}$ cycloalkyl, phenyl or naphthyl which is optionally substituted one or more times with $C_1$-$C_{12}$ alkyl or $C_1$-$C_{12}$ alkoxy, —CO—$C_1$-$C_{18}$ alkyl, —CO—$C_5$-$C_{12}$ cycloalkyl, and —COO—$C_1$-$C_{18}$ alkyl;
a is 1, 2, or 3;
a' is 1, 2, or 3; and
Ar[1], Ar[1'], R[103], R[103'], D, E and G are as defined in claim 1.

3. The polymer according to claim 1, comprising at least one unit of a formula selected from the group consisting of formula (Ia), formula (Ib), formula (Ic), formula (Id), and formula (Ie):

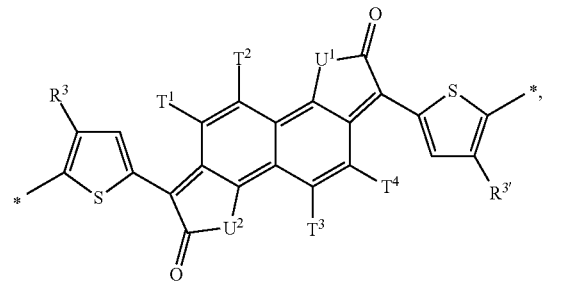

(Ia)

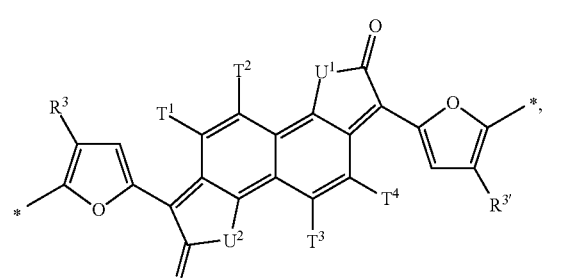

(Ib)

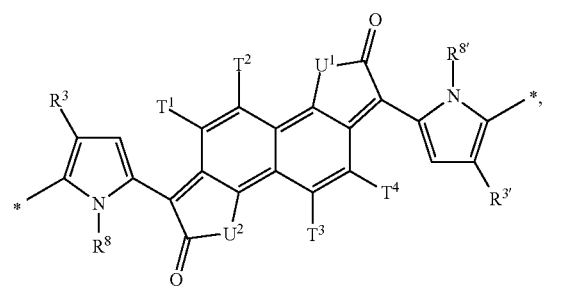

(Ic)

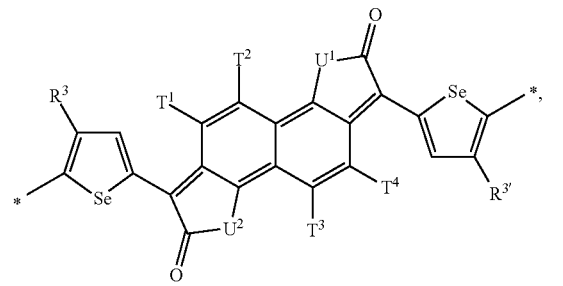

(Id)

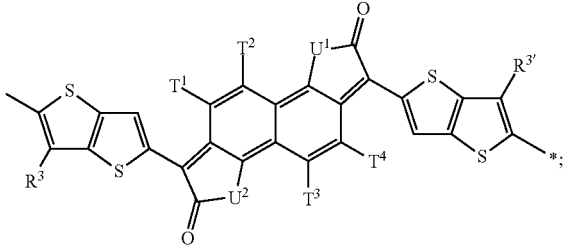

(Ie)

wherein
$U^1$ is O, or NR[1];
$U^2$ is O, or NR[2];
$T^1$, $T^2$, $T^3$ and $T^4$ are independently hydrogen, or $C_1$-$C_{25}$ alkyl;

$R^1$ and $R^2$ are independently a $C_1$-$C_{38}$ alkyl group;

$R^3$ and $R^{3'}$ are independently hydrogen or $C_1$-$C_{25}$ alkyl; and $R^8$ and $R^{8'}$ are independently hydrogen or $C_1$-$C_{25}$ alkyl.

4. The polymer according to claim 1, comprising a unit of formula

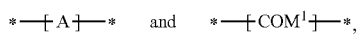

wherein

A is a repeating unit of formula (I), and

—COM$^1$- is a repeating unit, which is Ar$^1$, or is a group of formula

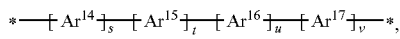

s is 1, t is 1, u is 0, or 1, v is 0, or 1, and

Ar$^{14}$, Ar$^{15}$, Ar$^{16}$ and Ar$^{17}$ are independently a group of formula

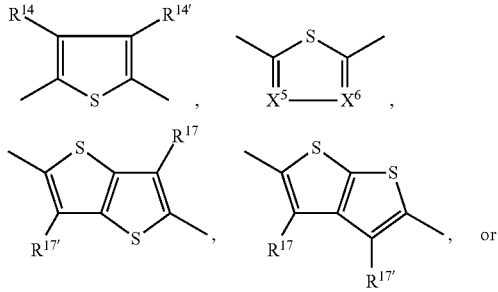

wherein one of $X^5$ and $X^6$ is N and the other is $CR^{14}$, and $R^{14}$, $R^{14'}$, $R^{17}$ and $R^{17'}$ are independently H, or a $C_1$-$C_{25}$ alkyl group.

5. The polymer according to claim 4, wherein A is a repeating unit of formula (Ia), (Ib), (Ic), (Id), or (Ie):

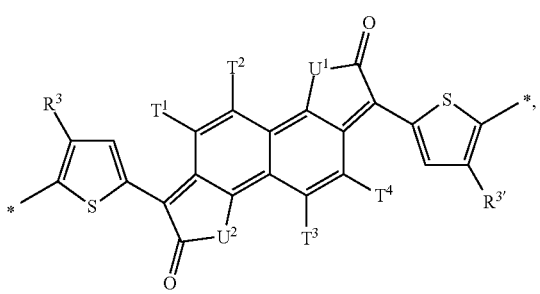

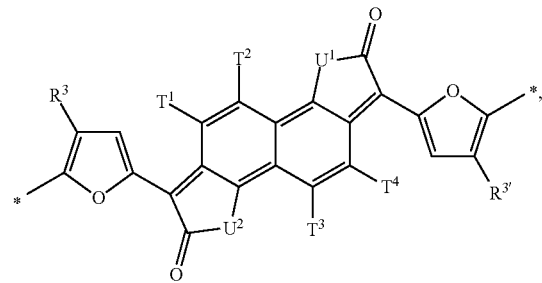

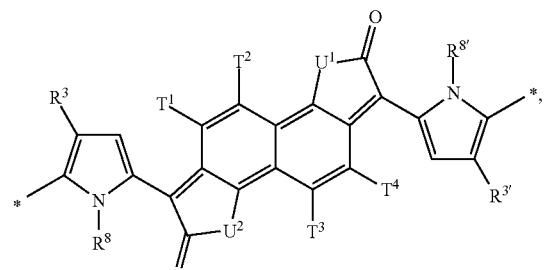

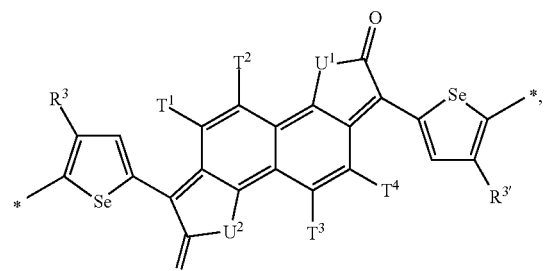

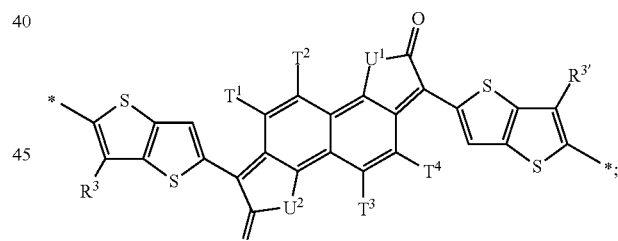

wherein $U^1$ is O, or NR$^1$;

$U^2$ is O, or NR$^2$;

$T^1$, $T^2$, $T^3$ and $T^4$ are independently hydrogen, or $C_1$-$C_{25}$ alkyl;

$R^1$ and $R^2$ are independently a $C_1$-$C_{38}$ alkyl group;

$R^3$ and $R^{3'}$ are independently hydrogen or $C_1$-$C_{25}$ alkyl; and $R^8$ and $R^{8'}$ are independently hydrogen or $C_1$-$C_{25}$ alkyl and

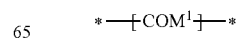

is a group of formula
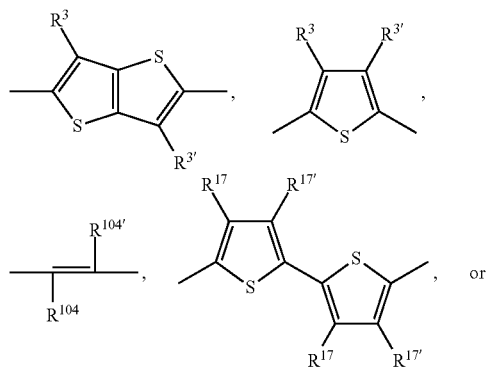
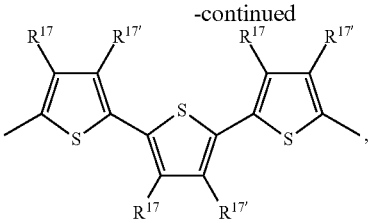
where $R^3$, $R^{3'}$, $R^{17}$ and $R^{17'}$ are independently hydrogen, or $C_1$-$C_{25}$ alkyl, and $R^{104}$ and $R^{104'}$ are independently hydrogen, cyano or a $C_1$-$C_{25}$ alkyl group.
6. The polymer according to claim 4, which is a polymer of formula
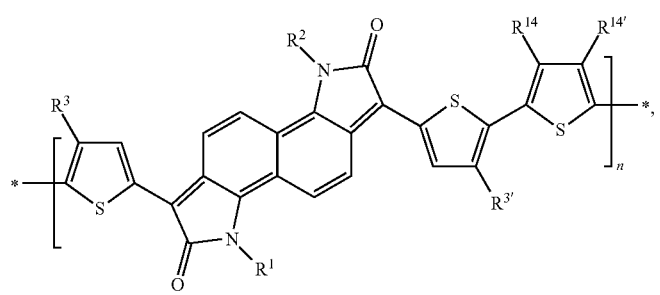 (Ia-1)
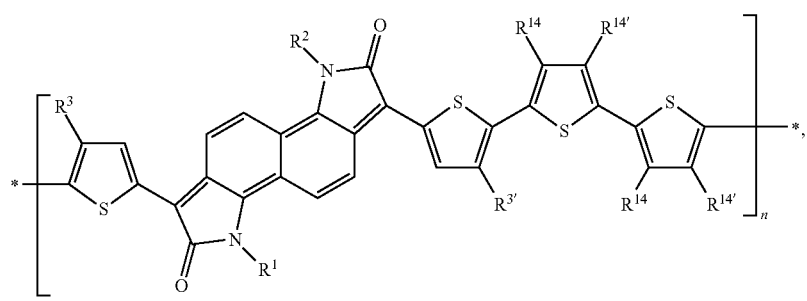 (Ia-2)
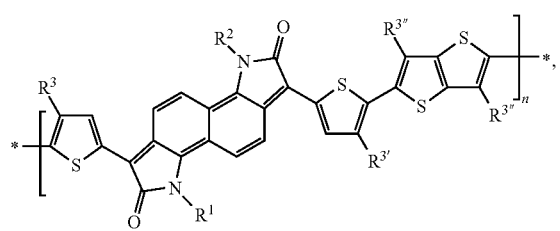 (Ia-3)
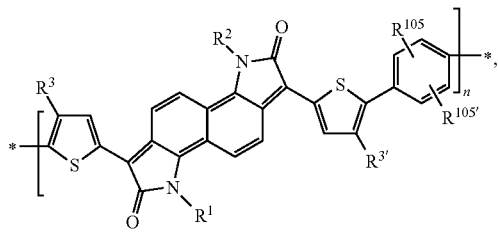 (Ia-4)
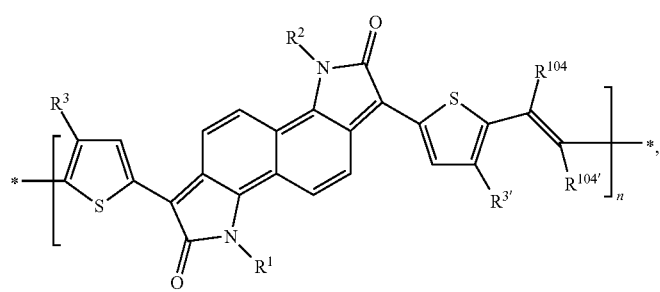 (Ia-5)

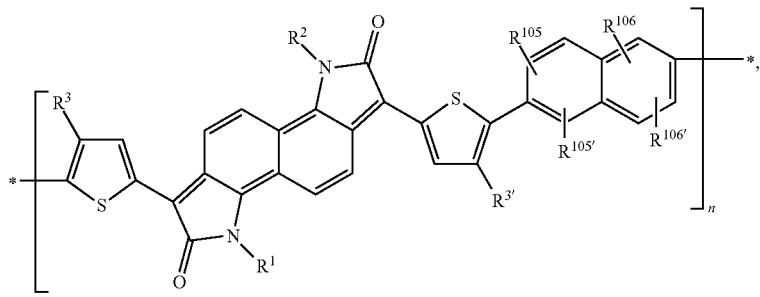
(Ia-6)
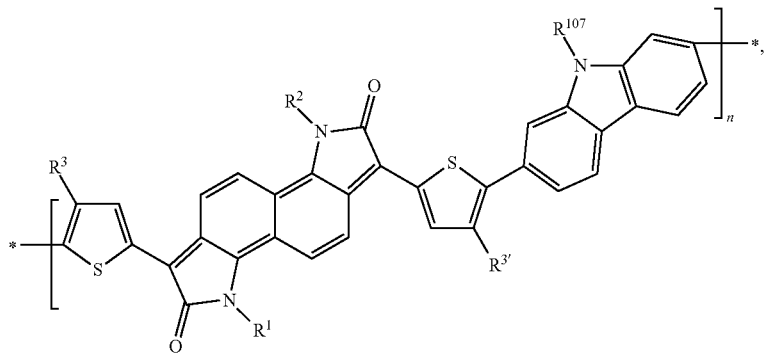
(Ia-7)
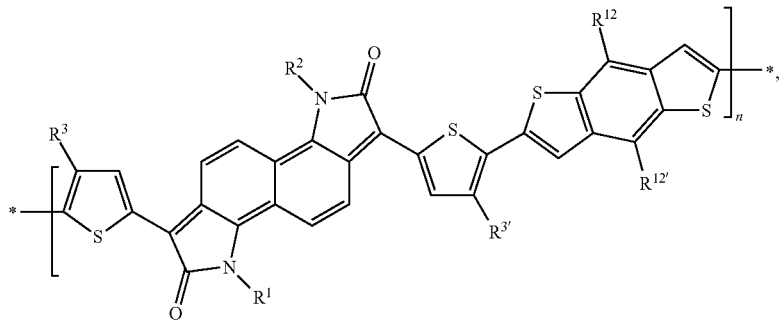
(Ia-8)
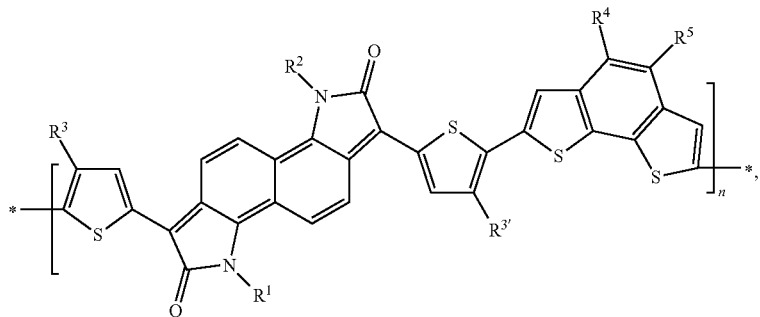
(Ia-9)
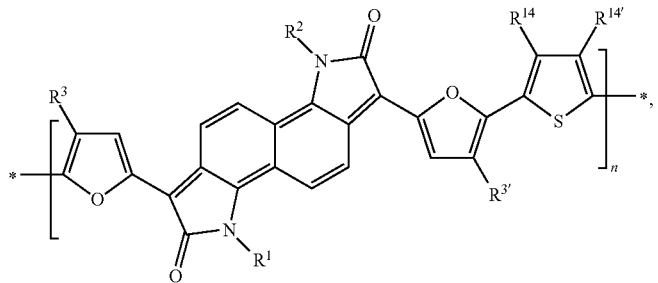
(Ia-10)

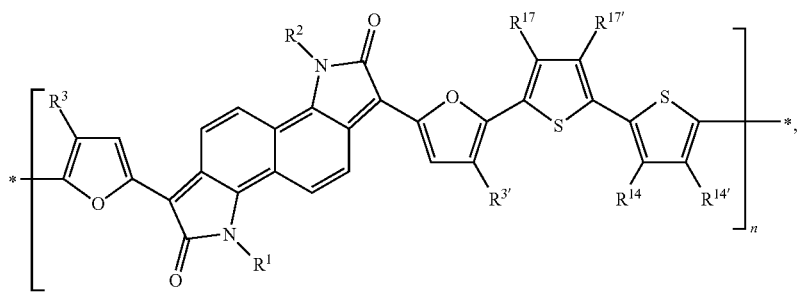
(Ia-11)
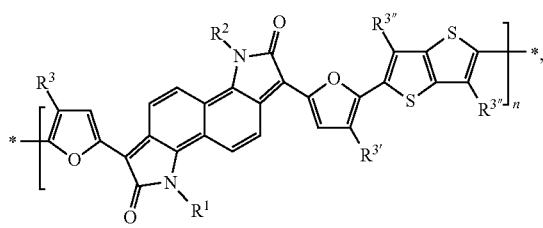
(Ia-12)
(Ia-13)
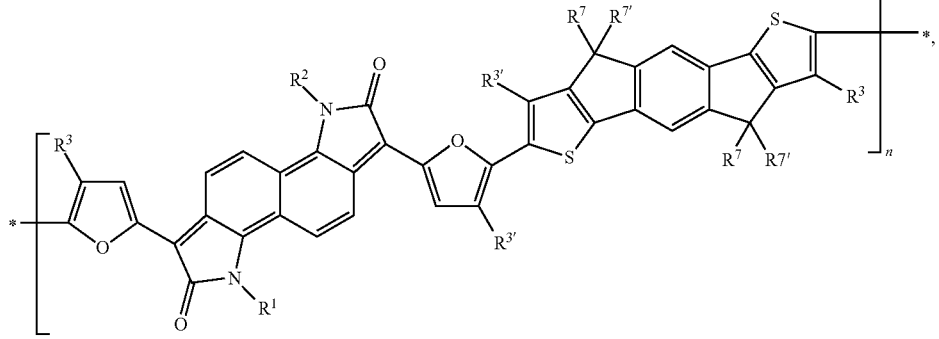
(Ia-14)
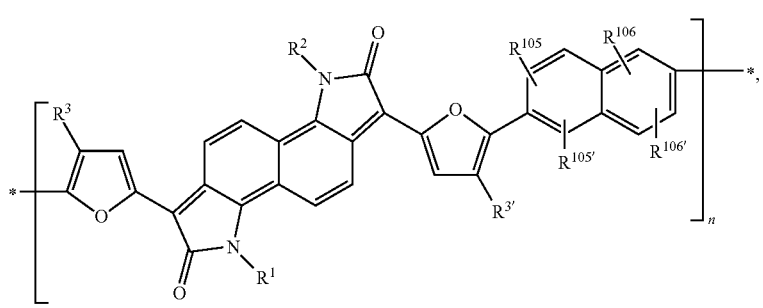
(Ia-15)
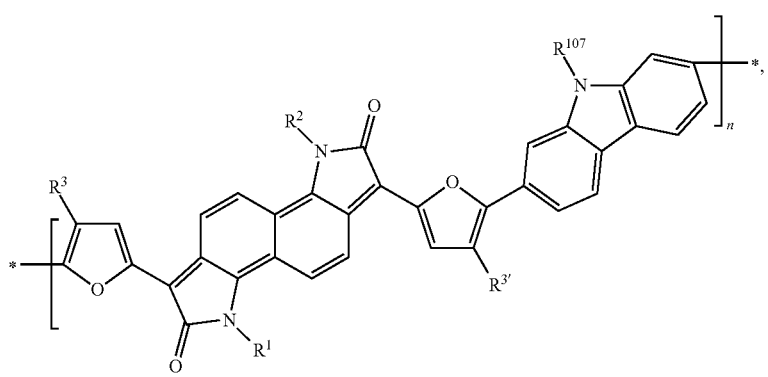
(Ia-16)

-continued
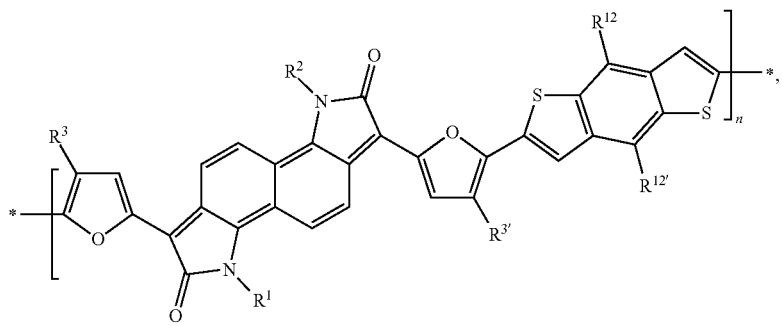
(Ia-17)
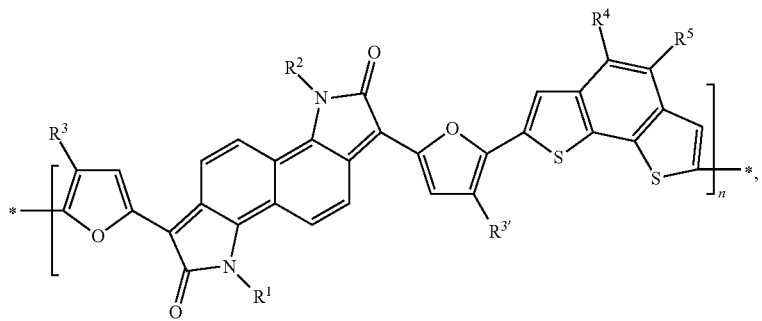
(Ia-18)
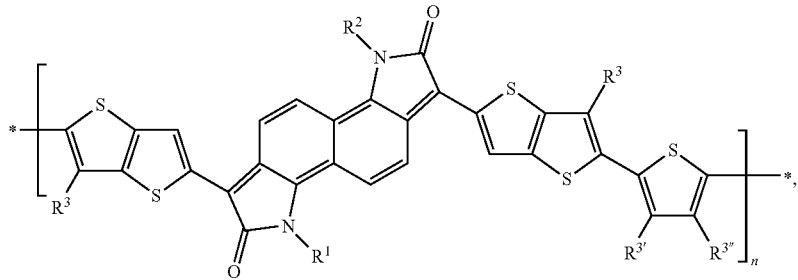
(Ia-19)
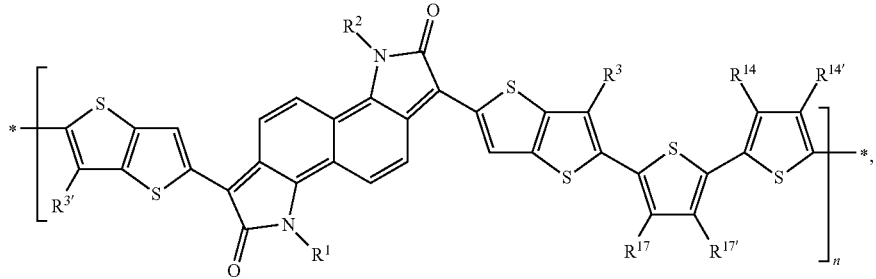
(Ia-20)
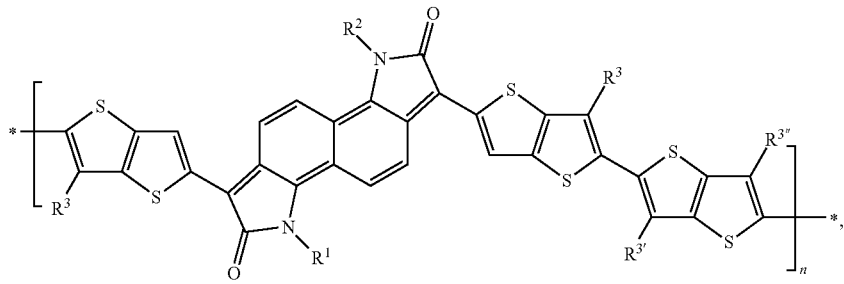
(Ia-21)

-continued
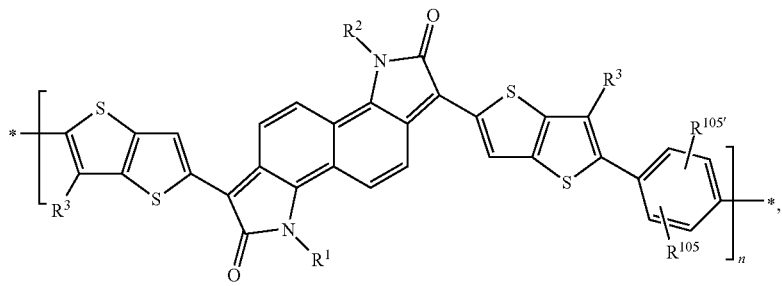
(Ia-22)
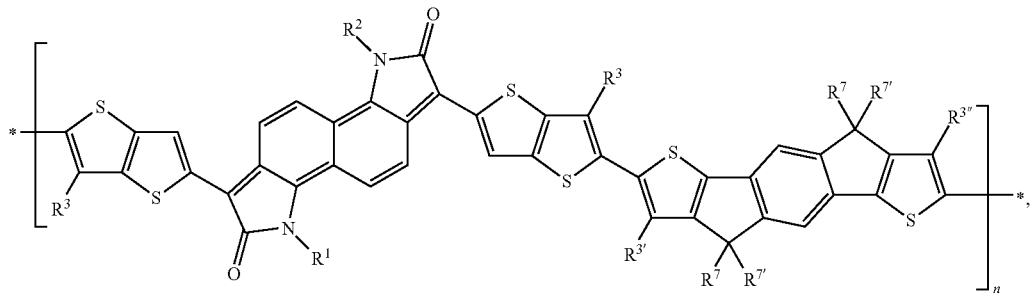
(Ia-23)
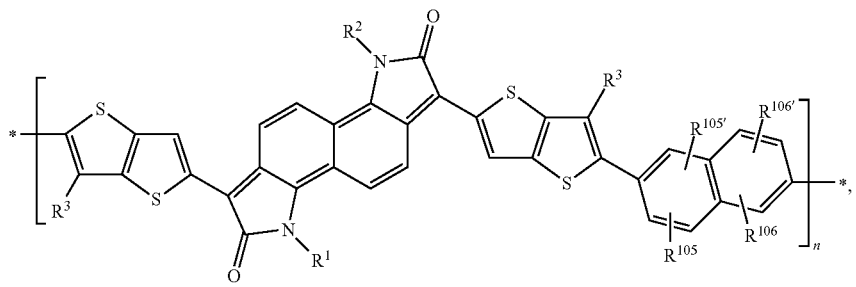
(Ia-24)
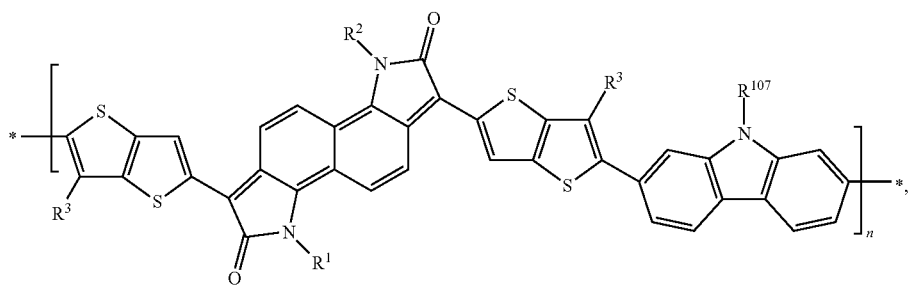
(Ia-25)
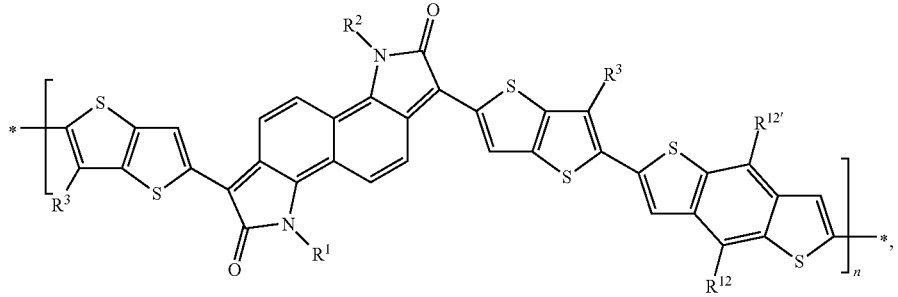
(Ia-26)

-continued
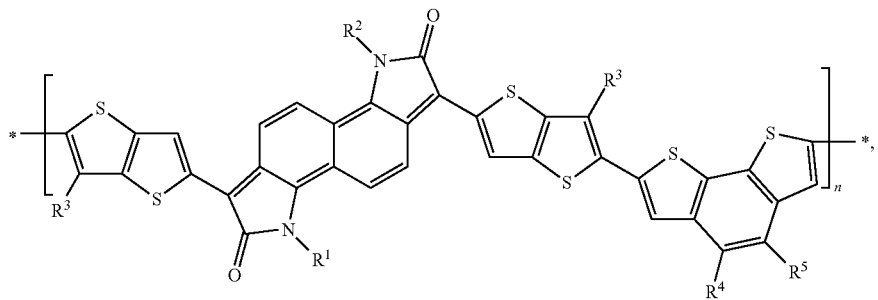
(Ia-27)
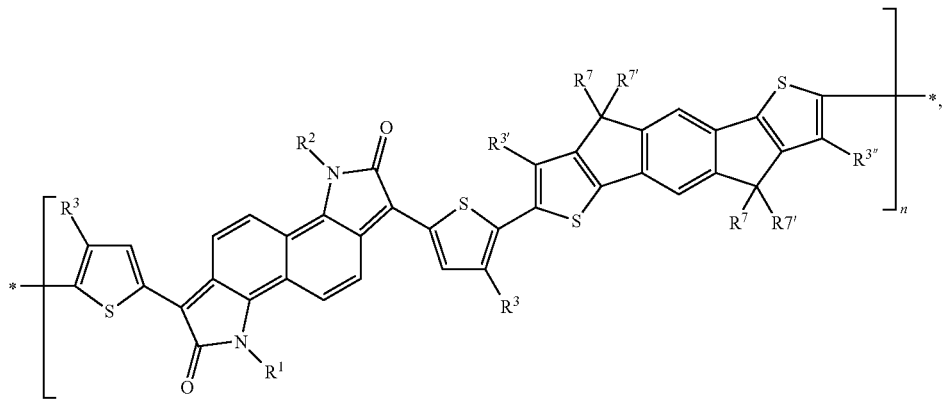
(Ia-28)
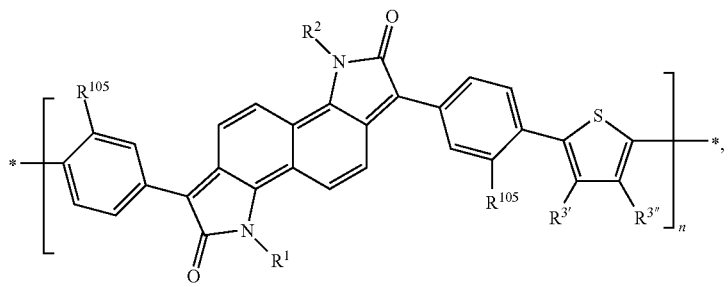
(Ia-29)
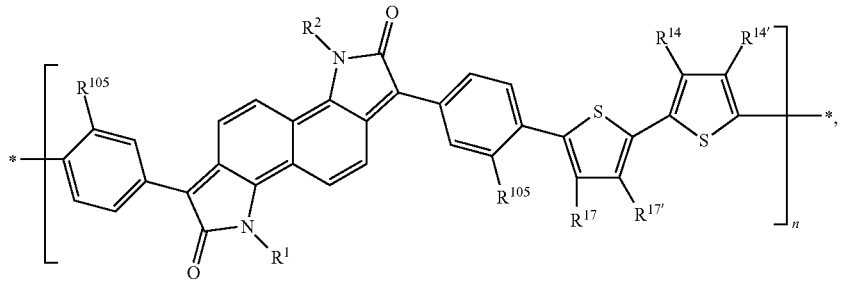
(Ia-30)
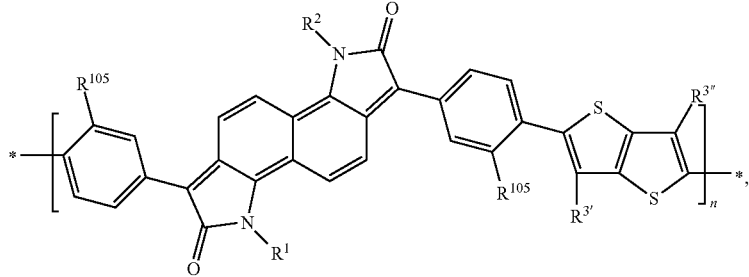
(Ia-31)

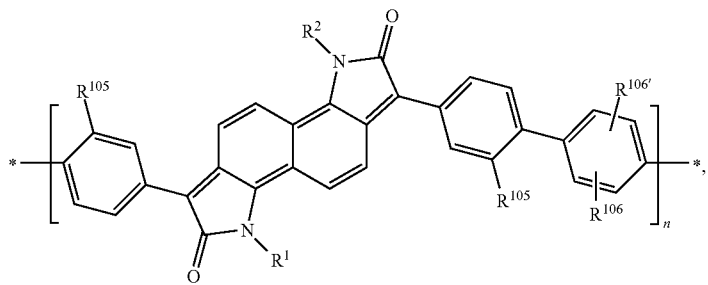
(Ia-32)
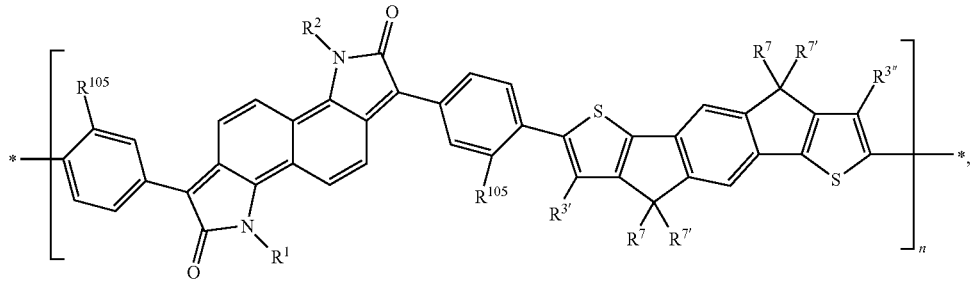
(Ia-33)
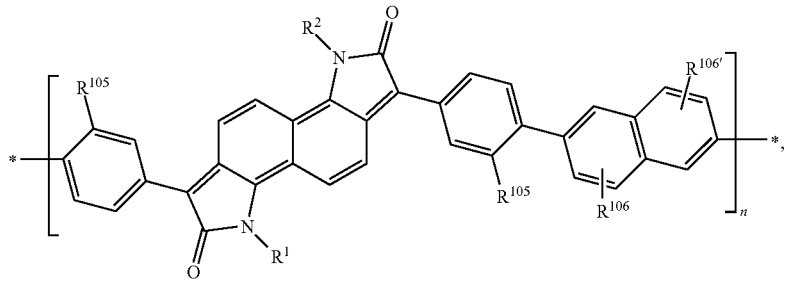
(Ia-34)
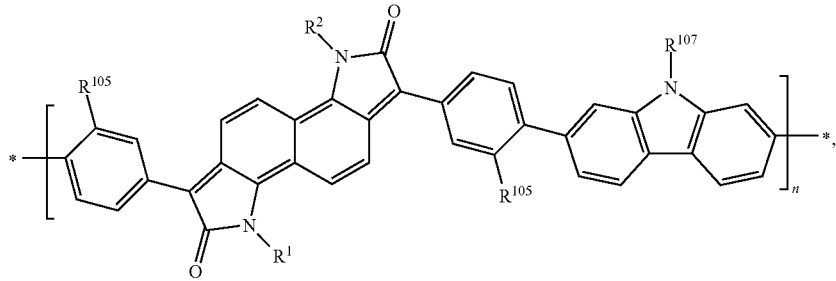
(Ia-35)
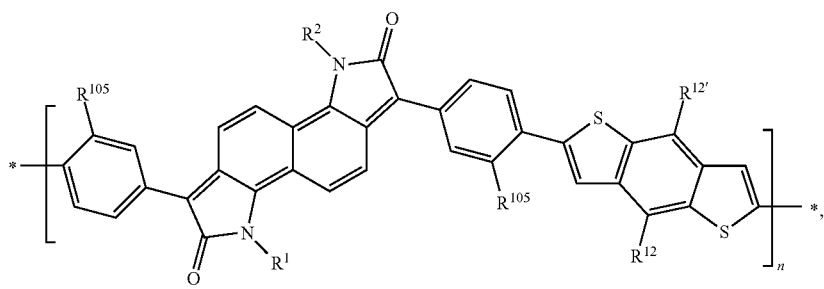
(Ia-36)

-continued

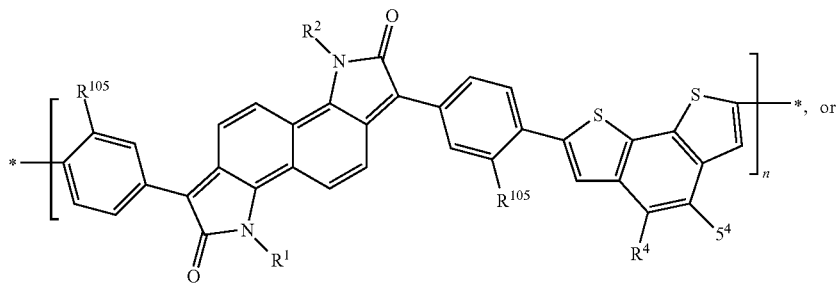
(Ia-37)

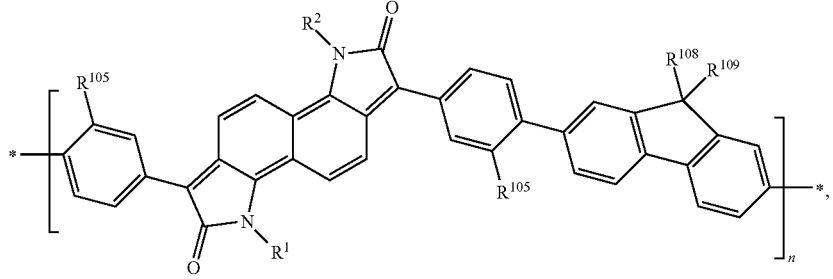
(Ia-38)

wherein n is 4 to 1000,
$R^1$ and $R^2$ are independently a $C_1$-$C_{38}$ alkyl group,
$R^3$, $R^{3'''}$ and $R^{3'}$ are independently hydrogen, halogen, cyano, $C_1$-$C_{25}$ alkyl or $C_1$-$C_{25}$ alkoxy,
$R^4$ and $R^5$ are independently hydrogen, or $C_1$-$C_{25}$ alkyl;
$R^{12}$ and $R^{12'}$ are H, or a $C_1$-$C_{25}$ alkyl group;
$R^7$ and $R^{7'}$ are independently hydrogen, $C_1$-$C_{25}$ alkyl, which is optionally interrupted by one, or more oxygen, or sulphur atoms;
$R^{14}$ and $R^{14'}$ are independently hydrogen, halogen, cyano, $C_1$-$C_{25}$ alkyl or $C_1$-$C_{25}$ alkoxy,
$R^{17}$ and $R^{17'}$ are independently H, or a $C_1$-$C_{25}$ alkyl group;
$R^{104}$ and $R^{104'}$ are independently hydrogen, cyano, $COOR^{103}$, $C_1$-$C_{25}$ alkyl,
$R^{103}$ is $C_1$-$C_{25}$ alkyl,
$R^{105}$, $R^{105'}$, $R^{106}$ and $R^{106'}$ are independently hydrogen, halogen, cyano, $C_1$-$C_{25}$ alkyl or $C_1$-$C_{25}$alkoxy, and
$R^{107}$ is $C_1$-$C_{25}$ alkyl.

7. A compound of formula

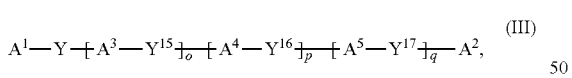
(III)

wherein Y, $Y^{15}$, $Y^{16}$ and $Y^{17}$ are independently a group of formula

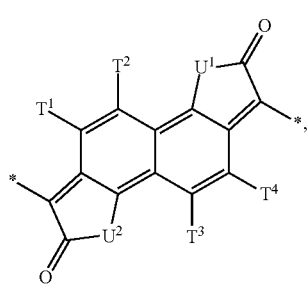

wherein
o is 0, or 1, p is 0, or 1, q is 0, or 1;
$A^1$ and $A^2$ are independently a group of formula

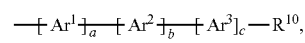

$A^3$, $A^4$ and $A^5$ are independently a group of formula

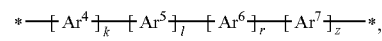

k is 1, 2, or 3; l is 0, 1, 2, or 3; r is 0, 1, 2, or 3; z is 0, 1, 2, or 3;
$R^{10}$ is hydrogen, halogen, cyano, $C_1$-$C_{25}$ alkyl, $C_1$-$C_{25}$ alkyl which is substituted one or more times by E and/or interrupted one or more times by D,

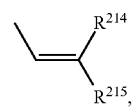

COO—$C_1$-$C_{18}$ alkyl, $C_4$-$C_{18}$ cycloalkyl group, $C_4$-$C_{18}$ cycloalkyl group, which is substituted by G, $C_2$-$C_{18}$ alkenyl, $C_2$-$C_{18}$ alkynyl, $C_1$-$C_{18}$ thioalkoxy, $C_1$-$C_{18}$ alkoxy, $C_1$-$C_{18}$ alkoxy which is substituted by E and/or interrupted by D, $C_7$-$C_{25}$ aralkyl, $C_7$-$C_{25}$ aralkyl, which is substituted by G, or a group of formulae IVa to IVm,

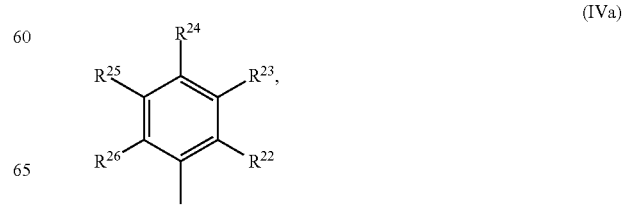
(IVa)

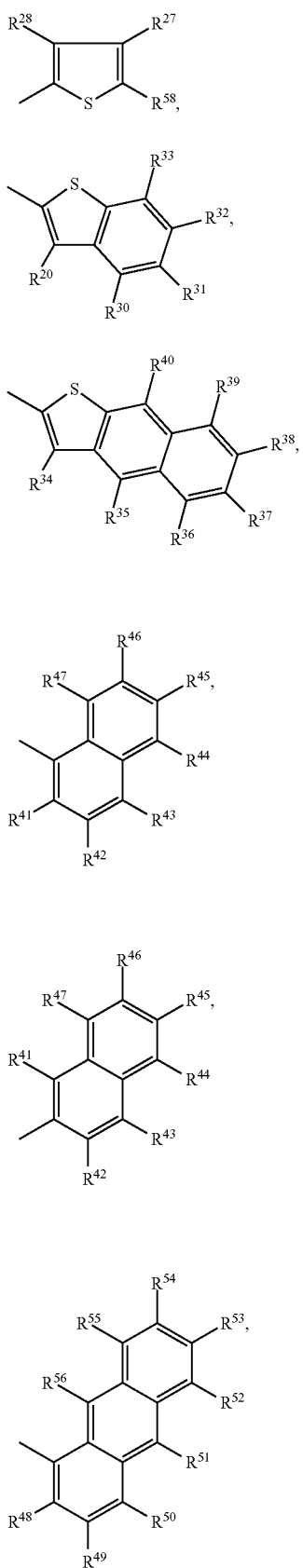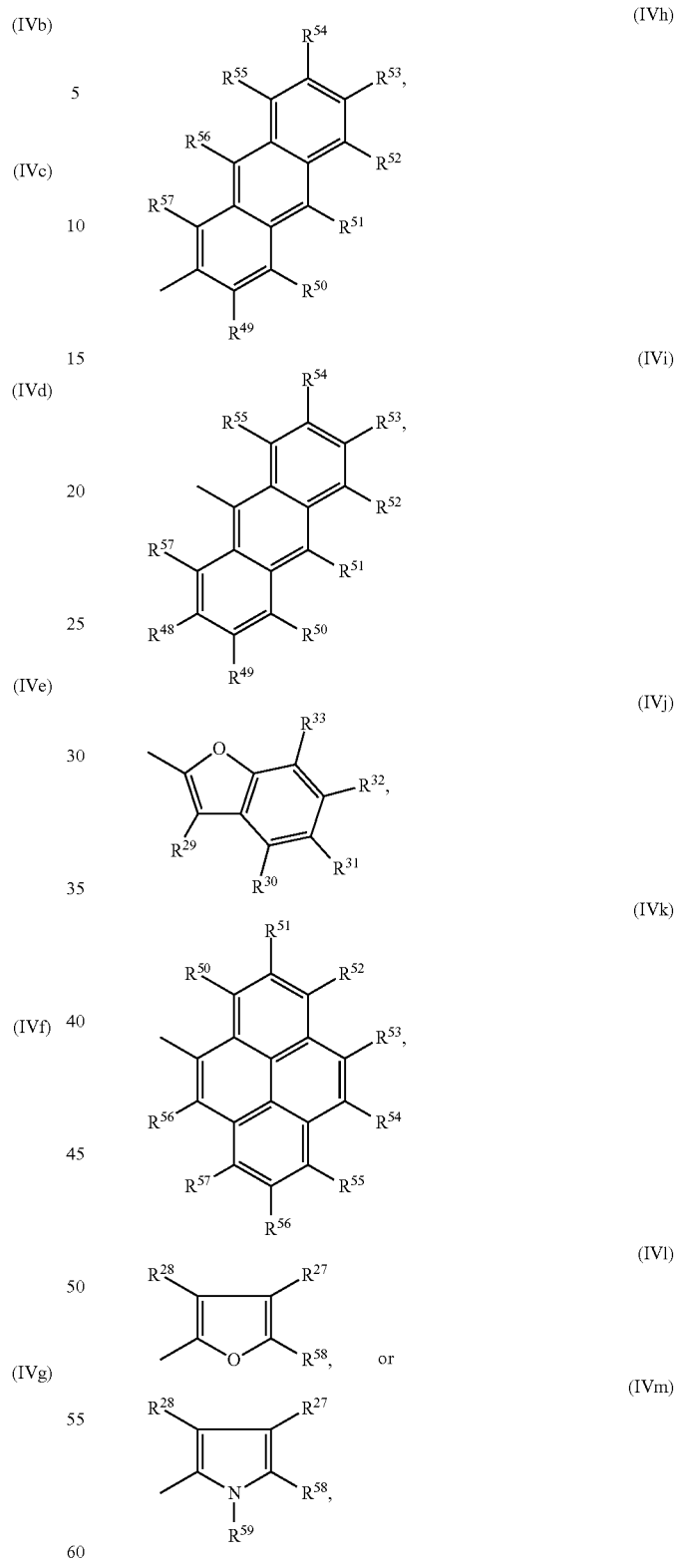
wherein $R^{22}$ to $R^{26}$ and $R^{29}$ to $R^{58}$ represent independently H, halogen, cyano, $C_1$-$C_{25}$ alkyl, $C_1$-$C_{25}$ alkyl which is substituted by E and/or interrupted by D, $C_6$-$C_{24}$ aryl, $C_6$-$C_{24}$ aryl which is substituted by G, $C_2$-$C_{20}$ heteroaryl, $C_2$-$C_{20}$ heteroaryl which is substituted by G, a $C_4$-$C_{18}$ cycloalkyl group, a $C_4$-$C_{18}$ cycloalkyl group, which is substituted by G, $C_2$-$C_{18}$ alkenyl, $C_2$-$C_{18}$ alkynyl, $C_1$-$C_{18}$ alkoxy, $C_1$-$C_{18}$ alkoxy which is substituted by E and/or interrupted by D, $C_7$-$C_{25}$ aralkyl, or $C_7$-$C_{25}$ aralkyl, which is substituted by G, $R^{27}$ and $R^{28}$ are independently hydrogen, $C_1$-$C_{25}$ alkyl, halogen, cyano or $C_7$-$C_{25}$ aralkyl, or $R^{27}$ and $R^{28}$ together represent alkylene or alkenylene which are optionally both bonded via oxygen and/or sulfur to a thienyl residue and which optionally both comprise up to 25 carbon atoms, $R^{59}$ is hydrogen, $C_6$-$C_{18}$ aryl; $C_6$-$C_{18}$ aryl which is substituted by $C_1$-$C_{18}$ alkyl, or $C_1$-$C_{18}$ alkoxy; or $C_1$-$C_{25}$ alkyl, which is optionally interrupted by one or more oxygen or sulphur atoms; or $C_7$-$C_{25}$ arylalkyl, D is —CO—, —COO—, —S—, —O—, or —$NR^{112}$—, E is $C_1$-$C_8$ thioalkoxy, $C_1$-$C_8$ alkoxy, CN, —$NR^{112}R^{113}$, —$CONR^{112}R^{113}$, or halogen, G is E, or $C_1$-$C_{18}$ alkyl, and $R^{112}$ and $R^{113}$ are independently H; $C_6$-$C_{18}$ aryl; $C_6$-$C_{18}$ aryl which is substituted by $C_1$-$C_{18}$ alkyl, or $C_1$-$C_{18}$ alkoxy; $C_1$-$C_{18}$ alkyl; or $C_1$-$C_{18}$ alkyl which is interrupted by —O—;

$R^{214}$ and $R^{215}$ are independently hydrogen, $C_1$-$C_{18}$ alkyl, $C_6$-$C_{24}$ aryl, $C_2$-$C_{20}$ heteroaryl, —CN or $COOR^{216}$;

$R^{216}$ is $C_1$-$C_{25}$ alkyl, $C_1$-$C_{25}$ haloalkyl, $C_7$-$C_{25}$ arylalkyl, $C_6$-$C_{24}$ aryl or $C_2$-$C_{20}$ heteroaryl;

$Ar^4$, $Ar^5$, $Ar^6$ and $Ar^7$ are independently $Ar^1$, and a, b, c, $Ar^1$, $Ar^2$, $Ar^3$, $T^1$, $T^2$, $T^3$, $T^4$, $U^1$ and $U^2$ are as defined in claim 1, with the proviso that, if o is 0, p is 0, q is 0, and $U^1$ is O and $U^2$ is O, $T^1$, $T^2$, $T^3$ and $T^4$ are each hydrogen, halogen, alkyl, or alkoxy; then the sum of a, b and c is equal, or greater than 2; and the further proviso that, if o is 0, p is 0, q is 0, a is 1, b is 0, c is 0, $T^1$, $T^2$, $T^3$ and $T^4$ are hydrogen, $U^1$ is O, $U^2$ is NH and $Ar^1$ is a group of formula

then $R^{10}$ is different from $OCH_3$, $OC_2H_5$, $O(CH_2)_2CH_3$, $OCH(CH_3)_2$ and $O(CH_2)_3CH_3$.

8. The compound according to claim 7, which is a compound of formula

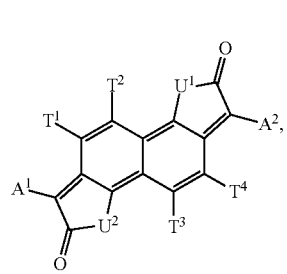
(IIIa)

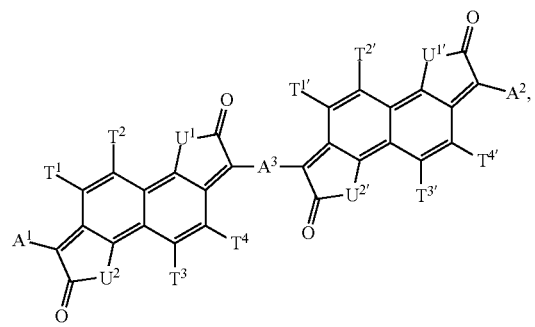
(IIIb)

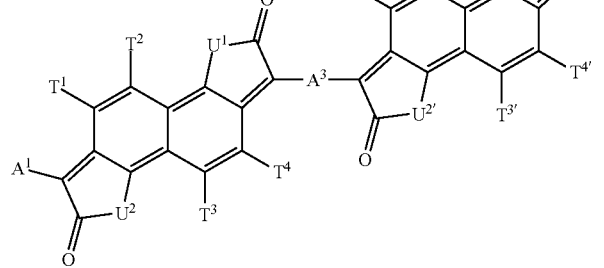

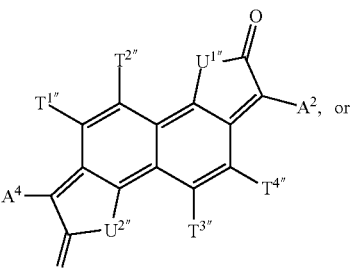
(IIIc)

-continued (IIId)

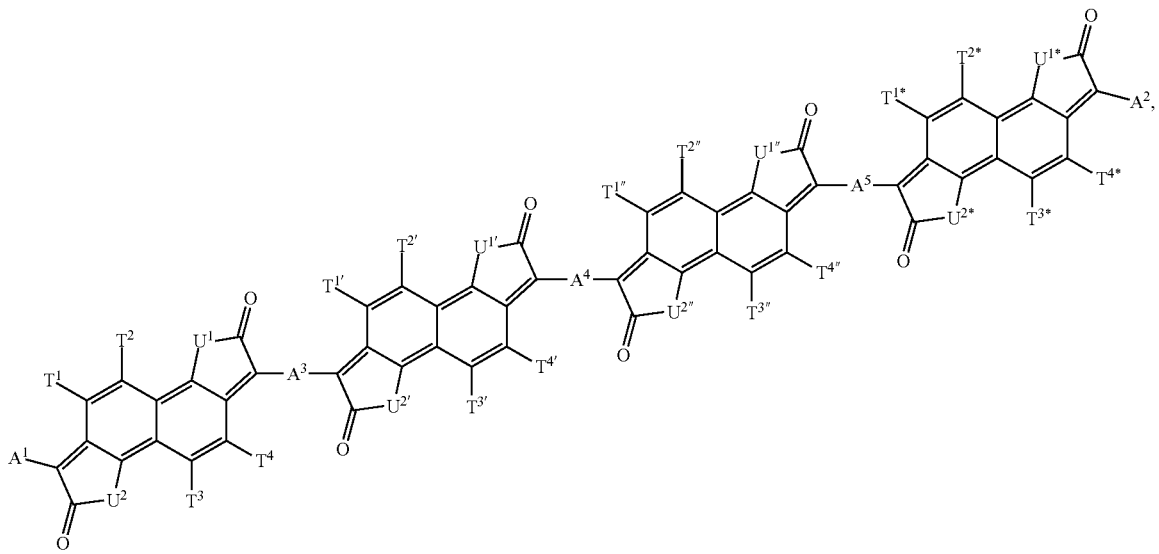

wherein
$A^1, A^2, A^3, A^4, A^5, T^1, T^2, T^3, T^4, U^1$ and $U^2$ are as defined in claim 7,
$T^{1'}, T^{2'}, T^{3'}, T^{4'}, T^{1''}, T^{2''}, T^{3''}, T^{4''}, T^{1*}, T^{2*}, T^{3*}$ and $T^{4*}$ are independently $T^1$, and
$U^{1'}, U^{2'}, U^{1''}, U^{2''}, U^{1*}$ and $U^{2*}$ are independently $U^1$.

9. An organic semiconductor material, layer or component, comprising the polymer according to claim 1.

10. A semiconductor device, comprising the polymer according to claim 1.

11. The semiconductor device according to claim 10, which is an organic photovoltaic device, a photodiode, or an organic field effect transistor.

12. A process for preparing an organic semiconductor device, the process comprising:
applying a solution and/or dispersion of the polymer according to claim 1 in an organic solvent to a suitable substrate and
removing the solvent.

13. A process for preparing a device, the process comprising:
employing the polymer according to claim 1 as IR absorber, or organic field effect transistor in the device, wherein the device is a PV device or a photodiode.

14. A compound of formula (V)

$X^2\text{---}(Ar^3)_c\text{---}(Ar^2)_b\text{---}(Ar^1)_a\text{---}Y\text{---}(Ar^{1'})_{a'}\text{---}(Ar^{2'})_{b'}\text{---}(Ar^{3'})_{c'}\text{---}X^{2'}$, wherein a, a', b, b', c, c', Y, $Ar^1, Ar^{1'}, Ar^2, Ar^{2'}, Ar^3$ and $Ar^{3'}$ are as defined in claim 1, and $X^2$ and $X^{2'}$ are independently halogen, $ZnX^{12}$, $-SnR^{207}R^{208}R^{209}$, wherein $R^{207}, R^{208}$ and $R^{209}$ are independently H or $C_1-C_6$ alkyl, or two of the groups $R^{207}, R^{208}$ and $R^{209}$ form a ring and are optionally branched; $-SiR^{210}R^{211}R^{212}$, wherein $R^{210}, R^{211}$ and $R^{212}$ are independently halogen, or $C_1-C_6$ alkyl; $X^{12}$ is a halogen atom; $-OS(O)_2CF_3$, $-OS(O)_2$-aryl, $-OS(O)_2CH_3$, $-B(OH)_2$, $-B(OY^1)_2$,

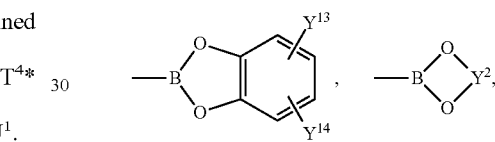

$-BF_4Na$, or $-BF_4K$, wherein $Y^1$ is independently in each occurrence a $C_1-C_{10}$ alkyl group and $Y^2$ is independently in each occurrence a $C_2-C_{10}$ alkylene group and $Y^{13}$ and $Y^{14}$ are independently hydrogen, or a $C_1-C_{10}$ alkyl group.

15. A process for preparing a polymer of formula (VII')

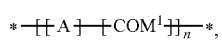

the process comprising
reacting a dihalogenide of formula $X^{10}$-A-$X^{10}$ with an equimolar amount of a diboronic acid or diboronate corresponding to formula $X^{11}$—$COM^1$-$X^{11}$, or
reacting a dihalogenide of formula $X^{10}$—$COM^1$-$X^{10}$ with an equimolar amount of a diboronic acid or diboronate corresponding to formula $X^{11}$-A-$X^{11}$, wherein $X^{10}$ is halogen, and $X^{11}$ is independently in each occurrence $-B(OH)_2$, $-B(OY^1)_2$,

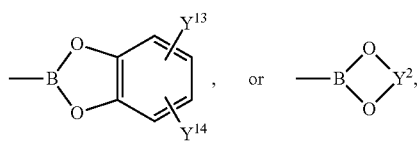

wherein $Y^1$ is independently in each occurrence a $C_1-C_{10}$ alkyl group and $Y^2$ is independently in each occurrence a $C_2-C_{10}$ alkylene group and $Y^{13}$ and $Y^{14}$ are independently hydrogen, or a $C_1-C_{10}$ alkyl group, in a solvent and in the presence of a catalyst; or reacting a dihalogenide of formula $X^{10}$-A-$X^{10}$ with an equimolar amount of an organo tin compound corresponding to formula

or reacting a dihalogenide of formula

with an equimolar amount of an organo tin compound corresponding to formula $X^{11'}$-A-$X^{11'}$, wherein
$X^{11'}$ is independently in each occurrence —$SnR^{207}R^{208}R^{209}$, wherein $R^{207}$, $R^{208}$ and $R^{209}$ are independently H or $C_1$-$C_6$ alkyl, or two of the groups $R^{207}$, $R^{208}$ and $R^{209}$ form a ring and are optionally branched, A and $COM^1$ are as defined in claim 4 and n is in a range of 4 to 1000.

16. A polymer comprising a unit of formula

 (X)

wherein $A^{1'}$ and $A^{2'}$ are independently a group of formula

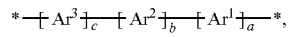

wherein a, b, c, p, q, $Ar^1$, $Ar^2$, $Ar^3$, Y, $Y^{15}$, $Y^{16}$, $Y^{17}$, $A^3$, $A^4$ and $A^5$ are as defined in claim 7.

* * * * *